US009474797B1

(12) United States Patent
Borca et al.

(10) Patent No.: US 9,474,797 B1
(45) Date of Patent: Oct. 25, 2016

(54) AFRICAN SWINE FEVER VIRUS GEORGIA STRAIN ADAPTED TO EFFICIENTLY GROW IN THE VERO CELL LINE

(71) Applicants: The United States of America, as Represented by the Secretary of Agriculture, Washington, DC (US); The University of Connecticut, Storrs, CT (US)

(72) Inventors: Manuel V. Borca, Westbrook, CT (US); Luis L. Rodriguez, Clinton, CT (US); Peter W. Krug, Stony Brook, NY (US); Vivian K. O'Donnell, Old Saybrook, CT (US)

(73) Assignees: The United States of America, as Represented by the Secretary of Agriculture, Washington, DC (US); The University of Connecticut, Farmington, CT (US)

( * ) Notice: Subject to any disclaimer, the term of this patent is extended or adjusted under 35 U.S.C. 154(b) by 0 days.

(21) Appl. No.: 14/309,548

(22) Filed: Jun. 19, 2014

(51) Int. Cl.
*A61K 39/12* (2006.01)
*A61K 39/00* (2006.01)

(52) U.S. Cl.
CPC ......... *A61K 39/12* (2013.01); *A61K 2039/525* (2013.01); *C12N 2710/12021* (2013.01); *C12N 2710/12034* (2013.01)

(58) Field of Classification Search
None
See application file for complete search history.

(56) References Cited

PUBLICATIONS

GenBank: FR682468.1. African swine fever virus Georgia 2007/1 complete genome. Dated Apr. 12, 2011.*
Borca, M.B., et al., Deletion of a CD2-Like Gene, 8-DR, from African Swine Fever Virus Affects Viral Infection in Domestic Swine. Journal of Virology. 1998, 72 (4): 2881-2889.
Chapman, David, et al., Genomic Analysis of Highly Virulent Georgia 2007/1 Isolate of African Swine Fever Virus, Emerging Infectious Diseases. Apr. 2011. vol. 17 (4): 599-605.
Lewis, T., et al., An African Swine Fever Virus ERV1-ALR Homologue, 9GL, Affects Virion Maturation and Viral Growth in Macrophages and Viral Virulence in Swine. Journal of Virology. 2000. vol. 74 (3): 1275-1285.
Moore, D.M., et al., The African Swine Fever Virus Thymidine Kinase Gene is Required for Efficient Replication in Swine Macrophages and for Virulence in Swine. Journal of Virology. 1998. vol. 72 (12): 10310-10315.
Zsak, L., et al., An African Swine Fever Virus Virulence-Associated Gene NL-S With Similarity to the Herpes Simplex Virus ICP34.5 Gene. Journal of Virology. 1996. vol. 70 (12): 8865-8871.

* cited by examiner

*Primary Examiner* — Nick Zou
(74) *Attorney, Agent, or Firm* — John D. Fado; Evelyn M. Rabin

(57) ABSTRACT

We have developed an ASFV Georgia strain adapted to grow in Vero cell line. The resulting virus, ASF-GVAV, efficiently grows in Vero cells although it still is able to significantly replicate in primary cell cultures of swine macrophages. ASF-GVAV virus was successfully used as parental virus to develop several recombinant ASF viruses. The development of an ASFV adapted to grow in an established cell line is a significant advance for research and development of vaccine candidate strains using genetic manipulation based in the process of homologous recombination. The GVAVS can be utilized as a basis for large scale production of ASF vaccines.

7 Claims, 2 Drawing Sheets
(1 of 2 Drawing Sheet(s) Filed in Color)

AFRICAN SWINE FEVER VIRUS GEORGIA STRAIN ADAPTED TO EFFICIENTLY GROW IN THE VERO CELL LINE

BACKGROUND OF THE INVENTION

1. Field of the Invention

The present invention relates generally to the field of viruses for vaccine development useful in the prophylaxis of African Swine Fever (ASF). More specifically, the invention provides a novel ASF virus for the development of recombinant ASF virus vaccine candidates, the genomes of which are modified from that of their parental Georgia strain (ASF-G) and are adapted for growth in Vero cells, resulting in the isolated, recombinant ASF-GVAV.

2. Description of the Relevant Art

African swine fever is a devastating highly contagious viral disease of pigs with mortality rates approaching 100 percent. ASF is endemic to Sub-Saharan Africa and maintains a life cycle in the wild through infection between soft ticks and feral pigs (wild pigs/bush pigs/warthogs). It causes major economic losses, threatens food security, and limits pig production in affected countries. The threat for an introduction of ASF in the United States is significant. The appearance of the 2007 outbreak in the Caucasus region (caused by the so called Georgia strain) and its further spreading throughout west Russia and Ukraine indicate that ASF is constant threat not only to Europe but also to Asia where swine represent the main source of animal protein and where the introduction and consequent high mortality caused by ASF would have devastating effects.

The disease occurs in several forms, ranging from acute to chronic with all infections being lethal. Importantly, there is no vaccine available to prevent the disease. Additionally, with the exception of few preliminary studies showing induction of neutralizing antibodies and partial protection against the challenge in animals immunized with a combination of structural proteins, no viral protein(s) mediating protective immunity or the immune mechanisms involved in protection have been identified.

Currently, there is no vaccine available for ASF and disease outbreaks are controlled by animal quarantine and slaughter. African swine fever virus is a large, icosahedral, cytoplasmic, double-stranded DNA virus; it is the only member of the family Asfaviridae, although it shares similarities with other virus families in the superfamily of nucleo-cytoplasmic large DNA viruses (Chapman et al. 2011. *Emerging Infect. Dis.* 17: 599-605). Attempts to vaccinate animals using infected cell extracts, supernatants of infected pig peripheral blood leukocytes, purified and inactivated virions, infected glutaraldehyde-fixed macrophages, or detergent-treated infected alveolar macrophages failed to induce protective immunity (Coggins, L. 1974. *Prog. Med. Virol.* 18:48-63; Forman et al. 1982. *Arch. Virol.* 74:91-100; Kihm et al. 1987. In: *African Swine Fever*, Becker, Y. (ed), Martinus Nijhoff, Boston, pp 127-144; Mebus, C. A. 1988. *Adv. Virus Res.* 35:251-269). Conversely, the use of attenuated virus strains obtained either by serial passages in cell cultures or by deleting virulence-associated genes through genetic manipulation of the virus genome constitutes the only methodology to induce protection. Thus, pigs surviving acute infection with moderately virulent or attenuated variants of ASFV develop long-term resistance to homologous, but rarely to heterologous, virus challenge (Hamdy and Dardiri. 1984. *Am. J. Vet. Res.* 45:711-714; Ruiz-Gonzalvo et al. 1981. In: *FAO/CEC Expert Consultation in ASF Research*, Wilkinson, P. J. (ed), Rome, pp 206-216). Importantly, pigs immunized with live attenuated ASF viruses containing engineered deletions of specific ASFV virulence/host range genes were protected when challenged with homologous parental virus (Lewis et al. 2000. *J. Virol.* 74:1275-1285; Moore et al. 1998. *J. Virol.* 72:10310-10315; Zsak et al. 1996. *J. Virol.* 70:8865-8871; Zsak et al. 1998. *J. Virol.* 72:1028-1035). These reports are a proof of concepts regarding the feasibility for the development of ASF vaccines by creating attenuated recombinant virus strains by genetic manipulation of field strains.

The core of the process of producing ASF recombinant viruses includes a homologous recombination event leading to the deletion of a specific virus gene and the insertion of a foreign marker gene which facilitates the identification and further purification of the recombinant virus. The process of developing recombinant ASFV from field isolates is time consuming and requires the availability of primary cultures of swine macrophages. Performing this process using established cell lines would be much easier since cells would be readily available and the process of homologous recombination much more effective. Thus, availability of an ASF virus acclimated to growing in a cell line would be useful and desirable for vaccine development.

SUMMARY OF THE INVENTION

We have developed an ASFV Georgia strain adapted to grow in Vero cell line; and the resulting virus, ASF-GVAV (ASF-Georgia Vero-Adapted Virus) efficiently grows in Vero cells and was successfully used as parental virus to develop several recombinant ASF viruses.

In accordance with this discovery, it is an object of the invention to provide ASF-GVAV for the development of recombinant ASF vaccine candidate strains using genetic manipulation based in the process of homologous recombination wherein growth in Vero cells makes said genetic manipulation easier.

It is also an object of the invention to provide an isolated polynucleotide molecule comprising a genetically modified DNA sequence encoding the genetically modified ASF-GVAV.

Other objects and advantages of this invention will become readily apparent from the ensuing description.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

DETAILED DESCRIPTION OF THE INVENTION

Figure 1:
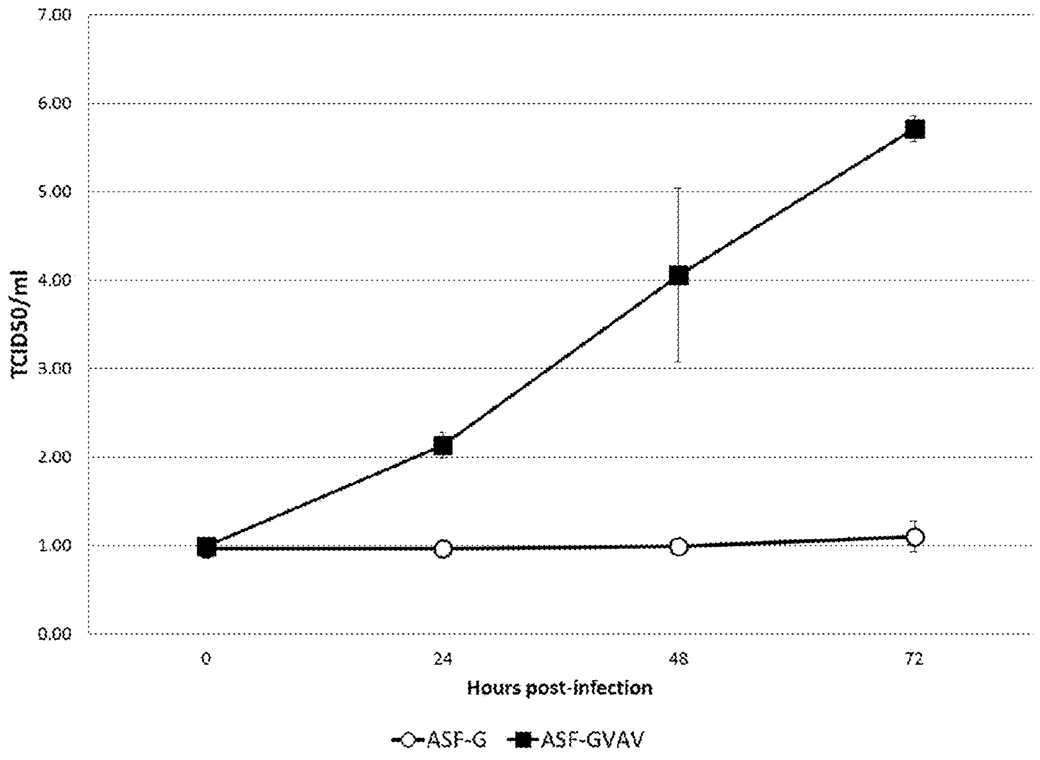
FIG. 1 depicts the in vitro growth characteristics of virus ASF-GVAV relative to parental ASFV Georgia isolate in a multi-step growth curve in Vero cell cultures.

We have developed and characterized a virus strain derived from the ASFV Georgia isolate 101, the virus strain currently causing the ASF epidemic in the Caucasus region, Russia, Ukraine, and other eastern Europeans countries. Our new virus strain has been adapted to grow in Vero cell line. We show here the process of virus adaptation, describe the mutated sequence of our ASF-GVAV virus and we give examples of its use for the development of different genetically modified virus strains.

The present invention provides ASFV adapted to growth in the Vero cell line, ATCC® CCL-81™, a cell substrate suitable for commercial production of ASF vaccines. In addition to such adapted ASF-GVAV, the invention provides a method for adapting a selected ASF to growth in the Vero cell line and preparing a Vero-adapted ASF without passaging in primary cultures. The ASF-GVAV of this invention can be used to develop recombinant ASF virus vaccine candidates.

In order to produce other vaccine candidates which are maximized for desirable levels of growth in Vero cells, we determined the genetic changes that occurred in the genome of the Vero-adapted ASF-G virus that altered its growth characteristics. We have discovered a large deletion in the nucleotide sequence of ASF-GVAV (SEQ ID NO:1), when compared ASF-Georgia strain (SEQ ID NO: 2). The present invention identifies the mutations that have occurred during adaptation to growth of ASF-GVAV in Vero cells. The nucleotide sequence of the Vero cell-adapted virus ASF-GVAV (SEQ ID NO:1) was compared with that of the original ASF-G virus (SEQ ID NO: 2).

A spleen homogenate from a pig infected in the field with the Georgia strain of ASFV was used to infect a sub-confluent monolayer of Vero cells and incubated for 4 days in a 34° C. incubator. Infected cells were detached and sub-cultured several times as described in Example 3. After infection was verified by immunochemistry, cells were expanded and frozen. Harvested virus stock having a titer of $5\times10^6$ PFU/ml was used to infect Vero cells. The infected culture was incubated at 34° C. until evident generalized CPE was observed and virus was successively passed under similar conditions for a total of 30 passages. Virus harvested after the last passage was used to produce a stock called ASF-GVAV (ASF-Georgia Vero-Adapted Virus).

In vitro growth characteristics of virus ASF-GVAV was evaluated relative to parental ASFV Georgia isolate in a multi-step growth curve where Vero cells as well as primary swine macrophage cell cultures were infected and growth was compared. Results demonstrated that ASF-GVAV exhibited a significantly increased virus yield (between 10-100,000 times more, depending on the time point considered) when compared to parental ASFV Georgia isolate. This result clearly indicates the adaptation of ASF-GVAV to grow in Vero cells.

The full length genome sequence of ASF-GVAV was compared with the parental ASFV Georgia isolate to determine those changes in the genome that occurred in ASF-G during the process of adaptation to grow in Vero cells resulting in the development of ASF-GVAV. Basically, a comparison between the genomes of the parental ASFV Georgia isolate and ASF-GVAV viruses demonstrated that ASF-GVAV possess a deletion between nucleotide positions 178,643 and 182,578 producing the deletion of the several ORFs; and, in addition, as shown in Example 4, there are further deletions, insertions, frame shifts, and amino acid substitutions.

It is understood that terms herein referring to nucleic acid molecules such as “isolated polynucleotide molecule” and “nucleotide sequence” include DNA, cDNA and RNA molecules and include both single-stranded and double-stranded molecules whether it is natural or synthetic origin.

For example, SEQ ID NO:1 is a DNA sequence corresponding to the genetically modified ASF-GVAV.

Furthermore, when reference is made herein to sequences homologous to a sequence in the Sequence Listing, it is to be understood that sequences are homologous to a sequence corresponding to the sequence in the Sequence Listing and to a sequence complementary to the sequence in the Sequence Listing.

For purposes of the present invention, two DNA sequences are substantially homologous when preferably 95% of the nucleotides match over the defined length of the sequence using algorithms such as CLUSTRAL or PILEUP. Sequences that are substantially homologous can be identified in a Southern hybridization experiment under stringent conditions as is known in the art. See, for example, Sambrook et al., supra. Sambrook et al. describe highly stringent conditions as a hybridization temperature 5-10° C. below the $T_m$ of a perfectly matched target and probe; thus, sequences that are “substantially homologous” would hybridize under such conditions.

As used herein, “substantially similar” refers to nucleic acid fragments wherein changes in one or more nucleotide bases results in substitution of one or more amino acids, but do not affect the functional properties of the polypeptide encoded by the nucleotide sequence. “Substantially similar” also refers to modifications of the nucleic acid fragments of the instant invention such as deletion or insertion of nucleotides that do not substantially affect the functional properties of the resulting transcript. It is therefore understood that the invention encompasses more than the specific exemplary nucleotide or amino acid sequences and includes functional equivalents thereof. Alterations in a nucleic acid fragment that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (1985. *Nucleic Acid Hybridization*, Hames and Higgins, Eds., IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms.

Substantially similar nucleic acid fragments of the instant invention may also be characterized by the percent identity of the amino acid sequences that they encode to the amino acid sequences disclosed herein, as determined by algorithms commonly employed by those skilled in this art.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988. *CABIOS* 4:11-17), the local homology algorithm of Smith et al. (1981. *Adv. Appl. Math.* 2:482); the homology alignment algorithm of Needleman and Wunsch (1970. *J. Mol. Biol.* 48:443-453); the search-for-similarity-method of Pearson and Lipman (1988. *Proc. Natl. Acad. Sci.* 85:2444-2448; the algorithm of Karlin and Altschul (1990. *Proc. Natl. Acad. Sci. USA* 87:2264), modified as in Karlin and Altschul (1993. *Proc. Natl. Acad. Sci. USA* 90:5873-5877).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

The term "substantial identity" of polynucleotide sequences means that a polynucleotide comprises a sequence that has at least 95% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 95%. Preferably, optimal alignment is conducted using the homology alignment algorithm of Needleman et al. (1970. *J. Mol. Biol.* 48:443).

Another indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification and isolation. In addition, short oligonucleotides of 12 or more nucleotides may be use as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions at those sequences as defined above.

By "variants" substantially similar sequences are intended. For nucleotide sequences, conservative variants include those sequences that, because of the degeneracy of the genetic code, encode the amino acid sequence of one of the ASFV proteins of the invention. Naturally occurring allelic variants such as these can be identified with the use of well-known molecular biology techniques, as, for example, with polymerase chain reaction (PCR), a technique used for the amplification of specific DNA segments. Generally, variants of a particular nucleotide sequence of the invention will have generally at least about 90%, preferably at least about 95% and more preferably at least about 98% sequence identity to that particular nucleotide sequence as determined by sequence alignment programs described elsewhere herein.

The terms "African swine fever virus" and "ASFV", as used herein, unless otherwise indicated, mean any strain of ASF viruses.

Accordingly, the subject invention provides an isolated polynucleotide molecule comprising a cDNA sequence encoding an ASFV that is genetically modified such that it adapted to grow in Vero cell culture wherein the cDNA sequence encoding said modified ASF-GVAV is SEQ ID NO:1 or sequences homologous thereto and contains one or more mutations that genetically enable the encoded ASF-GVAV to grow in Vero cells.

EXAMPLES

Having now generally described this invention, the same will be better understood by reference to certain specific examples, which are included herein only to further illustrate the invention and are not intended to limit the scope of the invention as defined by the claims.

Example 1

Viruses and Cell Cultures

The ASF virus Georgia strain was derived at PIADC from clinical material (spleen) of a field-infected pig kindly provided by Dr. Nino Vepkhvadze, from the Laboratory of the Ministry of Agriculture (LMA) in Tbilisi, Ga. The clinical material was macerated, resuspended in Dulbecco's Minimal Essential Media (DMEM) (Gibco, Grand Island, N.Y.) with 10% fetal calf serum (FCS) (Atlas Biologicals, Fort Collins, Colo.), clarified by centrifugation at 4° C., 20 min at 10,000 rpm and resuspended in Dulbecco's Minimal Essential Media (DMEM) (Gibco, Grand Island, N.Y.) with 10% fetal calf serum (FCS) (Atlas Biologicals, Fort Collins, Colo.). Vero cells were obtained from the ATCC, and sub-cultured in DMEM with 10% FCS. Growth kinetics was assessed either in Vero cells or in primary swine macrophage cell cultures prepared as described by Zsak et al. (1996, supra). Titration of ASFV from clinical samples was performed using primary swine macrophage cell cultures in 96-well plates (Primaria, Cambridge, Mass.). Viral infectivity was detected, after 7 days in culture, by hemoadsorption (HA). Titers were calculated using the method of Reed and Muench (1938. *Amer. J. Hygiene* 27:493-497) and expressed as $TCID_{50}$/ml.

Example 2

Full Length Sequence of ASFV Georgia Vero Adapted Strain

ASFV DNA was obtained from the cytoplasm of infected cells using the trizol method. DNA concentration was determined using Qubit® dsDNA HS assay kit (Life Technologies) and read on Qubit® 2 Flourometer (Life Technologies). One ug of virus DNA was enzymatically fragmented to obtain blunt end fragments in a length range of 200-300 bp using Ion Shear™ Plus reagent kit (Life Technologies) and incubated at 37° C. in Peltier Thermal cycler DNA Engine Tetrad 2. After shearing, fragmented DNA library is loaded onto a high sensitivity DNA chip (Agilent) and analyzed using a 2100 Bioanalyzer (Agilent) to assess the library size distribution and confirm a fragment size range between 50-500 bp, with a peak around 200 bp. Then, fragmented DNA is ligated to Ion-compatible adapters and library barcodes, followed by nick-repair to complete the linkage between adapters and DNA inserts using Ion Plus Fragment Library kit (Life Technologies). The adapter-ligated library is then size-selected for optimum length on a 2% Agarose Gel Cassettes (Sage Science) using Pippin Prep™ instrument (Sage Science). Library concentration is then normalized using the Ion Library Equalizer™ Kit (Life Technologies). Next the DNA library is clonally amplified onto Ion Sphere™ Particles generating template-positive ISPs using the Ion PGM™ Template OneTouch™ 2 200 Kit (Life Technologies) with the Ion OneTouch™ 2 Instrument (Life Technologies). Before proceeding to enrichment, quality assessment of unenriched template-positive ISPs is performed using Ion Sphere™ Quality Control assay kit (Life Technologies) and Qubit® 2 Flourometer instrument. The template-positive ISPs are then enriched using the Ion PGM™ Template OneTouch™ 2 200 Kit (Life Technologies) and Ion OneTouch™ ES instrument (Life Technologies) to eliminate untemplated ISPs and denatures DNA on template-positive ISPs. Using the Ion PGM™ 200 Sequencing v2 Kit (Life Technologies), enriched template ISPs are prepared for sequencing and loaded onto either Ion 314™ or Ion 316™ Chip v2 (Life Technologies) and run on the Ion PGM™ Sequencer (Life Technologies) which performs real-time measurements of hydrogen ions produced during DNA replication. Obtained sequences are then trimmed using Galaxy (Retrieved from the Internet: <URL: usegalaxy.org) NGS QC and Manipulation. Sequences are then aligned and analyzed using Sequencher 5.2.2 (Genecodes) and CLC Genomics Workbench (CLCBio) software.

Example 3

Development and Characterization of ASF-GVAV, the ASFV Georgia Vero-Adapted Strain A spleen homogenate from a pig infected in the field with the Georgia strain of ASFV was used to infect a sub-confluent monolayer of Vero cells and incubated for 4 days in a 34° C. incubator. No evident cytopathic effect (CPE) or hemadsorption was detected. The cells were detached, sub-cultured then incubated for 4 days at 34° C. Again, no CPE or hemadsorption was detected. Infected cells were sub-cultured again under the same conditions. Six days later, the presence of several cell foci of rounded cells was observed. Infected cultures were subjected to immunohistochemistry using serum from an ASFV-infected pig, resulting in positive staining with evidence of virus spread in the Vero cells. The cell cultures were sub-cultured two additional times; CPE became widespread in the cultures. Cells were then scraped, centrifuged at low speed and the cell pellets were resuspended in fresh media and frozen at −70° C. This stock has a titer is $5\times10^6$ PFU/ml. This virus stock was used to infect Vero cells. The infected culture was incubated at 34° C. until evident generalized CPE was observed. Virus was successively passed under similar conditions for a total of 30 passages from the initial infection with spleen lysate. The virus harvested after the last passage was used to produce a stock called ASF-GVAV (ASF-Georgia Vero-Adapted Virus) that was then used further for various studies.

In vitro growth characteristics of virus ASF-GVAV was evaluated relative to parental ASFV Georgia isolate in a multi-step growth curve (FIG. 1). Vero cell cultures were infected at a multiplicity of infection (MOI) of 0.01 $TCID_{50}$ per cell. Virus was adsorbed for 1 hour (time zero), and samples were collected at 24, 48 and 72 hours post-infection (hpi). Results demonstrated that ASF-GVAV exhibited a significantly increased virus yield in Vero cell cultures (between 10-100,000 times more, depending on the time point considered) when compared to parental ASFV Georgia isolate. This result clearly indicates the adaptation of ASF-GVAV to grow in Vero cells.

Figure 2:
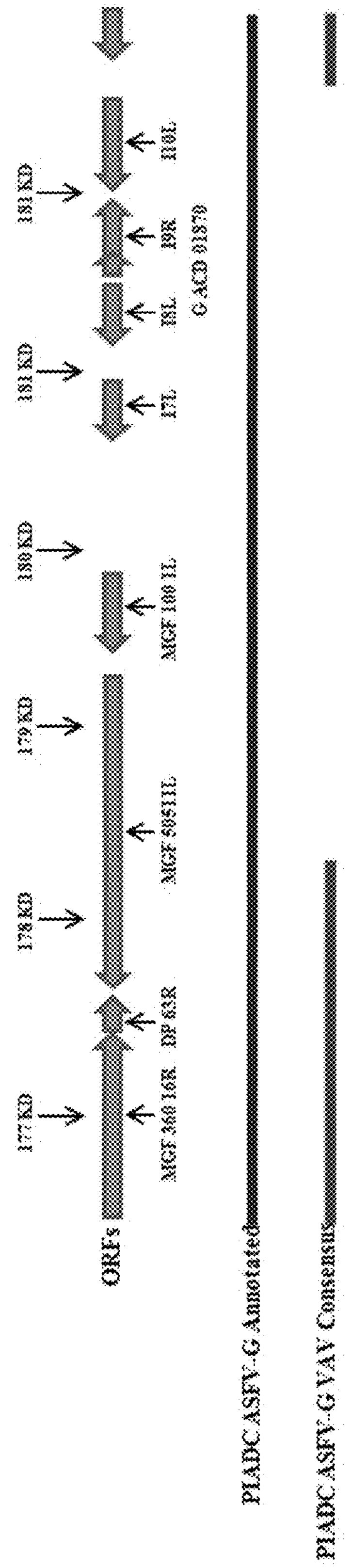
FIG. 2 is the representation of the mutation that occurred during passage of ASF in Vero cells and shows the deletion, the 4,054 nucleotide gap from position 178,524 to 182,578, observed in ASF-GVAV which differentiates ASF-GVAV from ASF.

In order to characterize the changes in the genome that occurred during the process of the adaptation of ASF-GVAV to grow in Vero cells, the full length genome sequence was obtained and compared with the parental ASFV Georgia isolate (Table 1 and FIG. 2). Basically, a comparison between the genomes of the parental ASFV Georgia isolate and ASF-GVAV viruses demonstrated that ASF-GVAV possess a deletion between nucleotide positions 178,643 and 182,578 producing the deletion of the following ORFs: MGF 505-11L, MGF 100-1L, I7L, I8L, ASFV G ACD 01870, I9R, I10L, and I11L (Chapman et al. 2011, supra). In addition, it is also found (i) nucleotide insertions (T and A) in the non-coding region at position 434 and 441, respectively; (ii) a double nucleotide (TT) deletion and a nucleotide insertion (T) at positions 1602 and 1620, respectively. These mutations produce a frame shift in sequence of ORF MGF 360 1L; (iii) an amino acid substitution (Cys131Tyr in ORF EP424R) in nucleotide position 71002; (iv) a synonymous (A to G) substitution at nucleotide position 97391 inside ORF B438L; (v) an amino acid substitution (Gly257Ser in ORF CP530R) in position 126174; (vi) an amino acid substitution (Gly127Glu in ORF E199L) in position 166065; and a nucleotide deletion (T), a nucleotide substitution (T to C) and a nucleotide insertion (T) in a non coding region at nucleotide positions 182582, 182 591 and 183303, respectively (Chapman et al., supra).

TABLE 1

Mutations observed in ASF-GVAV compared to the parental virus.*

| Position | Gene | Variant | Amino Acid Change |
|---|---|---|---|
| 434 | Non coding | Insertion - T | |
| 441 | Non coding | Insertion - A | |
| 1602 | MGF 360 1L | Deletion - TT | Frame Shift |
| 1620 | MGF 360 1L | Insertion - T | Frame Shift |
| 71002 | EP424R | G - A | Cys 131 Tyr |
| 97391 | B438L | A - G | Conserved |
| 126174 | CP530R | G - A | Gly 257 Ser |
| 166065 | E199L | C - T | Gly 127 Glu |
| 182582 | Non coding | Deletion - T | |
| 182591 | Non coding | T - C | |
| 183303 | Non coding | Insertion - T | |

*Numbering of nucleotide position presented in the table is based in data reported by Chapman et al. (supra).

Example 4

Examples Using the GVAVs to Produce Recombinant ASFV Viruses

The ASF-GVAV was used as parental virus to develop different recombinant viruses. Basically, ASF-GVAV virus was used in transfection/infection procedures along with recombinant plasmids seeking to delete specific virus genes using protocols currently used in our laboratory. As a summary, four different mutant viruses were developed with ASF-GVAV virus as parental virus using Vero cells as cellular substrate; the mutant viruses lack ASFV genes encoding for the thymidine kinase (Moore et al., supra), 9GL (Lewis et al., supra), CD2-like (Borca et al. 1998. *J. Virol.* 72:2881-2889) and NL (Zsak et al. 1996, supra). Most of these recombinant viruses were obtained in purity after few successive plaque purification steps. These results indicate the efficacy of ASF-GVAV virus to produce ASF recombinant viruses.

We have developed an ASFV Georgia strain adapted to grow in Vero cell line. The resulting virus, ASF-GVAV, efficiently grows in Vero cells although it still is able to significantly replicate in primary cell cultures of swine macrophages. ASF-GVAV virus was successfully used as parental virus to develop several recombinant ASF viruses. The development of an ASFV adapted to grow in an established cell line is a significant advance for research and development of vaccine candidate strains using genetic manipulation based in the process of homologous recombination. The GVAVS can be utilized as a basis for large scale production of ASF vaccines.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. An African Swine Fever-Georgia Virus (ASF-GV) encoded by a mutant DNA molecule having the nucleotide sequence of SEQ ID NO: 2 except for a deletion between nucleotide positions 178,643 and 182,578 producing the deletion of the following ORFs: MGF 505-11L, MGF 100-1L, I7L, I8L, ASFV G ACD 01870, I9R, I10L, and I11L and one or more of the following changes: (i) nucleotide insertions (T and A) in the non-coding region at position 434 and 441, respectively; (ii) a double nucleotide (TT) deletion and a nucleotide insertion (T) at positions 1602 and 1620, respectively; (iii) an amino acid substitution (Cys131Tyr in ORF EP424R) in nucleotide position 71002; (iv) a synonymous (A to G) substitution at nucleotide position 97391 inside ORF B438L; (v) an amino acid substitution (Gly257Ser in ORF CP530R) in position 126174; (vi) an amino acid substitution (Gly127Glu in ORF E199L) in position 166065; and a nucleotide deletion (T), a nucleotide substitution (T to C) and a nucleotide insertion (T) in a non coding region at nucleotide positions 182582, 182 591 and 183303, respectively.

2. An African Swine Fever-Georgia Vero Adapted Virus (ASF-GVAV) encoded by a mutant cDNA molecule having the nucleotide sequence of SEQ ID NO:1.

3. A method of developing recombinant ASF viruses for possible ASF vaccine candidate strains comprising:

a) producing a genetically manipulated African Swine Fever recombinant virus by combining, in a cell culture, African Swine Fever-Georgia Virus (ASF-GV) of claim 1 or 2 and plasmids having ASFV DNA incorporating a genetically manipulated targeted change, wherein co-culture of said ASF-GV template virus and said plasmids results in homologous recombination events;

b) introducing a reporter gene as part of said recombination events;

c) purifying said genetically manipulated African Swine Fever recombinant virus on the basis of said reporter gene;

d) expanding said genetically manipulated African Swine Fever recombinant virus; and e) evaluating said genetically manipulated African Swine Fever recombinant virus as a vaccine candidate strain.

4. An isolated or recombinant mutant DNA molecule encoding a African Swine Fever virus, said molecule having the nucleotide sequence of SEQ ID NO: 2 except for a deletion between nucleotide positions 178,643 and 182,578 producing the deletion of the following ORFs: MGF 505-11L, MGF 100-1L, I7L, I8L, ASFV G ACD 01870, I9R, I10L, and I11L and one or more of the following changes: (i) nucleotide insertions (T and A) in the non-coding region at position 434 and 441, respectively; (ii) a double nucleotide (TT) deletion and a nucleotide insertion (T) at positions 1602 and 1620, respectively; (iii) an amino acid substitution (Cys131Tyr in ORF EP424R) in nucleotide position 71002; (iv) a synonymous (A to G) substitution at nucleotide position 97391 inside ORF B438L; (v) an amino acid substitution (Gly257Ser in ORF CP530R) in position 126174; (vi) an amino acid substitution (Gly127Glu in ORF E199L) in position 166065; and a nucleotide deletion (T), a nucleotide substitution (T to C) and a nucleotide insertion (T) in a non coding region at nucleotide positions 182582, 182 591 and 183303, respectively.

5. The isolated or recombinant mutant DNA molecule encoding an African Swine Fever virus adapted to growth in Vero cells, said molecule having the nucleic acid sequence is of SEQ ID NO: 1.

6. An expression vector comprising the DNA molecule of any one of claims 4 and 5.

7. A host cell containing the cDNA molecule of any one of claims 4 and 5.

* * * * *

SEQUENCE LISTING

```
<160> NUMBER OF SEQ ID NOS: 2

<210> SEQ ID NO 1
<211> LENGTH: 178524
<212> TYPE: DNA
<213> ORGANISM: African swine fever virus

<400> SEQUENCE: 1

gaatatacca tattattgct attgccatca atgagaatgc cacgtaggca taggtcatcc      60

tatggccgga ccaatccatg gctgcactta aaaatatcaa aaaagtttaa gttttgggcc     120

ggcgttaaaa tttaaacctt ttctggttga tctttagcca tgtatagctg cgatgtttgg     180

tgccttatct acatgctatt ggcattcctg atattcgcac taaagtgcta tgttacaacc     240

gtcttatgcg tgatttttat ccaccttatt ggccgaaggg ccgccttgta tttcctgtta     300

ggtggtttgg ccgtattcta ctggtggcaa gcagctatca ataaaattta atggctctca     360

cttaagatcc ttgctgtaag cgggcgttta catactttga tcaagaaaaa aattattttt     420

ggaccccccc ccatgtttta tacaaaaatc atataataaa gtggcgacaa tcaacatatt     480

aatcaaccac agcattttat gatgtgttaa tcaacatata ccatattaat caaccacagc     540
```

-continued

```
attttatgat gcgtcaatca acatattatt acggagagcg tcaatcaata taatattgag    600
aacagcgact tgataccgtg tatggtggtg gcggcggcat gttgtttgta acagcatttt    660
tcatcattcg aagcttacaa aagatatgta taagatagca tattaatgtt attaacagta    720
atatcaataa ggcgtagcta tagatcttca ctttggtaga ccaataatcc atggttgcgc    780
ttaaaaatac caaaaaaaac attaagtttt ggagggtaag attggttttt caccattggt    840
aaagattatt attctaaatg tttaccccat agatgtgaaa caatgattct tcatatatta    900
acatattttt tgacttatac ttttcttcat ctagtaaggc gttaattttt tccggatctg    960
tcgtttttat tgataaaaga gaagagtctg gactgtaatt tttaaataat aagatattta   1020
ttaatatcca attattcgtt tggctcgcta tttccatgct ctcttcgaaa gcatcagctc   1080
ctaaatctat acaaaggaat aagttacctt cacaaaaatt cattaccgag gtaatcattg   1140
cccgattaat gtcagccccc aacataaaac aataatatat agttgtataa ttacaatcat   1200
acatacaggc caactgcatc atttcatcaa tgtctatatt tgtcttctct ttgttataaa   1260
tttcatgaag gtcaaagacg ttgttataag caaccccaca tattaaccgc caatctttaa   1320
aatgactata tcgttgataa aaatattgga tggcttcagt aagcttatat agtatcgcca   1380
tactatacca atacctagtt agcatttcgt tgaatgaaat attatccaat gtaaagttaa   1440
ttgataatgt atctagttca ccaaaaattc ttaatttcag ttgagcatta tttaggaaaa   1500
ggggattatc agataataat tcatggcata gaataatatt actgctagtt ttaacatact   1560
gtacattata aaatatttct aaaattttat tttcactcaa agctttcctc gcacctaact   1620
tttggcatag gtcctggtgc actccatatt gacagtaacc aacccaaagc tgatgtctgc   1680
accccattcg gtaaacagct ctattaaacc atgattgttt tcctgtacag ccttcattaa   1740
tgcaacattt aatgttaaac catgtttaaa acttgctgtt tttattaata tttgttcatc   1800
tatacaagta tgataaatcg taattggggc ttcatgccac cacaaaccac aacgctctaa   1860
aatacaataa tcatctttta acacaggctg tgtagctagt actttttag taagtgcttg    1920
taaagtagat ggcatcttct atctgcaaaa taattatttc cgaaaaaaaa atcaaattaa   1980
aatactaaat tctatttttt tttttaataa agcctgtaaa ttatataata aatctcgccc   2040
accgtattat ttccggacac aactttttat acctcattat atttttagat ctatagtttt   2100
ttaacaaggc attaattttt tctggatctg tcgtttttaa agataaaaga gagacgtttg   2160
aactataata atctttaaat gataatattt ctactaatat atcatgattc ttttgttttg   2220
ctaattctaa gctctcttcg aaagcattag ctcctaaatc tatacaaaag aacaagttat   2280
tcatataaaa gtttttttacc gaggtaacca ttgcccgatt gatgtcagcc cccaatacaa   2340
aacaatagta aatggttaaa aaattgctat ctctcataca ggccagatat atcatttcat   2400
caatattcat atcaaccttt tttatatgat acatttcatg aagatcagac acgttattaa   2460
aagaaagccc acatattagc cgccaatctt taaaatgact atatcgttga taaaaatatt   2520
ggatggcttc agtaagctta catagtatcg ctatactata ccaatatcta gttagcattt   2580
cgttgaatgt tatttcattc aatataaagt tgatcgatat cttctctaga aaacaacaaa   2640
ttattacttt taattcctct atattctgga aaaggggatt attagataac aatttatggc   2700
ataaaataat attactacta gttttaatac gatgtatttt ataaaatatt tgtacaatat   2760
ccatttcatt caaaattttt gcgcctaact cccggcagaa attccaagta tgctccgtat   2820
tgacagtgac taagctagag ttgatgtctg caccccattc agtaaacaac tctattagat   2880
catagttgtt ttcctgcaca gttttcatta atgcgagatt taactctaaa ccatctttaa   2940
```

aaattgctga ttttatcatc aattgattat cctcattagt agaaagcata attggagctc 3000
catgccacca caaaccacaa tatttcaaaa taaagtagtg ttctttagat atgtgctgtg 3060
tggccagtat ttttttagca agagcctgca gagaaattgg agtagacata ttttttttg 3120
caaaatggtt taagttttc aagaatacag attggataaa ttaggttgtt gacttagtta 3180
caggaggtat taaatattat gtagacataa aaatgagatc ctccaaaaaa ataaacaaca 3240
aaaaaaatat gtttaatatt aaaatgacaa tttctacatt gcttattgct cttattatac 3300
tacttattat tattttagta gtgtttttat actataagaa acaacaacca ccgaaaaagg 3360
tctgtaaagt agataaagat tgtggtagtg gagagcattg tgttcgtgga tcatgtagct 3420
cattgagctg cttagatgcc gtaaaaatgg acaaacgaaa tattaagata gattctaaga 3480
tttcctcatg cgaattcact cccaattttt accgttttac ggatactgct gctgatgagc 3540
agcaagaatt tggaaaaaca cggcatccta taaaaataac tccatctcca agtgaatccc 3600
atagccccca agaggtgtgt gaaaaatatt gttcatgggg aaccgatgac tgtacaggtt 3660
gggaatatgt tggtgatgaa aaggagggaa catgttatgt atataataat ccacatcacc 3720
cggttcttaa atatggtaag gatcacatca tagccttacc tagaaatcat aaacatgcat 3780
aaataaatac attaggctca tcgtatcttt ttaaaatcca taaatattcg tttgatatat 3840
gctgaaattt ttataaaaaa aataactatt tcctataaat catctagaaa tagtcctcgt 3900
tttgatcggt ttatatctta taatattgtg catcgatgca caactgcttt ttttggtcct 3960
tctggaacat cattatattt tctttcatta atataccatt cagatgtaaa cgttgaataa 4020
tttttatggc aacaatctac cattgaatta tatttagtaa catctaatac atcgtttgtt 4080
ttatcaggct cagctctata atcttgataa tttttgttat cagcttctaa agctccatca 4140
ttatttttca aagaagtatc cataattatg tttggtaaaa atactttaag ttttaatgtg 4200
atatttaaaa tggttgttat ataaatttac cgcttacagg taatctttat tcagtgtcat 4260
aaactatact tttgatgatt cagtattttg tgaatcagta catttattat cattaatatt 4320
tttaggctgt ttttccaatg ttttattgtt gcaatgagcc tgctcctcct ttgacgagga 4380
agtgtctgtt ggagtcatct gtttaggaag agtatcatcc atatctatta tgaagaaaat 4440
atataaatat tgatatacaa tcaaaaatat ttttgatcac gtctttgtta tctatcgata 4500
ttgttgataa cgtcttgaat aacctacatc atttttttac ataaaaaaat agatataatt 4560
tttattatat ctcaattatt ttaaagataa ttatcaatac agcaaatatc ataagctaac 4620
atatttttcg aataatagtt ttttagtaaa gtattaatct tttcaggatt ggtttctttt 4680
gataataaga taggattcgc tttataaatt tttaaagata atatattcac aatgatagaa 4740
taaccgtata tatctgctaa tgtcttactg tgttcaataa cattagcccc taaatccata 4800
caaaagaaca tattttcaat acaaaagttt tttaccgaga ttaacattgc tcgattagcg 4860
ttggctccca atgcaaaaca gtagtaaatg gtcaaaaaat tattatcgcg catacaggcc 4920
agctccatca ttttattaat actcatatga attttcgttg tgttacatat ttcatgaagg 4980
tcaaacacat tgttgaaaga aagtgcacaa attaatcgcc attcatcaaa atgcctgtat 5040
tcttgacaaa aatattgaat agcttcttta agattatatt ttaccgctat gccataccaa 5100
tatttggtta gcatctcact aaatgagatc tcatttaaca tagaatttgt tgttaaatcc 5160
ttcaactccc aataaatgat catccttaaa tccaccatgt ttacattttg taaaaaaggg 5220
ttattagaaa ataattcatg acacaaaatg acattactac ttgttatttt acactttgtt 5280

-continued

```
tcaaagaaaa atcgtaaaat ttcacttgtc tcaagctctt ctttagctcc caattttcgg   5340
cataggtttc gagtatgctc gttattaata aaaagtaacc cataattaat atttgcaccc   5400
cattcagtaa acaacatgat tagatcatca ttgttttcct taactgccaa taccaatgca   5460
gtattaagcc ttataccctc tttaaagcat aatgtcctta tcattatttg attatcatca   5520
tctatataca ttgagatagg agcttcatgc caccataaac cataacgctc taaaatataa   5580
taatcatctt tagatacgtg ttgcgtggcc aatgcccttt tagcaagtgc ttgtaaagtc   5640
gatggctgca tgtttattct gttaaaaaaa atcaaattat cgggtaaaca taaggatcaa   5700
cccgtagtta atatttgcag tagtattttt taacaatgaa ttataataaa aaaataattc   5760
attactatct attataaaac ccatctttaa ctttaaagaa gaactagatc atcttttttt   5820
tgttgtgtca gaacttcttc aatttattac ccacatttta tctaaaaaaa taaaaactac   5880
atcatatctt gtttcttcat caaattatca taccatttat agggtgtagg ttgggaacat   5940
tccatcatgt ggtaatcagg gtatttatat attttttgat agtaacatct atttggcaga   6000
tgtattgtcc aacaatcatg tctaataaaa tcattttcac ctatgggggga atcatcttaa   6060
aaaccttatt cctacagatt ccattttgac agtcccagca aaagtcacaa tattttccat   6120
gagtacacca atgttcaagc tctctttcgg gaggaatgct gccaatttta tgtttttttag   6180
cttctaactc tctgtacaac atcagttggg aaagcagaaa gaagattacc aggagaacca   6240
ttaaatatat aatagtctgc aaactacgtt tgcgaatgta atttgcaact aaaacacaac   6300
ccacaaggta aaatccataa gttaataact tttgccattt tcgtatgaca gcctcgtgcc   6360
attcatggtt gtgttgtggg cattctgttc ggtaaacttc atgaggcttt atagaagtta   6420
catagtaggt acagaattca ttgtgacgaa aaacactgca gttagctatg tagtcatttt   6480
caagaatggg agaatggttt tcaaagacct tattcttaca gatgccatct tgacagtccc   6540
aacagaacct acaatgattt gcataggtgc accagtattc aagctccttt tcaggagggg   6600
ttcttgttag atccaggagc tctagctcat atgtataaag aagagttgga atggatagta   6660
aagtaaatat ttgcagacca agcatggcta cttgtgaaca agtggctgct cgtcaacaaa   6720
tagctgttta tcagcaaata gctgtttatc agcaacaact aattatcagc aaatgctgct   6780
tgtgggtaag ccaataaata ggccataccc ttgaaaggag aattcagttt gataaaaaaa   6840
ataacgagtt ttctaataac ccggtcaagc atttaataaa tgaatagcat cacacgtctg   6900
catcgtgcat tctgcctgga aaatgggccc atctctaata tatttacact gacggtgaat   6960
catacagtgt tccatgggat agctatgctc ctgtacagga ggcatatctt ttagaacttt   7020
attcttacaa agaccatctt gacaagccca gcaaaaccga caatttttca catattgaca   7080
ccagtatcta agctcctctt ccaggggatt gtcggtcgaa aacccctgta gactagctag   7140
gccagctagc agcaagccga ggtaactaaa gaacctcatt gtagtgttat attacgaaaa   7200
aacatgttaa aatttggaaa aaaaagccct ttttatagat ctggaaaaaa attttcacaa   7260
atctaattaa aagccttaca gatcatcctt ttcataaatt ttcattaaca attggtgggg   7320
gcggttgtga ggtactggat cagaacaatc cataacatgg taatgtccat ttccttcacc   7380
atatgtacac tggttatacc agcgagaaac ctcacaagat gtcaaataac tgttctcaac   7440
aatcaatggc atgctcttat tcaccttgtt cttgcaaatt ccatgtgcac attcccagca   7500
aaacttgcag ttttccatgt aagtacacca gtatccaagt tcttcttgtg gaggattatc   7560
cgttgaacga agatgccctc ctgcctgagt aggtagtcct aagacctgat tggccagcag   7620
gccaagaatt tccaagaaga tcaccaacat tgctacggct ggctgaacag ctggcagata   7680
```

-continued

```
gctagctaat tagcaaacca agtgactcgc cctctctact cttaatatga gaatttaaga    7740
ttcggtccgg ctttttccc atgttttaca gggaaaaggt atttttagcc tatgaatgta     7800
catggttccg cacattaaaa aaaataaaag aaattattta atattggctg ttattttctt    7860
tcaactagca acaagccagg taactaaaga acttcattgt agttttatat tacggaaaag    7920
gttaaatttt ggacaaaaaa atcatatcta attaaaaatc ctcacagatc tttcttttca    7980
taaattttca ttaacaattg gtaggggcgg ttgtgaggta ctggatcaga acaatccata    8040
acatggtaat gcccatttcc ttcaccatat gtacactggt tataccagcg agaaacctca    8100
catgttgtca agtagctgtt ttcaataatc aatggcatgc tattattcac cttgttcttg    8160
caaattccat gtgcacattc ccagcaaaac ttgcaccttt ccatgtaagt gcaccagtat    8220
ccaagttctt cttgtggagg attatccgtt gaacgaagat gccctcctgc ctgagtaggt    8280
agtcctacga cctgattggc cagcaggcca agaattccca agaagactac caacattgct    8340
acggctggct gaacagctgg cagatagcta gctaattagc aaaccaagtg actcaccctc    8400
tctactctta atatgagaat ttaagatccg gtccgacatt tttccgatat tttacaagaa    8460
aaagatattt ttagctacaa atacacttca tatatcccta aaaaaacaaa aatttattta    8520
attttaacta ttattttctt tccactctct ctttaagatt ttgtaaggat tccagggctt    8580
tggttcagaa caggccatta catggtgaat cccctgtcct agatcataca tacatttatt    8640
tagccagcgg gaaactatac atgattgcac atactcattt tcaagaattg ttgtattctc    8700
caatttgccc tcacaaaggc cattttgaca attccagcaa aacttgcagt tttctgtata    8760
agtgcaccag tattcaagtt cttcttgtgg aggattatcc gttggatgaa gttgtccagc    8820
tggttgatta ggtagcccta agacctggtt gcaattcatg gtatggtaga tacccttatc    8880
taaatcatac atacatttat ccagccaacg ggaaaccaga catgatttca catactcatt    8940
cttgtaaatt actgacccat ctattttgtt tatacaagtg ccgtcttggc agtcccagca    9000
aaattggcaa ctttccatgt aggcacacca gtattcgagt tcttcctctg gaggctcctc    9060
tgttggacga agttgtccaa cgagctgact tgaaacctgg ctggccagaa ggccaagaat    9120
tcccaagaag atcaccaaca ttgctacggc tggctgaaca gctgactgaa tagctagcca    9180
attagcaatc cactgtactt ttcataagat catttaagat tcggtcggca tttttttcaat    9240
agtttgctag gaaaaaattt ttaattttat agattcacac tacttcattc tcatgcttag    9300
gaaaaaaaca aactaaatct tacaatgtat ctggatctaa tgagaagcta gaattcatct    9360
tttttcaaat cctttctggg atgttcattc tttttccact ccttccttgc aattttataa    9420
ggattccagg gctttgggtc agaacagttc atgctatggt aaatgtgctc ctccacatca    9480
tatctacata ggtcacccca gcgggaaacc tcacaatatt ttacatagtc attctcaata    9540
atacttgtgg agttgtttcc ccaaaccctg ctggtacaaa tcccatcttc acaatcccag    9600
cagaaccgac agctttccac ataagtgcac cagtatccaa gttcattctc tgggggttca    9660
aatgttagag gaagatgtcc acctacccga gtagaagtgg aggatgaaac caggttgcta    9720
ctggccagca ggccaataat tcccaggata atcaccagca ttgtgctcaa ccagcaacgg    9780
ctagcaacga ctagcaactg actagcaata gctagaaatg gctagcaatc agtagtagct    9840
aacgctctac tctttataag aaaatttaaa attcgatcag attttttttag aattgagaat   9900
gagtaaaacg cttatattct ttttctagct agaaaaaata agctagttta agataggatt    9960
tcccttacta acggtttaat ttttagcaaa ggtataggta aaatacactt gtacttagct   10020
```

-continued

```
gcaaaaaaat aagcttatgg cgtataagcc gccataagtt tatttaatta aaatgttaaa  10080
ctctgtgata agactggaat cttaggcagg tttgatgtgg agaacagcat gaaatacaag  10140
agtgcctgtt acacgaataa gttctctcaa accggggatg gtcatactca catctatgaa  10200
atcctggtct aggagattca tttgatgcat gatggccgca cccacactta tgagacactg  10260
aagaactaaa gggtttaatt ttgatctgaa tggtactata taggatgatg gcaatccata  10320
tcaagattag agcaatcaaa atcacctcct caagaagcat gatgtagcct taaatcttag  10380
actgctttaa accttaggcc ctcactatct ttaatgaagg agtttaaatt ttgatccctt  10440
tttcaagacc catttagaag aaaaaataaa gtttatatca atctaattca taagtcatct  10500
ctttcataaa tcttcatgta ttctctatgt ggataagtat gggatgttgg atttgcgcag  10560
tccatttgat gatctgtatg gtttttgggt ccttcataat aactacatat accattccag  10620
cgggaaaccg tgcaatttat aatccagtca ttttgatgaa taactggcca atctgtttga  10680
atcctgtttc ggcagatacc gtggacgcat tcccagcaaa agtcacattg gtttgcgtaa  10740
gtgcaccaat aaactagctc atgttcagga ggataacggg ttggtagtaa atcttctaat  10800
ttacgtatag gagcggcttg aaggacaacc acccccagta gtactagaat cagtaccttt  10860
atagtggcca ccctacacta gacctctaag ttgaagacaa agaactaaaa tttagagccg  10920
tttaattact actaataatt atattttta ttgtctacaa taggattcta ttaaaaaata  10980
atgattttta ccaagaaata tttttataaa aaattaatat attttgtaat aaactttatt  11040
tccaatgact gttaaaataa ggaaactatc cttagttagt cgaggaagat ggttaggtta  11100
tttcgcaatc cgataaaatg tttattttat cgtaggtctc gtaaaatcca ggaaaaaaaa  11160
ttacggaaga gtttaaaaaa gctaaatttt taccaccctc cagaagattg ttgtcaaata  11220
tatcgtttgc tagaaaatgt tcctggagga acttacttta ttacagaaaa tatgacgaat  11280
gatttaatta tggtcgtaaa ggattcggtg gataaaaaaa ttaaaagcat taaattatat  11340
cttcatggaa gttatattaa gattcatcag cactattata ttaatattta tatgtatctt  11400
atgagatata cccaaattta taaatatccc ttaatttgtt ttaacaaata ttataacatc  11460
taagtaaata ttcttggaat ggattttctt atagaatggt tacaggatat gtcagcgaca  11520
ggcttaataa caaatttgtt aatatttttt tgttaaataa atgaacaggc caccatttaa  11580
tattacccgt tgcaaaataa gaaaaaaaaa caaacttata gttacaaatc atcttgatta  11640
atcacatgtc gttttaactc aatgaaccat tctaaatctt tgggttgtga acaattcatg  11700
ttatgttgat agtgtatcct aaagtgagct tcatacatac accggtcatg ccaccgggaa  11760
actgtacaat taacaatata atcattttgc gtaataatag ggtggtcact aaacacttta  11820
tttttacaca ttccatcttt acaggtccag cagaagtcac agtgttttgc ataggtgcac  11880
cagaacttga gatccctttc aggaggccta cgcatttgca tcggattatc tgtggaaaga  11940
ggtaggttca ttattatgtt cgtcatcaaa attcctaaaa gaacatagaa gccaagaaag  12000
ataagcagtc ttgtagcggc ttgcattcgc attcgtgagt attgtttgcg aacatagctt  12060
atgagagcaa tggtagctat catacaaaga caagtatgtt tgatattctc agtgtcaatg  12120
accctatcct cctttatttg cattaactca tcaaaccaat cataatatgt gggatttgta  12180
cagctcatga tgtgaaagcg gcgtatccta gagtctgtaa agtagctaca tctttcatta  12240
tagcgagaaa ccctacatat ttgtatgtaa tcattttttt tgatgagagg gtgtttttca  12300
aaaaccttat ttttacaaac cccgtgtcga caattccagc agaagtcaca cgattttgca  12360
taggtgcacc aatactcaag ctctctcttt ggaggtctcc gggtcattgg taactctcct  12420
```

-continued

```
gttcctggaa aagattggct ttgaatgacc ggctgcatga ccgccagtac caaaaggaac  12480
acaatcacct tcatggctgc aacttataag ttgcaactta tgggttgcaa tactgcaacg  12540
tataggttgc accttataga tcgcgactca aaaggtatga aaaccttacc ctcaatacag  12600
aatttaagtt ttaatcctga taatgtatct gtttatgaaa aaaaattttt tttactcatg  12660
tatgaattct tatacgaatc ataatatgta ggctgagaat aataattcat atacggtgtt  12720
gcgggctcaa taaaaatttt gttaccacaa aaaataaatg ctggattttt aagatatata  12780
tctattaatg actaaaccct ttatacgctg taggctgaaa acaatccata taatgaatat  12840
acggtgattt gggtttaata aaatacatac aacggtcaaa atagcgggca atactacatt  12900
gactaatata atcattttgt ttaataagag gcatatcatc ccacacttta tttttacaaa  12960
taccgttcct acattcccag cagaaatcac agtgttttcc atacgtgcac cagtattcaa  13020
gctctcttat aggaggcgta taagtccttg gtaaattttg tttcatataa aagatggaaa  13080
ggggtcgatt taaacccggc tgagatagcc aaatcaaaat acataaaaga gcaagtagtt  13140
tcatagtggt atttagatgt aaatttttat agtatgcaaa tacaatgtaa cctacaaata  13200
caatactaaa tacaaggtaa aaacaacaat gtcttataat gattggccaa taatcacccc  13260
cccccccccc attttttccat gaatatttca tttcctgtat agggtctagg atgtgaacac  13320
tccatgttat gatgattagg cattttaact gatatttcat aaaaacaccc ccaggaattg  13380
cgattaacta tacagtttac aatcgaattc atcgaattag actcatttgt tatcttattt  13440
ttacaaatgc cattttgaca atcccagcag aagtcacaat tctttacata cgtacaccaa  13500
tatggaagct cctccttagg aggatgctgg gttcttggta attctggtaa ttcatgtgca  13560
agaatgagga ctgagtagcc caacaaaagt cctagaacct tcatgttgtg tccaaatggc  13620
acctgtcatt ttaaaaaaga tttaaatttt gctaccgcaa aaaaaatcca gtatgtattt  13680
ttttaataca tataattatt gaagtcttat aagataaagc cgagaacact atattttgta  13740
tagatgatgt atccggtatt caaactctct tataagtaca tgtaggaaat ggtcaattat  13800
tcaagattgg ctgagataac aacaaaacca aaatactcaa aagcataagt aatttcatgg  13860
ttgtactcag tcgtagattt ttgcagatcg caaatgcaac gcaaccagca aatacaaagc  13920
taaatacaag gtaaaaacaa taatacctta taatgattgg ccaattctta tccctccatt  13980
tttccatgaa catttcatgt tcataaagtc taggatacga acaacatttc atgctatgat  14040
gattaggtat tttaagtgat atttcataaa aacaccacgg ggttgttggt gattgatagg  14100
taagaataag gatggttgaa taacctagta aaagtcctag aaaaaccttc atattgcgtt  14160
cataccacag atgttattta aaaaaaatat aaattttaca gtatgtgata tacacatacc  14220
acaaaaatgt tcttatatta actaaaatat gtgggcagag agcaattcat ataatgaata  14280
tatggtattt taggctcaat aaagtacata caacgatcaa taaaacgggt aatactacat  14340
ttactgatgt aatcattttg aacaataaga ggcatatcat ccaaaacctt atttttacaa  14400
ataccattct tacaatccca gcagaaatca cagtgttttc catacgtaca ccaatattca  14460
agttctctca taggaggcgt ataggtcctt ggtaaaattt gtttcgtata aaagatggaa  14520
aggggtcgat ttaaaactgg ctgtgctaac caaaccaaaa tactcaaaag aacgaaaagt  14580
ttcatggttg tactcagacg cagattctta caaagcgcac atacaaagca gcctgtatat  14640
gcaataccaa tgatgaaata gagacagtat tgctttatag ataattgttg atggtcaccc  14700
cccccccccc cccatgtttg catgaatatt tcatttcctg tatagggtct aggatgtaaa  14760
```

-continued

```
cattccatgc taaagtgatt aggcatttta gatgaaattt catataaaca ggattgagtc  14820
ttggaatcac ggaaaactct acagtttaca atagaatgat tggagtcaat gaaacgagat  14880
tccgttatct tatttttgca aatgccatct tgacagtccc aacagaaatc gcattgtggt  14940
acatacgtac accaatatga aagctcactc ttgggaggat gctgggttct tggtaagtct  15000
ggtaattcat gtgcgagaat gaggactgag tagcccaaca aaagtcccag aagaaccttc  15060
atgttgcgtc taaatgacac ctgcacttac aaaaaaaaat ttaaattttg aatataacac  15120
aaaaaaacca ccttaaaatt tcttatatta tttcttggat ctgccccgac gtcatacaat  15180
gtattaaaat tatagaccaa tcatcttttt gtatataggc taatcatctt tatatataga  15240
ttttagatgt ttgcttgttg tatcaactta actgctagcg aagaaaatgg ataaaaactt  15300
tctgtatttt tataggttga aatcatttta tgcacatcgc taggatctaa tattttattt  15360
tgaagaaccg aatgtgggct taaaattttt ttcttagaaa aaagtagaat cataatattg  15420
ctatgttttt gtttaatgat ttcttgtatc tttttgtat acgggttggc acccaaacct  15480
atacaaaaat atacattact caaataacta ccttctatac ataatctttt ttccccacgt  15540
attttcctat ttatttccct atttatggaa ttaaaggata tcaatctctc taaggcacgg  15600
tcaaggtctg cgcctaaggc aaaacaataa tatataccta atttattccc agggcgtgca  15660
caggcaagaa acatcatgac gtttagccct aaacgtatat tttcctgaaa atacgcatga  15720
tgaacttcat caatattacc taagtatatg gccgtttgta aacgccaaag atctaaatga  15780
ggaaattttt tactaagata atgaataggt tttgtgagat taaaatctat ggcgaactta  15840
taccaaaatt ttaatacaag tgtatttctc gtcatttctt cttcttttc atctaaatat  15900
aagataaaac gattgtaaac aaagtctatc aataggtgaa aatcattgct attaaagctg  15960
tcgagaatca aaatattgtc ataataaatt tcgatcgcca gtaaaacctt ttttcgtttg  16020
acgagataaa caaacatatt atacaaccct acatctaaaa attctggatt ggctcctagt  16080
tggatacaca ggtctttagt ctgcttcgtt ttggcacaca tgatgccaaa attaatatca  16140
gcaccccata aaacaaataa cttgattaga tcagtctggt tttccttcac agcttttact  16200
aaggctctgt caagctcata gctgtcgaca tcagagcatg acatagagcc accggttacc  16260
attttacatt gcttacaaaa acctatgggt ccgttttccc accatagtcc aagctgttgt  16320
agaataaaaa tatcatcctc atgataattt gaaaaagcct tggtttctat caagactttt  16380
tttgtaagaa cctgtaaaga gttcatcgta ttattatgaa taacaggagt aaacgtaatc  16440
aattataaaa gtgatttttt cgaaaaaaac tttagatggt tgaaaatgat aatgtacatg  16500
ttcatacaaa aaatagatgc agtgatgtct aaaatcaaaa tttaattttc tatgtaaaaa  16560
gtacagactt acttatttgg gttaaattgt ttattttaaa ctttaattaa ccgtttgagt  16620
tagcgatgtt tgatttatct tccatactca tccggggggg gggggtcctt atagctctga  16680
cattattgtg gattattgaa tataatgaat acttcataga tgctaaacat tttaatagta  16740
gttctgaggc ttaattgtac tctataaatt tataaaaact ttttgatcaa aatttaattt  16800
cttataaaaa gagtacagac gtcgcttgtt taagcttcat catgtttcat tcattacttt  16860
ctacaattac gggggggggg agtcccctca tagctttagt attgctatgg tttactaatt  16920
attatgtaga atttatagaa gcatatgtac ctgaaagtat acctactcta taaaattaaa  16980
taatttcagt atattttttt tatgaataga acggaaatga tataaaaata atttaatatt  17040
gcaaaaaaaa ttcataatgt tggtatgtat tataaacata atagcatgtg taatttataa  17100
actgactcct ctatataatt attagatgag gtaccaacct acttatgata tgccgatgat  17160
```

-continued agatattgta tactataaaa caaaattatt ttaaatgtat tcatggatac attataacat 17220
ttttaccgca aattgtctct cagcgaagaa aatgaatgaa acgtttctgt atattcatag 17280
gttgaaatta ttttacgcac ttcactaggt tctaatattt tcttatgaag tattgaatgg 17340
gggcttaaaa gtcctttctt aaaaagaagt ttcatcataa cattcttttc ttgtctaaga 17400
agagtttctt gtattttttt tgtataagga ttggcaccca aacttataca aaaatgtaca 17460
ttactccaaa taccataatt tgaaaagaaa gttatttccc tatttacttc atgattaatg 17520
aaacctatca acgtctctaa ggccgtattg atatttgcgc ctaaggcaaa acaatagtat 17580
atacccaatt tattttgagg gtacatacaa gcaagcgaca tcatgtcatt tggatctaaa 17640
cgtatatttt cctgaaaata tgcatgatgg atttcatcaa cattacctaa gtatacagcc 17700
gtttttaaac gccaataatc taggtgagga aatttcttac taagaaaacg aataggtttt 17760
ataagattaa actctatggc gatcttaaac caaaatttta atacatatgt atttttttatc 17820
atttttttctt tttcatctaa atttaagata aaacgattgt aaataaagtc tatcaacacg 17880
taaaaatcat ggctatcaaa actgtcgaga atcgaaatat tgtcataata aatatctata 17940
gctaataaga ccttttgttg tttaattaga tcaacaaaca tattatacaa ccctacatct 18000
aaaaattttg gatcagctcc tagttgaata cacagaactt tcgtcctttc cgtcttggca 18060
catatgatgc cataattaat gttggcaccc cataaaacaa ataacttgat tagatcagtc 18120
tggtttttct tcacagccct caccaaggct ctgtcaagct catagctgtc aacatcagaa 18180
catgacatag agccactggt taccatttta cattgtttac aaaaacctat gggtccgttt 18240
tcccaccata atccaagctg ctgtaaaata aaaatatcat cctcatgata atttgaaaaa 18300
gccttgtttt ctatcaagac ttttttttgta agaacctgta aagaattcat cgtattatca 18360
tgaatgaaag cagtaaatgt aatcaattat aaaattgact tattgaagag aaatgttaaa 18420
tgagtgaaat cggtgtttat gatgatgtac atgatcatac gaagaaacac gttcactggt 18480
gtccatgatc aaaatttaat gttttacgta aaaagtacag atgttaactg tttagtttaa 18540
acataaattt aacctttagt ttaaacccta gttaatgatg tttaatattt cttctatact 18600
cattcaggga agtgtaatga ttctaatact gttgttatgg attattaatg aaaactttac 18660
agatgctgga gggaataatt ttaatcatac tgttttaatg tagctatata agctttcatc 18720
aaaatttaat ttttttttata aaaatacacg aattaaacta aagtctaaac tttagtttga 18780
ctatttgagt taatgatgct taacttatct tccatgctta tcaagggggg gtcctaatag 18840
ttttgatact attgttgtgg attgttgaat ataataaata ctttatagat gctgaaatgt 18900
ttgaaaataa tagtacatca atgttgtaag tttgatcaaa atttaatttc tcataaaaaa 18960
ggtacacatc aacattgctc atttaagttt catgatgttt gattcattac ttcctacaat 19020
tactgggggg gggggggggt ctttaatagc tttagcattg ttatggtttg ctgactatta 19080
tgtagaattc atagaagcac gtttagatag taatatcact gcagtgtaga ttatgaaata 19140
catactaaac taatttcagt atattttttt tgttcatata agttaaggta caaaaatgat 19200
taaacattgc aaaaaaagaa aatcacaatg ctattataca tagtgatcat agtggcttgt 19260
atcatttcta aactagttcc aaatgaatat tgggcaatac atctattttt tatcattatg 19320
atttttatgg tatatatgta tgaaaagtta gatatacatc aaaaatctca gttctggaat 19380
tataccatgt caggcttatc tggacataac gtacaggtaa catgtaagtg ttactaaata 19440
ctatgaagta tctatttttt ttgttgtaaa aaaaagaact tgatagtatt ttttaaaaaa 19500

-continued

```
taaaataatt aattgtacgt caacttcctt attttattct ttaaaaataa ctcgtaagta  19560
ttatttatct attttttgaa aaaatagatg taatcggttt catcatttag gtgtgtattt  19620
ctttttagca tctatcaaga attcattgtt tagtgatatg aaaacaatga atgatcatta  19680
tcttctattt aacaaccacc taaataaatg aacgtctttt tcatcttaac tgattaccaa  19740
aagttatttt gcgaaaaggc atacatatga tcaatatcag acctacaatg aatatttcca  19800
taatatccct ttattgtaat aattctattt ttgcattccg atatctcatc atctgtgcta  19860
ttatatgttt ccataactgt ttcatcatca aacataaatc ctgttaaata ggcaaaagac  19920
tttaatcccg gatagatttt taccattttc ctgagagccg tgtatagctt gtaataaatg  19980
gccaaaaata tgcaataaag cgtagaaaga gagtaatttt tggcataaaa gattttgaag  20040
gtttgatgaa tggctaaatc gcatataata taagatacga ttttaaagcg cacctgttca  20100
cgcagatttg ttgaaaaatt cgtggaaaga tttaacaaat aaaaggttat taatagttgc  20160
tcatcattcc ccttatacga catcgtcaga cgctctaata ttttactact aggcacatct  20220
gccacatgtt gaacatttaa agcctgttct tcttctgtgt tacggcaaaa gagccgtgcg  20280
tattcaggtg aagctcccca ggataacaac gtccttgcta cggctaaatt tttttgacg  20340
atgactttta tcagaaataa gtctttattt ttgcattgat cactatgcga atttgtatag  20400
ttgacgccgt tgcattgagt acattgatat aatgttttac aattccagcg tagccctaaa  20460
tggtataaaa gaactgtatt ttcgacataa gcatgctgat taacgatgtt tttgagacaa  20520
cacgtcgtta aggacaccat attgtctcca atttgttaga taaaagtctt tactaaaaaa  20580
atagattttt agttttaaca atcgagattt tattatttgg atgcatcatc aaaaagattt  20640
ataagtataa gaggttgtat aagaaaaaaa tgatgttata ctatttatgt taaaatttaa  20700
tttatcatat aaaaagtaca gatttaatca gttggttaaa ctatttagtt aattaaacta  20760
aatagtttaa ccatttagtc agactacttg gttagcaatg tttgagcttt cttccattct  20820
tatccggggg ggggggtcct aatcgttcta atactattgt ggatagttga atataatgaa  20880
gactttatag atgctataat gatgaattct agtatgcctg tataaaataa ttaacctttt  20940
tgatcaaaat ttaatttttt tataaaaagc tacagagtag tgttttatta aacgtggctt  21000
atttaaaagt tacacaatgt taaaatctct acttacttta attctttgtg gggttttatt  21060
aactttatcc atattatggc ttactactta ccatgtagaa cttatagagg caatagatga  21120
tttctacgac tgaaatatag aatagtccat tttctatttg taaaataatg atttatattc  21180
tttcctaaaa atgatacttt atatggtttg aaaacaaata ttaacaactt gatttttttt  21240
tctataaata aactataaat gaaaatagta aaactcatag agtcttataa gtgaacatct  21300
tcataatgtt actcaaacgt tggactatta aaaaatattc cgtgtgcatt attgctttta  21360
atcagtatga ttactttata cgaagccgct attaaaacgc ttatcacaca ccgaaaacaa  21420
attttaaaac accccgatag ccgtgaaatt ttactagctt tggggttgta ctgggataaa  21480
actcatattc ttgttaaatg tcgtgaatgt gggaatatga gtcttaccgg aaaacacagt  21540
acaaaatgta ttaacattaa ttgtctactt attcttgcca taaaaaaaag aataagcgta  21600
ttgttgatac cttgatagga atgggcgcgg atgtaacata tatacatctt ttaaagaata  21660
agataaaact gtcatacaac cagctgtcta tgcttaaaag caactcgcag atttcattga  21720
aggagcttca tgctatatgc tatcttttat atggtcggct tcccaaaaaa attaaacaag  21780
ggatgcgact gtgtaaaaca atggcgggac tatgtggtga acttttatgt gcatttttag  21840
ctccgtaaat gataatatgt atttaaaaca aacagatatt accaaaatat attctatgta  21900
```

-continued

```
cataatatct gggaaattat tttttttct catacccta aatataaaaa tattgggttt 21960
cttcactaaa ctttagaggt aaaaattttt ctttgttttg caccatcatg tatgggttta 22020
ggctgtccca gggattgttt atttgaatat ttcctaaata ggaacacaac gccatgatca 22080
tatatctttc attctggtaa gctttttgat acatcttcaa agatgccgta cctccgagtg 22140
tgtaacagca aacaaacgtc cgtacttttc catgggtcgc agcccattcc attccgtagc 22200
tcagcatctt ttgctgtatt tttttattcg ctttataaaa aaagtttttc atccattcca 22260
cgttctcata aaaacaggca cttaaaaaga gcactagggg tagtgtagtc ttattataga 22320
atgtaggaat gtatgtttta gttatttttt tcaacgcgtg ttccatacta tgttttaccg 22380
ccataaaaat acaaaaccaa taccaacttt ttctataaaa ggttttgctg tacacatata 22440
aacgagcaaa atatatttca aactctatat tctttttata aaaaaactcg agacagtcgt 22500
ttatgttacg actttttcta aatacctcaa aaacagtaat taattcactg tcgctgtgga 22560
aatgttcgta agctaactgt ttaatgtctt taggggtcaa ttcttttttt gggagcagtg 22620
gtttgagatt cggcaaaggt cgtctaaagt agtgagcgaa cttttcattc gctccccaac 22680
acaaaagccg ataagccagc atgtagttat cacgttttac cgcgtaaata agcaaatagt 22740
ttatattgat acatgtacca tgttgctgcc cgtttggaca tatgttgccg cattctgaac 22800
acttatgaat gagatcatag ttcttacaac ataaccccaa acgggttagt acttctttgt 22860
cacgttttaa aaactcgaca tgattcttta atgttaatgc tttgagcgca atgttaaata 22920
aactctgcat tttattaaaa tgaggttagt atcatgtttt agtataaaat ttagcggctg 22980
tttacataat gctaaataaa cttaacgttc ctactaaacc aaaaaaaatc aaattgacta 23040
agtcatagag aatttgacga tgttggtagg taatttttta acatggtata tattttttta 23100
gggtcggtta tattaggtaa taaaagagga cgtgccgtta aagtattttg cttaagatcc 23160
tttagatcct tacaaaaata tagattgttc gtctgatgat gccactgtgt tgcagtgatg 23220
gcttgatcaa tatcacctcc caagacaaaa cagtagtata tcgttaaaaa gttgtaatct 23280
ttcatacaag ccaactgcat cattttatcg atgtccatat gaacgatctt ttgctcgtat 23340
atttcatgaa ggtcaaatac attgttgaag taaatggcgc acatgagtcg ccacatacta 23400
aggtgcccat atgtttgata gaaaaaggag atagctcttt taagcttata ttttactgct 23460
atggcatagc agtatttaac gaatacgttc atgggtacat tatctaagat ataaaatatg 23520
aaaaacttta actctcgatg aatctcttcc cccatttcct gtacatttag agcttccaac 23580
ataggatttt tatcaaatat ttcatgacat aaaataatgt tattgctcgt tttatgacgc 23640
attaaaccgg tgaaaatttc cttattattt aaactatctt tagctcctaa ctttcgacac 23700
agctcctgag tttgttccgt cctagcacag gtcagcccat aataaatgtt tgctccccac 23760
tcggtgaaca gccttattac gtcatagtta ttttctttta tggccatgat taatgccaca 23820
tcaagatgaa gaagttcccc cttaaagggg gttgagctta aaataacgta attacagtag 23880
tgacataagc taatgggctt gttttgccac cataagccac aatattttaa aatataatga 23940
tactcctcag gcacgctctg tttggccaca gcctttttgg ccagggtttg caaggagagc 24000
atgataactt cttgaaaaaa aaactcaaat taagttccta cttttttaaa atattagtat 24060
ggacagatct accatcatat gaaggaattc tttcatcgtt aaacactgaa gagataatac 24120
tttcatcgta tagagaatat catgtcaatc catatattga atgttatata tcattaaacc 24180
catcattaat atagtgttta tgtgctatgg acaggttttt tgaatgataa tcttttaaca 24240
```

-continued

```
tacgttttat aacttcggga tcagtttctt ttaaagataa agaatcattc atgttataac  24300
aatttaatga taacatgctg gcaatgaacg agttgtcttt ttgatgcgct agagtctttc  24360
cctcctcaaa ggcattggcg cctaagtcta tacaaaagaa tatgtttccg atattataga  24420
actgaataga atgaaacatg gcctgattga tatcagcccc taagacgacg caacagtaat  24480
aaatcgttaa atagttatag ttcttgcgac aggcccactt tagcatttca ttcatgtcta  24540
tgcgaatcct ctccttttcg tacacttcgt gaagttcaaa cacattattg taaaaaaggg  24600
cgcacataag ccgccaccga tgtagatgag catatctctg ataaaaatag caaatcgcct  24660
ccttaaggtt acattctatt gccatcgcgt accaatattt agtaaacatc tcgcttaata  24720
tatcggtttc taccattaat ccctccagtt gttcataaat cattcccttt acttcaaaac  24780
gatttatggt atctaaaatg ggattattag aaaatacctc atggcagaaa atgatgttac  24840
tgctagttag atcacgtttc aatgtgtaaa aaaatcgtaa aatttcctgg tcatttaact  24900
gttctttggc acctagctgc ctgcacaggt ctcgggtgtg ctccgtgttg acagaaagca  24960
aaccgtagtt gatgtttgca ccccactcgg tgaacaattc tattagatcg tgattgtttt  25020
cctccacagc tttcaccaag gccgcgttaa gatttgtgcc gttcttaaaa tacggcgtcc  25080
atattttctt ttgatgatac atgatagggc cattatgcca ccatagaccg cagcacttca  25140
aaaaatgagg atggcatttg gccggatact ggctggccag cacctttttg gtgagagtct  25200
gcagagagag gaccatattt cttttttttg aaaaaatcaa attaaaaaaa tcatgcttgt  25260
ttagcataca tgtaatattg ttataattac gttataatta cgttataatt acgttataac  25320
tatattataa caatggtata acaatggtat aacaatgtta taacaatgtt ataacgatgt  25380
atcattgatg tcatcattca actaggccaa catacttttt aatttatagt tttttaatag  25440
atgatatatt ttgttaggat ctgcttcttt taacgttaat agcgaggagt ctgcactata  25500
aatgtctaat gataaatgat gagatatcaa atagtaattc cgttgctctg ctagggcctt  25560
tgcctcttca aaggcgtcgg ctcccagatc tatacaaaag aacaagttat ccatattata  25620
aaatcgtacg caggcaagca tagctgaatt aatattagct cctaagagaa aacaataata  25680
tatggttaaa aaattgttat cttttgtgca ggccatccgc atcatttcat ccacgtccat  25740
gcggatcttt tccttttcat acaaattatg taggtcaaac agcttattaa aacaaagagc  25800
acagattaac caccacgtat ttagatactt aaaatgttgg taaacataag aaatggcctc  25860
cctaagatta tcctgcaatg ccactataaa acagtatatc gttaacatat caccatccga  25920
catattactt aatatgtcgg tgtcttctac taacctttc aacttccaat atatggatga  25980
ccttatttcc cttataatga cataggctgg aaagggatta tcattaaaaa gtttaagaca  26040
taagataata ttactgctag tagtgccagg gtgtattaat ttaaagaaca tgtgcataat  26100
cttcttttta tccacgcggt acttggctcc taattcccag caaaattctc gaacaggcgg  26160
cgtattggcg caaattaacc catagttgat gtctgcgccc cattctgtaa acagttttat  26220
taactgatag ttgttttcct ttgtagccaa cattagtgcc gtattaaggt ccaagccgtc  26280
tgcaaagctt ggcagcttta tcagcatatg tttgcaatca agggaaattg gggccttata  26340
ccaccatagt ccgcagcgtt ctaagataac atggtactca atagatactt gctgtctggc  26400
tagtaccttt ttggcgaagg attgtaagga aggaaacatc ctgtttcttt ttttttaaaa  26460
atcaattatc tttgttcata atcaagaaaa atccccatat ttattgagtg ataatttttt  26520
aacatgcaat ttattttttc agggtccgta acgatcgaca acagagaaat aaccggattg  26580
taatgcttta atgataaggc atgggctatc agataatttt ccttttgttc tgccaaagct  26640
```

-continued

```
ttgccctcct caaaggcatc ggcacccagg tctatacaaa agaacaggtt tccaagatta  26700
tagttttgta tggaaacaag catggcttga ttgatgttgg ctcccatgat aaaacagtag  26760
taaatggccg aatagctata atcttggatg caggctatgt gcatcatttc atcaatatcc  26820
atgcggaccc tttctatttc gtacagctcg tgaaggtcga acacgttgtt gtaaaaaagg  26880
gcgcacatga gccgccacct atgtagacgc gggtatttct ggtaaaagta gcggatagca  26940
tctttgaggt catagtccac cgctatcgcg taccagtatt tggttaaaac agtgctaaag  27000
ctatcatcat ggtccagcat gaaggttatc tccatgagcc ctcttaactc ccacatgatt  27060
tccccctca gatccagatt atctataatc cttaaattgg ggttattgga aaacacctcg  27120
tggcaaaaga taatattgct actggtttta tcgcgcgttg tatcaaagaa aatttttaaa  27180
atatactctc tttctaaata ttctttggct cccagctctt tgcacagatc acgggtattt  27240
tccgtgagag cacaaatcat tccatagtta atatctgcac cccattcagt aaacagcttt  27300
atcaagtcat gattattctc cttcacggct ttcatcagtc ctatgtttaa ctcgatacct  27360
tgactaaaac aggttgacct tataaataat ttattgcgtc gaatatgaag cataatgggg  27420
ccattatgcc accacaggcc acaacacttc aggacatgat attgatctac cggtatacac  27480
tgcccggcca gtactttctt cgtgagggat tgcagggaag gcaacatgcc tttccatcct  27540
ttgacggaaa tcaaattatc tactaataac tatcagtgtt tatattaagt atttagatat  27600
tatcccgggc tggatacgta gtatcgctat tcacatgtac ttccaactct agccggagcc  27660
tgcagggtca tttattttta atattgattc ttttttgtat ttaatcattt agagaaggtc  27720
atcataggag ccagatgttc tctctccaga acttatgtcg aaaaacatta cctaaccgta  27780
aacttcctga atttttgac gaatatatat tacaactgct gggattatac tgggaaaacc  27840
atggaactat tcaacgagca ggaaacaact gtgtgcttat acagcaacat accctcattc  27900
ccgtaaatga agccctgaga acagcagcat ctgaagaaaa ttatgagatc gtgagccttt  27960
tattagcgtg ggaggggaac ctttactatg ctattatagg ggctctagag ggcaaccgcc  28020
acgacttaat tcgtaaatat gatgaccaaa tcaaggacca tcatgaaatt ctgccattca  28080
ttgacgatcc agtcatattt cacaaatgcc atatcatgcg gcaatgcttt tttgattgta  28140
ttttatatca agctgtaaaa tatagtaagt ttcgcgttct tctttacttt aaacatagat  28200
tagaggatga tttgcccttc actcatttac ttattgaaaa ggcatgtaaa gatcataatt  28260
atgaagttat taaatggata tatgaaaacc tacatatcta caatatgata gatacctttg  28320
aatgtgctat tgcccataag gatctacatc tatattgttt ggggtataga tttatatata  28380
acagaatcgt acccgataag tatcatcatt tagatattcg catgctttca agcctacaac  28440
tcctacataa ggtggcagcc aaaggatact tagattttat cctagaaacc ttaaagtatg  28500
atcataataa agataatata aatattattc taacacaagc tgcaacctat aaccatagaa  28560
aaattttaat ctatttcatt cctcaatcaa cccacgcaca gatagaacaa tgtttactag  28620
tggcgataaa agcaaaatct tccaggaaaa ccttgaactt actactgtct cacctaaacc  28680
tttccatcaa cctcatcaaa aaaataagcc attatgttgc cacttacaat tcaacaaata  28740
taataggcat tctgagtatg cggcggaaaa agaagatata tttagatatc atattgacaa  28800
aatttgtaaa aaaagctatt tttaataagt ttgtcgttcg atgtatggat acattttcta  28860
taaacccgga aagaatcctt aaaatagccg cgcgaataaa taggatgatg ttagtgaaaa  28920
aaatatctga acatgtttgg aaaaatcatg cggttagact taaataccct aaacatgcgg  28980
```

-continued

```
tacacacgat gaagcataaa gatgggaaaa atagactcat gaactttatc tatgatcgct  29040
gttattacca tatgcaaggg gaagaaatct ttagcctcgc aagattttat gcaatccatc  29100
atgcaccaaa gttgtttgac gtttttttatg attgttgtat cctagatacg atacgattca  29160
aaagccttct tttagattgt tcacatatca taggtaaaaa cgctcatgat gctaccaata  29220
tcaacatcgt gaacaagtat atcggcaacc tgtttgttat gggagttctt agcaaaaaag  29280
aaatcttaca ggactatcca tccatttatt ctaaacaata catgccttag tttatttttt  29340
ttgcggccga aacattattc ttaccctaga aaacgcttat agtcatctta aatcataggt  29400
aaggaagatc atcatatttt ttgaaacgta attttttaac gcatgatcta tgatttcagg  29460
gtccgtgctt ttaggcaacg gggtggtggc cggactataa atctttaggg ataaaatgtt  29520
ctttataagc tcataccctt cccctaaagc tgtagtaccc tcttcgaaaa catcagcccc  29580
cagatctata caaaagaaca tgttttctat attatagtac tgtattgagc taagcatggc  29640
ttgattgatg ttggcgccca ggacatagca gtagtacatg gttgaaaggt tgtggtcttt  29700
gatgcaggcg atccgcatca tctcttctat gtccatatgg atcttgtcct tttcatacgc  29760
ctcatgaagg tcaaacacat tattaaaaca aagagcacat gttaaccgcc acgtattcag  29820
gtgtgtatat ttttggtaaa aatactgtat ggcctctttc aggttatagc gtatggctat  29880
agcgtaccag tatttgagta gtaatgtact gagcgaaaac tcattattta gcagatcggt  29940
ttttactatt aactccctta actcccagaa aatttctatc ctcattttta tattatttac  30000
tttttgtaat atcggattgt tggaaaacac ctcatggcat aaaataatgt tactactagt  30060
tttatgaaac tttagatcta taaaaatttg taaaatttct tcttcattca aggtttcctt  30120
ggcacctagc tctcgacaga ggtcccaggt gtgctccgtg ttgacagata ccagcccgta  30180
gttgatgtcc gccccccact ctgcaaacag ttttataagg ttgtagttgt tttcccttac  30240
agccttcact aacgccgtat ttaggtttaa gccctcttta atacctgctg attttatgag  30300
ccttaggtta tgatcaaacg tgatcggagc atcatgccac cataggtcat aacactttaa  30360
aagataatgt tggttcgtgg gcacgcattg tccagccaac acctttttgg tcagagattg  30420
cagggaaggc aacatgtctc ttcatctttt aaaaaaaaat caaattaatt agccgaataa  30480
atttttcttt cgagggcttt ttaaaagagc tctttaagag ctctttaaga gctttttaag  30540
agattaaaaa attattcttg ctggcattct gccaagtatg cggcattcct atcatctata  30600
gtatattatg agaatattcc caaatgatgg ataagttttt tgatttataa tcttttaata  30660
aactgcttat ttcttcgggg tcctttaagt ttagtggcaa ggaagcatct gagctgtaaa  30720
tatccaaagc caaactatgg ctcagaaaat tataaccttt ttgttccgct atggcacgac  30780
cctcttcaaa ggcattacca cccaaatcta tacagaaaaa tatattaccg atgttataat  30840
attgtactga agtaagcata gcttggttga tgttgccccc cagcgcgtaa cagtaatata  30900
ttgttaatgg attgttatcc ttggtagaag ccagacatat catgtcatgg acgtctattt  30960
ggatgttttc cttgtggtac atctcatgaa gctcatatat tttgttataa tacaggagac  31020
attttaatcg ccattcatta agatccgtat atttctcatc tagaaaacaa atggcgtcct  31080
tacaatcgta ttgtactgct ttggcgtacc aatacttcac tagtaaacca tttaactcgt  31140
ccgtttcttt tatttctatg agcccccata gtcttttata aattaagccc cttaattgta  31200
taacaaattt gttttctaaa ataggattat tcataaaaat ttcatggcac aaaataatac  31260
tgccgctggt tttattgtgc attatcctgg taaaaatacg gaaaatatcg ttgtcctcta  31320
gagtttcttt ggcgcctagc tgtctacaca actctcggat gtgcttcgta ttgatagaaa  31380
```

```
gcaaaccata gttgatattt gcgccccact ctgtaaagag ctttatcaga ctatagttgt  31440
tttccttaac agctattatt aatgccacac gaaggtctat atcttctcct aaaaatcctg  31500
attttatttg tattcggcca cgatccatac aaagcttgag aggagcatca tgccaccata  31560
ggccacaata tttcaaaatg cagtgttcat ctattgacaa acactggctg gctatcgtct  31620
ttttgacgag ggtctgcaga gagagcggca acgacatgtt tctttttcac caaaaaaaat  31680
caaatgttct cgtctttaaa ggttaattca tgttcttaaa atgttcattt catgatagtg  31740
attaataata tggtttaata acgctagaag gcttgtttat aagacagtca taagcagtct  31800
ataagacagt ctataagcag tctataagac agtctatgac ttagtctata actataattt  31860
ctggatgggc tgtaagatac tcttcggctc gtttcagatt ttttgaagta tatgtcttta  31920
gcatatcata tatttcctgg ggttcggtta catctaatac caaggtcaca tcacggctga  31980
aaagctgctt tactaagaaa atgttgctca agttatacat ataagctttg tgcgcaatga  32040
gttgtgccct atcaaaatcg gcagccccca aatcaataca gaaaaacatg tttaaagtat  32100
tattgttata gatagaaaga ttcatgccat aatcgagact agcccccaac ctatgacagt  32160
aataaatggc cgcgtaattt ttttcccgca agcaagcaaa tttcatcatc agattagggc  32220
tgatgcaaat ctctttttca cgacacaact cgtgtatgtc aaaaatgtta ttaaaataaa  32280
ggctacaagc tacccgccaa tagaggtgat ttttatgcct tttatagaaa tagtgaatag  32340
cctttgtaaa attatgtcgt aatgccaggg caaaccaaaa ctttgttaat aggtggtgcg  32400
ccgtatcccc cgtcaacgga atgtttgaac aggtgtacgt aactgtgtct aaagtggttc  32460
tagttacggt ttccaagagt ggattatgac aaaacatgtc ataacccagc agaactcctg  32520
cacaggattt tagcctggcc acttctttta aaatttccag aagacggggt tcggatacag  32580
gcgttaagcc tcccagttcc gcacacagcc gctttagata cacggcagga acacgtataa  32640
gcccatattc aggatttgcg ccccaatcca caaataaacg tataagttca agattatcgc  32700
tcttcacggc ctttactagc gccgcttcga gacaaagatc atcctcagaa aaacactgta  32760
aatgtttata cgaaaaaact tgcttacaat tgttacatag gtgaatagga cctaaatccc  32820
accacaaacc aaaacgctgc aacgtataat catagtcact tgaaagataa ttgcatgcca  32880
caactttttt ggccaacgtt tgtaaagaca acatactaag tttaaaacat cttaaatcta  32940
agctagctaa ctttcaagaa aaccctctat ccctaagaat atatcttata actagactta  33000
tagcagtaaa aatcaacttt ggttattctt tttaatataa aacgtctaat tacttgcaaa  33060
ggactataaa gcccattttc ctcagctaga atttttattt tttaatgaag taggggggata  33120
tgttttccct tcaagacctt tgccgaaagc atctttttat tcttcccgat gtttttggcg  33180
agcatgtact acaacgatta ggactgtatt ggagatgtca cggctccctt caacgcatag  33240
gagacgacca catactcata cgacgggatc tcatcctttc caccaacgag gccttaagaa  33300
tggcgggaga ggaaggaaac aatgaagtag taaagctctt gttactgtgg aagggaaatc  33360
ttcattacgc cgtcatagga gccttgcagg gtgatcaata tgacctgatc cataagtatg  33420
aaaaccaaat cggcgacttt cattttatct taccattgat tcaagacgcg aatacgtttg  33480
aaaaatgcca cgctttagaa cgtttttgtg gtgtttcatg tctgctaaaa catgctacaa  33540
aatacaacat gctccctatt ctccaaaaat accaagaaga gctgtctatg agagcgtatc  33600
ttcacgaaac cctatttgaa ctagcatgcc tatggcagag gtatgatgtc cttaaatgga  33660
tagagcaaac catacatgtt tacgacctaa agattatgtt taatattgcc atctccaaga  33720
```

-continued

```
gggatctgac tatgtactcc ttaggatata ttttcctttt tgatagaggg aacaccgaag  33780
ctacgttgct aacgcaacat ctcaagaaga cagcggccaa agggctcctc cactttgtgc  33840
tagaaacgtt aaaatacggc ggcaacatag ataccgtcct gacccaagcc gtaaagtaca  33900
atcatagaaa acttttagat tattttctgc gtcaactacc tcgtaaacat attgaaaaac  33960
ttttgttgct ggccgtgcag gaaaaggctt ctaaaaaaac attgaactta ctgttgtcac  34020
atttaaacta ctccgtgaaa cgcatcaaaa aactaccgcg ctatgtgata gagtacgagt  34080
ccaccttggt gataaagatt ttattaaaaa aaagagtgaa cctgatagat gccatgttgg  34140
aaaagatggt aagatatttt tctgcgacga aagtgaggac gatcatggat gagctttcga  34200
ttagtccgga aagagtcatt aagatggcta tacagaaaat gagaacggat atcgtaatcc  34260
atacttctta tgtttgggag gatgatctag aacgtcttac tcgtcttaaa aatatggtat  34320
acaccataaa gtacgaacat gggaaaaaaa tgttaattaa agtcatgcac ggcatataca  34380
aaaacttatt atacggcgaa agggaaaaag tcatgtttta tttagccaag ctctatgttg  34440
ctcaaaacgc ggccacccaa ttcagagaca tttgtaagga ctgttacaaa ctggatgtgg  34500
cacggtttaa accgcggttt aagcaactaa tattagactg tttagaaatt attactaaaa  34560
aatcttgcta tagtatcctg gaaatcttag aaaaacatat tatttccctg tttactatga  34620
aagttatgac tgaagaagaa aaaaacctat gtttagaaat attatataaa gtaattcatt  34680
ataaaacaat acaatgttaa aattcaatag atatccatca ttaatattga ttatattttc  34740
gaatattatc ttctatggtg caagataatc atctagcgcg tgaaacatgt cctcttctct  34800
tcaggaactt tgtcgaaaaa agctgcctga ctgcatactt ccagagtttt ttgacgacta  34860
tgtattgcaa ctgttaggac tgcactggca agatcatggt tcccttcagc gtatcgagaa  34920
gaaccagata cttgttcaac aggaacccat ccatatcaat gaagcactca aagtagcagc  34980
atcggaaggg aactatgaaa tcgtagagct gttgttgtca tgggaggcag atccccgcta  35040
cgccgtcgta ggagccctag aaagcaaata ctatgacctg gtttacaaat actatgacca  35100
agttaaagac tgccatgata tcttgccgct gattcaaaat ccggaaacat tcgaaagatg  35160
tcatgagtta aacagcacct gttcactgaa atgcttattc aagcatgctg tgataaatga  35220
catgctgccg attcttcaaa aatatacaga ctatctggat aggtgggagt attgcagcca  35280
gatgctgttc gaactggcat gtagtaaaaa aaaatatgag atggttgtgt ggatagaggg  35340
agttctaggc gtcggcaaag ttacatctct tttcaccatt gcgattagca acagagacct  35400
acagctgtat tctctgggct actcaattat ccttgagaat ttgtactcct gtggacagga  35460
ccccaagttt ttactaaatc atttcctgcg agacgtttca ataaaagggc ttctaccctt  35520
tgtaatcaaa accatagaat atggtggaag caaggagata gccataactc tggctaaaaa  35580
atatcagcat aaacatattt tgaaatactt cgaaacctgg gaaagctagg ttcagtatgg  35640
tgtactcact attgtagtga atcgtatcct gtaaattttg taaaaaagct taaacttttg  35700
accacatcat attgttttag aaatctcaaa ccagtgaaca acagtcttat catacattaa  35760
aattccagta aaatttatat ttttttggt aaacaaatgt tttctcttca agacatctgt  35820
cggaaacatc tttttcaact tcctgacgct tttgatgaat atatattaca agcgctagga  35880
ctatactggg aaaaacacgg atctcttcaa cgaataagaa aggacgctgt gtttgtacag  35940
cgaaacatcg tcctttctac caatgaggcc ctgagaatcg cagcctcaga gggaaacgaa  36000
agggtaataa aacttctgtt atcatgggag ggaaattttc attatgtgat cataggagct  36060
ctagagggtg accaatatga cctaattcat aagtatgata gtcaaattaa agactaccac  36120
```

atgattttat cattgatcca aaatgcaaat acctttgaaa agtgtcatca gttatccaat 36180
agtaatatgt ggtgtcttat acagaatgct ataaaatata atatgctccc tattctccaa 36240
aaacacagaa atattctgac acatgaggga gagaatcagg aattgtttga gatggcatgt 36300
gaggaacaga aatatgacat agttttatgg ataggacaaa ccctaatgtt aaatgagccg 36360
gagtttattt ttgatatcgc cttcgaacgg atagattttt ctttattaac aatgggttat 36420
agccttcttt ttgataacaa gatgagtagt atagacattc atgatgaaga agatcttact 36480
tcattaccaa cagaacacct cgaaaaagca gccactaagg gatgtttctt ctttatgcta 36540
gaaactttaa aacatggtgg aaatgtaaat atggcagtct tatctaaagc tgttgagtat 36600
aatcatagaa aaattttaga ccattttatt cggcggcaaa aatgtttatc acgtgaagag 36660
attgaaaacc tattattaac cgccataacc aattgtgcat ccataaaaac gttaaactta 36720
ctcttgtctt acctaaacta ttccgtaaaa aatatcattg gaaaaatagt acaacatgtc 36780
ataaaagatg gtgattatac catcatatta cttttaaaaa aaaagaaaat aaacctagtg 36840
gaacctgttt taacaggttt tatagattat tactatagct attgttttat aaaacatttt 36900
atccaagagt ttgctattcg tccggaaaaa ctgattaaaa tggccgcgcg aaaaggtaaa 36960
ctaaatatga ttatcgaatt ccttaacgaa aaatatgttc ataaagatga tcttggaact 37020
atatttaaat atctcaaaac cctagtatgt accatgaaac ataaaaaagg aaaagagaca 37080
ttaattgttc ttattcataa aatatatcaa gatattcatc tggagactaa agaaaaattt 37140
aaattattaa gattttatgt catgcatgat gcaactatcc aatttctatc tatgtgcaaa 37200
gactgtttta atttagccgg ttttaaacca tttgttttag aatgtttgga tattgctatt 37260
aaaaaaaatt accctgatat gatacaatat atagaaattc tatcgaaatc tgagtaaaat 37320
ttattttttt gatcagagta agaaaatgtt ctccctccag gagatctgtc gaaagaacat 37380
ctactttcta cctgactggc tcggtgagca tgtgattcag cgactaggtc tgtactggga 37440
aaaacatggt tctcttcagc gaatcggaga caactatgta cttatacaac aggacctcat 37500
catccccatc aatgaagccc taagaatggc aggggaggag gggaatgatg aggtggtaca 37560
actcctatta ctatgggagg gaaacattca ttatgccatc ataggagctt tggagagtga 37620
ccattatagc ctaatacgta agctctatga ccaaatcgaa gactgtcacg acatccttcc 37680
cttgattcaa gacccaaaac tctttgaaaa atgccatgaa ttagataaat cttgtaacat 37740
tttatgtctc gtattacacg ccgtaaaaaa cgatatgctt tgcattcttc aagagtataa 37800
aatgcatcta agtggagagg atattcaagt ggtgtttgaa acagcatgcc gttcacaaaa 37860
aaacgatatt gtgtcatgga tgggacaaaa tattgcaata tacaaccccg aagttatttt 37920
tgatattgcc tttgataaga tgaatgtgtc cttattatct atagggtata cgcttctttt 37980
caatcatcat ataaataata cgaacgaaaa tattaattct ttattgacac aacatcttga 38040
atgggctgcc ggcatgggcc ttcttcattt tatgctggaa actttaaagt atggcgggga 38100
tgtaacgata atagtcttgt ctgaggccgt aaaatatgac cacagaaaga ttttagatta 38160
ttttctccgt cgaaaaaact tgtaccaaga agatcttgaa gaactattat tgttggcgat 38220
acgtgcagat tgttctaaaa agaccttaaa cttgttatta tcttacttaa actattccat 38280
aaacaatatc cgtaaaaaaa tattacaatg tgtaaaagaa tatgaaacga ccgttattat 38340
aaaaatttta cggaaaagaa agataaatct gatagagccc attttggcag actttatagg 38400
atatcatagc tatacctata tggtagattt tatgcgtgag ttttccatcc atccggaaaa 38460

-continued

```
aatgatcaaa atggctgcac gagaatcgag ggaggacttg atcataaaat tttccaaaaa  38520
agtttgcaaa gagcctaaag atagacttca ctatctcaaa agcttagtgt atactatgcg  38580
acataaagaa ggcaaacaac tgttaattta tacaatccat aacttataca aagcttgtca  38640
tctagagagt aaagaaatgt ttaatttggc acgattttat gcacggcata atgcagtgat  38700
ccagttcaaa tcgatttgcc acgatctctc caagctcaat attaatatca aaaacttgtt  38760
gttagaatgt ttaggtattg ctattaaaaa aaattacttt caacttatca aaacaataga  38820
aacggatatg cgttatgagt aacattttta gatgagggaa gattctacca aactaactaa  38880
gacctttcgc tagaatgtat cttattgtta atatagatga gatatgtcat tgtgaaaaaa  38940
tagattaggt aggttgtgaa aaacagatta aacttaaaat tatgtgtatt atgtaaaatt  39000
ttagaaataa aaatttattt tttttattga gggtacggaa aatgttctcc ctacaggacc  39060
tctgtcggaa gaacattttc ttccttccaa atgattttag caagcatacc ctacaatggc  39120
tgggattata ttggaaagag catggatccg tccatcgagc agaaaaagac agcataatga  39180
tacagaatga attggttctt tctatcaatg atgctttaca gcttgcagga gaggaggggg  39240
acacagatgt agtacagctc ttgttattat gggagggaaa tctgcattat gccatcatag  39300
gagccttgaa gactgaaaaa tataacctaa tatgtgagta tcatagccaa attcaggact  39360
ggcatattct cctacccatg attcaagatc cagaaacatt cgaaaaatgt catgatttaa  39420
gccttggatg tgactttatt tgccttctcc aacatgctgt aaaatacaac atgctttcta  39480
ttcttgtcaa atataaggag gatctactaa atgcaaggat taggcatcgt atccaatccc  39540
tgtttgtttt ggcatgcgaa aatcggagaa ttgaaattat tgattggata ggccaaaatc  39600
tgccaattcc tgaacctgat gccattttta gcattgctgt tgctacaaga gatttagaac  39660
tgttttcctt agggtacaag attatttttg attacatgca aagacaggga atcattcaat  39720
taaccaatgg agttcgcatg gttgtgctaa atcgtcacat tagcatggca atagataatg  39780
gtcttttacc ttttgttctg gaaactttaa aacatggtgg gaatatacat agagccttat  39840
cttatgcagt aacacacaat agaagaaaaa ttctggatta tcttattcgc cagaaaaata  39900
tagcccctaa tacaattgaa agacttttat atctggccgt gaaaaatcaa tcttccagga  39960
aaactttgaa cttgttgcta tcttacataa attacaaggt gaaaaatgtt aaaaagctgg  40020
tagagcatgt agtaaatgag aaatccactc ttgtgttaaa aattttatta gaaaaaaagg  40080
aaaatctagt ggatgctgtt ttaacaagac ttgtaaaaca ttctacatat ttccaggtga  40140
gagaatttat ccaggagttt tccatcagcc cagaaaaatt cattaaaata gctgtgcggg  40200
aaaagaaaaa tgtgttaatc gaggctattt ctgaagatat ttgggaaaat cccacagaaa  40260
gaattactta tctcaaacag atagtgcaca ccataaaata tgaaagtgga aggcgatttt  40320
tggtagacat cattcacagc atttaccaaa gttactcact aaaacacgaa gatattctta  40380
aactggcaac attttatgtc aaacacaatg caatcaccca ttttaaagac ctctgcaaat  40440
atctttggct gaacagagga acagaaagta agaaactgtt tttagagtgt ttagaaattg  40500
ctgatgagaa ggagtttcct gatattaaaa gtattgtgag tgaatatatt aactacttgt  40560
ttactgcagg agctattacc aaggaagaaa tcatgcaagc ctatgatgct ttagagtagc  40620
catgtattaa cattctgaaa gtagaataaa atatactata tactaaaaac caaattagcc  40680
atttttaact atcttcttct taaaaactct ggataaaaat ttattttttt taatttgggt  40740
agggaaaatg ttctcccttc aggacctctg tcggaagaac accttcttcc ttccaagtga  40800
ttttagcaag catacccctgc atttgctggg gttatactgg aaggggcatg gatctatcca  40860
```

```
aaggataaag aatgatggtg tgcttataga gcatgatctt actctttcca tcaatgaagc  40920
cttaattctt gcaggagaag agggaaacaa tgaagtagta aagctcttgt tactatggga  40980
aggaaatctt cattatgcca tcataggagc tttgaggact gagaactata acctagtatg  41040
tgagtaccat agtcaaattc aggactggca tgttctcctc cctttgattc aagatccaga  41100
aacattcgaa aaatgtcatg atttaagcct tgaatgtgat ctttcatgcc ttctccaaca  41160
tgctgtaaaa tataacatgc tttcgattct tgttaaatat aaagaggatc tactaaatgt  41220
actatttagg caacaaattc aaggactatt tattttagca tgtgaaaatc ggaagcttga  41280
gattcttacg tggatgggtc aaaatctgcc aattcctgat cctgagccta tttttagcat  41340
tgctgttgtc acaaaagatt tagaaatgtt ttccttaggg tacaagattg tttttgaata  41400
catggaaaac caaggacttc atttaaccca ggtagttcgt atggttatgc taaatcatca  41460
ctttggcatg gtaataaata aaggactttt accctttgtg ctggaaattt taaattatgg  41520
tgggaatgta aatagagcct tatcttatgc tgtcacacaa aataaaagaa agattttaga  41580
ccatgttgtt cgccaaaaga atatacccca taaaaccatt gaaagaatgt tgcatctggc  41640
tgtaaaaaag catgctccca ggaaaactct gaacttgtta ctatcttaca taaattacaa  41700
ggtgaaaaat gttaaaaagt tgttagaaca tgtagtgaaa tacaactcta ctcttgtgat  41760
aagactcttg ttagaaaaaa agaaaaacct gctggatgct actttgacaa gatatgtcaa  41820
agattctaca tactttcagg tgaaagaatt tatgcaagac ttctccatca gcccagaaaa  41880
attcattaaa atagctgtgc gggaaaagag aaatgtgttg atcaagggta tttctgaaga  41940
tatttgggaa aatcccgcgg aaagaatcag gaatcttaag cagatagtgt gtaccataaa  42000
atatgaaagt ggaagacaat tcctgataaa tatcattcac accatttacc agagttattc  42060
tttgaaacct gaagaaattc ttaaattggc aacattttat gtcaaacaca atgcaaccac  42120
ccattttaaa gatctctgca aatatctttg gctgaacaga agaacagaaa gtaagaaact  42180
gtttttagag tgcttggaaa ttgctgataa gaaggagttt cctgatatta aaagtattgt  42240
gagtgaatac attaactatt tgtttactgc aggagctatt accaaggaag aaatcatgca  42300
agcctatgct ttggagtatg ccatgtatta aatttctgaa tcagtaagca atagatagat  42360
tttagaatat gctgtattaa gttagtttct gaataagtaa ttaatagata gattttagtt  42420
tatgtaaaaa tgttaacatt tgttcataag ttttagatac cattttagag ttactttttt  42480
agatattact attttagcca ttattatctt aaataatcac tattttagat aggtccccgt  42540
attaaaaacc aaattaacca ttatctatgt ttttaataat actttttaaa aaccctccat  42600
aaaaatttat ttttttttcat aaaagtagag aaaatgttct ccctacagga tctctgtcgg  42660
aagaaccttt ttcttccact tgagccctta ggcaagcatg tggttcaacg gctgggatta  42720
tactgggaag gccatggttc agttaaacga gtgggtgatt gctttatatg tgtagaccag  42780
atttggatgc tatcaatcca taaggctata caaattgcag cctcggaagg aaatgagaac  42840
attgtcaagc ttttcttact atggaagggg agtctacaat atgccatcat aggagcctta  42900
gagggcaggc aatatgatct gattcaaaaa tattacaacc aaattgggga ctgccatcag  42960
attctaccac tgattcaaga tccagaaatt tacgaaagat gtcatgaatt aaatgttaca  43020
tgtacctttc aatgcttatt tcaacatgct ataagagata acatgctgcc cattttccaa  43080
aaatatggag aagatctgaa tggaaacagg agaatggttc aacttctgta tgagatggca  43140
tgccgattac aaaattatga tatcatcaaa tggataggat ctaacctgca tgtttataac  43200
```

-continued

```
ttggaagcca tttttagcat tgcttttgtt agaaaggatt taactttgta ttctttaggc  43260
tacatgcttc ttctgggtag aatgagtact gaagatagaa actttatctc aatcataaca  43320
cgccatcttg aatacgcatc aaaaaaggga ctttttgact ttgtactaga atctttgaaa  43380
tatggaggtc aagtggatac agtgttgttt caggctgtaa aatacaacca taggaaaatt  43440
ttggcccatt ttattcatga aattccccgt gaaacggttg aaaagctgat actccatgct  43500
gtggagtcac gggcctccag aaaaacattc aacctgcttt tatcttccat aaactactgt  43560
gtgaaccctt ttgtcaaaaa actactgcac gctgtggtga aacacaagta catgcttatc  43620
ataaagcttt tgctcgagcg gcccaaaaag aagataaacc tggtagatgc tgctctattc  43680
aaacttgtaa aatactctac ttatacagaa atagtaaaat acatgggtga gttttctgtg  43740
gacccaaaaa gggtggtcaa aatggcagca cgactcatga gagtggacct gattaaaaag  43800
atttctaatg atgcatggga agataaacta gagagaatca agcaccttaa acagatggta  43860
aataccatga accacagaaa tggaaaaaat ctattgatgt acaatattca caatattact  43920
ggatatacct atctgaacac caaagaagca tttaacttaa caagatttta tgctgtccac  43980
aatgcaacat gtttgtttaa agaaatgtgt aaaagctgtt ttgtacatga taaaatacag  44040
ctcagagaat tgcttgaaga ttgtttacat attgctaata ggcatgatta tatccagatt  44100
gcagaaaccg cagatgaatg tatcaaatat atagatctta ttacatttaa gtaaaccatg  44160
tatatatcaa gtaaatccag attaaatcag gctaattgta aatagttgta gataccatat  44220
aatgaatgtt ttattaggat agtagttcag ttaagatagt agtttagtta agatagtagt  44280
ttagttaaga tagtagttat gttaagatag tagttctgtt aagataatag tttagttaaa  44340
actagttcat gttaagttaa tagttttgtt aagacaatag ttcatttaag tcaatagttc  44400
agttaagtca atagttttgt taagtcaata gtttagttaa gtcaatagtt tagttaagtc  44460
aatagtttag ttaagtcaat agttatatta agacattagt tctgctaata cattagtttt  44520
gttaagataa taaaaattta tttttttca tcagggtaga gaaaatgttc tccctacagg  44580
agctctgccg gaagaacatt tacattcttc cttacccctt ggctaagcat gtacttcaac  44640
aactagggct gtactggaag ggacatggat ctcttcaacg aatcggagat gaccatgtac  44700
tcttacagca ggacctgatc ttttccatca acgaggcctt aagaatggca ggagaggaag  44760
gaaacaatga agtagtaaag ctcttgttac tatgggaggg aaaccttcat tatgccatca  44820
taggagcttt agagggcgac cgatatgacc ttatccataa atattatgat caaattgggg  44880
actgccacaa gattcttcct ttaatccaag acccgcaaat ctttgaaaaa tgccatgaat  44940
tgagtaactc ctgtaatatt cgatgccttt tagaacatgc agtaaaacac gacatgcttt  45000
ctattcttca aaaacacaag gagcaaataa gattacacat ggcattaacc caaatactat  45060
ttgaattggc gtgtcatgaa cgtaaaaatg acatcattag atggatcggt tattccctgc  45120
acatacacca tctagagact atttttgatg ttgcattcgc ccataaaaat ttatccttat  45180
acgttttagg gtatgaactt ctcatgcaca aagtaaatac agaggctgca tatatagaat  45240
tacccaattt gctatcatat caccttcgaa ctgcggcggc aggaggtctt cttaacttta  45300
tgttagaaac aataaagcat ggtggatatc tggataaaac ggttttatcc gcggctatca  45360
ggtacaagca taggaaaatt gtggctcatt ttattcatca ggttccccgt aaaaccgtta  45420
aaaaactgtt actctatgct gtgcaggctc gggcccccaa aaaaacactg aacctacttt  45480
tatcttcctt aaactactcc gtgcacacca tcaccaaaca actcgtacac aatgtcgtca  45540
tctacagttc cacgcttatc gtaaagcttt tactcatgcg gcgaaaaaac aagttaaacc  45600
```

```
tagtagatgc cgttttagcc agacttgtaa aatattccac ctatacagac attgtacaat  45660
tcatgggtga gttttctgtg agcccagaaa gggtgatcaa aatggctgca cgggaatcca  45720
ggacctttct gattgaaatg atctccaaag ctgcttgggg aaatcaccca cagacgttga  45780
ttcatcatct caaacaacta accaatacca tgaagcctca atctggaaaa gaccacatca  45840
tatataccat ccactatatt tatctaaact ctaatatgct ggtagcggag gaggaaaaaa  45900
atatttttaa attagcaaaa ttttatgcga atcataatgc ggtaaacagg tttaaacaaa  45960
tttgtgaaga ctattatata ttagatgcac gatttaaaac acttatttta gaatgttttg  46020
aaattgccgt ccagaaaaac tatcctagaa ttgcaaatat tgtggatgac tatattcgat  46080
tcctttttta caggggaaat ataaccgagg aagaaattcg tgaagcctat tctttaaaag  46140
atgctgaggt ttatgtagat ttaaaatggt tacaacaagg agaaatggtt taaaccaaat  46200
ccggtttaaa ctaaatccaa tttaaactac atttggttta tcattagtca ttgaaaccat  46260
cgaaaaaaaa gctatttgtt tatccccata aactcatctt ttttttgtct caaagtttga  46320
cactaaaatt cagtgtttta tagtgtttat aattaagtgt tttgcatgca ttgcagaaat  46380
tttcatcttt tttaattggt tcaataccac atgtcataca atatgttgtt tgattatcaa  46440
gattaacttt atgaaaggaa agtaagtgag ccgcaaattt aaaagtaaaa tatctttcat  46500
ttaaaatgat cttatgaatg tattttcgat aaggaggaat gaaagcattt gccaaaataa  46560
atcgcataaa aggcttggaa aaacccatat cttctaatct tttgtgggta taaaccctat  46620
tttggtgttt tacaaaaact tcattgttat aatagtcgtt atagctatca atcatttttt  46680
taagtcctat aatgcccaag gttgcacgca taaagccaca gtttctgctc caaaaagcat  46740
gcacctgtaa agggtgcttt tcatataacc aattacaaaa tttcattccg caacagtagc  46800
atgttatttc agtgggggat gtatagaata atccggcatt cgaaaatttt tcataatttt  46860
ttatgtcatg gattgcgaag ctttgatttc gtgcatctat ggagctatag cctacatatt  46920
taggttttac ttcaaataat cgcaaagaga tgtatggatc tatcgtattt attttaggaa  46980
acatttcata attttaaatt cttatatata atataaaaaa aattacaaac atttgtaatg  47040
atcatcctca attgaaggct gagttgtagg ctttattttt ctaattatac gaagaaggta  47100
ggttctcata aagccttcaa gatgactatt gatgtttcca atacattttc tcaatgagtt  47160
cataaaccca gacattttgc taatggcttg gcaaagtgcc aacaagttgt ccacaaagta  47220
ctggtagatt gccactagct atagctagct atagtgagcc aacctctctg tatgtatttt  47280
atatatttca ttttttaata gatttaatat ttttataaaa aatatttagt tttttataca  47340
agaatgtcga caaaaaaaaa gcccacaatt accaagcaag agctttactc cttagtagcg  47400
gcagataccc agttaaataa agcattgatt gaaagaatct ttacaagtca gcaaaaaata  47460
atacaaaatg ctttaaagca caatcaagaa gttattatac cacccggaat caagttcacc  47520
gtcgttacgg tgaaagctaa acctgctcgc cagggccata atcccgccac aggagagcct  47580
attcaaatta aagctaaacc tgaacataaa gccgtaaaga tacgagcatt gaaacctgtc  47640
catgatatgt taaactaaac tataaagtca tattcttctt tatcgttatt atcttcaata  47700
tatttttgcc aatcgaaatc gaataaattc agatcctgga catttaaata cttatcatcg  47760
tacattttaa tataatttaa acatgagttg ttgtcaaaaa cttttagcgt ttttgttaaa  47820
attatcatat gaataatttc cttattaaga gttgccggaa taatacaaaa cctattttta  47880
ggtacatcat ccatgataat agtaaaatta gtaaaaattg tttcttgttt ttcttttgtt  47940
```

```
tcaaataaac gttgtaaggt taaaggtttc tcgttcaatg gtttctttga agataaaaag  48000
aatgtataat ctggtttaaa ggtatttttg gtttcaatcg tgattccatc tgcttgagca  48060
tatactaaac cagaccaaat ataacggtcc actattacaa tataatttag cttaagtagc  48120
actgcaattt ctgcgataaa ttcactacga tgttttgtaa ataatttatg taattgttcc  48180
gatgacattt ctatggtttt atttaacacc tgcaatataa gatcaccggt ggtcgtgtct  48240
ggattaggaa aatgtataca tatagcatta taatccatgc attccaatgt ttcttttaat  48300
ttcattgcct gtgtgctttt tcccacacca ttgattccct cgatggcaat gagtattcca  48360
cgcatgatta ataaaaggaa aaaaagaatt cagtttttaa catttcttac aaatcttttt  48420
ttatacaaca ttgtacaaca ctgcattagc ggtatatgat gttatagctt cattaaatat  48480
ttgcttttat ataatcttta ccaacctata tttggtagat cactgcagat ggtcataaat  48540
aggccataac taagataaaa attatttcag acgctactac ggtagtatta ttaaaatcat  48600
gtgtggcaat gtatgacgtc ttaatagata aaacatttaa ggaaaacaaa tttgaataaa  48660
aaaataattg ttatgatggc gttgttacac aaagaaaagc ttatagagtg catctatcat  48720
gagctagaaa atggcgggac aatattgctt ctaacaaaaa atattgttgt gtcagaaatt  48780
tcatacattg gcaatactta taaatatttt acctttaatg acaatcatga tctgataagc  48840
aaagaagatc ttaaaggagc aacatccaaa aacattgcta aaatgattta taattggatt  48900
ataaaaaatc ctcaaaataa taagatttgg agtggtgagc cgcgtactca aatttatttt  48960
gaaaatgatt tatatcatac aaattacaat cataaatgta taaaagattt ttggaatgtt  49020
tcaacttcag tcggtcctca tatctttaat gatcgtagca tttggtgtac taaatgcaca  49080
tcctttttacc catttaccaa cattatgtcg cccaatatat tccaataaat tagatatctt  49140
tgctattaaa atagttaaaa accttatagg ataattaggt actttattac gataaattat  49200
gatattttat aattagttac tttattataa ttaatctctt tattaatgaa ttatcataag  49260
ataactaatt attttttcc atatatcaga taataaatct gatatgggct aaaagtatgt  49320
ttcaaactat ttacaataga atttctgtta agaaaacata cataatttga ataaaatttt  49380
tttaaatatc accgaaacaa tcaacatggt gttaatagag tttttaacag gtttcttcta  49440
tttatatgga aagagactgt tttccattag taaagtcatg gacatgatat gtctagacta  49500
ttataccatt attcctgctc ctctggcgat gatgttagcg gcaagactaa aaaactatga  49560
cctcatgaaa cgactgcacg aatgggaaat ctctattgac tacgctctac ttgtagtaga  49620
tgatgtgccg tctattgact attgcttaag tcttggcgct agatccccga ctagagcaca  49680
aaaaagagaa ctgctgaggg acaacacgtt taatcccgtg tataagtatc ttatgaactg  49740
ttccggcttc ccaacaaaga gagaaaaaaa cattccttgt gatgttcaat gcgaaagact  49800
gcaaaaaaac attataaaag aactggtatt taactgctct gtactgcttg aaatggtact  49860
gcacacagaa agagaatatg catacgccct acactgtgct gcaaaacata accaattgcc  49920
catcctcatg tattgttggc aacaatccac agacgcggaa tctattttgt tgaaaacctg  49980
ctgttctgat aagaacatca attgttttaa ctattgtatt ctatatggcg gcgcccaaaa  50040
tttggatgct gcaatggtgg aagcggcaaa gcacgatgcc cggatgctga taaactactg  50100
tgtcatgctt ggtggaagat ccttaaacga agcaaaagaa acggctgcca tgtttggaca  50160
cattgaatgc gcacaacact gttttaaact gcagtcttac gtcgtggaca catcgaatac  50220
agacgacact gattaaagcg acaatcttac gtcatgaacg actgtctttt gagtatctat  50280
acttacatta tattttttta tgaaaaaaat ataaaggttg tatacaaacc tttgtataca  50340
```

-continued

```
agaaatttgg atcattaaac aataattaat ttggacacag gaaacgatct agatcgatca  50400
aaaagctatt ttttttgcac acagaacatt tagataattg agagattact ttccatactt  50460
gttaagcttt tttacacaca ggaactttgg attctgttca ggaagttttt catagacatt  50520
atgtttacag ccagtaataa taattttggg ctttttctta aaccaccggt ggaaaacatc  50580
cagcttgtaa agagggaaat gcatgtagag aggttttggt agtcatggtt aagagatttg  50640
actaactcca tgtttcctgt aaagactgcc cagtcccaag cagtaaaacc tctatgatag  50700
tctttttgag tcggatctgc tccaaatttt atgagagaaa gcatatttaa agaacggccc  50760
cgtattgcgg ccttcatcac aggagtcatc ccattaaaat tcggtaaaca aattctggtc  50820
ccattttttc cgaaatagcc caacacccct tccaggatta aatgattttt tttctcagct  50880
aaataatgta aagcagagtt tccatcttta tccctcctat gagggttaat tatttctcca  50940
ggataagatt cttgttcaaa aagaaatttt aaaaagtcta tacgtccgta gatgcatatc  51000
cacatgaata ccgaggatcc atttttatcg catctattga caatccacgg atctgtttta  51060
aaaaattcct caaatagtgt aagattccca tttctaatat gtttttttaat ccatttaaca  51120
aacaagtttt ctatctccct ttctggaaac atgtgttcca ttttgaatgt cgcccctact  51180
ccactatatg attttactcc tttaattttt aatgtccttt tttttcggac ttctttggat  51240
aagctgttta ttaccatctt taaatgcctt atagcgggga ggagccaggc ccttttccca  51300
tatgtgcggt aattcttggt gtttatgctt gcctttggca taaccaggcc agtatttttc  51360
gatatattca gggtttgttt ttacgtattc tttaaaggtc cgataggctt cttgaataca  51420
ggtaggctca ccggtataat ttccatgttc atcttccttt aaaaagccat taaccctgtc  51480
ctttctccac ttaagattgt gctttccaaa aatgcgatca agatcttgcg cctgctgggg  51540
tggaatcata aatccctttt taggtcgaag ctttttattt tttccatagc ttcggccatc  51600
gcgttgcgaa acagtggtta ggacgcctga tagtctttcc atgggcgtcg catctaatcc  51660
tatccatcca ccctgatgaa tatcaatggc aacaagctct cctttatttt gggcaagcca  51720
agtttccaag aatgccatgc tttcttccca gggataaggc ccgccaacac cacgggttgt  51780
ccaatcttgc aaggactcca ggtccgacac ctggtaaggc tctaaagaag acggttcctt  51840
gtttttgtac tgcaaataag atttaatgac ccatttatac catgtgtcga accgcagcgt  51900
ggcgcctcca aagtgaaagc cgtcgttgat tttaggatat ctgcaacata tttcaaccgt  51960
acgtttgagt tctgcaaaag cggccttcca aggaagtctt tcgctgcggg taagacggtc  52020
tattttgccc tgcgtgccat agcgtatggc atgtcgtgcc aattgcaaca attctgacac  52080
cgatccgtgg gccccgatcc agtttatcgg ataggcaacc tccgaagggt ttaaaagatg  52140
ctcgtaaaag cgtggatctt cagatgccaa ggcgtctgca aaggggataa tgctagaaaa  52200
cctgtctaga catacgtttt ctgtgtttac ttctaaaggt agaaaaatgg ttgcgtgagg  52260
cttttgaacc tgcttgttca gcggtctgca tatgctttga ataatgtctc taggactatg  52320
tcgcggcgct gcaaaaaata ccgcgtttag ttctggaacc tctacgccct cttgaaagag  52380
tcgacagttt aataaaataa cgggttcctt tgaggaacaa aattctgtaa atgttttgag  52440
gataacctgt cgcggcaggg ttgagtgagc tatcagggca tagacccctt ggtctaccaa  52500
cgccgcgtat agctccttgg cctgtttaat atcacgggta aataccagca ttttaggagc  52560
cggtatattg gtttttaaat aggctaaggc cattataatt tgctttacta tgatctgttt  52620
cgtggtctcc tctttggtac tcggttggtg ggccaattta ggcgcggcta ccatctgcaa  52680
```

-continued

```
ttcaaaatca tttacatagc cggcctctat gccttctcgc agatagtagc gaaaggcaac  52740
gccgccaaaa agttcacgat ttttcatgga aagcggggtg tcgtacctgg gcgttgccgt  52800
taaaaaaagt cggtgccctt ttttaaagtt gagcaacacg tgggtaaagg gccgtgtctc  52860
ccattcgccg caaatccggt gacattcatc gctaataata agatcgaaat catccaccag  52920
tagcgtggag gattggtagg tggcaatcac aagaagagaa ggggcctccc gtatccgttt  52980
tgcaataaag acaggattgg tggtcatttc tatattgtcg tgatttagca caatgcgggt  53040
ctggtcagac cccacaagca aaacgttctt caaagaaatt ccatactgat agagtttttc  53100
cagagtctgc cgtagtaggg acaggcccgg caccaggtac aaaacttttc cttgaagata  53160
attggagagg ataagatagg cgacgcgagt tttgccgcat cggcaggcca tctgcagaat  53220
ggccctccca cttcgccgca gctcctgata gcccatattg gccgcctcct tctgataaag  53280
tcgatcctcg attgcagtcc gtgtctcatc tgtagaaaaa aataatacgt catctgcgaa  53340
atgttcatct tccacaggag ttatcaccag gtgtctcagt ttctccttgc ttatcagcgg  53400
atcagagggc aaagatggct caaccactat cgtggaatca ttcatctcat aggcgggaga  53460
atcacacaaa gtatagctta tgtccagaca gtttgcaaca tcctcagcca attgttttat  53520
tttttcgggt aaaagacata cgagttcttt gtttttgacg cgaaaaaact gtgcacaata  53580
taacacccct gcttcaattt tttgcgcatc cttctttgta gatgtttcca atgtgaaaca  53640
atacttccat tcatccgtaa aacaggttgt ataagatcca tcatgaagcc tagcggccaa  53700
gtttcctgtg tgcccaactt tatgtaagga ttgggcctcc agccagggat gaaccgccac  53760
gtaaaatcct gcgcacatgc tatatcaaat tgcagtttct taataactgt acacaggatc  53820
tgaaaaacat gtgattacaa aatttagata agaaatattt aatattaaaa atcacagaat  53880
acatgtcact gtgtagagag aaagccaaaa actcctcttg accgccgtgg gaaatcatcc  53940
agggtagtag gttgtgtttc ataaagttgt atgccgtagt gatcaccgtg gactccagat  54000
ggttattggc atctttgcaa tactttgcca tcttggcaga aaagacgata aatccacaaa  54060
ttctacccca gttgataaga tccttaaaca gctcagtcac aaccccagta aactgggttt  54120
taatttcttg aacactcgta agagaaaagg taattgtaac ctgtttgttc aaacactcat  54180
cataataggt taaaattttt tttatttgtt gttgatatgg gctaagctca tgctctgaaa  54240
tatcattaat gtaatattta atatatccca ctagtatttc attaatgata ttatgatata  54300
ttaactcttc tccctccata gcggcaccct atattttttt atttaggttt caatgttatc  54360
acaattgcga tacaattgtg atacaattgt gacacaactg tgttgtatac aacaaatgtt  54420
aggccacgta tagcaaccta tatgttaaga aatattttta tcccaacatt agttggaaac  54480
gagcagccgc aaagaagtca tttaaaataa gccatttaaa gatttagaat ttatatgtat  54540
acaactgtac aatggaagca gttcttacca aactcgacca ggaggaaaaa aaggctctcc  54600
aaaattttca tcgttgtgct tgggaagaaa ctaaaaatat tataaacgat tttcttgaaa  54660
tccctgagga acgatgcacc tataaattca actcatacac aaaaaaaatg gagcttttat  54720
ttacccctga attccacacc gcctggcatg aagttcctga gtgcagagag ttcatattaa  54780
actttttgag actcatttcg ggacatcgag tggtattaaa aggccctaca tttgttttta  54840
caaaagagat caagaatctg ggcattccta gtaccatcaa tgttgacttt caggccaaca  54900
ttgaaaatat ggatgatcta cagaagggaa atctcatcgg caagatgaat atcaaagaag  54960
gctaaataaa acaactaaca tcaaaaaaca ttaaaggcta tgttgtggac gatgcctttg  55020
tctcaatagt ttcgaggtca tccaataact catgtaacgt aaaaaagttg gtccattttt  55080
```

ttgaaaacat taaaagacgt tcgtcttcat aaataaaaaa gtcattcgaa ggaaaaatga 55140
tatactcaat accatagtct tgtaatattt tttttaggtc tctcagggtc cagggattta 55200
ccaggcttct acgcgaagtg agcatcataa aaatatctaa tattttttgc gccataagcc 55260
agcgcggatt ctcattggcc cacaaatcaa caataattct cttatcaacc gtgagcattc 55320
ctacttgatt cgaagaaatg attagatgcc cagcagtcca ccccatgagt agataacgca 55380
gcgttgtaga aatgtcacat atggaaggca ttcctccaca acatgaaccc aaattaggat 55440
gcgtgtgaaa cacaaacata gcaggcttgt tggccaccct gctataaata tcagcaggca 55500
tcatagcctc gctgccaaaa taaatgttct ctcctgccct ataggggctt ggaatgattt 55560
ccactatctc gggtacaccg tttatcatat taatgcggcc gcaccattca cggtcatcgt 55620
ccaaaaattt tttgatggca ccccgaacat tgtcccagtt aagcaacaga gtattcacaa 55680
tctcattacg ctccgcccag tattccttaa aacttctttt agacttgctg agctgttccc 55740
aggattcgaa ctcagtccaa tgtttttttt cttttgggga agacttccct tttgaaacat 55800
tttttgcggc tccaccatct acactatgat tttccaaaat aatctccttc atcgtttgag 55860
ttatatgggc attgctaagc accttagtgg taacctgttt acctatgtga tttagcagaa 55920
aaccaagttt gtccatttgt gtctcaacca tttattctta acaaaacaaa aaaaattaaa 55980
aatcatcgtc gtttaaaaag agtttgaagg caaacgcatc atccttaaca cagttctgat 56040
actgcgtagg tcttaactcg aaaaagttgg ttttttctac ttcattaaga aagaatttag 56100
tcatctgagg aaaagggttt cccaccttat aaatgctttt gcactgcatc atgaagcaca 56160
aattatctgt aaagtagcgt atatattgaa atagcatttc ttttgaaaaa ccgggaactc 56220
ttcctcttgc cttgtcaaag gcatagttaa taaactcatc caccaactcc acagcctcct 56280
tcaaaatttt gtgaatgatc ttttcctcgg gaatgttata cacgtaattt gagataagaa 56340
aacacgcaaa actacagtgc atcccttcat cacgtgagat aaactcatta tagcttacaa 56400
gccccggcat aatattctgt tccttaagaa actggatcgc cacaaagtgg ttttgaaata 56460
aaatgccttc tacggcggcg aagcccacca gccgctcacc tagagtgttc ctgtcggggt 56520
ccatccactg ccgcacccac tgcgccattt tttttatgat agggtgtttt tcaatgccgc 56580
taaagatgcg ctgttgttcc ttctcatccg ggatcagcgt ttttacctgt attgagtagg 56640
cttcgctatg aacgcactct tgggcagcct gcattgtata aaagtataac acttccttta 56700
ctttaatttc gcgcataaaa ttggttaaaa ggttttcgat aacaatttcg tcggcaacaa 56760
caaagaaggc taaaatttgt ttataaaatt cgcgctgtgg ctttggcatg gcttcccaat 56820
catcaatgtc cttacacatg tccacctcct gcgccgtcca cgtcaaactt tctaattttt 56880
tataccagtt ccaacattcg ggtgctgaa taggaaaaat agtgaaacgt tgggaatttt 56940
caattagtaa ttcctccata tttgaaataa atattaacat cttcaaattt attggctgcc 57000
atggagacgt tttttattga gacgttggca tctgatgtgt atggaaaggc gttaaatgtt 57060
gatttagata gactatcgca ggcgcaggtt aaatataccc ttcaagagct tatttcctac 57120
tgcagcgctc taaccatttt acattatgac tattcaaccc ttgcggcgcg tctttcggtg 57180
taccagctgc accagtcaac ggcctcctcc ttctcaaagg cggtgaggct gcaggccgca 57240
caatcctgct cacgcctgtc cccccagttt gtggacgtcg tttacaagta caaagccatt 57300
tttgacagct acattgacta tagcagagat tacaagctgt ccctcctggg gatagaaacc 57360
atgaaaaatt cttatttgtt aaaaaataaa gatggggtca tcatggaacg cccgcaggat 57420
gcttatatgc gggttgccat catgatctat gggatgggaa gagtggtcaa tatgaaaatg 57480
attctgctaa cctatgacct gctttcccag cacgtcatca cacacgcgtc gcccaccatg 57540
ttcaatgcag gcaccaaaaa gccacaactc tccagctgtt tcctgctaaa tgtaaatgat 57600
aatttagaaa atttatatga tatggtcaaa acggccggca tcatttcagg cggcggcggt 57660
ggaatagggc tgtgcttgtc aggaatacgg gcaaagaata gttttatttc tggtagtggt 57720
cttaaaagta acggcataca gaattatatt gtgctgcaaa atgcttcaca atgctacgcg 57780
aaccagggag gcctacgtcc cggagcctac gccgtctact tagagctgtg gcaccaagac 57840
atctttacat ttttacaaat gcctcgccta aaaggacaaa tggctgaaca acggcttaat 57900
gcccctaatc tcaagtacgg cctatgggtc cccgacctat tcatggaaat acttgaagac 57960
caaatacaca acagaggcga cggcaaatgg tacctctttt cgccggatca ggcccccaat 58020
ctacataagg tctttgattt ggaacggtcg cagcacgaaa acgcacaccg cgaatttaaa 58080
aagctttact atcagtatgt tgctgaaaaa aggtacaccg gcgtcacaac ggccaaagag 58140
attatcaaag agtggttcaa aacagttgtt caagtaggga atccctatat cgggtttaaa 58200
gatgccataa atcgtaaaag taatctttca catgtaggca ctatcacgaa ctccaatctt 58260
tgtattgaag tcacaatccc ctgctgggag ggtgataagg ctgaacaagg tgtttgtaat 58320
ctggccgcag taaatctagc cgcctttata cgtgaaaatg gctacgacta ccgtgggctc 58380
atagaagcat caggcaatgt cacagaaaat ttagataata ttatagataa tggctactac 58440
cccacagaag ccacgcggag aagcaatatg cgtcaccgac ctattggcat cggggtcttt 58500
ggcctagccg acgtgtttgc gtctttaaaa atgaaatttg gttcacccga ggccattgcc 58560
atggatgagg ccatccatgc ggccctatac tacggggcca tgcgacgatc catagaactt 58620
gcaaaagaaa aaggaagtca tcccagcttt ccggggtctg cggcctcaaa gggtctactg 58680
cagcccgacc tatgggttcg ctgtggtgat ttagtttcct cctgggaaga acgcgtggca 58740
cagacgacgc agggtgtgtt gacgccgaaa aggtggtcgc agctacgcct ggcggctatg 58800
cagggacttc gaaatggata tgtcacagct cttatgccca ccgcaacctc ctcaaattct 58860
acaggaaaaa acgaatgttt tgagcccttt acatccaatc tatatacacg tagaacgtta 58920
agcggggagt ttattgtttt aaataagtat ttaatagacg atttaaaaga aattaatctt 58980
tggacagaag ccattcaaca gcagctacta aatgcgggag gtagcattca gcacattttg 59040
gatataccgg ccgagatccg cgatcggtat aaaacctcca gggaaatgaa tcaaaaaatt 59100
ttaacaaaac acgcggccgc acgaaacccc tttgtatccc aaagtatgtc cttgaactat 59160
tacttttatg aacctgaact aagccaggta cttacagtgc tcgtcctagg ctggaaaaaa 59220
ggtttaacta ccggttccta ttactgtcat tttagccctg gagcgggtac ccaaaaaaag 59280
attataagaa actctgagaa agcgtgtaat gcggactgcg aggcgtgtct tctgtaggtg 59340
tctcgcggta aaagagcagc ggggaccata tggtaaaccc caacaagagg ataatgaata 59400
aaaaaagtaa acaggcatcc attagttcca tattaaattt ttttttcttc tatataatgg 59460
aatattttgt tgcggtagac aatgaaacct ccttgggggt ttttacttct atagagcaat 59520
gtgaagaaac gatgaaacaa taccccggcc tccattatgt cgtttttaag tatatgtgtc 59580
cggcggatgc agaaaataca gatgttgtat atttaatacc ctcgttaacc ttgcataccc 59640
ccatgtttgt agaccactgt ccaaatcgta ccaaacaagc acgacacgta ttgaaaaaaa 59700
taaacttagt gttcgaggaa gagtctattg aaaattggaa ggtttcagta aatactgtgt 59760
tcccccatgt tcacaacaga ttatctgcgc cgaaactttc catcgacgag gctaatgaag 59820

-continued ccgtagaaaa gtttttgata caagcaggac gactcatgtc tctgtaaatg tctcttcctt 59880
tatgggtgac gtctcttcct ttgccgagga agtctctgtt atgggcaaga ggtttgaaac 59940
aacgcaagga ctctgcttaa tctgctgtct cacaaaggga atcaaactac ctgctttcgt 60000
atttttaatg tagtaattac ccttgttgtg atgaatttta agaccatagc gtagtcccag 60060
tactttatta atgaatttta aaattgtttg agggtccgtt ttattgggct ttttaagctt 60120
aaactcaaag ctgatcgcgc ttaaatcata ctgaacaaat tcatcaacga gtttcgtcat 60180
taattgttca ttggtcaata tattagggtc ctgaacgcat ttaaagccgc acttagttaa 60240
tagcataata gcgtacatat gagattgaaa actataatta aattgtagat catgatgctc 60300
tgcgtgttgc atggcccatt gatgaaagtt taattcctga gtttgtaaca tagtgagcga 60360
ctcgtatact gtctttccgc ggcttatttg gacacggcca gtatagttct gttttgtcat 60420
aaaactattg tattgttcaa caaatttggg agtaatttta tgaccgtgcc atgcataaaa 60480
ttcgagtagt ttatactttt catacgcaaa taggtcttgc tggtctactg tgatgccttc 60540
ctttaagttt tgtttaattt gtaaagcttt attggcatca atggtttcag ccgaggcaat 60600
gtttacatag tcctggtgtt taatttccat tttaatgctt gtatattgtt tgactgtctc 60660
cagcttttca cccgtcagta taaacacctt agcgccggtg tcggcgatct ggttaataaa 60720
tcgggttata aagtgatttt ttgatagatg ttgtatccgc attgtttcga gccatagatg 60780
gtagtatgga gttttataat atatcggcct acctgtttcc ttactatacg tgaaggaaag 60840
ctggtgattg cttatggtct gaaaaagggt gtcacgtttt tgtaacgtaa acatttcaat 60900
gtcttcgatg gtttctggat agtaattttg tttcccctgt aagcagattt tataacactt 60960
actttttaat tcacgcacgc ggcccaacat ttggcaacat gtttctacgt cacacgacat 61020
attgttaaaa aagccgtata aaacatcaaa tctcttatct tcgtatgaaa cacccgctga 61080
aatcgtgggc gtatagataa ggatatcaac gagcccccaa taatacgata cattattaaa 61140
atgggattcc cgttcatgag cagtgctttt agaactataa aacccaattt ttttttccgg 61200
aaactttttt tggataaatg attgcaacag ccgggcctcc attaatgaat ttgtagggat 61260
aacaattttt ttgtcttcta gcaaatcctt taaaaggtta tttaaccaag tttctcgtga 61320
agaggtaaaa taatacgtgt catgctgggc ccttttatat tgattccagt gaaagaagat 61380
agggacatcc ccgcgaaaac gctgtagaat attatacgtt cgatttccta ggtttgcgtc 61440
caagcatata acataatttg ccgtttcgag catccacatg aaaatggcaa aagagggagc 61500
aaagtatttg tgcaggccgc tattgaattg attaaaaatc gattctacct catccaaaat 61560
aagtaggtct acaggctcgg ctgtggaggt tagccggaaa agtgattcta cctgaatgat 61620
gactctttcg tagctgtcca aatctccagt tacttcgctg tacaatgtga aattcggtag 61680
ccgggattgt atatttttttg agaagatctg tcgaaacgtc acaaaccgta tggtttgttg 61740
ttttgaaata gaattattgc cgtagtattt ttgcaaatag ttgcgcagtt ggacggtttt 61800
acctattttc atttgagcct ttacaacaag cgtagggact cgttcatatt ctcgcatact 61860
actttcatca tagatgtgtt tttgagtatc aggcagttct tcaaagagaa tggactcatg 61920
aacctctatg ctctttgtca tcacttggtc cacatatgtt tccacaaaat tatttgtgcc 61980
ggaaaggctg cccatgagaa ggctatgttt attgtcatgg cgacagtgtt gatacacttt 62040
gtttcccgtg actcttaaaa ttagggtatt gtccttatca tgcatacgct tacatatttc 62100
gcagtaactt ggacttgtac gtttaaacaa tactaaattt ttatgaacac ggaggaagca 62160
atgattttta catagtgttc ctgcaaattt taatacctct tcaagttcac tttgttggat 62220
agtatcgcag gaactcggtg ttgtttcttt tacatttgtg aagatacaag gtaaacacgt 62280
cgtttcaaag gggttgcta taagggtatc actcttttc gtggttgtac tggtctcaaa 62340
cacctctgca agctcctcat taaacatttt aacacgcatg ctaccttttt tatgagaccc 62400
tatgatgcga aaattttgaa tacttttgtt gacctggggg tcaacaaaag gataaacgtg 62460
tttgggaaga ttttctaaca ctttggatgt aaagactttg gcctcattat tgtttaatac 62520
tgagtatgta taaagtatga tatgaaagga gtatttaagt tctcgctttt tatttaatcc 62580
gatagaatct gttagcaaaa tttgttcacg cgttagattg atgttataag gtaaagaata 62640
tgtctcgtaa aatacatcca tgatgacgtt aattatcatg tcaaggatgt catagacatt 62700
gtcttcgaca ttatcattgt catcaacatt gtcatcagag tatgacttat ttaccggaaa 62760
gtcgatgtca aattttaagc gctgaggcaa aaacccaaat accacttcgt ggaaacactt 62820
ctgctcaaag ggctgagccg cctcccactc ccaaaagtca tcacgacttg aaaaaactct 62880
aaaaagatta ttatattcat ctcgcaccac gaagtgattc tttaaggttt cgagagaata 62940
tttatcctct acggcttctc cttgggagtt acagcgaaga aacttgaatg tttcttgcat 63000
tttgatattt aaaattaaat caattatgat gcggccgcta atgcggcggt tgacgcggcc 63060
gcgccgctga cgcagccatc atacataaag cggcatggcc gttttataac gactagtcgg 63120
ccgttatatg acgaactata taaaaatgaa ttcttttaat tagagttaag tattgttgat 63180
tgtataatcc atcatggttg agccacgcga acagtttttt caagatctgc tttcagcagt 63240
ggatcaacaa atggacactg taaaaaatga cataaaagac attatgaaag aaaaaacgtc 63300
ttttatggta tcattcgaaa actttataga acgttacgat accatggaaa aaaatattca 63360
agaccttcag aataagtacg aagaaatggc ggccaacctt atgaccgtca tgacggatac 63420
aaaaattcag cttggagcca ttatcgccca acttgagatt ctaatgataa atggcactcc 63480
acttccggca aaaaagacaa caattaagga ggctatgccc ttaccttcat caaacacgaa 63540
taatgaacaa acgagtcctc ccgcctcagg caaaacaagt gaaacaccta aaaaaaatcc 63600
cacgaatgcg atgttcttca cgcgtagcga atgggcatcc tcgaatactt ttcgagaaaa 63660
gtttttaaca ccagaaattc aagccatatt ggatgagcag tttgcaaaca agaccgggat 63720
cgaaagattg catgccgagg gtctttacat gtggagaacc caattctctg acgaacagaa 63780
gaaaatggtc aaagagatga tgaagaagta atatttttgg taaaaatatt tttatcaaaa 63840
ttttttacca aataataaaa atatttttac tttttttctt cataatatac atagaatgcc 63900
tacaaaagct ggcacaaaaa gtaccgcaaa taaaaaaaca acgaagggct cctccaaatc 63960
tggttcttcc agaggccaca ccggcaaaac ccatgcttct tcgtccatgc attccgggat 64020
gctctataaa gatatggtaa atattgctag atctagaggc attccgattt accagaatgg 64080
atcgcgtctt actaaaagtg aattggagaa aaaaattaaa cggtcaaaat gaatataatc 64140
aggaaactta agcctggaac aattagcctt gtgctgggac ccatgtttgc cggcaaaact 64200
acgtttctta ttcattgcat ttacatgctc gaacgtttgg aaaaaaaagt agtcttcata 64260
aaatctacca aaaacacccg agacaaaact attaaaacac actccggtat acagctacga 64320
cccaaacaat gtaaaatcat agaaagcaca cagttatctg acgtgggttc tctcaccgat 64380
atccatgcag ttgtcgtaga tgaagcgcat ttttttgacg atttaatcac atgccgcact 64440
tgggcagagg aagaaaaaat tattattctt gcgggactca atgcttcctt cgagcagaaa 64500
atgtttccgc ccatcgttcg tatttttcct tactgcagct gggttaagta tattggccgc 64560

-continued acctgtatga aatgtaacca acataatgca tgctttaatg tgcgtaagaa cgcagacaag 64620
acgcttatcc ttgcgggagg aagtgaactg tacgtaacat gttgtaacaa ctgtctaaaa 64680
aatacattta ttaagcagtt gcaacctatt aaatattaaa aatcttatac aataatggat 64740
cattatctta aaaaattaca agatatttat acgaagctcg agggtcatcc ctttcttttt 64800
agcccgtcga aaaccaatga aaaagagttt attactctgc taaaccaggc cttggcctca 64860
acgcagcttt accgcagcat acaacagctg tttttaacga tgtataagct agatcccatt 64920
gggtttatta actatattaa aacgagtaaa caagagtatt tatgcctgtt aattaatcct 64980
aaactcgtta ctaagttttt aaaaataacg agctttaaaa tttacattaa tttcaggctg 65040
aaaacttttt atataagtcc taataagtat aataattttt acaccgctcc ctctgaagaa 65100
aagactaacc atcttctaaa agaagaaaaa acttgggcaa agattgttga agaaggagga 65160
gaagaatcct aagtcgctta catttttttt tgctattttt atagaatgta cacgcatgtt 65220
gatgttgtcg gaatagctga agcctcagcg gccctctacg tgcaaaaaga tagggatcgc 65280
tacttagacg tgctaacaac cattgaaaac tttatttacc aacacaaatg catcataaca 65340
ggggaaagcg cccacctact ctttttaaaa aaaaatattt atctttacga attttactcc 65400
aacaatgtgg cggagcacag caaggctttg gcgaccctgc tttataaact tgatccggaa 65460
tacctcactc gttacacagt actcattacc aaaattccca accattggta tgtgattaac 65520
gtagatcagc gagaatttgt gcgcctatat gccatcccgg cagttaaaca acacttaccg 65580
attcccattt tacccttcta ttgcaccagc gcactcaccc agcaagaatt gttttgttta 65640
ggacctgaac tgcagttaat acaaatatat tccaagctct gtaaccccaa ctttgtcgag 65700
gaatggccta cgttgctcga ctacgaaaaa agcatgcgga tgttattttt agaacagttt 65760
ccgcaaagat tggaaatgac gggcgggaag aaggaggaga aggaaaagca tgaaagtatc 65820
attaaaaaaa taatactaga aatggtctct acccgtcagc gaatcgttgt tgggggttac 65880
atacaaaaaa acctgtacaa ccatgtactc aagaatagaa atcgtttaca gcttattacg 65940
agcttaaata tttatgaaga aaaagatatc atccagcaat tttgtgattc aaatggactg 66000
aagatcaaaa tacgtatcaa caatccgctc ttgcctacaa atccggaatt acggcgtttg 66060
actatttatt ttaatcataa taatgatgat gatcagtcat atctaatagt agatatgtac 66120
aacacgggaa gctatgagct agtgcctaca aatcagataa acacgcttga tggcagcttt 66180
ttaataggaa caccottcgt gcaagcgcga tttttgttgg tagagatctg ggtgcttatg 66240
cttattgcgc agcaaactaa aaaggacacc aaaaaaataa tacaattttt tataaatcaa 66300
tatgaaatgc ttatgaatag tccttggccc agtatggagg cccttttttcc ctcaagcagt 66360
aaaagatatt taggcaacta tgtagaccct aacgcgctca taaagtgggc acaactcaaa 66420
ttaaaaagaa taccgccttt ttatcctgga aagccggatg aagaatcatg ttaagccgat 66480
taaaaaatca tgttaagctg gttgaaaaat catgttaagc tggttgaaaa actcttggtg 66540
aaagcacgga tgtaatatta acattggccg ctcgcatttc gtgttgaaat acgatggaag 66600
agcgacggct atctaccatg ccgatatcgg cctggacatc acagttcatg cacttgtaga 66660
tgggatgact cgcgttatag atggcaggct cgccacagtt tctacagatg taggagatgc 66720
agccatccga gtcgtcgtgc gatttttcta tgatggtttg catggcgccc tgcgccgtaa 66780
gcacccaatg ctccatttct cccagacgaa gacctccgtg cgatcgtttg ccgtccaacg 66840
gctggcctgt gagggcatcc gtgggcccat agcttgcaac ggcgtatcgg tcatccagca 66900

-continued

```
caaattttg caggcgctgg tgataggtcg gtcctatgaa gatggccgca tcaaagtact  66960
cgccggtctg gccgttgaac attttttggc atccattgaa gcgtagacct tcttgcgcca  67020
gtctttctga aagaagctgc acattaatag gcaggaatgc ggtgccgtct gttaccaccc  67080
cctgtagggc atttgctaga ccaaccgtgg tttctatcat ttgaccgttg gtcattcggg  67140
agggatgtga gtgggggttt acaatgaggt cgggctgcaa tccgtcctct gtgaagggca  67200
tgtctgaagt gggcagggcc agcgccgcaa tgcccttgtt cccgctgcga gaactcattt  67260
tgtcgcctat attgagattt ctttcatagc gcaggcgcat gaggccaaag atctcgtcat  67320
taggcccatg gggacgcatc acagcatcca cgacggccgg ctcatcgaag ccgtacatga  67380
cagaccggtc gatgtatttg ttgagttcgt ctttttcgcc ccgtattttg gccacttttc  67440
ctataatgat gtcgcccttt ttgaccaccg ttcctacggg cacgaatcca tctacaagct  67500
tttcgtaatt agcaccaggc ttaagatttt tggtgattaa agggtcgggc ttcccaaacg  67560
actctatatc gctttctaat tctacttttt cttctcggta gaaggtgccg gcaaagccgc  67620
ccctgtcaat aaaggactgc gacacgatca cagagtcctc ctgattgtag ccgccgtaga  67680
tcatataagc cacaatggta ttaagcccgt tgggtatgac atagttatgt gctatggtct  67740
ttacaagcgg catttcattg taaaactgga agaagcggtt catgtcgaca cgatatggcc  67800
agctaaagca ataccagccc cccgtttgcc ggccttggtt tgtttcatag gtaacacgcg  67860
caggttgggt acagtttgcg tagggggaca ctagggcggc aaggcccaaa atagcttggg  67920
gcacgtccac gtgtgtgaaa cgacgcgtta catcatgttt atgtttgcgt agctcgatga  67980
tggagaaggc aacaagacag ttttccgcct cctcgggggt aatgaactca cagatgccct  68040
gtgctacgag atcttcaagt gtaagcgttc cggctaaaat gtcttttgcc atttgaggcg  68100
taaatcgcgt attttgaatg aaagggattt tatgtttttc ccagtcttta tcgccttttt  68160
ttctggcctc tgcggccttg tagcaggctt gattgtattt ttcaatatta ttatctacaa  68220
tgagtagggg gcgggtcagc ctaccgacgt ccaaccaaaa ttctacttcg tctaccatgc  68280
tatcccagta gatggtggta tggggatgca caaccttgcc ctcacggcga agcattctat  68340
accgctgagc aagctcaaag gcattggtgc agcagccgat ccattctccg ttgataaata  68400
cgcgcgctag gccctttcgt acaatgtcct tgttggaaac atcggctaac tgttgaatgg  68460
ccggatctga tagaaggcgt tgttttaacg aaagtacttc tccggcggtg cagacattgg  68520
cagtgatggc taactgttta gacatgccta ctttttcacc agtatcggct gactgggcta  68580
cgcagatgta tccaggatag gatgcgtgca cgcgacgcat catgtcagcc ctttctgttt  68640
gtttggatgc gttggtggtg ttatgagtat ttaccgtacg caatgctgaa atggtattta  68700
ataaattttt tctttccaaa ctttgagtag atactctgtt tacaatgggg cgctgtcgca  68760
ccatgatggt tttatttcct gaaatgatag actgttccat actgcgatta agatcggagg  68820
cggtattttt tgataaagcg gcagaaaatg cctcgataat gtttcgctga gtaagctcct  68880
caaaggctgt ttgtttaaga agttctttga acccattgat gatgggtgct atcacggaag  68940
tattaaaaat agccttaaag gccttggcga gtgagacccc tgagccgtgc acccgcttgg  69000
tgcggtagct atcacggtcc gtgggtggaa acacattcat aatgacaaga agtattttat  69060
gaataagcag gcctaaaaag cgcagctttc gtacacgtgt atctgcggtt tggcccatgt  69120
gtggcagcaa tattttgtct aaaatagtaa gttgtctttc atttaagtat tgtaccgcat  69180
tttcatcgct tttgtaagca gatgggtttg agacaaattt ggaaaccttc tcggataaaa  69240
actggataat tttttctcgg ttcagctcgt gttggaccgg ttgaaatatg ggtctaaaa  69300
```

-continued

```
catgaatgga tttttccaga atttctatca tgaaggtatt cacaagggag ttggattcta  69360
gatcaaatac cacttgctca atgatgctgt catcgcctgt cattccaaac atgcgaaaga  69420
tgagatacca aggtatgcga agttttgaga acttggtgct attgatttca atggtaatgg  69480
cgccggtggt catgtagcgt ataataattt gagagctatt ttcgaaggca cctcccggtt  69540
gggagataaa ctcgccgcga atgatttcat tattcccttg ttgcatggta tggtaatgga  69600
tgtgaagcgt gttaaagcgg atgttttcta agaggtctac gacccattcc ccgcctcggg  69660
ctataaagta gccgccgggt tcattagggt cttctcctat ttcttttttt gcggtttttg  69720
ataggtgatg agtgtggcag cggttgctgc cccgcatgat gggaaatgta gatacctgaa  69780
aaggaggaat acttgctcgt tttacctcct gccgaccatt gctgtagtgc gccgttaaaa  69840
taacctcggc ggctagatta accgggcccg aataggaaag gccacacagg cgtgccttat  69900
tgggtagtaa atttatcttg tttccctgtg aatagtttcg atgttgcggg cgttcaatgt  69960
tcacatctgt aaagttaaat tggatctgaa ctgattcccg aagcttatct atttcagtat  70020
ggtcgcgttg gtctttataa gtaatatcca cgttaaacat ttgttttaca atttgcggaa  70080
ttccattgtc cataagatcg tcgaagcttt tgatgttata ccctatcaat cctgtagagt  70140
ttactgcagc ggagataaag ctcagcatat cagcctctgt aagctcctca ttatccacgg  70200
tttcaatggg gccgtaggtt atttgcggcc gcaagggttc catgattatg aagtactaca  70260
ttaatattca gttattcttt aaaataaatc tttatttata aatcttattt ataatataag  70320
aatgccttat gcaagagaca tcacaaagtt tattacggca acggaaccag aggtgggtct  70380
tcccctgttg gcgctgcagc gctccaaatc catcataggg gttattcttc ttgtaataag  70440
tttgttattt attttcattg gcattattat attatcagtg agtagtggtc ataccacagc  70500
agcctctata tttatcgtat tgagtcttat cctaggtggc ggtggttttt ttcttattta  70560
taaagataat tcttaaccca cataaaattt gaaaaaatat agagtaagaa aatgtccaat  70620
tactattatt actatggcgg ggggagatat gattggttaa aaacagtaga acccactaat  70680
tttttaaaaa tcgggttgcc ttaccaggca cacccattac atcttcaaca tcaggcaact  70740
actcccccat ctatcttaga aaaatttaaa cgagcagaca ttcttcttaa tgaggtgaag  70800
gccgaaatgg acccactcat gttacaacca gaaaccgaaa aaaaactatt ccagatattg  70860
agtagtattg atatgttcaa aggtctgcga aaaaaagtag aattcacgta caatgctcaa  70920
attgttacga atgcttggct taaaatgtat gagctgctaa ataccatgaa ttttaataat  70980
acatctcagg cattttgcaa ttatgagctt ccaggagggt ttataagtgc aattaaccat  71040
tttaattata caatgatgca ttaccctact tttaactggg tagcttcctc cctttacccc  71100
agttcggaaa cagatgccct ggaagatcac tatggtcttt atcagtgcaa tccggataac  71160
tggttgatgc aatctccttt actgaaaaaa aatatagatt ataataacgg ggacgtaacc  71220
atcgctagca atgtaaaaaa cctagcgctt agagccacac aaaggctgac gcccatccat  71280
ctatatacgg ctgatggggg tattaatgta ggacatgact acaataaaca ggaagaatta  71340
aatcttaagc ttcactttgg tcaagccctt acgggtttgt tgagtcttag caaaggcgga  71400
aacatgatac tcaaacacta taccttaaat catgcattta ctctttcttt aatatgtgta  71460
ttttctcact tttttgagga actatacatt accaaaccta cctcctctcg gcccacaaac  71520
tctgaaacct atattgtggg taaaaacaga ttacgcttat ttacccccaa ggaagaacaa  71580
gtccttctaa aacggctaga attttttaat gatacgcccc tcgtagacct aagtctttac  71640
```

-continued

```
caaaatttac ttgaaagcgt ttactttgcc gtagaaacaa tacatctaaa acaacaaata  71700
gaatttctaa acttcggaat gaaatgttat cgacattttt ataacaagat taaactactt  71760
aacgattatt tagctccgaa aaaaaagatt tttcaggata ggtggcgtgt gcttaataag  71820
ctttatgttc ttgaaaaaaa gcataaactt aagctttgtg cctcctaggg atctgttgct  71880
taatttaaca gatgcaatct taacagatgt aaactaaaaa gtgtgttcat acaaggattg  71940
tatttatgaa tatttattaa catataaggt tgtgatgtaa cactgtataa cctatataac  72000
tacactatga agcacggcgt ataataattt atattgaaca cgatgttgac tcatttattt  72060
gcaaacaaat atttgtttgc aagacgtttg catgcattta ctaatatgtt gttgactagt  72120
ttatttgcaa actagatgtt tgattgcaaa ctagatgttt gcacgtattt atttgaacta  72180
atatacactc cttgttttat ttgttatata cacagcatac ataagtgtat attgtttaca  72240
cttatgttta taactcgacg taataacatt ttacacgctt tttttttgca aatcttaata  72300
atattgtatg ataaatcaaa caatgtctta tatatgtggt ttattatttt aggcgccgca  72360
agatgtactc cattctcatt gcatgcttgg tgttattact ctgtctagtt atatatgtcg  72420
gtcatcgtgc cgatcatgca cgaaaatatt tagaaggaat gtggcatgga gatccggttt  72480
ttctaaaaca gtcggggcta caatcctttt atctctacat acaacctgac catacatgtt  72540
tttttagcat tgtgaataaa aatggtgaaa agctgatgga aaccaaaata ccttgtacga  72600
taacaaataa aatatatatg ttttttaaac ctatttttga atttcatgtt gtgatggaag  72660
acatacatag ctacttccct aagcagttta actttctgtt agatagtaca gaaggtaaac  72720
ttattttaga aaacaatcac gttatttatg ctgtattgta taaggataat ttcgccaccg  72780
cactaggaaa aacggttgaa aaatatataa cacaaaatta atcatgtttt ctaacaaaaa  72840
gtacatcggt cttatcaata agaaggaggg tttgaaaaaa aaaatagatg attatagtat  72900
attaataatt ggaatattaa ttggaactaa catcttaagc cttattataa atataatagg  72960
agagattaat aaaccaatat gttaccaaaa tgatgataag atattttatt gccctaaaga  73020
ttgggttgga tataataatg tttgttatta ttttggcaat gaagaaaaaa attataataa  73080
tgcaagtaat tattgtaagc aattaaatag tacgcttact aataataata ctattttagt  73140
aaatcttact aaaacattaa atcttactaa aacatataat cacgaatcta attattgggt  73200
taattattct ttaattaaaa atgagtcagt actattacgt gatagtggat attacaaaaa  73260
acaaaaacat gtaagtttat tatatatttg tagtaaataa tatttttaat tacttaaaat  73320
ttttatatat aagtttttga tactatatta taaaacatat gttcataaaa tgataatact  73380
tattttttta atattttcta acatagtttt aagtattgat tattgggtta gttttaataa  73440
aacaataatt ttagatagta atattactaa tgataataat gatataaatg gagtatcatg  73500
gaattttttt aataattctt ttaatacact agctacatgt ggaaaagcag gtaacttttg  73560
tgaatgttct aattatagta catcaatata taatataaca aataattgta gcttaactat  73620
ttttcctcat aatgatgtat ttgatacaac atatcaagta gtatggaatc aaataattaa  73680
ttatacaata aaattattaa cacctgctac tcccccaaat atcacatata attgtactaa  73740
tttttaata acatgtaaaa aaaataatgg aacaaacact aatatatatt taaatataaa  73800
tgatactttt gttaaatata ctaatgaaag tatacttgaa tataactgga ataatagtaa  73860
cattaacaat tttacagcta catgtataat taataataca attagtacat ctaatgaaac  73920
aacacttata aattgtactt atttaacatt gtcatctaac tatttttata cttttttaa  73980
attatattat attccattaa gcatcataat tgggataaca ataagtattc ttcttatatc  74040
```

-continued

```
catcataact tttttatctt tacgaaaaag aaaaaaacat gttgaagaaa tagaaagtcc  74100
accacctgaa tctaatgaag aagaacaatg tcagcatgat gacaccactt ccatacatga  74160
accatctccc agagaaccat tacttcctaa gccttacagt cgttatcagt ataatacacc  74220
tatttactac atgcgtccct caacacaacc actcaaccca tttcccttac ctaaaccgtg  74280
tcctccaccc aaaccatgtc cgccacccaa accatgtcct ccacctaaac catgtccttc  74340
agctgaatcc tattctccac ccaaaccact acctagtatc ccgctactac ccaatatccc  74400
gccattatct acccaaaata tttcgcttat tcacgtagat agaattattt aatatgtact  74460
atatattaat tatttaacct ttcaagctgg tcttcattta aatttaaaat ccactaataa  74520
aatgtatttt ctagtagcag atcatcgaga acatcatgtg attccttttc ttaaaaccga  74580
tttccatcac atgcatcaaa atcctataca aaaaaatcaa gctctcctag aaatcaaaca  74640
gctttttact ggagattatc tcatctgcaa aagcccttct accattctgg cctgtattga  74700
acgaaaaacc tacaaagact ttgcggcttc tttgaaagat ggacgttata aaaatcgcca  74760
aaaaatgctg tcgctgcgag aacaaaccaa ctgtcaactt tattttttttg tagaaggccc  74820
ggcatttcct aaccctcaaa aaaaaattaa tcacgttgcc tatgcaagca ttattactgc  74880
tatgacgcat cttatggtta gagatcatat ttttgtcatt caaacgaaaa atgaggccca  74940
cagttcccaa aagcttgtgc agcttttttta tgccttttct aaggaaatgg tgtgcgtcgt  75000
tcccacctcc ctcaccccca cggatgaaga gctatgcatc aagctatggt cttctctttc  75060
tggtatttca ggcgtgatag gtaaaatctt ggcaaacact tgttccgtag ctcatttggt  75120
tcatggaaag ctttcatcgc agaatattga tcagttaaaa actccctcca accgaccatt  75180
ccccaaaaaa gtaaaacgta tgcttataag cattagcaaa ggaaataagg agttagaaat  75240
aaaattgctc tcgggggttc ccaatatcgg gaaaaaatta gctgccgaaa ttttaaaaga  75300
tcatgcgctt cttttttttc taaatcagcc cgtagaatgc ttggcaaata tacaaatcgt  75360
tcaaaaaacc cgtacgatta agttgggaat gaagcgagcc gaagcgattc attatttttt  75420
aaactggtgt ggctctgccc atgtaaccga tgatagccaa aatatcacag aggcgtcgcg  75480
gtccacaatg caggtcgcga cgcagtccgc cgcaatacag cccgctgcaa cgcagccatt  75540
gcacgaagta tcagatgatg catcatcaga tgcttcatca cccgtagggt atcaaacatt  75600
atctaaagaa atgttattga acacagcctg atgttaataa ttcactacat ctaaagaaat  75660
gttaacctcg atactaaaaa gtcattgaac acaactactg gggcgctaag ttgtccaaca  75720
catctaaaga aatgtcaaca tcctcgatgc taaaagggtc atcgagccgg tcaataatgt  75780
cttccccaaa aagtccggga gaactgtagg ccgagatgtc gtccatggag ctatcttccc  75840
cagagcacac aaagtcctct ccaaaaatca taaagttaaa tgcaccgggc ttacttaaca  75900
gcttttcgct ttgaataata gtgttgagtt ctgtcagcgc aaactctctc acaatattca  75960
caacccagga gggctcttta atttcataca gcgttaagaa acttatacat aaaaattcta  76020
tagagtaaag caaggcgctg gcaggatctg ttacccgtag gtgtttaaat gtagtgtgat  76080
attcattcac aacgttaggc agcacctttt ccaaatcctc cttttcctcg tacgacaggt  76140
gctttacaag cctttcaaca tgtataggag gcttgttaaa tgtactaacg tgccgcaaac  76200
agttataatt atataagaaa atacgtacgg cagagtcgac cgccatgagc cttggatcat  76260
ccattgaggt aggtggtggc ggggcaccct ggccttccct gatgtctgcg taggagcgcc  76320
cctccatggc ccctatggcc tctatcacag caggactgat atccaaaatc ttggccgtct  76380
```

-continued

```
tgattatttt tccgtaatcg aaagtccatg gctcctgtgg aggcttgggt tgtgtttcgg  76440
tggagggcgt ggtcatatct ttctttattt gaatagaacg gatcgacatc ttttccttat  76500
cgtactggtc tttataatta ttataatagt catgaactaa ttcgggttga gaaagatgat  76560
cgtatataat ataggtaaaa agtccgcact tgacacattt tttatcctgg aagtcgtgta  76620
atcctccctt ggggcagcgt gactcgtaga aggcataaaa ggtgttaaat tctaagctcg  76680
cctttagggc tgtttggacc ttttttatgt ttaattgccc cacctcatgt tgtagcacgt  76740
ggcatacaga acagcgtaga tcggcaagtg cataatggtt gtcaattttt tttatgacgt  76800
ctttgcgtgt tacttcaatc tcggcgggtt tctgcgaact gtctacggcc ttgtaaacgt  76860
aaatggtcca cttatgagga agcccccttt catcgtatag ggttgaaatg ggaagccttt  76920
tatactcaaa cagccgagtc cgttggtcgg ctcttcctgt gttaggatca aatatgttat  76980
aaaatccttg ctgagcaagc agggcctttt gctcgccata agcattttcg tacgttttga  77040
attctgcaag ttcggagtta aaattaggtg cattttgtaa atacttaaga aataattcat  77100
aggctctaag gtaaatgaga gttgaggttt tttcctcatc ccgtcctccc caccacaccc  77160
gcaggctttc ttcttgaaaa tagatgtcat tcagacgcgt caactgcgta aaatcaggcc  77220
gatatttaga ggtataaatt ttatcataaa attctttttg cgataatagc tcggccgggg  77280
tacgtcctat cacggtttta aactcatatt cagcctcctt gggagtccgt ggtttgtgca  77340
tagggatgct gccgtcaata cggcgccactg tggcagcata atcatacatg gggtccagca  77400
gaatctctgt caaaagtacc ttggtgtcgt cctgcacgct aagcccttgt agcccatttt  77460
ggtggataat ttttttgaaa gcctcccgaa aattattagc aatccactga tccgtaatct  77520
cagatagctg atttattata ccgctatatt gctgcatcat tttctccaaa agaaaggtca  77580
cgtatgcatt caaagagcta tccgccttca ttccatgaat ggtaatcgta agaaattctt  77640
tatttttttg cgagctataa atgagattca aaatataggc atagatgtag atcacagcat  77700
acagctgcgt taaaggatcg taatcctctt ccttttaat atttcgatg ctatacacga  77760
gcggcaggca gacatttacg gctatattgg caaactgttt cacgtctaca agctttccaa  77820
agtggataaa cgtgcaggcc ttcatggttt cctgccaaat aaaaacacgg agcttactat  77880
taagatcgcc gatgatgccc acatctgccg tacgatcctc ttgaataaaa tgggccagct  77940
cttcgccaca aattttgcaa aagtaggagt aaataagccc ctggttgttt tctttctcct  78000
tgtttattcc tgaaaatttc attagcttgg ttcgcatggt gtcgtaggac gcttctgccg  78060
cttgaagctg tataagcatg tccacatggg gacaaagcag cttaaacccg caggctttgc  78120
atagattcca attggtggta ttgttttttt ccttgtagag tacacgaata ctttctaata  78180
cttttaataa ctccgcgtat tgaagacccg aacgcaactg ttttaccagc ttgagatgag  78240
cacatgcatt tttttcttgg agttcccact gtttttttaat gtttaggtat tctgttgtaa  78300
taagttctgc ctcctgtttc ccacaggctt taatgacttc ttgaaggatg ctgttagggt  78360
catccacttt accctccatt gtaagaattt cacgtatagc atccgactgc accctaccta  78420
tttttcttc cataatttta aaatactgtc tcgcctgggt aatgacctct gtgagcttca  78480
tgtccacctg ctgcagaatc atttgctcct tttcacgctg ttcagcatgt tgtaaaaact  78540
tttgttctac agggttccaa agcacctcca aatagcctgc tctatatagg tcataaagca  78600
agggcatgta tcccgatgta aaaaccgggg acaccgagta catcgtagac aactctttta  78660
aaaaaaatat cacgcgctta atgttctcct ccggttcaat ctcctcggtt tcaacgatat  78720
tagatatatg actgccctga tcctcacggt ctagctttcg gtgtaccatc tcctctgcta  78780
```

-continued

```
gccgattaat gagccagcta tgcccgccgc tccgcaaaaa cttataaagt tcgatatact  78840
ggtgcgtaaa ctggatgatg ttttccttgg tggttacgac aacccccttct ccgttttttt  78900
tccaggtttc ttgatccacg catttcataa atactcgaat aaaattggtc aaattggctc  78960
ctgaggcgac gtagcccaag gtttcaggcg agaaggagcc tatctcagcc atacgcataa  79020
aacactgcgg ggaaaaagtt tttagccgca acttaagtcc atagatttca atgggggctt  79080
ctgcgggaac ggccaggtgc gtcccattaa ttaaaaaaat ttctttgcgt gtgctagggc  79140
gaacacgtaa ttcctttttt ttttcactca cgatggggac cacatcgggg tctaccagca  79200
gttgacgtat gtaggcctct atgggcatgg atagatcggg cagctttgac tgctcggcgc  79260
gaacatggtt cacaaaatct tttagagtga aaagaaagtc tattaaacgt atgtttttta  79320
tatcattaga ccctttaagg gtagagtaga tttcatccac tagtgcctcg atttcctcat  79380
tattgagcga taagatatct gtgccacggt ggactatttg cgcgatcgta attacttcct  79440
ccattagata gaaactgaat attatattta aaataaatac aaaatgtcaa atgaaagttt  79500
tcccgaaacg ttggaaaact tactttcaat gttacagacc aaacagcaaa acgcaattca  79560
gtcagaggtg attgaatggc tgcacagctt ttgtgaaacc tttcacttaa aaatacactg  79620
ccataaacag tttattccta gcggggaaaa aaaacgagct aaaatacccg ctcaagaaac  79680
acagggaaac acgcagccct cccaccatgt gtaccgggtt gttctctcca gagcacagcc  79740
agtcaaagca caggaatctc tgctaacaac catgtgcaac ggactggtgc tagatgcaaa  79800
cacatggaca tgcctagcca ttcctccgcc tgcgcccttt caacaggcga cccgccaggt  79860
ccaacacttt taccgtaaca atttctacga agtggttccc atccaggatg gcacccttct  79920
cacaatctac cactgggatg accctgaata tggcccctcc tggtgcctag caagtaccca  79980
cggatatgat gtgagtaact actgttggat aggcgacaaa accttcgccg agcttgtata  80040
cgaattgctg cagcagcact ctacctgcga cgtcaccctg gaaaaaaata aaacgcgggg  80100
aacgcgtctt ttctttgata acttaaatcc cgattactgc tatacgattg gaatccggca  80160
ccataattta cagccgctca tctatgaccc tcaaaatatt tgggcgattc aatctacaaa  80220
cctaaaaacg cttaaaacgg tatatccaga atactacggc tatataggca ttccaggaat  80280
tcagagtcaa gttcctgagc ttccccagta tgatttacct tatctaatac gatcttataa  80340
aactgctatg aatcaagcca aaaatgctat aaaaaatggc aaaaaagaca agggatactt  80400
taattatggc tatttactca tttcgcgagc gcctgccatt actaaaagta cttctaatgt  80460
tttgttaaaa tcgcctctgc tggtattttt acaaaaaagt gtgtaccaga aaaaacacaa  80520
tatctctaac agccagcgac tagaatttat tatactgcaa aactacttga tgcagcattt  80580
tcgagatcat ttcattgctc tatttccgca gtacatatcc tattatacga aataccaaaa  80640
catgttgaat atgattatcc atagtattgc aactaaagat aaagatcatc cctttgcagg  80700
agccgtggta aaaaaagtgt tggaagatat tgaaaacgcc gaaaacatta ttgatcatac  80760
aaccattcaa aactatgccc atcaaagcaa gtacgccatg ctttacttgt caattatttc  80820
ccatttttaa tctaatacgg ccaaagccgc gggtttttta ataaactaac atttaaaaaa  80880
actgttttat taaaaattat aatactttta ttatatatgg aacatccatc tacaaactat  80940
actcccgaac agcaacacga aaaattaaaa cattatgttt taatccctaa acacctttgg  81000
tcttatatta aatacggaac gcatgtccgg tactacacca cacaaaatgt tttccgagtc  81060
ggtggctttg tgcttcaaaa tccctacgaa gccgttataa aaaatgaggt aaaaacagca  81120
```

-continued

```
ataagactgc aaaatagttt taacacaaaa gcgaaagggc atgtaacgtg ggccgtccca  81180
tatgataata ttagcaagct atatgccaaa ccagatgcaa ttatgcttac catacaagaa  81240
aatgttgaaa aagctcttca tgctttaaac caaaacgtac tgacgctcgc atcaaaaata  81300
cgttaaatat aatttttgta gaggataaaa agctatttta gctaaaaaat aattcatata  81360
cgtttatgca gaggaagaac ggtggctttc aaattcagat tgcatccacg tagaccgtag  81420
cgtttttttt gcttctggtt tatatcgtaa accgtaataa acatcatcat ttgtatccgt  81480
tggatctttt tcccactccg gataaaaaat cggttttctt ttttttggtc gtttttttgca  81540
gtaagctgta aattaaggga atatagctta tcgaaaagtt gttcctgatc catataaata  81600
gcagcatata ttaaaaaaaa taaaaaaaga cgcttcaacg agtcagtacc actgcttgcc  81660
aacgatttac gttggttggt gcattatggt gatatagtaa tgagtgcctg cacaagtgct  81720
tgcacaagtg cctgcacaag tgcttgcaca agtgcttgca caagtgctta cacaagtgct  81780
tgcacaagtg cctgtacaca ttactgcatc gccaaagcac ctgcaatgcc tacttcctca  81840
acagagtacg ataactaaat gcttttaagc accgcttgcg tcgatgtgtc cttcggggca  81900
atcgggttca attggatcca atattattag tcataattac ctaatactta ttcaatttta  81960
tcttttttac cttgtaagat ttaaacagcg ttttagcttg tttaaagcaa cgtttaaaac  82020
aagctaaaat gctgtttaaa acaacgtttt aaacaagtta aaacaaataa gcttataaat  82080
ataccatgac aaaattagcc caatggatgt ttgagcagta tgtcaaagat ttaaacctaa  82140
aaaatcgagg gtcccccctcg ttccgcaaat ggctcacatt gcaaccctca ctgctgcgct  82200
attcgggtgt gatgcgtgct aacgcctttg acatcctaaa atatggctat cctatgcagc  82260
agtcaggtta tacggttgct acgcttgaaa tccactttaa aaatattagg tcttcctttg  82320
ccaacattta ctggaaccgt gatagcgagg agcctgagta cgtctgctgt tgtgccacct  82380
atcaatcgca cgatggcgaa taccggtatc gatttgtttg gtaccaaccc ttcatagagg  82440
cttataatgc catagaggcg gccctggatc ccctggaaac cattatcctg aacctcattg  82500
cggcacgaga tctagacttc gttgttcaca tatttcctta taataagggc catgaagact  82560
atttggcctc cacgcaactt attctcaaaa tctttattgc gacgctttta atggacattt  82620
taagaattaa agacaacacg ttggacgttc acttaaattc cgactatatt attgtgatgg  82680
agcggctttg gcctcacata aaggatgcca tagaacactt ttttgaagcc cataaggact  82740
tactagggta cttaattgcc tttcgcaatg gggggaactt tgcaggaagt cttagaccct  82800
cctgtgggca aaagattgtt cccctaacga ttcgagaggt cctacaaatg aatgatatta  82860
atttagccgt atggcgggag gtgtttatta tgcaggaatg ttccgactta gtcatcaatg  82920
ggatagcgcc ctgtttcccc atttttaaca cgtggacgta tttgcaaggt attaaccaga  82980
tttttttttga aaacacgtct ttgcaggaga aatttaaaaa agattttatt gcccgagagc  83040
tttccaaaga aattatcaag ggccaaaaaa cgttgaatga caaggagttt aaaaagttaa  83100
gcctacatca aatccagtac atggaatcct ttctacttat gtcggatgtt gccattatga  83160
ttaccacaga gtatgttggc tatacccttc aatccctgcc gggtattatt tcgcgatcca  83220
gctatttatc cccccatcgtg aaaaacattt tgatggacga agactctttt atgtccctac  83280
tatttgacct atgctatggc gcctacgtgt tgcataaaaa agaaaatgtg attcacgcgg  83340
atttgcacct gaataacatg acctactacc atttcaaccc aaccagtttt acagatcgca  83400
acaaaccagg aaaatacacc ttaaaggtca agaatcctgt gattgccttt ataaccgggc  83460
ccaaagtcga aaccgaaacg tacgtgttca agcacataga tgggttcggc tgcatcattg  83520
```

```
actttagcag agccattatg gggccaaacc atgcaatcaa gcttgagcgg cagtacggcc  83580
tcgcttttgt aaacaccttt taccgcaatc aaagtgagca tattttaaag gtattacggt  83640
actattttcc tgaaatgcta accaatcgcg aaaacgaaat acagggggtg attttatcaa  83700
actttaattt ctttttcaat agcattactg ccattgattt ttacgccatt gctagaaacc  83760
tacgtagtat gctttctttg gactatttac acacctctga ggtgaaacga aacgtagaaa  83820
tttcgcaaac atttttggat acatgtcaat ttttggagga aaaggccgtg gaatttttgt  83880
ttaaaaatct tcatactgtc ttatctggca agccggtcga aaaaacggcc ggggatgtgc  83940
ttttacccat cgtatttaaa aaatttttat acccaaatat tcctaaaaat atattacggt  84000
cttttaccgt aatagatgta tacaattata ataatataaa gcgttattct gggaaagcta  84060
tacaaacgtt tccaccctgg gctcaaacca aagaaatctt gacgcacgcc gagggtcgta  84120
catttgaaga tatttttcct agaggagaat tagtttttaa aaaggcttac gcagaaaaca  84180
accatttgga caaaatttta cagcgtattc gtgagcagct tgctaatgaa aatttgtaag  84240
gcttgcagtt cttgtatggt cagaacctat gtcgatggaa acattatttt tcgctgcagc  84300
tgcggcgaaa gcgttcaagg ggatagtcag aacttgctcg tctctagcaa ggtgtaccac  84360
accggggaaa tggaagataa gtacaagatt tttattaaaa atgcaccctt tgaccccacg  84420
aattgccaaa taaaaaagga ttgcccaaat tgtcatttag actatttgac acaaatctgt  84480
attggaagcc aaaaaatcat tatattggtg tgccgctgtg gctatatgag caacagagga  84540
taaaccatat catcccaccg aattatgaca ttcctttaaa accgtccgcc taaatagttt  84600
tcacaccttt ggtggcagac tattttataa aaagtaatgt tggttcatga agataaagtg  84660
tgccaaagaa acttttataa acaaatgatt aatgtaggtg ctagtcgtgt gtacttaaac  84720
agggtattct atagccaagt attttctata gccaagtatt ttctatagcc agtattagtc  84780
aagtatttag atgtcagggt atttttatag ccagtatttt tctatatgta caaactattc  84840
cagtaaacat atgtgtgttc tttattgagc agcatcatgg cattaacaag tttattaaac  84900
tgctctaatg ggcattaaat gacaactcgg tgcttagcaa aagtgcctat accttttaac  84960
aattagggcc gggaggcatt cccagctttt ttctataatc agccatacag taccccctgag  85020
cctcatacac gggaataagg tccttccatt ccttgttggg atcggcgggc cagctctcaa  85080
atgaggtgtg aatgtaaggg tcctgttctt tttccttaat gaagcgttta atctccattt  85140
gatgttgttt actttttttgt ttgcggcgga gcgtgttccg caccaatacg taaaaaatac  85200
caagaatcac acataaaaga attattaaaa aaaatatcat catcgcgggg tttaaaaaac  85260
gatcccatgc aacaggaatc gttcttaaaa ccttgtctgg cagggctgta aacatgaagt  85320
ctcctcctat aatcggggtg ggactgtagc ctaacagttc aaggtcctgt cgttctagat  85380
acttattggc gaactgccca ccctttgccc ccgttttttt attaatcaag cagcgctgca  85440
ttttccacca ttctaaatct tcaggagaaa gctcaatgcc atatatcaac tttaacgtta  85500
ttgcatcttt ttcaatatcc ttatcaattt ggctgagctt ttgagcttta agcgggtcta  85560
gtgtgtactt ccatttaaac ttagtgtcct gtagtttggc tacatgaaat acggaacatt  85620
tcggcggggc ctttgtgacg cccttacact gcggaagttt atcattagga caggcgcata  85680
gatgagactg cgccacagca tcgcgaacta catcgcagac ggagtacatt ttcctcctat  85740
gttaaacaat aaattttttt catagctgaa atttgtgggc ctatcttttc ccttgcccgg  85800
ataataatta taagggagtg ttgaaacatc tgggagagaa ttgcttaaaa aatgggtttt  85860
```

-continued

```
tgggaggggt aactgcgact gttgtacgtc gttggccagg gagattctat atgccgggct  85920
aaaggtgcaa cgttcctgtg aacaacttag tacgcgcgtt gttaatacaa atggactggt  85980
attagcaaac ctcgtaaact cttccggact tgtttgtttt tgtatgatgt ttagcaggga  86040
gtctgccttt tcgagaatcc aaagcgtcgc attgtagtaa aataaaaata gcgacttatc  86100
ggcaggcgtt gcaaaagcgc cgtatagaaa ataaagcagt aagtactggg gagacaccac  86160
aataaggtta tcttgaatga tagatatcgc tagctcttta aacatagtgc taaaaaaatg  86220
tatgtcgttc gtcttgaata tagggggact atagtccatg tagggctcac atatctcagt  86280
caggtgaagg cccatttctt ttatgacttc ttccgggttg tacgtcgcta acaccagcgc  86340
gggataggct ttgggcatat ccacggtaag tgttatgttt ttatcattct tatggtagga  86400
gtaagatggt tgtggaaatt ctgttttcca ctccgggact ttgcaggtaa ttctcagctc  86460
atttagagtc tggtacagga gggcgtatgc cgcaaagccg tgtatggcca cttgtttaaa  86520
gggaattgaa aacgttttac tttcgtatgt cgacttcaca ggaacaacgg gaatggggta  86580
atatttttct atgaggttat accgctgcaa atccttttta aacctgctaa aaacatcttc  86640
ccttggtggg ttatcaaaag gaaagcaaaa tgctaggtgt agcccggccc gctggtaatc  86700
ggggtgaatg attttaaggt ttttatacgt taatgtgggt atggtgttaa agatattggg  86760
gggcatatat gaaagatcag caacccacac aaagtccgtg cgcacccgca tggtctgcac  86820
atggatggcg cgcaccgtgc ccacctgctt gaagcccttt tcatacaaaa tgtcagcaag  86880
ttcgtaggcg tcctcaacgt ggttggggga aaacatatca aagtcgggtc tttctccctc  86940
gggataaatt gagctgcctt taagatgcag ggcataatca atggcaatcc ccccgtacaa  87000
aataagcttt ttctttatga taaattcgcg gaccacctcc aaagccgcct caatctccac  87060
ggcatttgcc tcacgttttt gagcaatgag ccggtactta gaaacattaa aatcagtctt  87120
tagtaaagac gtcataaata gtgtttaata tatattaaag gtttgaataa aatactaaat  87180
agtaaaaatg gatgccctat taaaggaaat agaaaagtta tcgcagccat ccttgcagaa  87240
agaaaacaat gatgtatgcg atctctgttt tatgcaaatg aaaaaaattt ctaactatca  87300
gcttttatgc gaagagtgcg gtcagctgaa ggactggttt gaacctgaat ataatgaaaa  87360
attcacggta tattctcgtc taaagatcgt gggtgccaat agttcctatc accagcgcga  87420
tttggacaag gccaactcaa gtgactatag ctccttgcaa tttcatcaca ttttagagga  87480
gctcaaatcc ctaaatgtta agtatatgga tgcggggcaa aagccctttc ctattcaggt  87540
gttaaaagaa actgctcaca gttataacca agtacaacaa catcgggtca tacgcagcat  87600
tacaaagctt cagatcttag ccagtattct acgtagcatt tgtttaaaat taaacattgc  87660
ttgtacggtg gcagacgccg cgaggtttac tcaacttaat accaaaggga tctcaagggg  87720
catggatctt ctgcgctccc tatttgtaga caataaaatt actttaaacg ttgatttaaa  87780
ccctatagac agctttatta atagtaccta cagtgcctta caaattaaac aaatccacca  87840
agaactgcag gaggaaaatg tttataattt aaaagaaatt gttaagagct ttatattata  87900
cgcggatgag aagaacatcg gcgtcgatct taacaggaga accgttgtga ttgctacgat  87960
gtataatgtt ttacgccgtg cctactaccc catagaaatt gatacggtgg tgtatcaatg  88020
taaaatacga aaaaatacaa ttacacgtgc tcttaaaatg tatgaggatt actactccca  88080
ctttaagtct ctttatgagc agtatcattt aaacgcggca aaaaaattaa tttaaactaa  88140
acgtttaaac taaatgttta aactaaacgt taaaactaaa catttcgact aaagtttaaa  88200
acctagtcta acagcgggat gcccatttcc ctggggttcc atatttcaac aatttttga  88260
```

```
ccttcgggtg ttaccttgat gcagcgcatg acgagcagtg gaattttcct attaaagagt  88320
tcttgcttag ctatatcaat aggactgcta tattttttttt taagcattgt agatccatta  88380
attgccaatt gttgcgctct aacggcgacc aaccttgtgg cctcaaaggt ggttaaaacg  88440
ttggaggtaa tgcgctcgtt atcgggtata atgaccaatg tttgcgacga ggcctgcaca  88500
aagccctcgc agatggacgg agactccacg atctcgtcct tgtcctcgga ctcctcctca  88560
ctgtcgacga ggttctcctc ttccgtttcc acatattcct ccacgaggtc atccatgata  88620
agatcctcgt tgtcattatc agccatatta cactgttatc aaatgtactg tttaatacgc  88680
aaatggattt actacgtttt aattgtatgt cttcatgtgc aggctctagt ggaaagtaat  88740
tttctcacaa tttttggcac cgttacactt gtgcccacaa aaacccgcga ttttttttatt  88800
ttatattact tttggaagta cgagtttaac cagtcgcttt caaaccttat gcgtctatct  88860
cgccaaaaaa cgctcacagc ggtgttggat attaccttta aaaaaataac attaattttt  88920
accacagagg gcgtattgcg tatggattct acgaataagc caggcgtgcc actcgatata  88980
gacccccagt tcattgacct tgatagtatt ttaatggaac tggatcatta ggacctctcc  89040
cgcccattta aatttttagt ttctacaata ataaaatgcg cgaggaatca tgggaagacc  89100
acgataccat tcagctcacc gctcagcgca aatacctcgc cgaggtgcaa gctctagaga  89160
ccctttttgac tcgagagctt tcagtctttc tcacagagcc aggcagcaaa aaaacaaata  89220
ttattaatag aatcacagga aaaacctacg cacttcccag cacagagcta ctaagactct  89280
acgagcatct cgagcaatgt cgcaagcaag gcgccctcat gtattttttg gaaagacagg  89340
ggacctactc gggtctcatg ttggactatg accttaaact caatacaaat gctgttcccc  89400
cgctggaacc ccccgcgcta tcacggcttt gccatcgaat atttgtgcat ataaaaaaca  89460
gcagtgtgct gcctgagggc agccataaaa tccacttctt ttttacatta aaacctgaag  89520
tggttcaggg caaatatggg ttccatgtgc tcattcctgg tctcaagctg gcggcttcta  89580
ccaaaaaaag cattatagga tccctacagc acgatgccac cgtacaaaaa attctacacg  89640
agcagggcgt tacaaatcct gagtcctgtc tggaccccca ctccgcctcc gttccctcgc  89700
tcctctacgg ctcctccaaa ctaaaccaca agccctacca actgaaaacc ggctttgagt  89760
tagtctttga tagctctgat cccgactaca ttcccattca tcaaataaaa aatttagaat  89820
cttataattt agtttctgag ttgagcctta cgaatgaaca gggaagcctt gtaagacctg  89880
tctattgcgc ggcagacatt gccgctgaga aggaggaaga gatcccgacc gaggatcact  89940
cgctctccat attaatgcta catgatcccg aagcccggta tttacataaa attttaaatc  90000
tgcttcctcc ggagtattat gtagagtacc ccctatggag caacgtcgta ttcgctttgg  90060
ccaatacatc cgctaactat cggcccctcg ccgaatggtt ttcgcaaaaa tgccctgaaa  90120
aatggaatac gggaggaaaa gagaaactag aaaaactttg gaatgatgcc tcgcaccaca  90180
ctgaaaagaa aatcaccaag cggtccatta tgtactgggc ccacaaacat gccccccagc  90240
aatacaaaga aattgtagaa caaggctact tttccattct cgctgaatat gtgtatagct  90300
ataacggcat gcttgagcac tacatgatcg ccaaagtcat ctatgctatg atgggcaaca  90360
agtttgtagt ggacgtggat tcaaacggga agtacgtttg gttcgaattt gtgctaccgg  90420
gccagccaat gaatcaggga gaaatatgga agtggcgcaa ggaggtaaac ccggatgagc  90480
tgcacatcta tatttccgaa aacttttcaa gggtgatgga ccgaatcacg gagcacatca  90540
aataccacct cagtcaaccc catgaaagca atattttaaa ttattataaa aaactattaa  90600
```

-continued

```
aagcctttga acgctctaaa agtaaaatct ttaatgacag ctttaaaaag ggagttatca  90660
ggcaagctga gtttttattt cgccaaagaa gctttattca aactctggat accaatcccc  90720
acctactggg ggttggcaac ggggttctct ccattgagac catcccggct aagctcatta  90780
atcattttca cgagcatccc attcatcagt acacacacat atgttatgtg ccctttaatc  90840
ccgaaaaccc ctggacaaaa ctattattga atgcactcca agacatcatc ccagaacttg  90900
atgctaggct gtggatcatg ttctacctaa gcacggccat atttcgcggc ctgaaggagg  90960
ctctgatgct tttgtggctt ggaggcggct gcaatggaaa aacttttcta atgcgacttg  91020
tggccatggt attgggcgat cactatgcct ccaagctcaa catcagcctt cttacaagct  91080
gcagagaaac cgcggaaaaa cccaacagtg cctttatgcg gcttaagggg cggggatatg  91140
ggtactttga ggaaaccaac aaaagcgagg ttctaaatac gtcgcggctg aaggaaatgg  91200
taaatccggg cgatgtcacc gctcgagagc ttaatcaaaa acaggaaagc tttcagatga  91260
cggccaccat ggtcgccgcg tccaactata acttcatcat tgacacgacg gaccacggca  91320
catggagaag actgcggcat tatcggtcaa aggtgaaatt ctgccataac cccgacccca  91380
gtaaccccta cgagaaaaag gaagatcctc gctttattca cgagtacatc atggatccag  91440
actgccaaaa cgcattcttc agcatactcg tctatttttg ggagaagcta cagaaggaat  91500
acaacgggca gattaaaaaa gtgttttgtc ccaccattga gagcgaaacg gaggcgtaca  91560
gaaagtcaca agatacgcta cataggttta tcacagaaag agtcgtggag tcgccctccg  91620
cagaaactgt gtacaaccta tccgaggtcg tgacggccta cgcggaatgg tacaacacca  91680
acattaacgt aaagcgccat attgccctcg agctatccca ggagttagaa aactctgtgc  91740
tagaaaaata ccttcagtgg tctcccaaca aaacgcgaat tctaaagggt tgccgtattt  91800
tgcataaatt tgaaacgctg cagcccggcg aatcctacat tggggtgtcc acggccggca  91860
cactcctaaa cacacccata tgcgagccaa aaaataaatg gtgggaatgg tcccctaatc  91920
cctctgcccc tcctgagaaa gaagcgtctg caccaactcc ttagggaata tccttagaag  91980
catgtctttc ggcagagcca ttaccggtag caaaaaagca acattgagta tattatatgc  92040
cttagcctgc tcataagcgt cctttttttt catggtattt tatgttttta aatattttta  92100
attatttttt aaatacgatg aacagttcgt gctccgaagg ctgtttacta aaaatcggtg  92160
tgaatccgca ttctttaaat atggtttccc attcggggat ggtatggaaa tccatgtctc  92220
tacgaatagt atggtgccca agtgcgtcct gcaggctgtg aagccagaag gcctcctgac  92280
cttgatgaag gtcgtacatg ataagaaaac catcaggttt caacagatgg taaagcttgt  92340
taaaatcgtt tatcgtaaga tgatgcgccg ccataggtaa ccctatgagc tccacagagt  92400
tttcatgctg gacatcgtcc atatcggtat aaaacgtttc acagtaaatg agacgcttaa  92460
acgagtatcg atgacaaaca tttatttcca agtaggtttg cactacgttt ttaggtatat  92520
cgggaatcat gttgattaag gttgtttcgg gaaacttaat catctgacta ggcttcattt  92580
tcaactcttt aaaggatttc ccggagaagt gaaaatgggt ctttacgtat ttatgtaaaa  92640
atacctgaat gggcagaggg ggctcctcct cttcgttctc gacgcctccc aaaatatttg  92700
gaatttcctg acgtggcaaa agaaagttta tgtccacgtt tacgaatcca tcgaggacgg  92760
acacaaagct tggctctaat ctccattcca tatactgttt agaaacggga gatagcataa  92820
tcctaggcgt cacaatgcac gaagggtttt taatcaccgc atcgtggtaa gaaaagtgta  92880
ttccatttct tccagtataa agaagcctat gttcgtcgta gcagaaacaa ttaaggcggt  92940
atgcctcata catacactgt ttcaaagtac aaacacgttt taaaaaggtt tctgcattgg  93000
```

cggaggccaa gcggttttgc cattggtgga aggggttcaa tcctacaatg gccagctcgt 93060
ttaaaatatc ttcgcggcgc gctaaaatct gcaccataga agaatacttt agcatttttt 93120
tttcgcacca ttcgcgaaga tgtttagcta cattattaac cttattattg ataaagtata 93180
cgatggcatg ttggaagcct tcaaaaataa agagcccctc caaaagatca tctgccaata 93240
gaagatggat gttggtgtaa gcattgtcaa tattttgtag aaacggcgga atgcctgcca 93300
aaaccgcttc agcaagcata gctccgttcc gttgtttact gtccaataga ttcgtaagtt 93360
ttttgtccgc aacagacacg acggctagga tggttgcaat gtcagaaatg gcggcttgcc 93420
agaaataacc cgaaaagcac atgcgcgctt cttctataga taaaaacgaa aagcgagagg 93480
caatgtctcc gagctgcgtg agttgaagac ctttttctcc tctggttaaa aggcctgcca 93540
caatggcccg ctcaatggct gatgccagcg catccgtggg gggaggatcc agcatatcaa 93600
tctcctctgc cttaaacacg ccttccttat ttttttaat cgtttctacg acaatgctaa 93660
gaaaaatggc cccagggcct tccgtaatga tttcaggata ctgctgcact ggtatttgct 93720
caaagacgtg ttttgtgtaa agcgggtaaa agtgcccagg aaatactctc cctacacgcc 93780
cctttctttg ctcgatacgg ctttgagccg cggggcgcgt aataagccct cccgcccatt 93840
cgggatagta ggtttcaatg cttctgttcc acccgggatc tatgacgtac ttcagcgttt 93900
caatggtaag gcccgtttcc gcaacaaccg tggaaacaat gacccttctt aaaggttttt 93960
ccactttagc ggttaaggga tttttcaccc acagattctt aatttccgct ttcaggccaa 94020
ggtaggcctc attttcctgc gcaatcgcct cactatcgat cggcaaaatc aacattaacg 94080
gcagcttttc tttggcaagg tccatatttg cattattcag caacatcgaa aggaagcgta 94140
tttcagccat accgggcatg aaaattaaaa tatctgcttc cgtgggacga tcatgaatgt 94200
tttctttatg aatagtgaga gccgtttcgc aggcggtctt aatgtagttg ttggtgttat 94260
acagcggcca gtgggtttcc acaccgtact gtcgtccttc caccaaaata atgttttctt 94320
ttccgatacc aaaataggtt gagtatttat gggtatcaat ggtggcggag gttaaaatta 94380
caaagggaat acgcagcgcc cctatgcttc ctctttgcaa catgcgctga agcatacttt 94440
taatatacat gagcataagg tcgatgccta gggctcgctc atgggcctca tctataatca 94500
taaaggcata gcgggaagct atctcatcat ccgtcattgt atgtagctgc gccaacagaa 94560
cccccgcggt tgcataaata aggccccgat tgggttttc cgtcagaggc ttcgtttggt 94620
agcccactgt ttggcctaat atcatgtcgg ggtagtgggt tgaggcgccg atgtctttgg 94680
cgagggtcac cgcggttagg actcttggct gggtacaaat aaccgagcgt cccaagtatt 94740
tttggaaaga atgcgtgttt tcatttctca gaattctgaa cacgtgtacg ggtaaggccg 94800
tggattttcc ggaaccagtg cgtgacttta taatgagcac ccggtctgcg agggaggttg 94860
gaatggcccc tccaaactcc gggagacgtt gttttatcca agtgatgatg taatgaatag 94920
gaacatcatt cttgtgctca gcgggcacgt tatagagatg accaggctcc aataaagtcg 94980
gttttcccat attctattgt tttaaggatt gattgttcat aaatattttt atactctgac 95040
caagaaatta ttttttatt aagccggtta tttacgttgt tatggaacgc gaaggtccag 95100
tactgaaagt cctccgagtt gtttaatgtc aagggatttt ttgtaagata cgaaaaggcg 95160
tggtgctggc acctggtgca tggcagagac tcgataaagt tcagtatcca ttggatggct 95220
tcatattttt ctttccagct aggagcgtct gaaaaaaaga tagcatatag atgcaaggat 95280
cgccagtatt taggtcccca atgcaacatt tataaccttt tgaaaaatct cattccatat 95340

-continued

```
agaggtaaat atttttttc catggagaat ttttttgcac tcttgaaggg attgcgccac  95400
atcgtcaaat gtttttgtt ttccatgtat tttggcgtaa ttccagccag tatctgtgtc  95460
atggtcctta atgtcatccg ctaactgaaa ggcatgtcca aaacaatggg cagccctttc  95520
aatcatccca atgtcttcaa cggatccagt tcctaaaacc cagcccataa taaacgcgat  95580
cttaaaaaag ggaatggttt tttctggagt gtctactaac tgaccggaac ccgcgctgtt  95640
tagagagtgg cttacaaagg tacacagcag cgctcccagt tggttgggat ccggaaacct  95700
tggacagtgt tccttaatcc agtcgatttg ccggcaaata ttttgaaatc cttgcatggt  95760
tagcgccaga gcgctcatct gcgccttggc tacgccaaag cgggcccaca ctgtatcttt  95820
atttcgccgc ttcacatcgt tgtcaaagga gggcatatca tcgataatca aagaagctac  95880
gtgaaagtac tccgctgcta gggcggcctc tgccggataa ataggcgccc caaaggaatg  95940
ttgcaactga caggcccgaa caatttccat caggataatg ggacggatat acttcccacc  96000
tcttagagcg taagagcaag gctctgttag ttgtccctta aagtccccat cttcaatagc  96060
attatttaag atggtctcaa actcttcact aaaggtttta taatttttag gattcagtgg  96120
atgtattcca tgaaaaagcg cgacactacg cggtgctgtg attctaaaat acttaggttt  96180
gcgcgtatag gatattaaaa taataataag aactacaatg atggagatat agatgagatg  96240
caacatgctg agttgtctcc ccgcagggaa tggtcctttt ccgcgcttgt taacggtacc  96300
gaggaggcgt tgaaatcttt aggaaaggtg ctgtctagtt tggaatctcc aattcctccc  96360
gtatatttag gtatataatt attgtgtcta gaaattgttt gctttgaggt atcaaaatat  96420
tcagcctgac cgctatttct tttagaataa ttcggtatag ggcttgagta gttggcaata  96480
ctcttaaacc ggggcaccaa ggtaacaata ttttccatat aatgggtttg atacgctttg  96540
tttaaaaatg ggcttaccgg ctttatgctt gttagttgtg cattgagtac cggtatgtct  96600
tctaggattt gtggctttat agaatgatta gcaaacacag aatgtagtat attagatact  96660
tgtagcatat gtctatttgc ggaaaattcc tggtattctc tgccgtgttg cgaatctttg  96720
ggcggaaggg gaccaagcat cggcacgtcc gtgtaggtac tggtggattt tatgagttcc  96780
tgctctatgt tcggtttgac atgtggattt cctaaaggaa tacctctacc tgcaatccct  96840
ttttctaccg acgcaggtag attgtgcgct aaacacaaaa tattgtacac gtctttgtgc  96900
ggaatatatc cgttatagtg ctggcccggc atctgatcgc caaggtgctg ctcatgctta  96960
atggtaccct ttgttctgag tttaggaaga tcctcgtacg aaaaaaattt tgtgtgctcg  97020
ctgaacctcg tagaaggaac cgaactattt tttgggtttt ttaaggaagg caatgaggaa  97080
ggctgggtca gacaattttt ctgtgtgccc tttaagctag ccacctgcgg aaatgttttt  97140
ttttccgtac gaacaacatt gcgcctaatt aggttttccg tatgggttga aaaagcagga  97200
cgatgatttt taaaatgatt aaaaagttta ttttttggaa tggagctgta cggctccaga  97260
tcttgcgcat cgccgtaacc aatgtttttg tgctgagggt tcagcataaa agaaaagtta  97320
cgtagatcac tgagttgcaa tcccttttca gccttttcag gactattagt gtattcattg  97380
tatacaggcg cggctccatt tttgttgccg cagtaccggg aatttagtat attatcagaa  97440
taccggttat gacgcggcaa atcgctttcc caaagaggtg gatctgacct ataatcggct  97500
aacagctttg aagcataatc atgatacatt gtatataaaa gttaattatt atattgagaa  97560
ggcataatta cttcttgtag gggtacaaga ggctttgaat caggcaaact gacgggtttt  97620
gaatcggccg gctttggacc ggcaggtatc tttttaggtt gatcttcttc tagctcatta  97680
gacacggatg ggggagaaat aggaggaata atttcatctc cgcccttata tttgtcatgg  97740
```

-continued

```
atagaagaaa caattacatc catgtttgat ttattataaa tgtcgtttaa ctggtgattt  97800
aaaacataat aatgcaaaaa taatagggct acaatgcata tatatacgta aatagccgtc  97860
ttcgtttttc gtttttatc caccggcgga ttacaaattg caaaaaatac aactaatacc  97920
accgctgtaa tgattaaggc cacaatgaaa ggattttgaa aggatgtttt gaacggttcg  97980
cacgtataaa ttttttctcc taaattattg atacccgcaa taaaatctac attcatttta  98040
tatatttata aattatgaaa aatttagagt tacatctccg ccggaccaat cattgctaaa  98100
atttgaagat tcttcaaaaa ggcccgactg gttgaatgtc ttctgctcag gtttccaaaa  98160
attttccaag aatggatttt gaacaatagg ctcatcttga ttttcttctt caaggatatt  98220
ttctttgata tcaagaacag cttctttaaa ctcaggtgta tcttgattaa actcaggttt  98280
atcctgatca atcgcaaaaa tattatcttc ttcagatata tcctgtttaa tcgcaagaat  98340
agtttcttcc tcaggtttat cctgatcaat cgcaagaata ttttcttctt caggtttatc  98400
ctgaccaaac tcaacaatat ctttctcgct aaatccgttt ttagtgtgaa gctcttggtt  98460
ttgaagagaa ttatcaaaat ctattttagt tgttgtccta gaccgtggca cgggatagtt  98520
atctaatggt ttacttacta tagtcctcga atgtggcacg ggataattgt ttggtgactt  98580
gctggttagc tcttggcttg ttaatagttc ttgttttctc aataattcca tctctactac  98640
ttctttttga tccgctggtg tctctttttg gtattcttca ttagaaaaat gttcagaggg  98700
taatgtttca ataaactttg tgagtggata gctgctcttt gatgtagaag agcgttgaat  98760
ttgctgataa aggagttgaa caagtcgccg gtattcactc tgtctttttt catatttttt  98820
acgtagcgtg gagagatctg ctaagagcga cttgttttca gatgttaatt cttcaatttg  98880
atgaagaagg ctgcgattgt atgaactaag tcttgcatac gtttcttcta attctgtctc  98940
cggctccaca taggcctgtt ttcgcagaaa tttattgtat agttccattc tttttttgag  99000
cagaaaggta agactataat cttgcatttc tttcgtaact ttatggtagt tttctttccg  99060
gtttttgata ataaagggca gcattttttc tgttgtgata aaggtgccca gattgctaat  99120
gtagtcgcac agtagcaatt ccaagataga ttctttcttt tcaaggctta tagattggct  99180
gtattcttta ggtatgaaag aatcaacaat cgttgttacg aagtttgaaa agtttaatgt  99240
tttgctgtta atttgggtaa tgttacaaaa atatttgtaa aaactatcta gcatttttc  99300
ataaagtttt ttattttgtt taacccctaa aatatagccc tttacttgat actgatattc  99360
cgtaacaatg gaatgttttt tgtatagtgc atttttgtat aaaaagttat aaaaaatgtt  99420
gataaaatac gcaccaaggg tttcaaaaat acttataacg tgggattctt cctgatccat  99480
tatatcatat gtaatattat tttaataaaa aattactgac gaataacatg caaaaaaaat  99540
atgtttaaac ttattttaag ctagcactta tttaaaagtg ttttaaacac gttttaaatt  99600
gtatgttaat acacttaaaa attaagccga aatttgctcc aataaggatt acttttatca  99660
atgaccacct ctttactata aacggcttta cataatttta ataatgcttt agagccaaag  99720
ctgaaggcag tgggaagcgg cactgtacta tggtaaaaat gttgccgatg ttcatcctcg  99780
cggatgtaca caagtttcct atatccttta aacacaatat ggctaatttc ttccacatac  99840
tccttatcct gtttggaata gcggttgctt tgacgggaaa aattcgacat acaaatagag  99900
gcatttgtaa aaatggaaac aaatgcgttt ttacgaagat tggcgggtaa atcggtatca  99960
tcttggcagc aaataatcat cgaaataaaa cagtgacgat tttggtaaaa aaacttttta 100020
aaaatttctt ttgtaaataa tgggtgcagt tcggccgcgc agtcgtctaa tattaaaagt 100080
```

```
aaacgaggat taagattgat atagtttaac gtaaactttt catcctctgt aaggcataag 100140
tttttataca tatgaatgtt ctgtataata attttttttta aaagttgctg ataaagcgat 100200
gtaatctttt cttctttttt ttggtccgtt tgttcagcct ttaagcactc cacttttgca 100260
atatttttgt tttcctttttg ctgtatatcg atcggaagtt tatgatacaa tgtttttagc 100320
atatcgatgt tgtttactcg actgtagatg gaggacatca tagtttgccg ctgccagatg 100380
gcctccaaaa agcgttcagc gcccttgttg tcattttttt tttgcttatc ggcgagccac 100440
aagcggtagt gtattagagt tggatgtaca aaaccctcat atgaacgatt tgagggttcc 100500
gagggggcaa ccactaaaat ttgttcaata tggggttgca ggattttcat aatatgttta 100560
acgtacacgg ttttgcctgt ttttgagggg ccatatagca cagttgtttt atctataaaa 100620
tgatgtgctt tgaactgtag ttcaggaatt agcttccctg aatgggtcgt tagggccatc 100680
tctatattat tacaattctg cttttgtata taaaatttct ttttcgagtt tattattatt 100740
gttgacccac atatctaccc gtatcgtatc atcaggcaca ttgagcattt caagcgcatt 100800
atctaactgt ttttttgttt ttatcagctc gctttcttca tcgggggtta aattttcttt 100860
actaagcagt tgcttaattt tttcttcgca gtcgtctata aaatcatact ctcgagcttt 100920
tttgatattt ccagatgctt tttctaggtt ttttagctcc ttaaaggaaa gcagtccctt 100980
aatcccgcta tccgtgtgaa aggttgaatt atagatggag agccccggag catccgggcc 101040
agtttcttgt atatttttttg ctttttttgtg gtaaatagta tttcgtaaaa tctcttttcc 101100
tatctttagg tcttcctcat gacggtccaa aatccgtttt attatttcat tattttgatt 101160
aaaataattg tagcgctctc tgttggcctt aaagcttccc aggagtgtcc agttgcctaa 101220
ttgaatggat gaaacctctg agaaaatctg gtctttatat ttataataaa attcatcaac 101280
cttttgttgg ttgctgctat ccaccacatc ataaataatg aaggcaaact ctaggtcggg 101340
tttttctggg tagatgcttt ccgtagcggc ccgcaactct tcgtaattat cctcaatgta 101400
ataattccac ttataaaaag tatcctgagg tggaatatgc tgcgaaagat atctagtaat 101460
ttttgtgtta aagagaatgg gtttaaacgc cctcggattt tcaagcatat gtttaatgct 101520
ttggtgaagt tctatatttt gtaatatgtg ggctgctgcc ctatagccct gtggggtttg 101580
ggtgattgca tcaatatcgg cctgaagctc attaggcaca tttaatgttt tttgcatgat 101640
gtgtaaaggg atgcgctcag gatctgctaa atcggtgtat tctgtgcttg tacaagtgct 101700
tgcacaggta tctacattgg tatctgcaca catgcttgca caggtgtcta cattggtatc 101760
tgcacacatg cttgcacaag tgtctacatt ggtatctgca caagtatacg cactttgagc 101820
atgaagatta ggatcaaaca caaaatgttc tcgtaaaaag ctatcgatcg ttgttttagc 101880
ttccttgctt ttctgcgtct gggttttgca gctatctgct atagataaaa ttgtatttac 101940
taccgattca gagggaacat cattagtttc ctgtttcaaa gtatcaacta acgttattag 102000
ctcactgaga agagttttgg tcgtgtgggt aggttttgaa taggaaggca tccattcctg 102060
cagagctttg aagacatatc caataaagct agtcattata agacgtcgaa tatactgctc 102120
ccgcaaattt gtaaaagagc aaaaggccac cctgctatca tttttgaact gtttgtaagg 102180
gttcgtcctt tggtaaagct gtttaagcgt ttcttcggat atttcagtag agggatcctc 102240
caatacgttt ttgagaagct catcaatatt aaattctgcc atatcttaga gtttattata 102300
tacatattaa agctttaata taagggggggt ataacaatgg acgaaatcat caataaatac 102360
caagctgttg aaaaactttt taaggaaatt cagcaaggat tggccgcgta tgatcaatac 102420
aagaccttaa ttagtgaaat gatgcactat aataatcata tcaagcagga gtattttaac 102480
```

tttttaatga ttatttcacc ttatcttatt agggcgcata gcggagaaac gctgcgaaac 102540
aaagtaaata atgaaattaa acgtcttatt ttggttgaaa atatcaatac caaaatatct 102600
aaaacgctgg taagtgttaa ttttttacta cagaaaaaac tttcaacgga cggggtgaaa 102660
acgaaaaaca tgtggtgcac caataatccc atgctgcagg taaaaacagc ccacaacctt 102720
tttaagcaac tatgcgacac acagtccaaa actcaatggg tacaaacttt aaaatataag 102780
gaatgcaagt attgtcatac cgacatggtg tttaacacca cgcagtttgg gctgcaatgt 102840
cctaactgcg gttgtattca agaattgatg ggaaccattt ttgatgaaac acatttttac 102900
aaccatgatg ggcagaaagc aaagtcaggt atctttaacc ctaaccgtca ctatcggttt 102960
tggatagaac atattcttgg tagaaatcca gaacaagagt tggggaccaa acaagatccc 103020
tgcggaacca aggtgttgca acaactaaaa aaaattatta agcgcgataa taaatgcatc 103080
gcgcttttga cggtcgaaaa tattcgaaaa atgttaaaag agataaaccg cacagactta 103140
aataattgtg tttctcttat attgcgtaaa cttaccggag tagggccgcc tcaaatatca 103200
gagtcgattt tactacgagg cgaatacata tttacagagg caattaagat acgggaaaaa 103260
gtgtgtaaaa aagggcgtat taataggaat tattatccgt attatatata taaaattttt 103320
gacgccattt tgcctccaaa tgataccacg aatcgacgca ttttacaata tattcatttg 103380
caaggaaatg atacgctagc taataatgat agtgagtggg aatctatctg tatggagctc 103440
cctgaaataa aatggaagcc cacagatcga acccattgtg ttcatttttt ttaaagatga 103500
agatttttta gatgattttt tttagttttt taaaagacga aaaaattttt taaaagatga 103560
atattcttaa accccgcaaa ttactttttt ttaggtactg taacgcagca cagctgaacc 103620
gttctgaaga agaagaaagt taatagcaga tgccgatacc acaagatcag ccgtagtgat 103680
agaccccacg taatccgtgt cccaactaat ataaaattct cttgctctgg atacgttaat 103740
atgaccactg ggttggtatt cctcccgtgg cttcaaagca aaggtaatca tcatcgcacc 103800
cggatcatcg gggttttaa tcgcattgcc tccgtagtgg aagggtatgt aagagctgca 103860
gaactttgat ggaaatttat cgataagatt gataccatga gcagttacgg aaatgttttt 103920
aataataggt aatgtgatcg gatacgtaac ggggctaata tcagatatag atgaacatgc 103980
gtctggaaga gctgtatctc tatcctgaaa gcttatctct gcgtggtgag tgggctgcat 104040
aatggcgtta acaacatgtc cgaacttgtg ccaatctcgg tgttgatgag gattttgatc 104100
ggagatgttc caggtaggtt ttaatcctat aaacatatat tcaatgggcc atttaagagc 104160
agacattagt ttttcatcgt ggtggttatt gttggtgtgg gtcacctgcg ttttatggac 104220
acgtatcagc gaaaagcgaa cgcgttttac aaaaaggttg tgtatttcag gggttacaaa 104280
caggttattg atgtaaagtt cattattcgt gagcgagatt tcattaatga ctcctgggat 104340
aaaccatggt ttaaagcgta tattgcgtct actggggcgt ccagctataa aacgtgactg 104400
gcgtacaaaa agtccaggaa attcattcac caaatccttt tgcgatgcaa gctttatggt 104460
gataaagcgc tcgccgaagg gaatggatac tgagggaata gcaaggttca cgttctcatt 104520
aaaccaaaag cgcaacttaa tccagagcgc aagagggggc tgatagtatt taggggtttg 104580
aggtccatta cagctgtaat gaacattacg tcttatgtcc agatacgttg cgtccgtgat 104640
aggagtaata tcttgtttac ctgctgtttg gatattgtga gagttctcgg gaaaatgctg 104700
tgaaagaaat ttcgggttgg tatggctaca cgttcgctgc gtatcatttt catcggtaag 104760
aataggtttg ctttggtgcg gcttgtgcaa atcatgaatg ttgcatagga gagggccact 104820

-continued

```
ggttccctcc accgatacct cctggccaac caagtgctta tatccagtca ttttatcccc 104880
tgggatgcaa aatttgcgca caagcgttgt gacatccgaa ctatattcgt ctagggaatt 104940
tccatttaca tcgaatctta cgttttcata aagtcgttct ccggggtatt cgcagtagta 105000
aaccaagttt cggtacgcat tctttgtgcc gggtacaatg ggtcttccaa aaggatctac 105060
aagcgtgtaa acggcgccct ctaagggtgt ttggttgtcc cagtcatatc cgttgcgagg 105120
aaacgtttga agctgcccat gggcccccat ctgggacgtg ccctgaatcg gagcatcctg 105180
ccaggatgaa tgacatgcac ccaatatatg atggcccacc atatcatgga aaaagtctcc 105240
gtactgggga ataccaaagg taagcttgtt tcccaaggtg gggtacccg tatgcgggcg 105300
tactttattg tattcaaacc ctactggaac ataaggctta aaatgcgcat taaaatgcac 105360
caaatgtgtt tcttcgattt gactcaaagt gggttcggga tcgggtttcc cataactttt 105420
gttcacattt ttaatgttag agatcctgct attcagcaag tcttgggcca atataatctt 105480
gtcggccttc ccatcgttag caataagaca aaaagctcct cctgatgcca tatataatgt 105540
tataaaaata atttattgtt tttattaaat atggcggttt atgcgaagga tcttgataat 105600
aacaaagagt taaaccaaaa attaattaac gatcagctta aaattattga cacgctcttg 105660
ctggcagaaa aaaaaaactt tttggtgtat gaactacctg ccccttttga cttttcctcc 105720
ggcgaccctt tggccagtca gcgcgacata tactatgcca tcataaaaag cctcgaggag 105780
cgcgggttta ctgtcaaaat atgtatgaaa ggggatcgtg ccctcctttt catcacctgg 105840
aaaaaaatac aatccattga gataaacaaa aaagaagaat atctgcgcat gcacttcata 105900
caagacgaag agaaagcatt ttattgtaaa tttttagagt ctagatgagc ttttacgcaa 105960
tgttgtacag tgttgtatat atgtcttgta agcatttgtt gtagagtaat aagtaaaaga 106020
taaataaaaa tgactattaa aataaagccc aaaccattaa aaatattttt atctgttaga 106080
tttaatttaa taaatggctc atggaatgtg tggtgcgccg ctgcatgagg tgtggccgca 106140
tgggatgtgg tcgcataaga tgtagctaca tgggatgtgg catttgcttg catgtaagga 106200
tcatgatgtg ttgggtcttc atcccagcaa taatcgccat ctttatctag ctgaattgta 106260
taccccatta tatatcactt attatttttt tttaatgttt catgaatttc attataggcg 106320
gtgaaagggt cctcaggccc cttctgtaaa agattataga gatcttcgga cgctttatgt 106380
ttcgtgcgaa ttaaggcggg atataacaaa agagagggcc ccagttccaa acaaatttta 106440
cttagcgggc tcatattttg caccaagttt cccactactt gcgatgtttc ataacgcatt 106500
ttaaagagct ttatcataaa agtgttatgc aggccggtgt agtctggcct atagttaagg 106560
aaggggattt ctctggtacc gtcaaacacg atctcaagtc ctctagcaag cccgatcaaa 106620
atttcttcag caatggatga gtatctaatt cctacattac gaagcgtaag catttctata 106680
acatcatcta tttcctgcat agaggaatct attgtaggaa ttttaatatc atctgtgctg 106740
atttgttcat tcccaagata ggtaagcagc atattaattt tttctagctt tactagctta 106800
gtcttacgct cataatcatg atctttttta taaaaagagt tgggatcacc gttggaccgt 106860
agatgattaa taaggcggtc tacttgcttt gtactaggtt taatactttt ttcactatac 106920
tcgctttcag catagtggtt tttacgatct cttttagaaa tagctgtttt ttgagatgcc 106980
tcagactctg catatttttt tctatgcgta gaaagagaat aaccgcggtc attacgtgaa 107040
ctactgttgc atgcaaggcc tcggcgcgtc ttaccgctgc gcacactgcc attgcgtata 107100
ctgccatcgc gcacactgcc gctgcgtata ctgccattgc gtatactgcc gctgcgtatg 107160
ctgccgctgc gtatgctgcc gctacataca ctatcactac atatgctgtc agtacatacg 107220
```

ctatcgcggc gtatgccgcc gtgtacctta tcgccgcccc tacccgaggg ttttttagat 107280
ataatactgt gtggggagtc aagcgaaaat tcagggtcat taaagttaat gcccaatgac 107340
tttgccaatc cattaagctc ttcatcaaaa tgatcggtag gaaaactttg ttgcttgccc 107400
atgacctgtt tttcaagttc ctccaaattg gcttgctcat ttatatggag attattcata 107460
agcgtcgtaa ttccagcaag atttgctcct tctaaaaatg tggtgtcctc catcggatat 107520
actatactat ttaaaagctt ttaaataaaa atgtgtttgg aagaaatgct ctcttcaagc 107580
gtgtgtagct cagatataaa tgcctcctca gaaagctttc caccatactc ctttctcatc 107640
gtataggagg gcgccggttt aatgtaggaa atccactggg aggtaaaaaa ccggtacaac 107700
atatttagca gctcgcgggc ctcccacctt ttgggctccg tatagtgcac atcaacataa 107760
gaggcggcgc atgaaaagct gcaaaagttg ccgagaacgc ccatctcaat ctctcctcgc 107820
tcattttcac gcatataggt gggcacgaat tttgggacag tcttgaaata gagatgacat 107880
gtccagcatt taaagctaga atgggtaacc catttggaaa cagtggtgaa tacggagggt 107940
agcttttttt cgacctcggc ttcatcgtca ttcgtattta acgtatcggt ggcagttttt 108000
ttggattgca agcattcttc aatggtaatc ccggataagt ataaaatatt aggacaatta 108060
gtttccataa ttttgatagt tatttttata caacatggat ttaattaaag ataaatggag 108120
gacgaaacgg aactgtgttt tcggtcaaac aaggtgacga ggcttgaaat gtttgtctgc 108180
acatacgggg gaaaaattac cagccttgca tgttcgcata tggagttaat taaaatgttg 108240
caaattgctg agccggtgaa ggcattgaac tgcaactttg gccaccagtg cctaccgggc 108300
tacgaatctt taataaagac tccgaaaaaa actaaaaaca tgttgcgccg tccgcgcaaa 108360
acagaaggcg atgggacttg cttcaatagt gccattgaag cctccatttt gtttaaggac 108420
aagatgtata aattaaaatg ttttcctagt accggggaaa ttcaggtccc gggcgtcatt 108480
tttccggatt ttgaagacgg aaaaaaacatt atacagcagt gggtagactt cttgcaacat 108540
caacccattg aaaaaaaaat ccagattatt gaatttaaaa cgattatgat taattttaag 108600
tttcaaataa acccagtgtc tccccgcgtc atcattcatt taaaaaaatt tgcagctttg 108660
ttggaacaca tccctactcc atatcccata cgtgaaataa agcctccatt agaagactca 108720
aaagtatccg caaaatttat ggtcagtccg ggaaaaaaag tacgcattaa tgtttttctt 108780
aaaggtaaga taaatatttt aggctgcaac acaaaggaat ccgcggagac catttatacg 108840
tttttgaaag atcttatcag cgtacattgg caagaaattt tgtgcgtgtt accggtaccc 108900
gattaaagaa tgttttcatt aataaggtaa tcgactatgc taaaaagaat aacaagaaaa 108960
ataccttgaa gaactatacc aaagtaggta ggttttctgc atgtcacggc atggttaaaa 109020
ttgctaataa tgtagtccac aaaagcattg ctcaatacga ctaaaaatag taaaaaaagg 109080
ataagtgctc tttttatatc catatacttt aaaacttatt ttttacacta ataatttcct 109140
gcggccgcaa tataaactgt aggtcatcta taacgcccag acctgttaaa agtagagtac 109200
tatgttttaa gggatttaaa atatccgccg caagaatgtg aatataattt tcaaagtggt 109260
ttacaggaat gcgtaagcgt tttttttgc actgcggttg gtttagggtc gaatactggc 109320
aggaggtata tatattaata agaccgcggt cgatggtttc aatatcttca tagaattcaa 109380
tgcgcggcgt caaaagtttt ttaagatgtt gacataactc atcatacgtg taggactgga 109440 gggggaaag aagggtgtag tcaaagttaa aaatgttttt ttgaagaacc tttaaagcat 109500
gttccgcgtc cgtggtttcc aaaatatgtt ttatggtatg aatgtcattt aaatctacaa 109560
agtctgacag ctttgtgtag aactcggtga cggaggttat tttctggaaa tcggtttttt 109620
gaaaaagatt ttcaatgtgt ttgcgggttg agttgctttg cagtccatac aagacatcaa 109680
aaaattcaat cagcaaaaac ttatacaaat ggttaatata aaaagctttg ttggccttat 109740
tctgctgagg atatggttcc tctaggggat atagaatggc ttggtctata tccctaggat 109800
caatagtcaa tgttgcgatg ggaagctttt ccagcgtagc gggaagagtt tgggttggag 109860
cgtagtaaaa gtatagcccg gtttttccct ctgaaagaaa gcccacaaat tcttttttta 109920
tattttgcag caccgctgag ggtacgattt cgtactgttt atactgtttg ttgaaaaggg 109980
taataaattt ccaggtttct tcaaagcttg caatctgggt gggccgcaga tcaaagtcga 110040
tgggaatgtc gtcatgaatg taggatgata gtcttatagg aaaataaata gggcgatcgg 110100
tgtctgaatc gataagtaaa gcataacaaa agttatgcct gttgataagt tttttaccaa 110160
ccgtgtagcc gggaatgttt ttcacgtcat ggatatccca ccagttatcc ttgcacataa 110220
actcgctcat agactggatg acctccatca cagggtcatc ttcggtaaaa atatactggg 110280
cctcactgtt tttcagaaat cttttttgct gggtgatggc cattgggtag atcccttcgt 110340
ccgtgtcaaa gataatggct atcttcttcg atgggctaag aatttttttgt attgtgctgg 110400 gggacacctc aaacccgatg tcgccctgtt tatctttaaa aaagacacag tgaaggtcgt 110460
agcatatggc aacaaggtcc agaaagatgt cctgccatgt ggtgtcccat tgaagcagtt 110520
ggtttttttg ttcaacaaag gtttgtaaga taaggtttgc cagctccgcg ccgctggaaa 110580
acatgttgcc ggccccattc cccaaaatat agtactgcgg tgtgttggcc gcctttgcaa 110640
tttcaatggc aagggccttg ggggcaagat ccaaaattcg agcaagggaa taaaaaagcc 110700
cggcattgct aattccaagc atggtttgct ccaccccccac aatgcaaaaa atgtcgggct 110760
cttttatcgt atttaaaaac agttcatctg ctatctggtg gggtagaaag gcaatccggt 110820
tcaccggtat ttttttttcca taggacaagg tatgacgcga tgtttgtgta ttaagatcct 110880
ccaggtcttg ttctacaaac gtgtgcttgg tgaggcaggt attgttaata tagaaccgct 110940
ttgtgcccag cagggccttc gtcttttggc agcacggcag acagtaattt agggggtggc 111000
ggccttctag taggcttaga tgagggtagt caggatgcgg gcagctatag taggcaggta 111060
ccccctccgt gaaattccaa tactttacta gctccttgcg cttggctggc ggcatggact 111120
tcacctcggc ctctgagtaa atgacgggtg gccgtgggtg ctggcatagg acggagtaaa 111180
ccgttgcctg cgtgtcgtac ttgcgcaggt catacaggtc ggggtcctgt tcttgaagcg 111240
cacgtagctg agaggctccc tttccttgtt gtttatcgtg cagttgagag agtttattaa 111300
ccaaaatttt gtcaggcccg gtgatcaagt tatctaaaaa cacaaatagg taaacccaaa 111360
gatagttaaa ctcttcctgg gtaatgttaa acatttctat tttgatatct gtaaccctat 111420
ggtagatgcg aatgttgcgg ccgccgtaga ttgtttccca ccgggccgca acatttgtgt 111480
caaagaggta cgcatacgtg ttttggagca acgcaacatt gatgtccatt ttgcgccccg 111540
gaccggagga aataatgatc atccgttcga tttcgtgggg atcatacgaa taaatcccct 111600
ttttaaataa aaaattgtag accccggttt gctggaggcc ccgcacggaa ataatccctg 111660
cttgctcgta ttcccgccaa cgacttttga gctcggtaaa tcccttgcta gaaagcgtat 111720
agggccaaaa ggtggacacc gacatggagc tgatagaaat ttggatgtcc tcgttggagg 111780
gaaggggcag actccctcca cgaggaaacg cggcaggccc catatcatta attgtatgaa 111840
taataggatt tatgaaatta tttagggtgg acaccacgga gttaaagtcg tggcgctcgt 111900
tttctgacca attgctttcg ataaagtagt gcccattatt ttgtatggta agaataaagg 111960
cctttttatt gataaagcgt attaaaataa tagtgggtac acggaatgtt ttattgctga 112020
atttttcagg ctccgtggaa gttatgtggt gtttggaaac cacggtggga cctgttttac 112080
tataaaagaa caccaccagc tgaggaatat cgggagtagc tggaaatagg tcgaaaacat 112140
tgcgcacatt aatttgaata tttacgaggg gtgaaatttt aatcattgcc gaggtgacgg 112200
ccaacgtgcc gcgtgttagt ctattcccct cgtacttggc aatgacttgt tgtgctctgg 112260
catacgtaaa gtttattagt ttttgctcta ggagaagcct ctttttaaga ctggtcaagg 112320
atggagaaag agcaggatac tgtttttcca tttgtaaggg agattgtacc aatagtttaa 112380
aggcatcggg ggaaagaaga ggccaatact tcataataag gccgtaatag agtaagtcaa 112440
attggtaatt atcctctatg gcaatggaga tttggcgccg catgggggcc actagcgtgt 112500
tgaggtctgc tacaaagatg tgatgaatgt tttttatgag ctggaagctg tcgagcgctt 112560
ccacatagag ctcatctttt tgactttcca tagatgcgtc gatgttcacc ccacccacct 112620
gttgaaactc ctttttgtag tcgcgaatgt ctaacgccac cccgctaccg cttaacaata 112680
ggcgatacgt tacctgaagc gcattgtttt gaaaaaagaa aatgtgttgt ctataagggg 112740
ggatccctgt ggcaacgtaa atttttctc gaatgtcttt aaaagtgtct tcagggaaaa 112800
tactatactc gctatacatc gtctcaattt ctggcatcat cacgtttgtc tcctcgccac 112860
gatcctccac aaaaagtttt tcaaactcat ctaaatcatc gctatctcca cccaccacgt 112920
attgggaaag ctttttctcc caatcctcgc cgtaaaaatt ttgtaaaatt tctttgtcct 112980
taggggttcg ctgcaggtct ttgcggcagg cctgtaacac gtttgcagga acggatccca 113040
aaaaaataaa cgtcttcgtg tactcatttt ccacaggatt ataaagagta actcgtagag 113100
gatttgttaa aaagtcattt tggaaatcca ttatacccgg tatagaaaat aaaatttaaa 113160
ataaaaacgg atgatatcta tcatggaccg ttctgagatt gttgcacggg agaacccggt 113220
gattacccaa cgagttacaa atctcctaca aaccaatgct cctctactat tcatgcccat 113280
tgatatccat gaagtacgat atggagccta cacacttttc atgtatggtt ccctcgaaaa 113340
cggttacaaa gcagaagtaa ggattgaaaa catcccagtt ttctttgacg tacagattga 113400
gttcaatgat acaaaccagc ttttttaaa gtcgctactg acggctgaaa atattgtgta 113460
tgaacggctg gagacgctca cccagcgtcc tgtaatgggg taccgcgaga aggaaaaaga 113520
gtttgcacca tacattcgaa tattttttaa aagcctgtat gagcgacgaa aagccattac 113580
ttacttaaat aatatgggct acaacacggc cgcggacgac acaacctgtt attaccgaat 113640
ggtttcccga gaattaaaac tacctcttac aagttggata cagcttcagc actattccta 113700
cgagcctcgc ggcttggtac acaggttttc cgtaaccccc gaggatcttg tttcctatca 113760
gaatgatggc cccacagacc acagcatcgt tatggcctac gatatagaga cctatagccc 113820
tgttaaggga accgttccgg acccaaatca ggcaaacgac gtggtgttca tgatatgcat 113880
gcgcattttt tggattcact ccacagagcc tctagcgagc acgtgcatca ccatggcacc 113940
ctgcaaaaag tcctcagagt ggaccaccat tctatgctcc tctgaaaaaa atttgttgtt 114000
aagctttgct gaacagttta gccgctgggc tcctgatata tgcacagggt tcaatgattc 114060
tcggtacgac tggcccttta tcgttgaaaa atctatgcag cacggtattc tagaagaaat 114120
ctttaacaaa atgagccttt tctggcacca aaagctggat accattctaa aatgctatta 114180
cgtaaaggaa aagagagtca aaatctcggc cgaaaaatcg atcatttcct ccttttttgca 114240
taccctgga tgcctaccca ttgatgtccg caacatgtgt atgcagcttt accctaaagc 114300

```
cgaaaaaaca agcttgaaag cgtttttaga aaattgtggg ttagattcga aggtagacct 114360
gccgtaccat ctcatgtgga agtattatga aacacgagac agcgaaaaaa tagccgacgt 114420
ggcctattac tgcattatag atgcccagcg ctgtcaggac cttctggtgc gccacaatgt 114480
tatccccgat cgcagagagg taggaattct gtcatacacc tcgctgtatg actgtatcta 114540
ctacgcggga ggacacaagg tatgcaatat gctcattgcc tatgccatcc atgatgaata 114600
cggccgtatt gcttgcagta ccattgcccg aggtaagcgg gaacacggaa aatatcccgg 114660
cgcctttgtg atagaccccg ttaaagggct tgaacaggat aaacccacca caggtctcga 114720
ctttgcgtcg ctgtacccct cactcatcat ggcctacaac ttttcgccag aaaaatttgt 114780
agcctctcgg gatgaggcaa atagcctcat ggccaagggt gaatctcttc actacgtctc 114840
ctttcacttt aacaatcgtc tcgtggaagg atggtttgtg cggcataata acgttcctga 114900
taaaatggga ttgtacccaa aagtactcat cgatctactt aacaaacgga ccgcccttaa 114960
acaagagctt aaaaaactag gtgagaaaaa agaatgtatc catgaatccc atcctgggtt 115020
taaggaacta cagtttcgcc atgccatggt agacgcgaag caaaaggcgt tgaaaatttt 115080
catgaacacg ttttacggcg aggcaggtaa caatttgtcg cccttctttc tgcttcctct 115140
agccggagga gtcaccagtt cgggtcaata taatcttaaa cttgtctata actttgttat 115200
caataaaggt tacggcatca agtacggtga caccgactca ttatacatta catgcccaga 115260
tagtctttat acagaggtaa cagacgcata tttaaacagc caaaaaacga taaaacatta 115320
tgagcaactc tgccacgaaa aagtgcttct gtctatgaaa gccatgtcta cactatgcgc 115380
cgaggtgaat gaatacctgc gacaagataa tggcaccagt tacctacgta tggcctacga 115440
ggaagtactc tttcctgtgt gctttacagg caagaaaaag tattatggta ttgctcatgt 115500
aaacacaccc aattttaata caaaagaatt attcatccgc ggaatagata tcattaagca 115560
gggtcaaaca aaactcacca aaacgatagg aacgcgaatt atggaagaat ccatgaaact 115620
acgccgccct gaggaccatc gcccccctct tattgaaatc gttaaaacgg ttttgaagga 115680
tgctgtggtt aacatgaagc agtggaattt tgaagacttc atccaaacag atgcgtggag 115740
accggacaaa gacaacaaag cagtccaaat ctttatgtct cgcatgcacg ctcggcgtga 115800
gcaactaaaa aaacacggcg ctgcagcatc gcaatttgct gagcccgagc cgggagaacg 115860
cttctcctac gttatcgtgg aaaaacaggt acagtttgat atccagggcc accgcacaga 115920
ttcctccaga aagggggaca agatggaata cgtctctgaa gcaaaggcta aaaatcttcc 115980
tattgatata ttgttttata tcaacaacta tgttctaggc ttgtgcgcga gattcattaa 116040
tgaaaatgaa gaatttcaac cccctgacaa cgtcagcaat aaggatgaat acgctcagcg 116100
ccgagctaaa tcctacctac aaaaattcgt gcaatccatt caccctaaag acaagtctgt 116160
cattaagcaa ggcaatgttc atcgacagtg ctacaaatac attcaccaag aaattaaaaa 116220
aaaaataggc atctttgccg acctttataa ggaatttttt aacaacacca caaaccccat 116280
cgaaagcttt attcaaagca ctcagtttat gatacaatac tttgatggag aacaaaaagt 116340
aaaccattct atgaaaaaaa tggttgaaca gcatgctacg gctagtaatc gagctggtaa 116400
gcccgctggt aatccagccg gcaatgcgct gatgcgggct atatttacgc agctgattac 116460
ggaagaaaaa aaaattgtac aagccttata caataagggg gatgcaatac acgatcttct 116520
cacctatatc attaacaata taaattacaa aattgccacg tttcagacga aacagatgtt 116580
gacgttcgag ttttccagta ctcatgtaga actgctatta aagctgaata aaacgtggct 116640
tattttggct ggaattcatg tggcaaaaaa acatctgcaa gctttttttgg attcatataa 116700
```

```
caatgaatcg ccgtctagaa cattcattca gcaggctata gaggaagaat gtggcagtat  116760
taaaccatct tgctacgact ttatttccta atacttctta agaaactctt taaacaagga  116820
cttcgcatgg tcaaaggttc taaacccatg gcccttatga ttcgccaaaa aagcggtttc  116880
atcaagattt tctaaccctt tcacggatga agaaataagg tgttcggcct cgtttgccca  116940
ttttctatga ttttttttca cctcgggttc tagatctgtt ttctccatat actcattgtg  117000
gtcatatttt tttttgggag gaggcgtggg tggaggaatg ggtggaggaa gtacacccga  117060
ctttcccgct tcaaccgttt tataaaaaaa tagaagcata atacaaagaa taaggactat  117120
cgcaaatatg ataaccagtg tcccagtcga gggcattttg ttatataagt aacgtttttt  117180
ttatttttta taattcgaat gaagaaccat gttgaatagt cttctactca aagacatttt  117240
gttatacggt aaatgagaat ttataaaatc cgaatatcac tatcatactg tttatctgag  117300
aaggtctcac tgggtcctgt gatggagaac ccatactctg taatgctggg gtttataatg  117360
tggtcaggac tgacaagcac atttctgaac tgcgagagtt ctaggtttag acgcagtcgt  117420
aatagtcgct gtatatttgt aataaatatt agattgcgta tgaggcgagt gtcaaagcga  117480
tccttttccaa tttgtactaa ggtgggcttt tgtattccaa ctcccacttg tttaacgatg  117540
gaccagggtc cttcttcccg attttgttcc gtgatatagg tcagcacact attttctgta  117600
tatgaggtat gatgtcgcat attaatacct ggtgccattc caactggcgg ttgtgcaatt  117660
cgggctgtac cgggacccaa ccatcgtgga gttttataaa catatcgttc tagcgtattt  117720
aaaaattcct taaggttatt tacgagtagc atgaagggtg ctattaaaac aggtggatgg  117780
tttataacca ttgtcataaa ccattgcatt gcttcaatat cattttgtaa tgcttgacgg  117840
ggaggcgggg caggtaatcc acgtatgttg aataaagcgg ttaattgtgc accggctgtt  117900
tggggcgtaa tattttgtat taaatttatc atcgaattgg cttgcccggc atttcctata  117960
agatcgatta aattggttat ttgacctcga tattgttgta cccagttttg aatggcagcg  118020
atgatctcag gggttggatt gttttgaatt tcaggtgttt gtattagatt attcacttct  118080
cttcgtgtat cttcaagctg agtcctaaat gcatttaact cgcctataat ttggtttcta  118140
tcaataacat ttcttaaacc tcgaactgtt tcagccaatc gtatagtacg cacaatttca  118200
tgtaaggcct ggtttatgta tattgacatg ggatggcccc accgctcacg tccacgttga  118260
atacctgcgg ccaaactagg acctgcctcg tcataatcaa attgtgtagg ataaaggctt  118320
ccaaatagca ctttattgaa aatttggtca gaaagaaatt tagggcggcc catatttagc  118380
gcgttgtccc ctctaaagat gcgtgacatg tatccggcgt tgcctttgga tagtaactca  118440
ttcccatatt gagtaataga gaccgagaca taggggttta taagaagttt tagcataaat  118500
tctcgagtat ttatgggggg acgattcgga atgtttaata cctctgcaac atctggttga  118560
ggagccgtgg tgtccagaga tcgtactttt tcagccgaaa tgccgtacat aagacaagca  118620
atttcttcaa aactatagtc atagttgtaa atattggcaa gtggtataga tcgcatcagc  118680
gcatttacat tgataggtat aatattcata tcaaacaagt taaatatgcg ctcgcgctct  118740
ctattagagc caagagtgcg tgtttgacct ttcggcgaca ctattttgtg aatatgattg  118800
atttgctcct cttggtaaga gctttccacg aaggaaatta cgtcttgcaa tgttttacga  118860
agcgaataca ctgcattcat ccctattccc gctgttataa tgggtttatc gtctctgttc  118920
tcgctaataa gattaactcc accaaaagta ttttcattgt acatcatcac tgttttaaaa  118980
ctacggatat ttatgataaa tcggagagcc tgaatggcgt gggtataaaa gtgttcaaat  119040
```

-continued cgcgtgggag taatttgttc gcgagcaact accgtttcat tatagttttt catgataagc 119100
tgtactccgg gcatatctga gagctgtacc ggatcatttc ccagtaattt tcttgtgccg 119160
tatagtagtt taaactcggg ggagccgctt tcaaggttcg ggtaaagaag aggatcatat 119220
acctcattat tttctattct taggtcatgt aaataataga gcgaaagtga aaatggcata 119280
agaggctcct tattgtaccg ggacatatag ttttgaatga agtgttcttc tgtttcaaga 119340
tagatgggat gatcggtaag ctcgtgcagg acctccatgg cagaatctgc cagagtgtga 119400
gagcctctaa tgatcccgtc gatcactgcg accagtcgct ttcgcacaac atcgctcgta 119460
ttattttgtg cgtctcctag gggcataagc gtaacattgg gacgaaatac gccgccaatt 119520
ccccgcaggg ccgcctgacc gacggatagt cctgtcgcag gaacattgtt attattataa 119580
taaataacgg aatcattatt ggctcccaag agtgccgtca gattagggcg agctagttgg 119640
acatttgtgt attgtataaa ttgttttaga agctctccct ggctaataag aatattaaac 119700
attttgttaa atagtggaag attggctcta taattttctt taaggtaaat gggaatttct 119760
gttaaagtag aaataagatg ctgactcagg ccctggcgat tggtatcctt aataagccgc 119820
tgaagtataa gtcccaaaga cagaagaagc accgactgct ctgtggggtc gcctctatga 119880
ccaaagacgt tgttattgcg tgctaagtca gggtgagcat atcccatctc catcactgct 119940
tggctaaagt tcccattagc gaatgcatta ataagattta gatatatttt tccgctggga 120000
gcatcataaa atcgggtaat atatgaagct atgagctggt taaacaccat catcatacta 120060
cgattatttt gaataccata gtctgatccg tataggcgat aacgtcgaag gttgtttgcg 120120
gcatcattga cattggcata ggttctgagc gctatgttgt cccagtagct aagagtattt 120180
tcctcctggg cgttgttggt acgaataaga ttggagagtc taaagtctcc tagtgccacc 120240
tgctctacac gaagtccaga gttattctcc aaagcatcgt aaaatacgag tctactgaat 120300
actcttccgt attgttcaaa gcgttcagag gattggggat tgttatttat ttgaatatta 120360
gccgcgtccc ttctttgcgc cccacctcga agttgcagta cattataagg ctttgtaagc 120420
aaggtgtagg ttttattaat gatttggtta acccccctcca ggcccaattc accgccagga 120480
agcggccttc ctccggcatc ggtaggtggt ttaataagtt tgtcaattaa atgttcttcc 120540
aaccagtaaa atgagccagg attagatcta ttttcatagt attgaataat gtttttatca 120600
atatgcgggc gtagaagatc aagaaaatac ttcgtgtcgg ccatcaaaga atcaattaag 120660
gaaataagac ctgtaaaatc taaatgcact tgagcggtgc tggtttcagg gaagcgaact 120720
tgaaccattt tgttaaaact ggaggtcatt tcgaagatat tggtcaacag gagctgcatg 120780
attcgctgat tatctactaa ataccttgcg gccaactctt gctccggacg aactcctcca 120840
ccagcaggaa tacccacata tggtacaatc caagcaaaaa gagtttctgt ggttaaattt 120900
cggtcttggg ctgctgcagc cgcttcggta gtgggatcag ggtacaccat agaaagccgc 120960
atattgattt ctttaatgac taatcctgga tttctaatct cagagatggc cccgtgtttt 121020
cttccgagcc agtcaataag attggcgcgg ttcacgttgg cagcttgtgt ctctcgtaac 121080
cattcgataa tgcttttttg aatcgtatct aggtctaaac ctttaatgtt attacgaaag 121140
ttattaagaa gtacgtaaat agcactcaat aagttaagac ctgtaataac ggtttcatga 121200
aacagaaata ttttgttaac atctgtatct gccagtgact cagagccttg aataagtttt 121260
gaaacgattt gaattttatc ggtatgctcc tttttgagtt cattgatagc ctggcgaatg 121320
agttcttggt aggaaatttt gcccaattct tgttgcagac tgggatcttc aaacatctca 121380
ctaagctgtt tcctaaattt ttgtaccaaa tcccactggg agttgggctg cagcattcct 121440
gtttggacat ccacagagtc tatattgtat agtgccgggc gccacttggg ggtaggctgg 121500
gttgaaggac taataaacct atcggaggga agtaattgtg aggattgtgt atagccatcc 121560
tcatcaggaa gaatggagta gttggtttga ttcatcattc caaaatcatt catagttcgc 121620
gcttcctgaa caatgcgttg aaatttttcc cattcggtgc gtgtaatgac accgaatctg 121680
cggtttattt catttacaaa atggataagc gctttttttgg ttgcttcttg ttcaccatac 121740
tctaagttaa agtgttggta aatgacgttt atttctttga taagctgacg aatttcggtt 121800
tctgagtagt caccaatgtt aataagctca ataggacgca taaagataat gcgaataagt 121860
cctgagaaga ttccttccag ctcaggaagc atcgagatct gtacattttc atctctaaag 121920
gaaaacaact tttgataaaa ttcggcgagg cggggaaggc ggaagtaaag ctctgctgcc 121980
tcgggaatta cctcgggctc tagctcatcg gcacccccca atatcatacg cgtgggtata 122040
agtttgtaca cgggctcagg ccgttcaaac atgtcgtaaa tccctaatac aataaaaatc 122100
ttggcggcca tacttttcag catgaaggtg aagaagacgt cctcggtttc ccagcgggtt 122160
gatagggcgt cgttaactct cacagtagag aggtagaccc gctgagccgc ttcctcggca 122220
gtctgtgcaa gcgccatcct ttgtcctcca atttctgatt gatttagatt tttaagtccc 122280
acggaaagcg cagaatgttg aagatattca agcaaggttt tatagatttg caggggcgac 122340
atgggcacca tttgccgcag ctcctctccc ccaagcatgt ccccaatccg ggcaaaggca 122400
ttgatgatat ttttaagcgc ctgaaagtta gaaagagagc gcccgataag gtcgcgaatg 122460
tttttagcct ggcttgctct gacgggacgg agggtaccaa cgcttcggcc ttgttggatt 122520
tcagccgcaa ctttttcgta gtagtggccc gcaggagcat tatccgtaaa gacgttggag 122580
tcgttgcctg tggaggtggg aaaactttca aagacttgtg caagcgtgtc ccctgttgtc 122640
tcggtgaacc atcgtcctat aatgcgcacg ccatccagca tctgttggac tgtttgaata 122700
gaatctatgt tgtttacaaa cgttttggta atgtttttaa gataaagatc tagcccttcc 122760
agagctcgat agaatcggcg ttttacatca tactccagct cgatggcgct tacggttgcc 122820
ttccagtcta cttcctgggc acctccagga tttgggccca cgtgtcctct ggcaagatct 122880
acagccggag aattaatgcg cgcatttttt tccgtatcca actgcatgag gcgtcccgca 122940
atagcatctc cgagaatagt ggcatagttt tcctcgtagg attgaaactc ctgtttgtta 123000
tgcgttaaat tggagtaaat ctgggccaca taatagtaat acataaaggt gttaattgcc 123060
tggttgaggt caacctgcga tcgcgcggcc ttgctgagcc caagctcttc aactgttagg 123120
gcagcaccgc ctacccttgt acactcgcag tcctcctcgc ctccatactt tttttgcaca 123180
atatcggtat aaaaatcaat aatctgtagc aagcgagagc aggagtcata aagattttta 123240
aaattagggt cggttttaga tatctcctcc aaaacatttt taacaagcgt aagctgtgtt 123300
aagaaggttt cgcgttcttc tcgtgcggcc gcattggtgt aaaagccgat aagacttaga 123360
tcaagtgcga tggtgcccat atcattaatg cgcgaaagag catctcgaag cctcgttatg 123420
ttcggcgtca aggcaatttc tttaacaagt ttgatgccta ttttttttcac attttccaaa 123480 aagtcgttat aggcttgtgt gcttttattc aaaaattcca tgaggatgtg ctttctatcc 123540
agtctttgcg cttcaatcct cctatctagt ggcgttttct cctcatcgcc cccctttttg 123600
gcacaactgt tctcaaggat tttgtggcgt tcattaaagg tctgtcgcaa caggttcacg 123660
gctttttcaa actcagcaat gttttctgcg gagacaagac cactaaacct tttgaggtca 123720
agctccttgt caaactccgc ccagtttttg ctttgaaggt actgttcaac cttgagtcct 123780

-continued actttctgga gagccttatt aattttattc gcaacagacg cagcaatacc tagattacaa 123840
agtgtgtacg aaagtacttt tccaaaattt ttggttccca agacactatt tgtatcattt 123900
aaaagtttaa taatatccac ctcatccgtc tgcagtttat caagttcctt ttgggtggga 123960
gttaaaatat tgtcaataaa attcgttaaa atgttgattt gcaggttttg ttcatttaaa 124020
agtcgacgat atactgcttc aatcatggtg actgcattaa tgacttcctc attgggggct 124080
gctttggtta cctccgtcac catgcgctcg tgaagttgct taatggcgtc gtttaacagc 124140
ttgatatttt caagtgtatt ttctatactg ccgtgtacat caagatactc tgcgcgcagt 124200
ccatgagtta gggagttaat gtacagaact atttgtcgac atatactggc ggccccttcg 124260
gtggtatcta taagcttatc ctgacctaaa tcaataaatt cctggttaat ggcgtctgca 124320
atcattttac agacggtctc ctgtttttcc gcatttttta caaaggtgga accggctcga 124380
ggatcgggca gttgtttttt gatatcttta agaatatctt cgatgggctg ctttgtgtct 124440
actttgaacc ctattttggc aatcgccctg ataattcctt ctataatccg cagctttgct 124500
ttactcgata cggagtctat gtgataatct ttaatgtgtt gtacaggatt tttgtccccc 124560
ccgccattaa aatatcctcc ccctgaaaaa ggacgagttt gtctttgtat atgatcctgt 124620
aacttcgcat atatatttgc ttctgatgaa ggcagtggtc tactagaggt tgaagatcca 124680
cggttaccca ttataataaa aaaaataaag atttaaaact acaaatattt tgctgtttat 124740
aaacccaatc atataagact aactaaaaca ttaaatgtag gtgagataaa agcttatttt 124800
ttttaaaagt ttaataacca tgagtcttac cacctctttt tcttcttcct ttagaggggt 124860
tccataaatg gtttgaataa aattatgtgc tctaataacc ttgttaaaat caggtgcctt 124920
tccatattgt tcaatatgtt gcacagtctt ttgtgcaagc atatacagct tggagtcttt 124980
aggtacctcc gatgagggct cttgctcaaa caacgtttca aaggaggatg tgcattcatt 125040
ggtttcatta tcattttttt catgaatgtt ctccgaagat gctgaggatt ccgtctcctc 125100
ttcaaacagc acatgcagaa tcatattcca ttcttcttga gcctgatgtt cagtataccc 125160
ttgccctgca tatatacgag cagatttcac aatatcatac ttaacagtac taagcaatgt 125220
ttttatagcg gtcgtaacaa ttctaccgct attgataatc tcaacagaaa accaattata 125280
caggctaccc gcatgaaaca caacttgtga agatgatctt aaatccgttt tgaagatgac 125340
ctccattttc atggatatat ttaaaataaa atccattcaa ttttaaaatt ataaaataat 125400
aagaagatgc cctctaatat gaaacagttt tgcaagattt ctgtatggct acagcagcac 125460
gatccagatt tattagaaat tatcaacaac ttatgtatgc ttggcaattt atccgcggca 125520
aagtacaaac acggagttac cttcatttac cccaaacagg caaagatccg cgatgaaata 125580
aaaaaacatg cctactccaa tgacccttca caagccataa agaccttaga atcactcatc 125640
cttccatttt acattcccac tccagcggag ttcaccgggg aaatcggctc ctacaccgga 125700
gtgaaattag aggttgaaaa aacggaggcg aataaagtta ttttaaaaaa tggagaagcg 125760
gtcctagtac cggcggccga ttttaagccc tttcctgatc gccgactagc ggtctggatc 125820
atggagtcag gctctatgcc cctggagggt ccccccctata agcggaaaaa ggagggtggg 125880
gggaatgacc cgccggttcc taagcatatc tcgccgtata ctccgcgcac gcgtattgcc 125940
attgaggtgg aaaaggcctt tgatgactgt atgcgtcaaa actggtgtag tgtcaataat 126000
ccctatcttg ccaagtcggt ctccttgctg tctttcttgt cgctcaacca tcccaccgag 126060
tttattaagg tactgccgct tatagacttt gacccccttgg tgacctttta tctacttctt 126120
gagccctata aaacgcatgg ggatgacttt ttaattccgg aaaccatttt attcagccct 126180

-continued

```
accggatgga atggtacaga tctgtatcaa agtgccatgc tggagtttaa aaagtttttt 126240
acccagatta ctcgccaaac ctttatggac atagccgatt cggctactaa ggaggtagat 126300
gttcccatat gttactcgga tcccgaaacc gtacattcct atgccaatca cgtgcgtact 126360
gaaattttgc atcacaatgc cgtcaataag gttacaacac ctaacctcgt cgtgcaggcc 126420
tataatgagc tcgagcaaac caataccata cgacattacg gccctatttt cccggaaagt 126480
accatcaacg cactgcgttt ttggaaaaag ctgtggcagg atgaacagcg atttgttatc 126540
cacggcctgc accgcacgtt gatggatcaa cccacctatg aaacctctga gtttgcagag 126600
atcgttagaa atttacggtt ttcgcgtccc ggcaataact atataaacga gcttaatatt 126660
acaagtcccg ctatgtacgg cgacaagcat accaccggag atattgcgcc caatgataga 126720
tttgccatgt tggtggcctt tatcaacagt actgactttt tatacaccgc gattcccgag 126780
gaaaaggtag gggggaatga aacccaaacc agtagcctta cagacctagt tccaacacgg 126840
ctacactctt ttttaaatca taatctaagc aaacttaaaa tcttaaaccg cgcgcagcaa 126900
acggttagaa atattctttc aaatgattgt cttaatcaac tgaaacatta tgttaaacac 126960
acgggaaaaa atgaaatact aaagttactt caagaataag tatgttgata cctgtggtgt 127020
gttttacctg tgggtttcct attggaacct acgcggcaat tttgacaagg gctcgtaccg 127080
agtatattaa aaccaaaatg ggcggaacat tgccgcaaaa tatcccatta gatgcttctc 127140
tccagattga gttaaaagac ctcattacag ctctgggaat cccaatgcgg gtgtgttgtc 127200
gcactcattt aattactacg ttggattatc gtaaatatta ttaatatcta aaattgaaaa 127260
aatattttta atgttactag taaaaatgac tacacacatc tttcacgcag atgatctcct 127320
acaagcattg caacaagcaa aagcagaaaa aaatttttca tctgtatttt ctttagattg 127380
ggataaatta cgcacagcga agcgtaatac aacggttaaa tatgttacgg tcaatgtcat 127440
agtaaaaggc aaaaaagctc cgctaatgtt taactttcaa aatgaaaaac atgtaggaac 127500
cattcctccc agtaccgatg aagaggttat acggatgaat gctgaaaatc caaagttttt 127560
ggtgaaaaaa cgtgacaggg atccctgttt gcagttcaac aaatacaaaa tctcgccgcc 127620
attggaagat gatggtctca ctgttaaaaa gaatgagcag ggtgaagaaa tataccccgg 127680
cgacgaagaa aaatctaagt tgtttcaaat tattgaactg ttagaagaag cctttgaaga 127740
cgctgtgcaa aaaggtcctg aagccatgaa aacgaaacat gttataaaat taattcaaag 127800
aaaaatttct aatagcgcgg ttaaaaacgc agacaaacct ttgccgaatc ctatcgcacg 127860
cattcgtatt aaaatcaatc ccgctacaag tatactaaca ccaatattgc ttgataaaaa 127920
taagcccatt actttacaga atggtaaaac aagctttgaa gagttaaaag atgaagacgg 127980
cgttaaggcc aatccggata atattcataa gcttatagaa tcgcattcta tacatgatgg 128040
catcattaat gctagatcta tttgcatcag caatatgggc atttcatttc cgctttgctt 128100
ggaaatggga gttgtaaaag tttttgaaaa aaataatggg attgatgtga actccattta 128160
tggctcagac gatatttcaa ctcttgttaa tcagattgct attgcttaaa caatttgctc 128220
aaaacaagct tataaacgtt tcttaggtat gcgatacgta aatcctaatt ctttaataag 128280
ttctttttca gtagtgattt ttagaggtac taaagtttga tttttaaata atccatactg 128340
atttagctta taattctttt tttttaacgc agctcgaatt cttattaaat aagaaacggg 128400
acccgtaaaa tgaagtactg cgtatggctt ttcctcggct aaggccgtaa aaagatcaag 128460
ttgatatgtg ttttttttcc attcaataaa aagtacacac tttcgttctc cgcagacttt 128520
```

-continued

```
tacagaaaaa gaaagatcct ttatgcgaat gttgggcagg acgtgtttta aaagtttttt 128580
ttctggaaca ataataagaa gatccacgtc attaagcatt ttctcttcgc gtcttaagct 128640
accaacagca acgatgtttt ttgataaaat ttttataagt tgtccattat attcaaacgc 128700
aagtcgggag cgtaagtcat ttacaatttt ttttccttga ataagcgtta acattttata 128760
tttaatatta aaatcttttc attttatata ttatatacgc aaaatggcac ttgatggttc 128820
aagtggtgga ggctctaatg tagaaacatt acttatagta gcaatcattg tggttattat 128880
ggcaatcatg ctttactatt tttggtggat gccccgccag caaaaaaaat gtagcaaggc 128940
tgaagaatgc acatgtaata acggaagctg ttccctaaaa acaagttaaa acatgcaatt 129000
atatgcatgc atataaacgc atgcatataa acgcatacat ataaaatgcg taaatactat 129060
ataaaaaact ataacatatc aatcaaggaa tcaacacttt tataattttc cgtaatatat 129120
ttttcatcca taatgatgtc agagtacatg gtccctatgc gaggaacaga gcccataagg 129180
gtaggcgcgg caataccgta aatgggattc acggcggagt caaccgcagc atctgtcaag 129240
acctggactg gagacgacaa ggccattcgc aacaacacgt tggaaggctc tcttgcatta 129300
agccctgcct tttctagaga ggtaacctgt cccgttcttg tcatgagatc tgcgtacatg 129360
agtaaatgac gatggttggg acccttgtcc cccataaccg ttctaatttc actaataatt 129420
ttttgccgtg ccgcttctat gccgtaaagc tccatggtgt ctcctataga ggacgatacg 129480
atggtgtatg ggtcgatgtt atcatcaagc attgcgccaa aaatattagt cccgtttgtt 129540
ttgatggcgt agatattgtc tagtcttacc agtttcccct gggcatccac acggtggcgc 129600
ataagcttaa caacattcgc atttttgatg cctggtattc ctctaatcgt gctatttaat 129660
agtttatcca ccacatttac ggcaattttt tcatccgtag ccattcgggt attggtactg 129720
cgtctaaagg cgctttcccg taggtatatg cgaataatga tgggaatccc tgaggccgtg 129780
ttttccacag aatgcatgat gtaggtgttg gggtgtttag ctcttagact attaataata 129840
ctttctagac taatgctttt taatatcatg gttgttttgt ttaattccaa gcggatacac 129900
cagtttgcaa tatcctctgg gggctgtagt agaggatggt tttccagaaa atccgtcatc 129960
cattccacat cacttgcaaa atcggggtac atcacatttt tttttgtgct tgaatacgtt 130020
tcgtacaata ggtgccactg caatatcaac cgttcgaacg ttataagctc tatgctgtta 130080
gcaatttctt gcgcatatgt tttatttgtt tccacttccg ggttctttag acgtaaaagc 130140
atttcagagg attgttcagc ctctacgggc ttcgcgctaa agatctcctg gggccgcaca 130200
attcccgact tgttggttcc cccggccacg gaccggtggt gggagtccag catatattgt 130260
gtcaagggct ctgatacgga ctgcgccgcc aggattccca ctgcctcacc gtagttaata 130320
agactttgag tatattgtag ccttatgagg tccaggatgg cactcatctg ctcgcaggta 130380
atgtttaatg ttttaacggt tgccagttcg atgcgaataa gcatgcgcat cagagaggca 130440
gcccgtttaa gataaacggg tatgggcgtt tgtagtcgtt cctgaatgtt gttaataaac 130500
acgtatggaa gatttttgca aaacgttttg accatcgcgt atttttgtag aatacttttt 130560
tcgtcgaagg gaagcacgcc actggtggag ctcagtagaa tgttttttac gatgctggcc 130620
acgtttaccg gcacctgtct aacatctgta agcagctgac tgaaattaaa attttcgacg 130680
tttaggaaga tctgtcgata tttatctcta tcctttttaa ggcgtgaaaa ttcttcttca 130740
aacaagggcg attgtatccc ggtgtacttg aatttgtctt caagttcctg gtccgacagc 130800
atgatggttt caaaccgtac ggtttcaagc tggcgcgcat caaggccgtc ctctccgtac 130860
aactgctgca caagacgcgt atcgatggaa acccgtcggt aataatccac aatacaggat 130920
```

tgaaggccaa agatggcttt acggttggca tagcctgtgg atgatgtcga taatgctttg 130980
ttgatcaagt cgaatcttcc attcatttcc ccaaagataa attcagggga ggtaaggccc 131040
gcaatatagc tgttgcagat gaacccgtag gcctgcgcct ccagggcaaa cctggggtag 131100
tacaccaggg tcctaccgaa ggaaaactgg ggttgaatgc gttgtgtatt aatttcaatt 131160
tggccgatgc ccgccatgat gtgaatcata ttggggtttg agcccttggc gccagtggcc 131220
accatctgaa aaagcccatt ggtttccgga ttaatggaat tcataatcgg ctttaaaatt 131280
ctatcgggaa atttaagcgc attcagctgc aatttttcgt agaagtcatg cgttgtcagg 131340
cctataggcg gcatgatgtc tccatgaagc agccggttgt ttatttcctc cgactcaagc 131400
agcagttcat tgataatttc ttggacctcc tgatgtgcct ccggggttag gagcatgtcg 131460
gccgtggaca ctgtgaatcc ggcgttgcgc acgtagttta gggcgagctg ctgggtcgca 131520
aatatcattt tcaaggcctg ctgcggccca tacctacgcg aaataaggtg atagattcca 131580
ccggaggaac ccgctccgac ggcctttttg tcaaggacgc cttcaatgag ttcgccgttg 131640
cgtatttgtg tagagatgtc ctgcttgtta taatgcatgt agggtgcata cacttctgag 131700
taccatgtgg gggctcgttg ataattgatg ggggtctgcc tcagtagcat agatacaacc 131760
gatttgccat ccagcaggtc agttggggag tagttggcaa aacaaggtgg gtcggtttgg 131820
gttgtttgaa acaaccccat ggcgtgcagc ttgttcatca catttttccc catgggggtg 131880
ttcgtgcgtg taagcaaaaa gcttcccacc gtggagtcct gcacctgccc attaacggga 131940
cccgagctct ttgtggaaat gaaccagttt cgcacagaac aaagtagttc ggcctcaacg 132000
cggctcatga cgctccaggg aacccagaga ttcatctgat ccccgtcaaa gtccgcatta 132060
taccaggcac atgcgctgac attcatttga aacgtagaaa tttttgggtt ttcaagaacg 132120
acaatccggt gaacccctat gctgcttcgt tcgagagaag gctggcgatt aaaaaacgcg 132180
acgtcgccag tgacgacgtc acggtaaagg atgtctccta cctccagcct aaagtcttgt 132240
ttgagaccct caatgtcgtg aacggattgt gttatttgct tatacactct tgaacaacca 132300
gggtactggc gctttccatt taaaaaatag ggcattaatc tattaatatt ataatgttgc 132360
actgtttccg caacttgcag cgttcgtgca aaggaaatgg gatagccaac ctcgtccagg 132420
tgaaggtctg agttcccgca gatggtggac cggctgatcg accatacctg gctgcccagt 132480
agggatttac gaattcttcc ctccttgcga ggaagtcttc gcatgatgga gggagcaggg 132540
cgtgccccca tgacgatccc acgctttccc gtgcctccct gggttgcggt ggtggaaacg 132600
gaatccaaca aaaagttata gtaaagttgc tgtatggttt gcaaattgcg gtcaatattt 132660
aaaggtattt tttggccgcg cacgatttgt aggtccttcg ggatcagcag attctttcga 132720
accagatact gaatcacgtt gttaatgtcg tgaaagcttt gggggcctga cccgattccc 132780
aatctgatgc caggtcgtat gctgatgggg gggatctgaa tggccttaag cacaagtttt 132840
tcgggatggg agtttttact tcgccccagt tttacaacgg tgtcgtaggt tacgcgcgaa 132900
aaaatctctc tgatgatctg cgggtacagt ttgtcaatct tgccctgctg atccgcccaa 132960
aaggtaaaat aatcttccga gtccttaaca attttggggt gtactgcctt acagacgtag 133020
cactgctttc cttcggtttg gcttgaagcc gcttcaataa gacgcttagg cctaataagg 133080
tgctcgtacc tctttaggtc aacgatggga gccccgcagt tgagacatat aacccttaac 133140
catcgtcgta tttcggcgat gaagagcggc tgaagcaccg gagcatgcat ctgcagtatc 133200
ccagggtgtc ccatacattg cttgcgctgg tgtgagcaag tgatgcattt ataatggtga 133260

-continued tcggtggttc ccattcgcgc atcatagata ccccccttcgg cgggaagggt gccctcaaat 133320
aaattagaaa tggtaacctc cataacgcct tgcctcttat gatcattgtc accggcaata 133380
ttgaactgaa cggcggctat ttcggcatat ccagcctcca tatttttgct aaatacataa 133440
taaaacttca aatgttaaaa aaaataacat cggttggcat atttttttgt taaaaccaag 133500
tgttaaatga tttctaaaac atttatcggt tcacgaaaac ctaccgcacg ggcctgaaga 133560
ggaatgccag ttttgggggga aagctcggca tattccacgg taagctcttt tccataaaga 133620 tgtttttttaa ataaggcggg cgtgagtttt tgaaaaagag cataacgatc cgcgtacgtc 133680
aaatgcttag gagtgactac aaaccgcttt ttgtttggca attcgcaaac ccataaaatg 133740
gcgcctaagt cctttccctt ttttccctga gtatagtcca ctaaaataaa ttcagcgtct 133800
agcagcggtt tcagcttggc aagatgcgct gagtggtagt tgttgtatcc cggctcatag 133860
ggcccattgg cattgcgtac gatggctccc tcgtagccct ccttaataaa ctgcgcctta 133920
agcctaaggg cctcatccac attcttcacg ctaaaatttt caacttggtg gataaaggta 133980
agatcttcct tctgtttaaa aatatttgtt aatagctgtt gtctcttgtt ggaaggcatt 134040
tgaagctgat cactccaaaa acagtcaaac acgtaaaagt gcagctcgga ggaatctgtc 134100
ttcgcattcg cctgccccgc gatccattgc agaggtttgc ggtgtaaata aagctcacca 134160
tccaaatata ctctcacgtc tataaataaa taaagctgtt tgagctcttt tttaatattg 134220
tcaagaccta aaaattcctt tttcgtgcgc gaatacaaga gaatgctacc atcgccctgc 134280
tggcaggcca cagctcgaac gccattacgc ttgcgctgca cgatgggatc tgtttcttct 134340
tcaaaaaatg tcttaggaat tatattaaaa tattttacca gcataggggg gataattcct 134400
ctatttgtgt gggctccccg cttttgtctg gcatggcgat tatatttact aagggcgtcc 134460
ttgaatgcct gatggactac cgttgtggca ttttttttac ccaagttttt tccctcggta 134520
acacgtgtca tttttgatat ccgcaccgcc ccttcttcca caaaaaaattt tgtgaaaatt 134580 tcagcaacgg cgtcttttac atctgtggaa aacatctcat ctgtgatggg aatgatcgtg 134640
ttgtgctgca ccacttgcac acaaataatc catgaggcct tttttccgct tttcgtttca 134700
gactcaatcg gaggaaaaca aaaaatgttg tttgaatatt gcccaggaaa ttgatttagc 134760
atggttttaa caataaaata agcctatcaa ttttttttata atttgaatag ttattccaaa 134820
ttcaatatgg cttctttaga taatttagtg gcacgatatc agaggtgctt taatgaccag 134880
tctcttaaaa atagtactat tgaacttgaa atacgttttc aacagataaa ttttttatta 134940
ttcaaaaccg tatatgaggc acttgtggca caagagatcc ctagcaccat ctcccacagc 135000
atccgctgca tcaaaaaagt tcaccatgaa aaccactgcc gggaaaaaat tttgccgtcg 135060
gaaaatcttt acttcaaaaa acagcctctc atgtttttta agttttcaga gcctgcatct 135120
ctgggctgta aggtctcgct ggccatcgag cagcccattc gtaaatttat cttggactcc 135180
tccattctcg ttcggctcaa aaatcgtacg acctttcggg tatctgaact ttggaaaata 135240
gagcttacca ttgtaaagca gctgatggga agcgaggtct ctgcaaaact tgccgctttc 135300
aaaacgcttc tgtttgacac cccagagcaa caaacgacaa aaaatatgat gacgttaata 135360
aacccagatg acgaatatct ttacgaaata gaaatagagt atacaggaaa gcccgaatcc 135420
ctaacggcgg cagatgttat aaaaattaaa aacacggtgt tgacacttat ttctccaaac 135480
catttaatgc taacagccta ccaccaggcc attgaattca ttgcctccca tatactgtcc 135540
tcagaaatcc ttcttgctcg tattaagagc gggaagtggg ggcttaaacg cctcctcccc 135600
caggtgaaat ccatgaccaa agcggattac atgaaatttt atccgcccgt tggctactat 135660
gtaacggaca aagcagatgg aattagaggc atcgccgtca ttcaggacac gcaaatttat 135720
gtggttgcag accagttata cagcctaggt accaccggca ttgaacccct taaaccaacc 135780
attttggacg gtgaatttat gcctgaaaaa aaagaatttt atgggtttga cgtcatcatg 135840
tatgagggca atctattgac gcaacagggg tttgaaacaa gaattgagtc tttaagcaag 135900
ggcattaaag tcttacaagc gtttaacata aaagcagaaa tgaagccctt tatttcgcta 135960
acaagtgcag atcccaacgt gctcctcaaa aactttgaaa gcatttttaa gaaaaaaact 136020
cgcccatatt ctattgatgg catcatttta gtagaacctg gcaattctta tctaaataca 136080
aacacccttta agtggaagcc cacctgggat aacacattag actttttggt gcgaaaatgt 136140
ccggagagtt taaacgtacc agagtacgcg cccaaaaaag ggttttccct gcatctacta 136200
tttgtaggca tctccggaga gctttttaaa aaattagcgc taaattggtg tccaggatat 136260
acgaaactat tccccgttac acagcgcaac caaaactact ttccagtaca gttccagcca 136320
tcggattttc cattggcatt tctttattac cacccagata cctcgtcatt ttctaatata 136380
gatggaaagg tccttgaaat gcgttgtctt aagagagaaa tcaatcacgt cagctgggaa 136440
attgtaaaaa tccgggagga taggcagcag gatcttaaaa ccggcgggta ttttggcaat 136500
gatttcaaaa cagccgaact cacatggctt aactatatgg atccctttc ctttgaggag 136560
ctggcaaagg gcccttctgg aatgtacttc gccggtgcca aaaccggcat ataccgcgct 136620
caaacagcac ttatttcctt tattaaacaa gaaatcatcc aaaaaataag tcaccaatcc 136680
tgggttatcg atcttggaat aggaaaaggg caggacctag gacgttacct ggacgcaggg 136740
ataaggcatc ttgttgggat cgataaggat caaaccgcgc ttgcggagct tgtttatcga 136800
aaattttcgc atgctacgac ccgacagcac aagcacgcta ccaacattta cgtgttgcat 136860
caagacctcg cagagcctgc gaaagaaatc agcgaaaagg tacaccaaat ttacgggttt 136920
cccaaggagg gagcttcttc cattgttagc aacctgttta ttcactatct tatgaaaaac 136980
acgcagcagg tggaaaacct ggccgttctg tgccataagc ttcttcagcc ggggggaatg 137040
gtgtggttta ccaccatgtt gggagaacag gtcttagaat tacttcatga aaatagaata 137100
gagctcaatg aagtatggga ggctcgtgaa aacgaagtgg tcaaatttgc tattaaacgt 137160
ctctttaaag aggatatatt acaggaaact gggcaagaaa ttggagtcct gttacccttc 137220
agcaatggcg acttctacaa tgaatatctt gtgaacacag cgtttttaat taaaatattt 137280
aaacatcacg gcttttccct agttcaaaag cagtccttta aggactggat tccagaattt 137340
caaaacttta gtaaaagttt gtataaaatt cttacagaag ccgataaaac ttggacaagc 137400
ctttttgggt ttatttgtct gcgcaaaaat taaatatttt ttcataagaa gtactaccca 137460
ggttttaaag aaatagctaa aaatatcata tggatactgc catgcagctt aaaacgtcta 137520
ttggtttaat tacatgtcgt atgaacaccc aaaataacca aatagaaact attctggttc 137580
aaaaacgtta cagccttgct ttttcagaat ttattcattg tcattactct ataaatgcta 137640
atcaaggtca tctgattaaa atgtttaata acatgacaat taatgaacga ctgcttgtca 137700
aaacactgga ttttgaccgc atgtggtatc atatttggat tgaaactcca gtctacgaac 137760
tataccacaa aaaataccaa aaatttagga aaaattggct tctcccggat aatgggaaaa 137820
agcttatttc attaatcaac caagcaaagg gctcaggaac acttctatgg gaaatcccta 137880
agggtaagcc gaaggaagac gagtcggacc ttacctgtgc catacgggag tttgaagaag 137940
aaaccgggat tacccgcgaa tattaccaga ttctcccaga gtttaaaaaa tctatgtcat 138000

-continued actttgacgg taaaacagaa tataagcata tctacttcct tgcaatgtta tgtaagtcgt 138060
tggaggaacc caatatgaat ctttctttac aatacgaaaa ccgaattgcc gaaatttcta 138120
aaatttcttg gcaaaatatg gaggctgtac gttttattag caaacgccag tcattaaacc 138180
tggagcctat catcgggcct gcatttaatt ttattaaaaa ctatttacga tacaagcact 138240
aggatgccgc attaaaatgc cacataaggt aatacactag gaatgtcgca cacgcacaag 138300
aatacaacgt cgccggagat ttattatcta gtacacgttt tatgtatgta caatccgcct 138360
tcatttaata tattgagcgg atgtactatg tatttatttt aacaaaaaac attatttttt 138420
ttaatcttca tcatctgttt ttataaactc agtaatatca aaagtagctt gtggggtttc 138480
agagggttca ccttggttat cctccgtgag gataacatgt tcttcaggtt cgtcgtcact 138540
ggagaaccca tcatttaatt cctcttcact caacatctgt aaaaaatctt ccaagctttc 138600
gctatcgtta aaatcctcat catccataag aataatggta ccttcctcat cgtttcctcc 138660
ttgtttcgtg tctaaatagg cctgcatggc atttgcaaaa gtatcaaaat aggctgagtc 138720
agattgctgt tccaaaatat ggccttgcgt attaaatgtg gttgcatcgt tgttaaatgc 138780
ttgcaaatac agtaagggat ttatatccat tattattaag caaaaaaaat ttaaattatt 138840
tttcgaccga tgttaggtaa aattaaacaa ttgctatagg tgttaagcaa tgtttattga 138900
ttttaagtac tcaacaacca tgatgtaaat actatacagc acttttggat ttttaatcaa 138960
atccagatta atactaactt cttttgtgat acagttcgta ataatagtat cctgctcatc 139020
gttttgtaag atttctttta atatattttt ttttaccggg atactaagca attgattatt 139080
ttcttttaaa aactcctttt gatattcaat cgtcttattc attgaatatt tgtatataac 139140
tataattaca aatgttcaat gaattgttat tcatgtcggg agatggctat ttaaaaatca 139200
tgtcctattt ttctttgctc aataagcatc caaatatttt catggcgttt tattaattgt 139260
tcattattga acgtatcaca aagatcattt ataaattgca gatagtttat tatttctttc 139320
aagagagtaa caaacattac ttcagcagaa catataatag gtaattcagt ggcgttaaaa 139380
gaattttgat cttgttgata cgccaatggc gaggacttaa ggagatttgg gggtcttgcc 139440
caaaacccta ggctgctgtt cttgtttttt agggcgtcat aaagaaatga aagcacattg 139500
caaggcttaa gccgcgacat ctccttcccc ttgggccctt tccatatttt tagatctaag 139560
atctcatccg agcttataga gtaggtatag taaagttttt caaaaaagca tatctgcttg 139620
aagtcttttt tagaacgact ttcaagaagc atttctataa tgttaacaag ttttgttagg 139680
tttaaggcct gttcctgtgt aagctcctct tgcacgtgat agactgaaaa agtgtgctta 139740
ggaatgaaaa tactccccgt ggcactggcc tgttgtctgc caggtatata gtacacgctg 139800
ctgttagcaa gctgtaccgg cacaatttgc cccacttctg caacattatt ttgcgattcg 139860
gacgagggta tgacaatagt tacgggttca gtcaataggc tttcgccgag aataatatta 139920
ctgtcatttt taataatttt aacggccgct attaaatcaa aggcatttaa gtaagaaaca 139980
acagcagaaa atcttacatg catatatcct cttccgctat tattcgtacg cataataaaa 140040
caaggggagc gttgtataac gccagtaata ttaagaataa aactgttttt gaaacactta 140100
cccacataaa tgttttcaag ctccttcaaa agatgagcct ccacatttgt acaaaaattg 140160
gtaggatcat caatattcaa cgttgtctca aaaatttttt ggtcgatcat atctataaata 140220
tattctgtct atttcaattt aaataatata cgaataaata acgagattat tttattaaat 140280
aagcaatggt gtatacactt tgtatttact ttgagatata ctttgtgtat cacaacgtgc 140340
cctaagatgt gtgcacaagt gacggcattt tgtcgttaaa aaggtaaaac cagcggattc 140400
catcctgcat tccatttggt tgattacgag cctccatttc tttttgcaaa aggttattgc 140460
gaatgagtaa gcagagcttg atggcactaa tctttgtaag gtttaaactt atgcccaatt 140520
ggtcagcaat tttttgttgc tcctcccgtc cgcgtgtttc gcatacggct ccccggttta 140580
gcatgcgaat atcagtaatc tcattctttt ttaaaacctg gataggtggg cggattttaa 140640
atttaagggc ctttcccttg ctttccatat agcctatgac gatgtcgttt tcttttcgtt 140700
taacattaat attaagcata taaagcggaa tttcatgcca ggttttatct tctcgcgagg 140760
taataagtcg cacggagtcc tccgtggcat agcccactag agtgttgtca tccccaggca 140820
cgtggcttat aattttaaaa atgtccggaa atggctgaat atcttttttt gaaaaagcga 140880
tgaaaaactt tttataaacc tcgacaaggg cccccatacc tgcaagatta tctataataa 140940
gtgcttctag catcgtatag tgaaatgaag cggggtagtg gatgagtacc tgctccattg 141000
gctcatcctg aaaatccttc tgaaactttt catacaatac ttgaaagggt tctttggtct 141060
gcgagtgttc gaggtatttg gtaatacgga tgctgtgcat cgcgggaggc tgaaaatccc 141120
gaatatatgt ttcaatatct aataccggtt cctttttatg gttaagcacc gcagcgacgt 141180
acaaatgctc aggctttgcc ggcacatgca taatggtgca aagacgattc tgtatccata 141240
attccttgca ctggtttttt gagtagcata gagaaatgag cgccagcgcg aagttgtcct 141300
ctgagaagag tttattatcg atggtaattc cctgtatgag cttgggagtg gaaacagcct 141360
tccatagctc ggagtacgtc cacacggggc gtgccataaa caaagatata ataatattag 141420
aaattgtttt tacctcttgc tccccgtatc cataggcctc aaaggtattg aggacggtgg 141480
ctccgacgtt tgccggcgtg atggatggac taaggggcag actttccaac ataggcttat 141540
caatcttaat ctggttggtg aacccatcaa tggcgtgctt tcgcagcgcc ttatccccct 141600
cctgtattaa aatgtattct tttaattttt gtgcgtactt agcgagctct ggccctccat 141660
cgggtgttgt cgatacgtac aaataaattg tcacgttgcg ctcactgggg gggagctcca 141720
tgtgtgaatt ttttcgcacc accctcccaa atacctgaat aagccgggga atatcaaggg 141780
gcaatgacat aatcatctcg taccgcacgg cctgaaagtt caaaccctcc acaatcacct 141840
tggacccgat gagaatacgc agctggtggc cttccaggtt ggacgaggcg ttaaaaagag 141900
ccaggcttcg ttcgcgtaca gcgggctcta tttcgctgtg cagaatggtg aaccgtactg 141960
gaataaactg atggtcgcta tgtgtgtgct catcgcgaat cgcggcgcag atggagcagc 142020
gggtcgttcc cacaggggac gaaacttcat ttaaaatgcc attactttgt aaaatttctt 142080
gcaagataag aaccccccgac atgcggaccc gattgtggta aattaaaatt ttccccccggc 142140 cttgccgaat aatggaaaga atgtctttca tcatttgagt gtattttccg ctataaaagg 142200
ccaatcccga gatgtgcgtt ggtggctgca gcgacaaaaa gctgccactc acattaaagg 142260
gggctctacg cgaaggctca ataatctgta ccccgttttc cagaagccag tctgtgcttg 142320
ccatagaaag ggcggtgggg gtttccgtcg agttaaacag gccgtaagcc ttgggttccg 142380
tttgttttga aaattttggg ttgggaaaca ccatgtcata aatgctgtac gcattactcg 142440
agattttagg gtcagggccc agctgtttaa gcgtttcaag ctgatactca gacatggggc 142500
attcgatgaa atgtaagtac ggcaatgttt cgtctttata ggacaacatc tttccggcaa 142560
atattctttc ggggtaaaaa ttggtgttgg tatccaacaa aaaagatacc cttccggtgc 142620
tcagtctttc cacaagagct agggcgtcct ttttccattt aacggaatgc ccactgctgt 142680
caaacagttg ctggcgctgg aggggctggc cgttgggcag ctcatgccgc ggaaccaaaa 142740
ggtttaacag gtcgacgtat tccatgacac tcccggttac gggcgttgcc gacatgaaga 142800
cggccctggg ggcctggtga ggtggaaagg catccaggac atactgtaaa gcgatgccat 142860
aattatttcg ttcctggata ttgtacacgt tgtgtatttc atccgcaatg agcagtcctc 142920
ccctaagttg ctccatgatt ttttgattca cccggatgag gccgtttgtc tcggcctcgc 142980
taattttttg cacgaactga gatatatcgt tctcattcaa tgtatcttct gcttcgtcag 143040
aacgatgaaa cagagaaagc acatcaaagt ttttctcttc acccttactc gtaatattga 143100
aaagcttgga tgcaaattcc ttatagccgt aaaactgaaa aaagcctccg cggtttctat 143160
cggttaaacg gcgctttaac gtactaacga acccatttag atgccgtgat tcgaccgacg 143220
tggtgctgcc agactgcttt gcaatgtgaa gaagccggtg tagctcagcg acctccttgt 143280
aagaaacaaa tcccagctca ggacgtctta gcatttctgt ttgaatgatg gcgcgtgtaa 143340
agcctaccac aaaaatccag ggcgcatttt caataaaatt catgtagtgg ttcataaatt 143400
gacgcgcgat ggcaatcgcg gcaatgcttt ttcccgtccc ggtctgccag tttaataaaa 143460
gacgcgagta gggcgtgttg ggattttgaa agttttggac gaaaagctgg gcattatgca 143520
attggagacc cttgatggaa ggaaagggcg acgcgtaggg gtcacacgga aaaaacgctc 143580 gcccccccctt ctcgcagcca ggcccaccga tctggacaaa atgagcccgc agatcacgaa 143640
tgagctcttt ttggtcgaca ggaggggaaa tcaacgattt aaactccttt cttcgcgcca 143700
actgctgcaa aaagtctgcg gcatccaatt cgggatacgc catattatca taaaaaaata 143760 aacctttttta tgaaaacttt tatgtgattc tgtattgcaa ttgtttttta tgaatactgt 143820
aaataagcgt atcaacttgt ttttctaacg aagaggcgtt attctttttt tctggatata 143880
aaataataat aagtataata attaagacta aacagcaggc aatcactatc aaactcatat 143940
tatacttact tttttataaa aagtattata tcttatgaat gcgcaagttc agctaattgt 144000
tcgtcgcttg gaatgtggga ctgcagggag gtggagtttt tcctttttct aaagaatacc 144060
gggaaatggt ggtgaggctc aggttgttgt acatagtagc taggaggagg tttaggtatg 144120
ctcgacttgc agtcaatagt ccggttatag taaacgatgg caacgatgat aagaataata 144180
atgagcaaaa tcaaaatgcc caggagaatc gcagttgttc cgggatattt ggcgattgta 144240
tgggctaaaa ggccttgggt gctttgttta attccctcgc gggttgacag gttatgagaa 144300
agcagtggag acgtttcagt gtccatttat tacaattgaa cagttatatt aatctcaaat 144360
aaaatataac acaaaattaa ttatggccat gcaaaagtta tttacgtata tttacgagtt 144420
tattgaatat cgtaagatgg tgctgttgga agaaaaggta ccatatgata agtttgttca 144480
aatggtactt aatacaggat tttttcgtat taacgcggag acgctgaatc acggaatcgt 144540
atccgtgttt atctttggag caaatggcaa gtacgttcac cacggaggcg acatgagaac 144600
gcttttaacg aatacgctta atgaaaaaaa acattatgaa gaattaattt taatcgttga 144660
taagcccgtt ttaagcaaaa aaaatatttt agatataatc gtcgagcagc gcgctgcaaa 144720
tcccacgatt gtaataaaca tatatcccta ccacctgttc tgcattaaca ttcccaaggt 144780
gagtgccatt cctaaacata aactaattac tcaggaggag gcgcaggagt ttttaggtcg 144840
cgaatatctg caaccgcagg acctcatgca aattagcgcg tcagaccccc cggtggtctg 144900
gctgggagga agaccgggag actttgtgca aattgagcgg ccctcagaga cagctatgca 144960
cgctgttgtt atccgcttta tcaccaagtc caaaatttga gtcccgtgtt taaagatgac 145020
agacagctaa gtaagcatat ctgtaaaatt gtcgatgtcc tctgtggata gagcgctttc 145080
ctctgagcag caaatttttt catacatctc catgggggat ggcgaggctt taatagtatg 145140
taggtcacgt aagaactgtt gtatgatggg atatttgtct tttaaaaact ggggatgttt 145200
cataactgga attatttgaa agataaagac cttccatcca aagtagccaa ccacatttgg 145260
catttcggga cacgcggttt cataaggcat agaatagtga atagtgtact gatctttttg 145320
atacagcgtt tcaagtagtt ggcgaaatgt ttccgcgtcg agcgtgccaa aatcttgagg 145380
agcctcggtg tgctcctgtg tagagcagat cgtgatgatt ccccaggcaa gcgggagcat 145440
ggactctgga gggtggatat ccgtattggt ctcattattc gatcccagct gatgaatgcc 145500
gcacacgcga aacatggcct cgacgtagat gcccatagag ataggcggcg aaagggcaag 145560
accggattgt atttgcggca tatagtagga gggcaccgag ttttttattt ttcggttgaa 145620
tggggacttt atttctacca gcacggggat gcgtttcgtg gcctcatagc gtacgttgtt 145680
aaaaattgtt ttgatttccc aggactgttg agtgtatccc agcgttaggt gacaaaaccc 145740
atcggggcta ttactatgtc cggggtatcc caaataggtc ccatcaatat gaatattgtc 145800
acctatgacg gtggtttggc agaacaactc aagcagatct ttactaacac gctcaaaaag 145860
ggttccccag ctacaagcag cgcggttcaa attcttctta aaaagatttg ctttttccgc 145920
caaggttata taatagcttt tgtaagggtt taaacctaaa acgctggcaa ggtcagagcc 145980
acccacctga gtgcgacgaa tagcatgcca ggcatcggag cgctgctgag gagagtcttt 146040
aaacaggcgt acaaaggttt ccattatact tgttttaaca ggaattcaat ataaaaagtc 146100
aacacagttt gcaatttttc caatctcaag atatagccat acattttttt ttccaattgg 146160
cgaatatgtt taagctcatg tgtttcaata ttagcatccg gaaatttaaa tgcataaaga 146220
tgttcaaagg cctgatttat acacgtatca aaggatctgt ggtatgttat tagcttcagc 146280
atgtgtgcca gatcttcaag atggtctaaa tttatacggt tttccacgtg gtggatcatg 146340
tctgccacat cttgagcccc catccagggg atcacaaggt actccccctt aaagatgatt 146400
cgtcgttttt ttaaaaaatc atgaaaacgt tttaaagctt caagaaaggg gcagttgggc 146460
tttgacccca aaatgctgac gacgatatcc tcgggcatga tgtattcgca gtgaggatag 146520
tagtttacgg actctaattc agcggcccgc cgttttattt cgtatcttgc ccagttattc 146580
agagagtact ccacgcctcc gaccacaaca gacatcctat ctattaaaaa ataacaataa 146640
aaaccttatg aaatctatgt atagtggccg ctaaaatgtc tatattagaa aaaattacgt 146700
caagtccctc tgaatgcgca gagcatctta caaacaaaga tagctgttta agtaaaaaaa 146760
tacaaaaaga gctcacctct tttttggaaa aaaaagagac actcggttgc gattcggagt 146820
cctgcgtaat tacccacccc gccgtgaagg cctatgcgca acaaaaggga ctggacctct 146880
ccaaagaact ggagactcgg tttaaagcgc caggacccag aaacaacacg ggtcttctta 146940
caaacttcaa tattgatgaa acgctgcaga ggtgggccat aaaatacacc aagtttttca 147000
actgtccttt ttccatgatg gactttgaga gggtccatta taaatttaat caagtggata 147060
tggtaaaggt atataaggga gaagagctac aatatgtaga aggcaaagtg gtcaagcgtc 147120
cttgtaacac cttcggatgc gttttaaaca cggacttttc aacgggcact ggaaaacact 147180
gggtagccat ctttgtggat atgcggggcg actgctggag catcgaatat tttaattcga 147240
cgggaaattc tcctccaggt cccgttattc gttggatgga acgggtcaaa cagcagctat 147300
taaaaataca ccacaccgtg aaaacgcttg cagttaccaa cattcgtcac caacggtcgc 147360
agaccgagtg cggcccctac agcctgtttt acatcagggc acgcctcgac aacgtgtcat 147420
acgcccattt tatatccgct aggattaccg acgaagacat gtataagttt agaacccatc 147480

-continued

```
tgtttcgcat cgcataaact aataaagttt gaattcttta taggaataaa aatggaagcg 147540
tttgaaatca gcgatttcaa agagcatgcg aagaaaaaaa gcatgtgggc tggcgccctc 147600
aacaaagtca ctatttcggg tcttatgggg gtctttaccg aagatgagga ccttatggcg 147660
ttacccattc acagagacca ctgccccgct ttgttaaaaa tttttgacga gatcatcgta 147720
aatgccacgg atcatgaaag agcttgccat aacaaaacaa aaaaggtaac ttacattaaa 147780
atttcgtttg ataaaggtgt gttttcttgc gaaaacgatg gcccgggaat ccccattgca 147840
aagcatgagc aagccagtct tatcgccaag cgcgatgtgt atgttcccga ggtggcttca 147900
tgtcactttt tagccggaac gaacatcaat aaggccaagg actgtatcaa gggggggaacc 147960
aacggcgtcg ggctgaagct cgccatggtg cattcgcagt gggccattct taccaccgcc 148020
gacggcgcgc aaaagtatgt tcaacatatc aaccaacgcc tagatatcat tgagcctcct 148080
accattacac cctccaggga aatgtttaca cgtatcgagc tcatgcccgt ataccaggaa 148140
ctagggtacg cggagcctct gtctgaaaca gagcaggcgg atctttccgc ctggatttac 148200
cttcgcgcct gccaatgcgc ggcctacgtg ggaaaaggca ccaccattta ttacaatgat 148260
aagccttgcc gcacgggctc tgtgatggcg ctagccaaaa tgtacaccct gttgagcgcg 148320
cctaatagca cgatacatac ggcgaccatt aaggccgacg caaagcccta tagcctgcac 148380
cccctgcagg ttgcggcggt cgtgtccccc aagtttaaaa aatttgaaca cgtgtccgtt 148440
atcaacgggg taaattgcgt aaaaggagaa catgtcacct ttttgaaaaa gactattaat 148500
gaaatggtcg ttaaaaaatt tcaacaaacg attaaagata aaaaccgcaa aacaacatta 148560
cgagacagct gttcaaacat ctttatcgtt atagtgggtt ccattccagg aatagaatgg 148620
accggccagc ggaaggatga acttagcatc gcggaaaatg tttttaaaac gcattactcc 148680
attccttcta gtttttttaac aagtatgaca aagtctatcg tggatattct tctgcaatcc 148740
atttctaaaa aagataacca taaacaggtc gacgtagaca aatatacgcg tgcccgcaat 148800
gcgggaggaa aaagggcgca ggactgcatg ctactcgcgg cggaaggggga tagcgcactt 148860
tccctgctgc gcacgggact aaccctggga aagtccaacc caagcgggcc ctcctttgac 148920
ttctgcggca tgatctccct gggaggagtc atcatgaatg cctgcaaaaa ggtgacaaac 148980
attacaacgg actctggaga aaccattatg gtgcgcaacg aacagcttac caataataaa 149040
gtgttgcagg gaatcgtgca ggtattgggt ctagacttca actgccatta caaaacacag 149100
gaagagcgag caaagctgag atacggctgc attgttgcgt gcgttgatca agatctggat 149160
gggtgtggaa aaatccttgg actgctgctg gcctactttc acctgttttg gcctcagctt 149220
attatccatg gtttcgtaaa acgactgctt accccgctga tacgtgtgta tgaaaagggt 149280
aagaccatgc ccgtggaatt ttactatgaa caagagtttg atgcctgggc aaaaaagcag 149340
accagcttag ccaaccatac cgtaaaatat tacaagggat tggcggcgca tgacacccat 149400
gaagtaaaaa gcatgttcaa acattttgac aacatggtgt acacgtttac cctggatgac 149460
tcagcaaagg agttgtttca tatttatttt ggcggggagt cggagttgcg aaaaagagag 149520
ctttgcaccg gcgtggtgcc gctcaccgaa acccagacgc agtccattca tagtgtccga 149580
cgaattcctt gcagcctgca tctgcaagta gataccaagg cttacaagct ggatgccatc 149640
gagcggcaga ttcccaactt cttagacggg atgacgcggg cgcggcgcaa aattttagcc 149700
gggggggtga aatgcttcgc ctccaacaac cgtgaacgaa aggtttttca gttcgggggc 149760
tacgttgcag atcacatgtt ttatcaccat ggcgacatgt cgttaaacac aagtattata 149820
aaagccgccc agtattaccc aggctcctcc cacctctatc cggtattcat aggcatagga 149880
```

agttttggct ccaggcacct gggaggaaag gatgcaggat ccccaagata catcagtgtg 149940
cagcttgcgt ctgaatttat taaaacaatg ttccccgcgg aggactcatg gcttctcccc 150000
tacgtctttg aggacggcca gcgggcggaa ccagagtact acgtgcctgt gttgccgctt 150060
gctattatgg agtacggcgc caacccatcg gagggctgga agtacaccac ttgggcccgg 150120
caactggaag acattttggc cttggtgagg gcctacgtcg acaaagacaa cccaaaacac 150180
gagctactgc actatgcaat aaaacataag attactatac tcccgctgcg gccctccaat 150240
tacaatttca agggccattt gaagcggttt ggccaatact actacagcta cggcacgtac 150300
gtcatctcag agcagcgaaa tataattact attacggagc ttcctctgcg tgttcctacg 150360
gttgcataca tcgaaagtat aaaaaaatcg agtaaccgca tgacatttat tgaagaaatc 150420
atcgactaca gtagttcaga aactattgaa attctggtga aattaaagcc aaatagtctt 150480
aaccgtatcg tggaagaatt taaggagact gaagagcaag attccataga aaattttctg 150540
cgcctgcgca attgtttaca ttcacatcta aactttgtaa aacctaaagg tggcattatc 150600
gagtttaaca cgtattatga aattttgtat gcgtggctac cttacaggcg tgagctttac 150660
caaaagcgtc ttatgcgtga gcacgcggtg cttaagctgc gcattatcat ggaaactgct 150720
attgtacgct acatcaatga gtctgcagag ctaaatcttt cccattatga ggatgaaaag 150780
gaggcaagcc gcattctaag cgagcatgga tttcccccgc tgaaccacac gctgatcatt 150840
tcccctgagt ttgcctctat agaggaactc aatcaaaaag cactgcaggg ctgttatacc 150900
tatatactat ctttgcaggc tcgagaattg cttatcgcag ccaaaactcg tcgggtggaa 150960
aaaataaaaa aaatgcaagc tcgtcttgat aaggttgagc agcttttgca agagtctccc 151020
tttcccggcg ccagcgtatg gctggaggaa attgatgcgg tggaaaaggc tattataaaa 151080
ggaagaaata ctcagtggaa atttcattaa acgctaccgg ttttatgatg tccaataggt 151140
gttaagcaat cagttcatca acattttttt caagaatttg aaaagtttgg ataatgttct 151200
gaatactttt ttctaaaaga gttatcaaat cttcttgtga ggccttatga ataattgtta 151260
ataccatttc ttgcttatgg ggaacacact gataccccac aaagctaata tcaggaatca 151320
tttcataaat atatgttttt agcagatttc cgatggtatg ggtttcatct tttatcgtga 151380
taatggcctt tgtttttttcc tcatccatgg aaaacagcac aagttccggc tgcggctctt 151440
caaagttttc ataaattttt tgaatgcttt ggattcggcc aataatgatc cggcaggcgt 151500
tttttaaata cgtgcgaacg gcctggttga tatgtggcag cggcaccgct ggaaagcaaa 151560
gccccaggcg gtggtgacgc gggtctgagg tcatagagct ttgcttgtaa ccgctaagcg 151620
ccatatattc ttttttatcc gttgggtact gttcaatgtc aaggtgggaa aaatgtgttt 151680
taacggcaag attaaaggcg gcatgctttc gtcctatgcc ctttttaata tagatatcct 151740
ctataatcaa cgattttccg ggttgtagga agccaatctc aaaggtagga ttaaaaatcg 151800
ggtatttaag cttagggcct gccacctgga tgagatcgcg gctatagatg gttttaacct 151860
cacagctatt gtttaaactc cgcagagcaa ataccagtgt ctcgtttttc gcataaatcg 151920
gaatgaaatt aatgcggttt ctaataaatt gttccgtcat aaacaggtcc gtggaatcct 151980
cgatcttata cccaccgggc ttaatatcta gcatataatt gggaatttca tcttgcaaga 152040
cccgcgacag gccgtggacc gcggctctgc taatgccctt aaagtccata acaacattga 152100
ccgggacgag gggcaactgc tcctcgagct gaaatagttt tttggccgca tttttaataa 152160
agaggttgga aaagtctatc aaaaacggtt tgatttccac gttttggaaa attttttcca 152220

-continued tttgtattat aaatatatct atatatattc aaattatggt agtttatgac ttgctcgttt 152280
ctttaagtaa ggaatccata gatgtgctac ggtttgtaga ggcaaacctt gcggcgttta 152340
accagcagta tatttttttc aatatccaaa gaaaaaactc gatcacgaca ccccttctca 152400
ttacgccgca gcaggaaaaa atttcgcaaa ttgttgagtt tttaatggat gaatataata 152460
agaacaatag aaggccctcc gggccgccgc gtgagcagcc catgcaccca ttattgccgt 152520
atcaacaatc ctcggacgaa cagcccatga tgccgtatca acagcccccg gggaatgatg 152580
atcagccata tgagcaaata taccataaaa aacacgcgtc gcagcaagta aatactgaac 152640
tgaacgatta ttatcaacat attcttgcat taggcgatga agacaaaggt atggacagca 152700
tgttaaaact tccagaaaag gcaaaaaggg atagcgatga tgaggacgac atgttttcta 152760
taaaaaacta acgacgtaac aattaaacaa aaataaaaat cattataaaa tgaatcttga 152820
atacgtccaa gttgttcaaa aatttaatca agtactccta gaacttacca aaaaagtatg 152880
taccgttgtg ggcgggagca aacccaccta ttggtatcac cacattagaa gggtttgctc 152940
agaatgtcca tccatgccga tgagtatgat aggtccgtat ctgaatgtct ataaagccca 153000
aattctaaca agggacaaga atttttttat gaatttcgat cccgcgcata atgagtacac 153060
ctttatcatt caaaaactaa aagaagcagc ccgaaatatg ccggaagacg aattagaaca 153120
gtactgggta aaacttttat ttttacttaa aagctacata aaatgtaagc cctttattaa 153180
ttaaagaatt gatgcataac taataaatgg ccggtcgtgt taaaataaaa cagaaagagc 153240
tcatagactc tactgtaaaa aacaaaaatg tgatgaatct gttccatgaa attataggct 153300
caaaaggcaa tattaatttt agcgttgtct ggcccaagtt taaaaaaatc aaacagagcg 153360
tttatgacta catttccact ctttctgtgc tggaaaaagc aaacgttatg caaaactttg 153420
aagctgataa gaaactgttg gaactttttg tacaaaagct gtgggctgcc tatgaaggct 153480
atttcaaata tcccgagatt gaaaaatatg aggtggaagg ccaggtaaat ttcaatctcg 153540
tacctcagtg cgtcctcgaa aagtttagcc agttgtatag gataagaatc aattcagagc 153600
ttgtcacact catcctaaac agctgtgcct ttatgagtaa atataacgat tatattctca 153660
aaaaagatcc ctacatacta accataaccc ccggcctatg cttttccccc attcccaact 153720
tcgaggacct aaattttaaa catctttaca acagtgataa aaattctcag catgacaaag 153780
agtttatcat gtttatatta tataagcttt atacggctgc cctaggagtg tacaatgcca 153840
tctcgattcc agacatcgac gtagaagacc ttgaaaatat catcctatcc tcggtgagcc 153900
agattaaaaa acaaattccg cgctgcaaag acgccttcaa caaaattgaa tcttcggtac 153960
acctgttgcg caaaaatttt aacacatatt acagtgacta tgtgggctca ggctacaacc 154020
caaccatcat tatggaacag tacattaaag acatatcaca ggattccaag aacatatcac 154080
cacgcatttc ctaccagttt agaaccatca tcaagtatta ccgcgacatg attgccacca 154140
ggcatcaaac gatggacccc caggtattaa acctcgtaaa gcacgtcgaa aagaaattag 154200
atatgcttga tagagaaaaa aattagtata tatagttatg gtgaatcttt ttcctgtttt 154260
taccttaatt gtgattatta caattttaat tacgactcga gaactatcca ccacgatgct 154320
tattgtttct cttgtaacag attatattat tattaataca cagtatacgg aacagcagca 154380
tgaaaacaat acatttttca tgccgcaaaa aaattctttt aacgaatctt ataataaaga 154440
caaaaaatct aatatacata ttccctacca gtggctggcg cctgaactga aggaagctga 154500
gagcaagtac tggtggggca attatgatcc tcatagcgag cccgttctcg ctggcgcatc 154560
ttgaatatct tcatacgtgg cacgtcacca tcaaaaacat tgcccaacag cacgggcttg 154620
atataaaggt ggccattgtg gtctcaacat cgcatttaaa taattttttg ccaatttccg 154680
gggcgcttaa catcgaatgt ataaccttcc ccagttgcgg catcaaggag atagacctcc 154740
tatgggcgcg cattaaacta tttcaacatt actgcgccat cggtgcccgt cttttatggc 154800
tggtaagtgc tgacatcagg ccccctgttt cagcgtggcc agccatcgcc gacagtctaa 154860
aaaagggagc agatgcggtc gttattccct acccctcccg atggaacaat cttataccta 154920
ccgtcatcaa agaaatagtt gtccaccaaa aaaaatgcct tgtggcggtg gatgcacgcc 154980
accttgatac agatacccag attgtagggg ccgggatggg ctgcatcgtc ctaaccctaa 155040
aggcccttat ggtgcgccta agtattggca aacagcccgt taagatactg tggcccgacc 155100
ttcacggcac tgccgagggc attcctctgg agggggtgga ggttggctgg tttttaaacg 155160
cttatgcgca taaattaaat atacgctgcc taggggctga tcatattgcg cagcacttaa 155220
cttaattctt tatttaaaaa gtccacgcat ccagtggcgg cctacattaa gggcctacgc 155280
acataaatat acactggcta gaagtacgcc ttcatttaaa ccattgaatt atttatataa 155340
tggctgcaaa cattattgca acaagagccg tgccaaagat ggccagcaaa aaagagcatc 155400
aatactgtct gctagactcc caggaaaagc gtcatgggca ttatcccttt tcatttgaat 155460
taaagcctta tgggcaaaca ggcgcaaata tcataggagt acagggctca cttacccatg 155520
ttatcaaaat gacagtattt ccatttatga ttccttttcc tttacaaaaa actcatatag 155580
atgattttat tggtggacgc atttatttat tttttaagga actggacatg caagcagttt 155640
ctgatgtaaa tggaatgcaa taccacttcg agttcaaggt tgttcctgta agccccaacc 155700
aagtagagct tcttcctgtg aataataaat ataaatttac atatgctata ccggtagtgc 155760
aataccttac cccaatcttt tatgatcttt cgggaccgct agatttccca ttagatactc 155820
tttcggtcca tgtggatatc ctctccaatc atatacagct tcctatccaa aaccataacc 155880
taacaacggg tgatcgtgtt tttatttctg gatataaaca cctgcaaacg attgaattat 155940
gtaaaaataa caagattttt atcaaaaata taccgccgct ttcatccgaa aaaataaaac 156000
tatatatact aaaaaatcga atcagaattc cgctatactt taaatcttta aaaacgtcta 156060
agtaataaca tttttatagt ctactcctag ttccgaaata ggctgaattt ctttttttaag 156120 tcctttaaac caaggatgtg atacaagact cttaaaggaa agccgcttat tttcattaat 156180
tgttaaacat tccgtgataa actgttttcc cgtctctgaa atgttctcgg gaatataatt 156240
ttcccgtttc aggatatcat ttaaataaaa attttctgca cgaaatctaa aaagattaac 156300
cgcgaccata cctatcgtcc acacggttaa aggaagctgg tagtaataac cataataata 156360
aaattctgga cacacgtatt cccatgttcc aaacatatta tattggggac gggtttcgtc 156420
taatctaaca gcgcttccaa agtcaatgac cttaatgatc ttttgattta tgtctataat 156480
aaggttctca tccttaatat ccccatggat aaagcccttc tcataaatgt tttgtataat 156540
aagaataagc tggaatatta tttttttggc ttcggtttcc tcaagttttt taaagtaatg 156600
ataatgaagt agatcaacac tatttggaat atattctatg attagtatat gatacatagc 156660
attttcggta tattcgataa gcttaataac accgggagta tcttgcaggg ctttcaacac 156720
gatgacttca tttcctggaa tttctttttt agaaacgtac ttaaatataa tgggttgccc 156780
tacttgatga cccaaaaaga cgttatttct gccaccctca aacatgggtc tcgtcgcaat 156840
gaaatacatg tgctgcgttg tggagatcct ttccaccttt gctgtaggat aaaacgcata 156900
ttgtgcctgg ggattttttta acattttttt aagctgttgt tccggcctgg acatgtttta 156960

-continued

```
ttagctttat atataaaggg ttagaaggtt taatttcaat atatgcctta atgatgggat 157020
tatattcgta aaaggtatag cctaatccta cgtctttgtt tttttggtaa aaaaactgtt 157080
tgccctcgta ggatatgcta taggctttta cttcggcttt tacaagcggt tggcagggat 157140
tgggcaaacg taaatcgcgt tcaaagtttt catgaaaaag caaagcattt gtgggctgac 157200
acatcagaca gccgctttcg ccattgaagg cacattcaat ggccgccctt tttagtaaat 157260
cgcggaaagc agaattaaga tggctctttt caagcccccct ttcgtgaaaa cgctcatcaa 157320
tcgtttttttg ttcctgactg ccttcgggaa tactataaaa cattttttga ttagccaccg 157380
cgatgtacaa aaaaggctgt acggttttct cctcgggcgg tagcgcatcg tggctaccaa 157440
tgcgtataat gcgcgccttc acttgatcct ctcgggcctt atcccagtac ggctctagga 157500
tatgaacctg ccgcccgtat ttgagatcca atccctcagc tcctgtttta gagacgagta 157560
aaattttaat aacctctccg tgtatattca gcggcgaatt ccaaagctgc tggatcatgt 157620
cgcgctcttt agataaaatt ttccctgtaa taagcgtaaa tcgtgttatt ttggaggaca 157680
ggactaacgt atgggtcggc ccatcttccg caaagttttt caccataaga tctttcccat 157740
ccttatgaag gaggatggtg ttgtgccctt cttccaatac ttttaggggc tgaaggcact 157800
ggtagccctc tatttctaaa aagcgggcca cgacgtgaag gcccaattcc acaaactgtg 157860
agtaaatgag cacagggccc ggagacgttt taatattttt tagcatgcgt actattttgg 157920
gactagaatt ttctgtgaag gcctctttgg gcagctgctg aacagcctct gataattttt 157980
catcctcctt tactgttagc atttcggacg cgaagatgct gatcatacgg gaacgcacat 158040
agtaggagga gcctgactct tgctccgatc ctggcaggca gagggcggcg gcatttattt 158100
tttcatacat tcctgagctg gcgtgctttt ccgcgttttc aacgtctcgg gccagcagat 158160
attgcctata ctgctcgggt gacatttcaa ccttttctat aataagagga agctctgtgg 158220
ggaatagctt gttgagctca ttctggtttc cagcgtagct tatcataccc actaggcggt 158280
ttagtagttt gtccgcgttt aaagggctat tcgttgtttt attgacataa gcggtgtaga 158340
atctttcata gtgaagaggt aataagattc gcccgcttag catattaaaa cagggcacca 158400
tttcaaaggg gtccttcgaa cacggggtgc ctgttaaaaa cagaatacga atatttttag 158460
cttgcataat attattgtac agctggcggg catttgtttt atcattggcg ctattgataa 158520
ttcctctaaa gaggttgtgt gcctcgtcaa cgatgagcag gcatccattt agggaccctc 158580
ccgcctttat gatctgctgc cccatgttgt aagcgtctag ggacacaaac ctgaagcgcc 158640
gcgagatttt ttgtagctct ttggagtgat ccgtcgtttc cggatataaa agtttaataa 158700
gctttaacaa agactgttgg aagtttgagt gcaacgactt gggtgcgatc agaatcgggt 158760
tgtaaatatg tgaaagtgag atggcaagcg acaggctcaa aatggttttc cccatgccca 158820
tctggtgata gatgaggagg ccccgtgtgt tttccccctg gcctatccca aatttaggat 158880
ccgaaaaggc ggtgtaaatt aaaaactggt agtatttcag ggctcgtgca aagcgggcag 158940
tgagtgaggt gtctttgctt tcctgaagct ctttatattt ttcatatacc tcttttaggt 159000
atgcttctat ttggacgggg aaggaggtgt tgttgtgcac gcaagacatg actcgttata 159060
aggatcccat attaaaactt cattagaaga atagggctgc tgatagctag cgctgcactt 159120
aaaaatgggg tagccctttt tcttgtaaat ccggtgcctg tcgtagacct ggctagaaag 159180
cgggcttagt gtatctttaa tgtccacaac gatgcgtacc tttttttcat ccgatccctg 159240
ccgggtaata cgtcccaaga tttgctccat gttgtttctg cggggcgttg ccatgatgat 159300
cgatgtcata tgcttgaagg aaatgcctct acgcccgtag ccataggtca gcaagataat 159360
```

-continued ggaagcgctg tgtgcctgag aaagagcggt atttgaaacc ccgccgcata ggagcgccac 159420
ctccggaacg ataatttgaa catctttgaa ttctttggaa agcgcctgat aaaaaatttc 159480
taaaagtttg cgaaattcca cgaaaatgat gatgccatac ggctcatcgg tcccccattt 159540
gtgaggctca gcggtatgca gggagtaaag ccgctttgcc tcatttacga caagttgtat 159600
acgcgaagga tcttgaagta gtttatcaat ggtggcaatg gccgatacct tttcattaat 159660
atacacaggg ctaacgaagt caggatgtcc ctgatattcg atttccctca cgtacccgga 159720
aaaggttgtg gtgggactta cagtcctctg gggctgtcct agatggtgaa taataatctt 159780
gtccatacca tcgggccggt ccaggggtgt agcggacagt cctaatatcc gactaagttg 159840
tattttccaa aaaattttgt aattctccgg cgagtgtaat tcatgtgcct catctaacac 159900
gactagacca aagggctcaa agaactgctc aggcttcttg cgcagggtat taatgattcc 159960
cacgatgacg tcgtactctt tgctcgtcat gtcctttttc ttgcacgctg cattattgta 160020
agcagctaca cgtaggtggg gcaggagcaa tgttagctcg tcgatccact gtatttgaat 160080
cgccttggtg ggcacgatga ccagggtagg gtacaaaagt ttttgaataa tgctgatcgc 160140
aatacgcgtt ttccccaaac cggtatttag atgtaggtaa aagcgcccat agggggacag 160200
gagcttttta tgaatcttat cgaccatttc ttgctggtag ttaaatagtg gaaattctgt 160260
ttcaacgcat gggagggccc gcagcgacac ggggcgcgtc gtgtaaacca tgttaaacat 160320
ttcaaactgc ttttgcagca atatgggaaa ataaatgtat tccccctgca gcgtgaaggc 160380
agtttcctgt cttatggcta tgtgctttgg ctgcccgggt aatgcccgcg ccgtaacggt 160440
gagcgcctta agaacgcgcc cgaaatcatg ttgtaattta ctttgtagct tcttataatt 160500
tattcctatt ccagcaaagg atataatggc ctccattctc acgctggacg ggttatatgc 160560
agaggttcca aaattcttac cagaggcgtt acgagagggc tgtgctggca agaatcctct 160620
aagcttttat attcaacaaa ttttaaattt aatgggatgt gacggtaacg agtaccatgt 160680
tctttttacc agcagctccg aggaagcaaa tactcatatg atcatggccg ccgtgcgtcg 160740
ccatttgctg cggacgcagc aaaggcctca tgtcattatc ggagcagccg agccccctag 160800
cgtcaccgaa tgtgtgaagg cattggcgca ggaaaaacgc tgcgtataca ccatcatccc 160860
cctaaaaaat tttgaaatag atcctgttgc ggtatacgat gccatacaaa gcaatacctg 160920
cttagcgtgc atttcaggca ctaatgctgt tgtcaaaacg ttcaacaaac tccaggacat 160980
cagcaacgtg ttaaaaggta ttcccctgca ctcagaagtg agtgatcttg tttatcaagg 161040
atgtattcaa caaaatccgc ccgctgatag tttttcaata aatagtctct acggcttcct 161100
gggagtcggt gttttgggaa tgaagaaaaa ggtcatgcaa ggattggggc cgctcatttt 161160
tggaggaggg ctgagaggcg gaagccctaa tatacccgga attcatgcca tgtataaaac 161220
gctaacccag caaaggcctt ctatgaaaaa aaataaatac aatacatacg ctgttcatga 161280
aaactttaaa aaacatcagc atgtatatct acccataggg ggcgtgtctg cagaggacac 161340
gtctgcagaa aacatatcta caaaagacat gcctgttgaa ggcccgaagg gactcccggg 161400
ctatatttta tttagcgttg gccgtcgcgc cgaggagcta caaaaaaaaa ttttcactaa 161460
atttaatata aaggttggcc gtgttgttga cttacaagag atactgtttc gtatcaaaat 161520
accccaaaaa tactgggaga cattattgtt catccaatta agagataatt tgaccaaaga 161580
ggacataaaa agagttatgg ttgttttgat gcatttagat accatcactc ctcgtggctc 161640
tcttcctcct ccgagccact cttcttcttt ttcttaatcg tttttgtttg ttctataata 161700
agggaaaaga actccgtggg atcttgttcc ccgtacaggt tatctgcgac cataaggatg 161760
cttagaatgg taaacaggtg agaatacata agggtttgcg ttttaagaaa accctgacgt 161820
tgaatcataa ttgaaaacac cttgcaaagc cgactcatca gttgttctgt aatggcgtta 161880
agcattttct ggaatttttc ttggttttcg ggtgtgattt tatattcatg tagaaagtgt 161940
ttcacacctg aggagaagaa tctttcctcc ttcgagagcc catctttgat gatgggaagt 162000
tccttgatca gggcaaacca ttcctcctct tgggcttgcg gattctgaag atactgatgg 162060
cagatatggt ttagaatggt gcacacgtag ctaataagct ctgagctgat tctttggttg 162120
gttttcaaat gttggcgaaa gtagtttttc accgaagtgc atgtaataaa cgtcttcatt 162180
ttcttataat atacaacagt atgttgagtc tttaatttaa aattacaagg agttttctag 162240
gtctttatgc gtataggtgt ttctttgtcg taaattttca atagccgaca ttgtttgtga 162300
agcagtgttc tgagtagtga ctgtcgtgta aggctcagcc ggatgagcag gagcactcgc 162360
ggccgcaggt gcggccgccg gcccgccagt tgccatgact agtctgtccg taactgggtt 162420
gtccgtaact ggtttgtttg ttgctggtct gtttgttgcc ggtctgcccg tgactggctt 162480
gcctacactt gctgtagtcg ctccagctgg tttagaggta cctggttgtg gagtgacttc 162540
tacccactgc tgatcttgat aaggatttat aaactgtata tcttcctcct caatagcagc 162600
agcttttttc tttcttgaag agaatagata gattagaacg atgataatga tgactaagac 162660
cacgatagca atgagaatag tatacatatg tgtggagaag aagcttggtg tagtgactgg 162720
tgacaaacac tcaccataat gccgcggata aaccggttga aaaaattcag aatccattta 162780
agatactatt ataaataata tataaaaatg ttgtggcgca atgaaattac agaatttatg 162840
gaccaacttt ccaagtattc tcaagaaatc ttaaaaacgt ttaagcaatt gcgtcctagt 162900
gaatataaac aatacaatga atttttaaca caagttacac cgttgctgca aaaaacccct 162960
gaaaaaattc cagagttggt tgaccatata ttcaattacc tagacaacgt tgaaaaaatt 163020
tgtgagctcc tcgtgaatgc tagctcaatt attattagtt caaaaaatacg agaacaagta 163080
aaacacggaa tgagcttcag ctataaagcc gacctcgact ccttggcgga cattctctct 163140
caaaaacagt acgtgcttat gcatctttca aaaaatattg cggccgagta ttttaatacg 163200
tgtttaaacc aagggaaatc caagttagat ctcaaagctg cctctgtatt ttatagtagt 163260
cgttcccgaa cggcaagctc agcagaactc tatagaaaaa tgctatacgc ctatggttca 163320
ccgcaggaaa ttaattatta tactgaaaaa gcccgaaata agacgttgga tgtggaggag 163380
agcgacagca tggccatcat cgaacgaacg gcccgacaca acctttccct tatgcacccg 163440
ctagaagcca tggggcttac ctttggggca accaacacgg acgccgaccc ggaggatctg 163500
aaggacaaaa cggtgataaa tttaacgctc ccgcaggcaa cagaaagcat cacctaccat 163560
cttaaatccc taatgcagct aaaaaaagta agtacggctt caggactaaa tacaaacatt 163620
ttgaaagcat ttgataatat tatttccacc cctgtgaaaa aaaataaaat ggcctccaag 163680
ttggcgcccg ggatggatgt cgtgttcact agcgataacg gaaaaacatt ttttactaaa 163740
aacattttaa gcaaaaacat gctagcgggg cccaaagagc gggtgtttgc atataataat 163800
ctcattagta atttaaataa ctcctgtttc atacaaaatc acaacgattt tttaagacag 163860
caggactctt ggcccttcta tgacgcgcac aattttacca acaagttttt aatgcagcct 163920
attttttcgg ggcagacccg tcctcggctt cagggagcca tggaggcggc gcatgtggaa 163980
acgcatctca cggcattttt acaaagtatt cagccctcta ggccacaaga tccctctgtt 164040
ttggcttccc ccaagttatc tgctctaatc ttgaactaaa aacagccttt cttggactta 164100
aatgatggtc taccagtttt tgaaataact tagagaacta tgaagatttt catgaaattt 164160
aaattagaga tttgcaaagg ttacttgcgg tcattttctg ttgaattaaa taattattcg 164220
aatagtataa tgtctgaaga tattcgtcgt ggtcctggca gaccgccaaa gaaaagggtt 164280
gttcccaact ttgagcgcaa gggcattctg gaaaaaccag ttcggccaca aagccgtctc 164340
gagttttcct atgataaccc gctgatattt aaaaatcttt ttatttactt taaaaacctt 164400
aaaagtaaaa atattttggt gcgatgtacc cccaccgaga ttaccttttt ttcacgtgac 164460
cagtcgcagg caagctttgt tattgccacc atcgacggaa aaaacgtgaa ccattattac 164520
gccagtgatg tcttttggct aggcatcaac agagagctcg ttgaaaaaat gtttaacagc 164580
attgatcgct ctttttaaa aattaccatc gttcaccgct atgacaagcc tgaaaccctg 164640
tttttatct ttacggattt tgacattgac aaggagtgca cgtatcagat tacggtctcg 164700
gagcccgagc tcgatatgga ccttatcgaa atggaaaaaa gcatcagtga agaaagactc 164760
aagaactatc ctctgcgctg ggagtttacc tccaagcagc tcaagaaaac atttagcgac 164820
ttatcaaact acaccgagct cgtgaccatt gaaaaactcg gcggcgatac gccgctgcac 164880
ctgtatttcc aaaagtttaa ctccatctca taccacgaga tgtataaatc ttccaacaag 164940
atcaacctga cctcgaccat tcctaagtcg caggtgttcc agataaatgt taaaattgct 165000
cacatcaagt cgctggcctc ggctatggtc accgacaaga tccgcattct gtgcgaagaa 165060
aatgggaacc taatctttca atcggaaatg gatgccctta tgttaaatac gattaccttg 165120
aacaccacga tatagttcgg taacattaga tgttctaata tttagcatct aaataatacg 165180
ctgtagtccg gtcagggttg cgtcacagtt ttcccatttt tttgcctcgt cggcggtggc 165240
caccgttgcc ctatcattta cgcccggtaa gacaaagcta aaggcgttca gcggggcttg 165300
gcaatgcccg cccagcgtga aggagctcgg aggattttgc gcatcccgaa atcccttagc 165360
catgttgttt aacacttcgg ttacgtcaat cgagtgaagg gatcccttgg gatccgtgaa 165420
tgtaaagacg cagtttctaa agcgcatgta tgcgatggac gattcatcgg gggttttgaa 165480
ggtaacagtg ttccccttgc tgtacttaaa gggggaccat ccggtaaaat tataccaaat 165540
gaaagcaata ataattaaaa taaccaacac aatagttata gacaacacaa agtctgtagt 165600
gccgcccatt attaaataaa aatattttag accgccggct taaaatttac ttattgctca 165660
tagcttaagt ctattttatt catagcttaa gtttattgct catggcttaa gtctattgct 165720
tatagcttaa gtctatttta ttcatagctt aagtctattg ttcatggctt aagtttgttg 165780
ctcatagctt aactccatta ctgatagctt actgatcatg acttaaataa aaatattttg 165840
cccgcttaaa aattgtttag gtttgaaaaa ataagagatg gagggggcaa cttatcgtca 165900
ttgtgtttac ccccactgga agacatcaaa cggtaaataa ttataagaat caaaatgatt 165960
aatataaggg ttaaaaaagg atgattcatc acattaatta aaaacgtatt tataacgctg 166020
ttgcagttga aattttggta taggtcggaa atattgcccg agccttcgta ttctgcaatg 166080
ttctgacata tggtgagtcc ggagggggcac tgcttgttgg tcaaaatatt tctttgctcc 166140
gttgttttat aggcattttt atttccatta cacggagcaa acgcacattc agcccatagg 166200
gtgccggagt tcacacaggc acaatactgg ctatacgcat actcatcctt tgagcacaat 166260
ccctgtttat cgcatatgct cccaataata ttgtcatcct ccgccgtttg ttgatttgta 166320
tgcgagcgta aaatagcggc ccaggccttg ggctcctttt tttgcagctc ggaaatcgaa 166380
gggcctgtac agctaaagtc gacccaaata tcattgcatt tcgtggaaac tggcatgcaa 166440

-continued gacataattg aaataattaa taagtatata tcatggcaac aaattttttt attcaaccta 166500
tcaccgaaga agctgaagca tactacccac cttccgtgat aacgaataaa cggaaggacc 166560
tgggggtaga cgtatactgt tgctccgacc tagtgcttca acctggacta aatattgttc 166620
gcctgcatat taaagtagca tgcgaacaca tgggcaaaaa atgcggtttt aaaatcatgg 166680
cgagaagcag tatgtgcacc catgaacggc tgctcatcct tgcaaacgga attggtttaa 166740
tagacccggg ttatgtgggc gagctcatgc tcaagatcat taatcttggc gacacccccgg 166800 tccaaatatg ggccaaagaa tgtttggtgc agttggtggc ccaaggtgac catgtgcctg 166860
accatatcaa catcctaaaa agaaaccaaa tatttccgct gtttgcgcct accccaagag 166920
gcgagggtag atttgggagc acgggcgagg ccgggattat gagaacttaa ttttattttt 166980
tttcttaaca taatgggagg ctctacaagc aaaaattcct ttaaaaatac gaccaacatt 167040
atcagcaatt ccattttcaa tcagatgcaa agttgtattt ccatgttgga tggcaaaaat 167100
tacataggcg tattcggtga tggaaatatt ttaaaccacg ttttccagga tttaaactta 167160
tcattaaaca caagttgcgt gcaaaagcac gtaaacgagg aaaatttcat tacaaatctt 167220
tcgaaccaaa ttactcaaaa tttaaaagac caagaagttg cgttaaccca atggatggac 167280
gcaggaactc acgatcagaa aacggatata gaagaaaata taaaggtaaa cttaacaacc 167340
acacttattc aaaactgcgt ttcatccctg tcgggtatga acgtgctggt ggtgaagggg 167400
aatggcaaca ttgttgaaaa cgcaactcag aagcagtcgc agcaaatcat ctctaactgc 167460
ttgcagggga gcaagcaggc catagacacc acaaccggca tcactaacac ggtaaatcag 167520
tactcacact acacctcaaa aaactttttt gacttcattg cagacgcaat ttcggctgtt 167580
tttaaaaaca tcatggtcgc ggctgtagtt atcgttctaa tcatcgtagg gtttatagcc 167640
gtcttttact ttttgcattc acggcaccgc catgaggagg aagaagaagc tgaaccactc 167700
ataagcaaca aggtattaaa aaatgctgcc gtttcgtaat aatttaatta aaagtaaaaa 167760
aaaaggtatt gttatagtga tggcagattt taattctcca atccagtatt tgaaagaaga 167820
ttcgagggac cggacctcta taggttctct agaatacgat gaaaatgccg acacgatgat 167880
accgagcttc gcagcaggct tggaagagtt tgaacccatt cccgactatg accctaccac 167940
atcaacttcc ctgtattcac aattgaccca caacatggaa aaaatcgcag aggaagagga 168000
tagtaatttt ctacacgata ctagggagtt tacttcactg gtccccgatg aggcagacaa 168060
taaaccggaa gatgacgaag aaagcggtgc aaaacctaaa aagaaaaaac atttgtttcc 168120
aaaattaagc tcgcataaat cgaagtaaaa attgaagcga aaaaaagtag aaaaaaaatg 168180
tttggagctt ttgtaagcca ccgtttgtgg tcagatagtg gttgtacgac cacctgcatc 168240
acaaacagca ttgctaatta tgtagccttc ggcgaacaaa ttggatttcc ctttaaatca 168300
gctcaggtat ttattgccgg ccctagaaag gctgtgataa atattcagga agatgataaa 168360
gttgagcttt taaagatgat tgttaagcac aatctttggg ttgttgctca tggaacctac 168420
ttagatgtgc cctggtcccg taagagtgcg tttgttacac attttataca acaagaacta 168480
cttatatgca aggaagtcgg tattaaaggg ttagttttac acctaggcgc tgtggagcct 168540
gaacttatta tggaaggact aaaaaaaatt aagccggttg agggggttgt catttacctg 168600
gaaaccccgc ataacaaaca tcatacatat aaatacagta caattgagca gatcaaagaa 168660
ttgtttttac ggatacgaaa taccaggttg aaacagattg gtttatgcat tgatacggct 168720
cacatctggt cttccggtgt caacatctcc agctataatg acgcggggca atggctgcgc 168780
tcgctggaaa acattcattc cgtgatccca ccaagccaca ttatgttcca cctaaatgat 168840
gccgccacag aatgcggaag cggtatagac cgacatgcaa gtctttttga aggaatgatt 168900
tggaaatcat atagccataa aataaagcaa agcggtttat attgttttgt tgaatacgtt 168960
acgcgacacc agtgtccggc tatattggag agaaacctcg ggtcttccat gcaattacaa 169020
accgctttaa ccgcagaatt tactacatta aaatcgttat taaaataagg atgagtttta 169080
gcgaatgtcc cttagttatt agtgcatgca aaaaatttct acaaaagcgt attacaatag 169140
agaatgaagc acttataaat gccttaataa ccgctttagc gcagaccagc acgttgaatg 169200
atctttgttt attacctatt caaacctatt tgcttagtta taaaaatgct tttgagtgga 169260
tacacttcgt atgtattgca atcaccacta ttttggataa taagtataac tggaaggact 169320
gtacggtaga tattaattat atttttctcc atgtaaccta tatttacaat attaaaacca 169380
aggaatacct agactactgt tcttaaactt tattttttct atatttacgc caaagagaat 169440
atttaaagtt tttttgaaaa aaataatata tgtagataaa attcagttac atgatatatg 169500
tgtaaacatg tgtggtaaac aacatatggt tatgctttat aagataaatg cgcataatat 169560
atgtaaacaa aatatggtta tgtgttaaat gcatataaat gtattttaac gtatatcttg 169620
tgataatgga tatatgcatt tattaaaaga ggctgtattt attataaatc ttgctaagga 169680
tgccattgtc aacatatatc ccatgttgga caaattgcgt tgcgatccag ttcttttttt 169740
ttgattttgt ttaatgctat cctttttgaa gggatggttg tccaccatat ttattcgatg 169800
ttcaatgaat aggtctgctt tttcgtaagg cagtgaaggt cgttccaaga ctccttgaac 169860
gatggacgtg ttttcttgga tccacttaaa aagcacgtgg cattcaaaaa caggacagtg 169920
attggatcct tggatatgct ttggacagcc aatgcttgaa gagatgtagt cccttttctt 169980
taggacaagc ttctccacgc tggggcaaca gagatcgttc aagttctgga cggtcgcatt 170040
tggaatgttg aaacttcgta tccattcacc ctcgggtcct cccttatgaa gaaggagtat 170100
ttgctcatgg tccttagtaa tcttaaccaa atgttggaag atcatttttt tacctgcttt 170160
aaaggcctga agggtgtcag ttggcaaagc tattgaattc gggagtgggc tttcatcaag 170220
cgtgaaatgg tgaatgtgac gcgactggaa agaaaacgac cgttgattta ttttttcaaa 170280
gattgggtcg attccgccat gaaagaacag ctgcaagatt ttagaaggcg tatttttttc 170340
ccaataaaaa atgaccactt ctcgtgggat taaaatcgtc tgtgtcccat tttcattata 170400
taattggccc ataaagccat caacgtcaat caacaccaaa agcatggtat agagagcttt 170460
tagaaccgga gttcgttaaa aaaatacaaa gttcgtttaa aacgtgtaat gttactaaaa 170520
aaatgtaatg tttaaatgat aatgatacca catgcattaa tgaaaaaaac ttttaaattt 170580
ttgttttaat atttgcatga aaatggaaac atttttagtc tgtttatttc acaatgcaga 170640
tggtttacat caacagattc aggaaatttt gtatttattg cggatgcata tttacgaaac 170700
aaatctttac ttaaagcagg aactatcacg gcttatatat ccaaataggc aactttcttt 170760
tgtgttactt atgccccttt cccttctaag aaactgggat gacattgaat atttaacgga 170820
cgttgtagat gataagcaga ctctacatta cgcggcaaat ttgctgacaa actacgttct 170880
acatctatcc atgtttcaaa agctgacaaa accatacttc cttttagcgg tcaagcgggt 170940
cagcgaaaaa ctcaacaaaa agcagcgaca ttcattttac gaggtattgg taacctccga 171000
aaccttgaat aattatgaaa acctatctaa aaacatttta aatacgttga tgtttgccgt 171060
gcgctacgta tttaaaccta cgccgaacta ttcagaaatt ctcgcagagt tggaaaaaaa 171120
aaataaaatt caccatatta tttttaatat ggtaattacg gattttgcgc aaatccgtga 171180

-continued

```
acaacaaatg gataaacatc tgtgtgaaac aaataatgag cttcgtcagg aatgtaaaga 171240
aactattttt gatttaaagg tggtaggaaa tgtttagcca ataaactcat gcccgcattt 171300
tttacaggta caaaatatcg tggatggctc atcgagggcg cgtgtttgta cttctctgta 171360
ggtacacata cgctgcttgc agttgggaca cttataaagt tgtgacgtct tttcggcgac 171420
cttttgctgc gaacgtagag taatttctgt cttctccttt aaggcggcag aggggcaaag 171480
ctcggcgaac gtcatgctac caattgcctc cggttttagc tcgccagaaa ttagcttatt 171540
aagggcatcg ttatcctgtt gttggtgact tttttttcg cagttaataa tatgattgat 171600
cgtcccacaa cgggttgaat attcttctaa aaaggttttt tcttgttgct ggtacgtata 171660
atgataacac gaggcctcga ttttttgcgc gtattcggtg cataaatcag tatgttcctt 171720
aaaaaacata tgtttttgaa gcgttctaaa aaacatcatt tggatgatat cacgcatttc 171780
caaaataata tagggttcta gtcttttgga atctttcata actagatcgg tggtaatatt 171840
cttagtcata caatttatta aaaatggttt aatatattgt aaatattttt taggcgtgtc 171900
agcctgtaaa aaacattctt gttcaatctt atttgtaagg atagtatttt gcaaatactt 171960
atttagcaaa aatacgatag aatcgcgggc tatatgcatt ttcatataat ttttttttaa 172020
aatttaatac aaaaaaaaga agtatagact cttcttctag tccggttagt tcgttggttg 172080
cctcaacatg gagactcaga agttgatttc catggttaag gaagccttag aaaaatatca 172140
ataccctctt actgctaaaa atattaaagt agtgatacaa aaagagcaca atgtcgtctt 172200
acctacagga tctataaata gcatactgta cagtaactca gaactttttg agaagattga 172260
taagacaaat accatttatc ccccgctttg gatacggaaa aactaattgt aaccagtagt 172320
acatttaagg atagtttaag cagtaaatgt agaataacac agttaagcaa taaataacaa 172380
gtatatagga atatatagga atatatagaa atatatagaa atagctaagc ttaatactaa 172440
ttcagctttt tttttaacta aaacctgaat agatgcgaag tagcggacat atacatacta 172500
aaataagcca tacatttact ttcttcttga acatgaaacc ttttttctt ctgttgttgg 172560
tatataaaca ataggactgt ttgctgaggt tgtatgatct tctacaactg ctgtctcagg 172620
atgacgatgt ttttttaaac taaaagtgta ggatggaatg agtggaatat agttatggct 172680
cgacttatcc tgtttcgtac aggaatattt tttacaaata gaacgcaaca agcatatgaa 172740
taaaaacaga aatgatatac aggagcataa aatagatatg aacactaagg ggtagcagct 172800
tttataacgt tccgtatttt tcttagctat caattgattt accgtaatat ttatctcggg 172860
aaactttgtt ctacaatatt ttgtttggta ttccagaaac tcatgtcctg gcttattccc 172920
gcagcttaaa aaatgataca aaaatgtgtt attgttacta aaattaattc ttcttaagaa 172980
aaactgcgga agacgcttta ggtacgtctg ttcctgtttt agtaggaagt agtataaggg 173040
acaatttctt tttccacaca ttagattatt gtaatatagg taggttgggg tgttggagcg 173100
aataagtttt ctgagtatgt tataatctat gacttgtaaa tcgttatacc ttaggtccaa 173160
aaacttgagt tctttaccaa agccacctgc aatttcagaa atatttttca tcccgcagcg 173220
gataatacgg atgtcctgaa acgtctttaa aatacttgta ttgtagtgaa tacttatgtt 173280
attttttgt aaataatcta tgtcatgaca agtgcatgaa atgccagcag cattgcttgg 173340
tatagtatta tatgcaggaa gaactatact actattgaga atagtcacat tgtacttata 173400
ccatgtatta ttttctgata taaagtattt gcaggtgacc tgtggtttaa tcctacctgt 173460
taagccactt cctaaaaaaa caaaaaatat gaaaaccctt agcatcctgt atatactatt 173520
aaaaatttat aaaattttct gtttaaattt catttagaca aaaaaataat atatatacat 173580
```

cagcaagaaa ttatatacag attatataat tttctgattt ttttttgcca caataagcat 173640
cattatatgc attaaaatct caatactaaa cactaaaatc taaattctaa gcattaaatt 173700
ctaagcatta aattctatgc actaaactgt aagcactaaa atctaagtaa ctaaaatcaa 173760
cactaaatgt atgcaaccta aaatgtaaag cattactcat catcctcctc ttcttcatcc 173820
tcatcatcat aggttaagat atatgtgtca tcctccattt cttcacattc atcttcataa 173880
gcatcactgg gtattggtgg aacattggat gcagcatttt taaaatattc tatgtcttct 173940
ggtgaacact catctaatga tttttttgaca gtccttttaa cttccatggg atatgattcc 174000
aaatcctctt tatataagag tttacggtag cttttagctg catccacatt tgctggagaa 174060
tctggatttg gctcattgag cagtgaaatt acactaagaa gaatggtatc aatcttttga 174120
gccggagacc aagtcattcc ctgttcttca gcattgtctc cgtgtaagat agagatacat 174180
agttttccat cagagtaaat attaggatgc cacatttcag aggtgaatgt taatctgggt 174240
ggtgcatatg ggtattctgg aggaaaggcg atttttgcct tgaataagcc tccctcataa 174300
aaagtgtcag gtgggcccct taagatcaca tcccattcag tcatatcctt ctcattcacc 174360
gaaattttga aattctcaga gggattctct atcaggtgtc tgtactctgc tattaaaaac 174420
ctggaaacca tggttattta atattaatta aattccctgg tttattcctc cttaaaagta 174480
gatgaacctc ttttgttttt tattgggttc atttttacta aatttatgaa ctggaaaaaa 174540
ctttaacggc ataattatca aatgcgaagg gggatccgta taaaatccta gcttgccggt 174600
aatggctatt aagttaaatt tggtaccagt aacactaata tttaaaaagc cctgatcatt 174660
aactttccac attaaaagat tattatattc gaatgtttgt ccaatatgga caactttgtc 174720
accagatgtt acatttgatt tggttgttag tggctgaagc ttggcacaat caaaaataag 174780
cccattaaca ctaagatata gaggagtggg ttgatctatt ttctcatagt ttaatattcc 174840
atctttccac gtaatagctt gataattatc cgcagcaatg agttgaaatt tttataaatag 174900
tacaggggtt ttagttgtcg ttatacattt aaagggtgtt ttataaaaat aaaaataata 174960
attgttaaaa gtatgataat aatcgccaaa ataatttcat acattttttta taagaattat 175020
acatagtatg gtatttaaaa tattagctaa atttaaaaaa acttcatgat ttttaaaaca 175080
gggaaaaagg ggattaggtt gaataaaaaa ggtaagcact tgtctatata ttttttttac 175140
aatgttgcct tgagtcgcat ttttaactgg ctggggagta tcagagtgga atatcactgt 175200
agtaggtcta taaggtcttg ttaaaatatg atcggtcatt gttttcgtac tagtgtcatt 175260
tagggtcgac ctgatagctc gatataaagt tatagggat aacctatcaa atacagtctt 175320
atctgtgctg aaatgtatat cgtcttcttt atcactaata atattaggaa tggctgtcat 175380
taaataatta ctacttgttg ttgtgggtga aatagttgta ctggtattat tggaaatggc 175440
tgtcattaaa taattactac ttgttgttgt gggtgaaata gttgtactag tattattaga 175500
aatggctgtc gttaaataat tactacctat tacaagtaaa ctaatgctaa ctacattttt 175560
aacctcaata aacctaaaaa gccatactaa atacctaaac aacatcctgt tataatatga 175620
gcagaaaaaa aaataagtat aattagggaa ttattcttat tcgcttacta ttaagaataa 175680
ttcagaatct tatttagtta gaaactatca taaagtgaat aggactcatc gtcggatgaa 175740
gattccgttt cagagatagt ttctttttct tcctcagaat aatctgttcc tacaatagaa 175800
tcggtgtcat cctcagaaag agaagtattt aaatatggac tatctatagc aatatcctct 175860
tctatctcgc aatcctcctc ctccatttcc atagtgtgta ggagaatatt tttatcatca 175920
tgctcacttc tttttttgtt gaaagatgaa ccgtcctcaa tacggttcat gttaagttcc 175980
ttcatcttat gtataatttc cgtaatccgt gatgtttttg acatgtaaga tggttttaag 176040
gttatatcca caataacagg agaatctcta tcattttcat ttgataaact ttgatctttg 176100
atttcttcgt ctaaaattct tgtctttttt tgggtactag atgaaataga ggaattcata 176160
ttctgaaacg atatatcaag gggagctgga cgctttttc caattaaacc gtttttcgag 176220
atactatgat tagatgaatg atctttagcc aagctgtcct tggatatact atagttagat 176280
attttacctt taaataatat tcttctatac aagttattct taggtaaaga attagtatgg 176340
attcctatat ttttatctga aggagtgtcc atatcggaga acgtcctctt acgaatattt 176400
tgaccacgag ccatttcatc cactataggc agtattttgg ctggctatgg ttctttgttg 176460
tgacaattct atgagatttg attgcaaatc aatttttagt tttaaatata ttggtaccta 176520
ggacaaagaa agtatatata gccaataatt attccactaa attgatttcc agactgatgg 176580
gtatggagcc atgttgtctc tgcagacgat cgcaaaaatg gccgtagcaa caaacaccta 176640
ctccaagtat cactatccaa tactgaaggt ctttgggctg tggtggaaaa acaatacgct 176700
aaatggccct attaaaatat gtaaccattg caacaacata atggtaggag aatatcctat 176760
gtgttacaat catggaatga gtctggatat agctttgatt cgggcagtaa aggagcgtaa 176820
tatatcctta gtccagcttt tcaccgaatg ggggggaaat attgactatg gggcactttg 176880
tgctaacact ccatctatgc aaagattatg taaaagtttg ggagccaaac caccaaaggg 176940
ccgaatgtat atggatgctc ttatacatct ttcagatacc ttgaatgata atgatctgat 177000
tagggggtat gagatttttg atgataatag cgtgttggat tgtgtcaatc tcatacgact 177060
caaaataatg cttaccttga aggcccgtat acctctcatg gaacaactag accaaattgc 177120
cttaaaacaa cttctgcagc gatactggta tgccatggct gtacaacaca acttaacaat 177180
cgctatccac tattttgata atcatattcc taatataaag ccatttagtc tgcgctgtgc 177240
tttgtatttt aatgatccct ttaaaatcca tgatgcttgc agaactgtaa atatggatcc 177300
taatgagatg atgaacattg cttgtcaaca ggatttaaac tttcaaagca tttactattg 177360
ttatctttta ggggctgata ttaatcaggc tatgctaatg tctttaaagt atggtcatct 177420
ttctaatatg tggttttgca tagatttggg ggcggatgcc tttaaagagg caggggcgct 177480
tgctgagaaa aaaataaaag agtgttacaa cacatattag gtcttaatat ctttaagcga 177540
gagttgattc ccccctgtaa agatcctgat ccttatcaaa tccaaattct gttaaaaaac 177600
tacattctaa aaaatgtctc aactgttttt acatattatt gccagtagcc attgtttata 177660
tcagaaaata acccatttgt ttatcttttt ttgtggggca accattaaga cccgacgcaa 177720
aaaaagatta atcttttatc agatacctaa aacgttctat aagggagtct atgagatgga 177780
tcatattttg atggtcatag taagaagcaa gctttttggc gaaaacaacg gagttaaaga 177840
atttaacccg ctcatgtttg gataggactt ttaacagcga gccaaaacag tatttaaaaa 177900
tttggcaata gttttttttgg gatgcaataa acaaacactt gatcagtgcc cgcttcactt 177960
tctgatcaga catgtttgcc gcataacagg cctttttaaa cttagtaata taattatgtt 178020
ccgcaagcac cattaacaag ggaacgatgg gaagctgctt ttcttggtga aatttacgta 178080
aatattcgat ggccaccgct tggacgactg tgtaatttac taagttagaa atgatagctt 178140
tcatggttgt aaaaatatac ataggatttt ctttttctgt atacagtttg aaaagcttat 178200
gattacgtga aatgatggcc atttttaata caagatggta tagtgtatct ttaggtaaaa 178260
atgccttgca agccgcgatg atgtcgatgt tgtctccatg aacagcgata gaaactaatg 178320
tttccaatct aaatgttttt atctgcatta atagaagaat gcagtcaatg ttattatact 178380
taataatact gtaatacacc gaatcaatga ccgtcatctg agaatcaagc tgacttatta 178440
gtaaatttaa cgtttttttg gaggcatgac ctttgatcgc ggcactaagt gcacacagta 178500
tagcaaaatt gttaaataca tttt 178524

<210> SEQ ID NO 2
<211> LENGTH: 189346
<212> TYPE: DNA
<213> ORGANISM: African swine fever virus

<400> SEQUENCE: 2
gaatatacca tattattgct attgccatca atgagaatgc cacgtaggca taggtcatcc 60
tatggccgga ccaatccatg gctgcactta aaaatatcaa aaaagtttaa gttttgggcc 120
ggcgttaaaa tttaaacctt ttctggttga tctttagcca tgtatagctg cgatgtttgg 180
tgccttatct acatgctatt ggcattcctg atattcgcac taaagtgcta tgttacaacc 240
gtcttatgcg tgatttttat ccaccttatt ggccgaaggg ccgccttgta tttcctgtta 300
ggtggtttgg ccgtattcta ctggtggcaa gcagctatca ataaaattta atggctctca 360
cttaagatcc ttgctgtaag cgggcgttta catactttga tcaagaaaaa aattattttt 420
ggaccccccc ccatgtttta tacaaaaatc atataataaa gtggcgacaa tcaacatatt 480
aatcaaccac agcattttat gatgtgttaa tcaacatata ccatattaat caaccacagc 540
attttatgat gcgtcaatca acatattatt acggagagcg tcaatcaata taatattgag 600
aacagcgact tgataccgtg tatggtggtg gcggcggcat gttgtttgta acagcatttt 660
tcatcattcg aagcttacaa aagatatgta taagatagca tattaatgtt attaacagta 720
atatcaataa ggcgtagcta tagatcttca ctttggtaga ccaataatcc atggttgcgc 780
ttaaaaatac caaaaaaaac attaagtttt ggagggtaag attggttttt caccattggt 840
aaagattatt attctaaatg tttaccccat agatgtgaaa caatgattct tcatatatta 900
acatattttt tgacttatac ttttcttcat ctagtaaggc gttaattttt tccggatctg 960
tcgtttttat tgataaaaga gaagagtctg gactgtaatt tttaaataat aagatattta 1020
ttaatatcca attattcgtt tggctcgcta tttccatgct ctcttcgaaa gcatcagctc 1080
ctaaatctat acaaaggaat aagttacctt cacaaaaatt cattaccgag gtaatcattg 1140
cccgattaat gtcagccccc aacataaaac aataatatat agttgtataa ttacaatcat 1200
acatacaggc caactgcatc atttcatcaa tgtctatatt tgtcttctct ttgttataaa 1260
tttcatgaag gtcaaagacg ttgttataag caaccccaca tattaaccgc caatctttaa 1320
aatgactata tcgttgataa aaatattgga tggcttcagt aagcttatat agtatcgcca 1380
tactatacca atacctagtt agcatttcgt tgaatgaaat attatccaat gtaaagttaa 1440
ttgataatgt atctagttca ccaaaaattc ttaatttcag ttgagcatta tttaggaaaa 1500
ggggattatc agataataat tcatggcata gaataatatt actgctagtt ttaacatact 1560
gtacattata aaatatttct aaaattttat tttcactcaa agctttcctc gcacctaact 1620
tttggcatag gtcctggtgc actccatatt gacagtaacc aacccaaagc tgatgtctgc 1680
accccattcg gtaaacagct ctattaaacc atgattgttt tcctgtacag ccttcattaa 1740
tgcaacattt aatgttaaac catgtttaaa acttgctgtt tttattaata tttgttcatc 1800
tatacaagta tgataaatcg taattggggc ttcatgccac cacaaaccac aacgctctaa 1860

```
aatacaataa tcatctttta acacaggctg tgtagctagt actttttag taagtgcttg   1920
taaagtagat ggcatcttct atctgcaaaa taattatttc cgaaaaaaaa atcaaattaa   1980
aatactaaat tctattttt tttttaataa agcctgtaaa ttatataata aatctcgccc   2040
accgtattat ttccggacac aactttttat acctcattat atttttagat ctatagtttt   2100
ttaacaaggc attaattttt tctggatctg tcgtttttaa agataaaaga gagacgtttg   2160
aactataata atctttaaat gataatattt ctactaatat atcatgattc ttttgttttg   2220
ctaattctaa gctctcttcg aaagcattag ctcctaaatc tatacaaaag aacaagttat   2280
tcatataaaa gtttttacc gaggtaacca ttgcccgatt gatgtcagcc cccaatacaa    2340
aacaatagta aatggttaaa aaattgctat ctctcataca ggccagatat atcatttcat   2400
caatattcat atcaaccttt tttatatgat acatttcatg aagatcagac acgttattaa   2460
aagaaagccc acatattagc cgccaatctt taaaatgact atatcgttga taaaaatatt   2520
ggatggcttc agtaagctta catagtatcg ctatactata ccaatatcta gttagcattt   2580
cgttgaatgt tatttcattc aatataaagt tgatcgatat cttctctaga aaacaacaaa   2640
ttattacttt taattcctct atattctgga aaaggggatt attagataac aatttatggc   2700
ataaaataat attactacta gttttaatac gatgtatttt ataaaatatt tgtacaatat   2760
ccatttcatt caaaattttt gcgcctaact cccggcagaa attccaagta tgctccgtat   2820
tgacagtgac taagctagag ttgatgtctg caccccattc agtaaacaac tctattagat   2880
catagttgtt ttcctgcaca gttttcatta atgcgagatt taactctaaa ccatctttaa   2940
aaattgctga ttttatcatc aattgattat cctcattagt agaaagcata attggagctc   3000
catgccacca caaaccacaa tatttcaaaa taaagtagtg ttctttagat atgtgctgtg   3060
tggccagtat ttttttagca agagcctgca gagaaattgg agtagacata ttttttttg    3120
caaaatggtt taagtttttc aagaatacag attggataaa ttaggttgtt gacttagtta   3180
caggaggtat taaatattat gtagacataa aaatgagatc ctccaaaaaa ataaacaaca   3240
aaaaaaatat gtttaatatt aaaatgacaa tttctacatt gcttattgct cttattatac   3300
tacttattat tattttagta gtgtttttat actataagaa acaacaacca ccgaaaaagg   3360
tctgtaaagt agataaagat tgtggtagtg gagagcattg tgttcgtgga tcatgtagct   3420
cattgagctg cttagatgcc gtaaaaatgg acaaacgaaa tattaagata gattctaaga   3480
tttcctcatg cgaattcact cccaattttt accgttttac ggatactgct gctgatgagc   3540
agcaagaatt tggaaaaaca cggcatccta taaaaataac tccatctcca agtgaatccc   3600
atagccccca agaggtgtgt gaaaaatatt gttcatgggg aaccgatgac tgtacaggtt   3660
gggaatatgt tggtgatgaa aaggagggaa catgttatgt atataataat ccacatcacc   3720
cggttcttaa atatggtaag gatcacatca tagccttacc tagaaatcat aaacatgcat   3780
aaataaatac attaggctca tcgtatcttt ttaaaatcca taaatattcg tttgatatat   3840
gctgaaattt ttataaaaaa aataactatt tcctataaat catctagaaa tagtcctcgt   3900
tttgatcggt ttatatctta taatattgtg catcgatgca caactgcttt ttttggtcct   3960
tctggaacat cattatattt tctttcatta atataccatt cagatgtaaa cgttgaataa   4020
tttttatggc aacaatctac cattgaatta tatttagtaa catctaatac atcgtttgtt   4080
ttatcaggct cagctctata atcttgataa tttttgttat cagcttctaa agctccatca   4140
ttatttttca aagaagtatc cataattatg tttggtaaaa atactttaag ttttaatgtg   4200
atatttaaaa tggttgttat ataaatttac cgcttacagg taatctttat tcagtgtcat   4260
```

```
aaactatact tttgatgatt cagtattttg tgaatcagta catttattat cattaatatt   4320
tttaggctgt ttttccaatg ttttattgtt gcaatgagcc tgctcctcct ttgacgagga   4380
agtgtctgtt ggagtcatct gtttaggaag agtatcatcc atatctatta tgaagaaaat   4440
atataaatat tgatatacaa tcaaaaatat ttttgatcac gtctttgtta tctatcgata   4500
ttgttgataa cgtcttgaat aacctacatc attttttttac ataaaaaaat agatataatt   4560
tttattatat ctcaattatt ttaaagataa ttatcaatac agcaaatatc ataagctaac   4620
atatttttcg aataatagtt ttttagtaaa gtattaatct tttcaggatt ggtttctttt   4680
gataataaga taggattcgc tttataaatt tttaaagata atatattcac aatgatagaa   4740
taaccgtata tatctgctaa tgtcttactg tgttcaataa cattagcccc taaatccata   4800
caaaagaaca tattttcaat acaaaagttt tttaccgaga ttaacattgc tcgattagcg   4860
ttggctccca atgcaaaaca gtagtaaatg gtcaaaaaat tattatcgcg catacaggcc   4920
agctccatca ttttattaat actcatatga attttcgttg tgttacatat ttcatgaagg   4980
tcaaacacat tgttgaaaga aagtgcacaa attaatcgcc attcatcaaa atgcctgtat   5040
tcttgacaaa aatattgaat agcttcttta agattatatt ttaccgctat gccataccaa   5100
tatttggtta gcatctcact aaatgagatc tcatttaaca tagaatttgt tgttaaatcc   5160
ttcaactccc aataaatgat catccttaaa tccaccatgt ttacattttg taaaaaaggg   5220
ttattagaaa ataattcatg acacaaaatg acattactac ttgttatttt acactttgtt   5280
tcaaagaaaa atcgtaaaat ttcacttgtc tcaagctctt ctttagctcc caattttcgg   5340
cataggtttc gagtatgctc gttattaata aaaagtaacc cataattaat atttgcaccc   5400
cattcagtaa acaacatgat tagatcatca ttgttttcct taactgccaa taccaatgca   5460
gtattaagcc ttataccctc tttaaagcat aatgtcctta tcattatttg attatcatca   5520
tctatataca ttgagatagg agcttcatgc caccataaac cataacgctc taaaatataa   5580
taatcatctt tagatacgtg ttgcgtggcc aatgcccttt tagcaagtgc ttgtaaagtc   5640
gatggctgca tgtttattct gttaaaaaaa atcaaattat cgggtaaaca taaggatcaa   5700
cccgtagtta atatttgcag tagtattttt taacaatgaa ttataataaa aaaataattc   5760
attactatct attataaaac ccatctttaa ctttaaagaa gaactagatc atcttttttt   5820
tgttgtgtca gaacttcttc aatttattac ccacatttta tctaaaaaaa taaaaactac   5880
atcatatctt gtttcttcat caaattatca taccatttat agggtgtagg ttgggaacat   5940
tccatcatgt ggtaatcagg gtatttatat atttttttgat agtaacatct atttggcaga   6000
tgtattgtcc aacaatcatg tctaataaaa tcattttcac ctatggggga atcatcttaa   6060
aaaccttatt cctacagatt ccattttgac agtcccagca aaagtcacaa tattttccat   6120
gagtacacca atgttcaagc tctctttcgg gaggaatgct gccaatttta tgttttttag   6180
cttctaactc tctgtacaac atcagttggg aaagcagaaa gaagattacc aggagaacca   6240
ttaaatatat aatagtctgc aaactacgtt tgcgaatgta atttgcaact aaaacacaac   6300
ccacaaggta aaatccataa gttaataact tttgccattt tcgtatgaca gcctcgtgcc   6360
attcatggtt gtgttgtggg cattctgttc ggtaaacttc atgaggcttt atagaagtta   6420
catagtaggt acagaattca ttgtgacgaa aaacactgca gttagctatg tagtcatttt   6480
caagaatggg agaatggttt tcaaagacct tattcttaca gatgccatct tgacagtccc   6540
aacagaacct acaatgattt gcataggtgc accagtattc aagctccttt tcaggagggg   6600
```

-continued

```
ttcttgttag atccaggagc tctagctcat atgtataaag aagagttgga atggatagta   6660
aagtaaatat ttgcagacca agcatggcta cttgtgaaca agtggctgct cgtcaacaaa   6720
tagctgttta tcagcaaata gctgtttatc agcaacaact aattatcagc aaatgctgct   6780
tgtgggtaag ccaataaata ggccataccc ttgaaaggag aattcagttt gataaaaaaa   6840
ataacgagtt ttctaataac ccggtcaagc atttaataaa tgaatagcat cacacgtctg   6900
catcgtgcat tctgcctgga aaatgggccc atctctaata tatttacact gacggtgaat   6960
catacagtgt tccatgggat agctatgctc ctgtacagga ggcatatctt ttagaacttt   7020
attcttacaa agaccatctt gacaagccca gcaaaaccga caatttttca catattgaca   7080
ccagtatcta agctcctctt ccaggggatt gtcggtcgaa aacccctgta gactagctag   7140
gccagctagc agcaagccga ggtaactaaa gaacctcatt gtagtgttat attacgaaaa   7200
aacatgttaa aatttggaaa aaaaagccct ttttatagat ctggaaaaaa attttcacaa   7260
atctaattaa aagccttaca gatcatcctt ttcataaatt ttcattaaca attggtgggg   7320
gcggttgtga ggtactggat cagaacaatc cataacatgg taatgtccat ttccttcacc   7380
atatgtacac tggttatacc agcgagaaac ctcacaagat gtcaaataac tgttctcaac   7440
aatcaatggc atgctcttat tcaccttgtt cttgcaaatt ccatgtgcac attcccagca   7500
aaacttgcag ttttccatgt aagtacacca gtatccaagt tcttcttgtg gaggattatc   7560
cgttgaacga agatgccctc ctgcctgagt aggtagtcct aagacctgat tggccagcag   7620
gccaagaatt tccaagaaga tcaccaacat tgctacggct ggctgaacag ctggcagata   7680
gctagctaat tagcaaacca agtgactcgc cctctctact cttaatatga gaatttaaga   7740
ttcggtccgg ctttttttccc atgttttaca gggaaaaggt atttttagcc tatgaatgta   7800
catggttccg cacattaaaa aaaataaaag aaattattta atattggctg ttattttctt   7860
tcaactagca acaagccagg taactaaaga acttcattgt agttttatat tacggaaaag   7920
gttaaatttt ggacaaaaaa atcatatcta attaaaaatc ctcacagatc tttcttttca   7980
taaattttca ttaacaattg gtaggggcgg ttgtgaggta ctggatcaga acaatccata   8040
acatggtaat gcccatttcc ttcaccatat gtacactggt tataccagcg agaaacctca   8100
catgttgtca agtagctgtt ttcaataatc aatggcatgc tattattcac cttgttcttg   8160
caaattccat gtgcacattc ccagcaaaac ttgcaccttt ccatgtaagt gcaccagtat   8220
ccaagttctt cttgtggagg attatccgtt gaacgaagat gccctcctgc ctgagtaggt   8280
agtcctacga cctgattggc cagcaggcca agaattccca agaagactac caacattgct   8340
acggctggct gaacagctgg cagatagcta gctaattagc aaaccaagtg actcaccctc   8400
tctactctta atatgagaat ttaagatccg gtccgacatt tttccgatat tttacaagaa   8460
aaagatattt ttagctacaa atacacttca tatatcccta aaaaaacaaa aatttattta   8520
attttaacta ttattttctt tccactctct ctttaagatt ttgtaaggat tccagggctt   8580
tggttcagaa caggccatta catggtgaat cccctgtcct agatcataca tacatttatt   8640
tagccagcgg gaaactatac atgattgcac atactcattt tcaagaattg ttgtattctc   8700
caatttgccc tcacaaaggc cattttgaca attccagcaa aacttgcagt tttctgtata   8760
agtgcaccag tattcaagtt cttcttgtgg aggattatcc gttggatgaa gttgtccagc   8820
tggttgatta ggtagcccta agacctggtt gcaattcatg gtatggtaga tacccttatc   8880
taaatcatac atacatttat ccagccaacg ggaaaccaga catgatttca catactcatt   8940
cttgtaaatt actgacccat ctattttgtt tatacaagtg ccgtcttggc agtcccagca   9000
```

aaattggcaa ctttccatgt aggcacacca gtattcgagt tcttcctctg gaggctcctc 9060
tgttggacga agttgtccaa cgagctgact tgaaacctgg ctggccagaa ggccaagaat 9120
tcccaagaag atcaccaaca ttgctacggc tggctgaaca gctgactgaa tagctagcca 9180
attagcaatc cactgtactt ttcataagat catttaagat tcggtcggca ttttttcaat 9240
agtttgctag gaaaaaattt ttaattttat agattcacac tacttcattc tcatgcttag 9300
gaaaaaaaca aactaaatct tacaatgtat ctggatctaa tgagaagcta gaattcatct 9360
tttttcaaat cctttctggg atgttcattc tttttccact ccttccttgc aattttataa 9420
ggattccagg gctttgggtc agaacagttc atgctatggt aaatgtgctc ctccacatca 9480
tatctacata ggtcacccca gcgggaaacc tcacaatatt ttacatagtc attctcaata 9540
atacttgtgg agttgtttcc ccaaaccctg ctggtacaaa tcccatcttc acaatcccag 9600
cagaaccgac agctttccac ataagtgcac cagtatccaa gttcattctc tgggggttca 9660
aatgttagag gaagatgtcc acctacccga gtagaagtgg aggatgaaac caggttgcta 9720
ctggccagca ggccaataat tcccaggata atcaccagca ttgtgctcaa ccagcaacgg 9780
ctagcaacga ctagcaactg actagcaata gctagaaatg gctagcaatc agtagtagct 9840
aacgctctac tctttataag aaaatttaaa attcgatcag attttttag aattgagaat 9900
gagtaaaacg cttatattct ttttctagct agaaaaaata agctagttta agataggatt 9960
tcccttacta acggtttaat ttttagcaaa ggtataggta aaatacactt gtacttagct 10020
gcaaaaaaat aagcttatgg cgtataagcc gccataagtt tatttaatta aaatgttaaa 10080
ctctgtgata agactggaat cttaggcagg tttgatgtgg agaacagcat gaaatacaag 10140
agtgcctgtt acacgaataa gttctctcaa accggggatg gtcatactca catctatgaa 10200
atcctggtct aggagattca tttgatgcat gatggccgca cccacactta tgagacactg 10260
aagaactaaa gggtttaatt ttgatctgaa tggtactata taggatgatg gcaatccata 10320
tcaagattag agcaatcaaa atcacctcct caagaagcat gatgtagcct taaatcttag 10380
actgctttaa accttaggcc ctcactatct ttaatgaagg agtttaaatt ttgatccctt 10440
tttcaagacc catttagaag aaaaaataaa gtttatatca atctaattca taagtcatct 10500
ctttcataaa tcttcatgta ttctctatgt ggataagtat gggatgttgg atttgcgcag 10560
tccatttgat gatctgtatg gtttttgggt ccttcataat aactacatat accattccag 10620
cgggaaaccg tgcaatttat aatccagtca ttttgatgaa taactggcca atctgtttga 10680
atcctgtttc ggcagatacc gtggacgcat tcccagcaaa agtcacattg gtttgcgtaa 10740
gtgcaccaat aaactagctc atgttcagga ggataacggg ttggtagtaa atcttctaat 10800
ttacgtatag gagcggcttg aaggacaacc acccccagta gtactagaat cagtaccttt 10860
atagtggcca ccctacacta gacctctaag ttgaagacaa agaactaaaa tttagagccg 10920
tttaattact actaataatt atattttta ttgtctacaa taggattcta ttaaaaaata 10980
atgattttta ccaagaaata tttttataaa aaattaatat attttgtaat aaactttatt 11040
tccaatgact gttaaaataa ggaaactatc cttagttagt cgaggaagat ggttaggtta 11100
tttcgcaatc cgataaaatg tttattttat cgtaggtctc gtaaaatcca ggaaaaaaaa 11160
ttacggaaga gtttaaaaaa gctaaatttt taccaccctc cagaagattg ttgtcaaata 11220
tatcgtttgc tagaaaatgt tcctggagga acttacttta ttacagaaaa tatgacgaat 11280
gatttaatta tggtcgtaaa ggattcggtg gataaaaaaa ttaaaagcat taaattatat 11340

-continued

```
cttcatggaa gttatattaa gattcatcag cactattata ttaatattta tatgtatctt  11400
atgagatata cccaaattta taaatatccc ttaatttgtt ttaacaaata ttataacatc  11460
taagtaaata ttcttggaat ggattttctt atagaatggt tacaggatat gtcagcgaca  11520
ggcttaataa caaatttgtt aatatttttt tgttaaataa atgaacaggc caccatttaa  11580
tattacccgt tgcaaaataa gaaaaaaaaa caaacttata gttacaaatc atcttgatta  11640
atcacatgtc gttttaactc aatgaaccat tctaaatctt tgggttgtga acaattcatg  11700
ttatgttgat agtgtatcct aaagtgagct tcatacatac accggtcatg ccaccgggaa  11760
actgtacaat taacaatata atcattttgc gtaataatag ggtggtcact aaacacttta  11820
tttttacaca ttccatcttt acaggtccag cagaagtcac agtgttttgc ataggtgcac  11880
cagaacttga gatccctttc aggaggccta cgcatttgca tcggattatc tgtggaaaga  11940
ggtaggttca ttattatgtt cgtcatcaaa attcctaaaa gaacatagaa gccaagaaag  12000
ataagcagtc ttgtagcggc ttgcattcgc attcgtgagt attgtttgcg aacatagctt  12060
atgagagcaa tggtagctat catacaaaga caagtatgtt tgatattctc agtgtcaatg  12120
accctatcct cctttatttg cattaactca tcaaaccaat cataatatgt gggatttgta  12180
cagctcatga tgtgaaagcg gcgtatccta gagtctgtaa agtagctaca tctttcatta  12240
tagcgagaaa ccctacatat ttgtatgtaa tcattttttt tgatgagagg gtgtttttca  12300
aaaaccttat ttttacaaac cccgtgtcga caattccagc agaagtcaca cgattttgca  12360
taggtgcacc aatactcaag ctctctcttt ggaggtctcc gggtcattgg taactctcct  12420
gttcctggaa aagattggct ttgaatgacc ggctgcatga ccgccagtac caaaaggaac  12480
acaatcacct tcatggctgc aacttataag ttgcaactta tgggttgcaa tactgcaacg  12540
tataggttgc accttataga tcgcgactca aaaggtatga aaaccttacc ctcaatacag  12600
aatttaagtt ttaatcctga taatgtatct gtttatgaaa aaaaattttt tttactcatg  12660
tatgaattct tatacgaatc ataatatgta ggctgagaat aataattcat atacggtgtt  12720
gcgggctcaa taaaaatttt gttaccacaa aaaataaatg ctggattttt aagatatata  12780
tctattaatg actaaaccct ttatacgctg taggctgaaa acaatccata taatgaatat  12840
acggtgattt gggtttaata aaatacatac aacggtcaaa atagcgggca atactacatt  12900
gactaatata atcattttgt ttaataagag gcatatcatc ccacacttta tttttacaaa  12960
taccgttcct acattcccag cagaaatcac agtgttttcc atacgtgcac cagtattcaa  13020
gctctcttat aggaggcgta taagtccttg gtaaattttg tttcatataa aagatggaaa  13080
ggggtcgatt taaacccggc tgagatagcc aaatcaaaat acataaaaga gcaagtagtt  13140
tcatagtggt atttagatgt aaatttttat agtatgcaaa tacaatgtaa cctacaaata  13200
caatactaaa tacaaggtaa aaacaacaat gtcttataat gattggccaa taatcacccc  13260
cccccccccc atttttccat gaatatttca tttcctgtat agggtctagg atgtgaacac  13320
tccatgttat gatgattagg cattttaact gatatttcat aaaaacaccc ccaggaattg  13380
cgattaacta tacagtttac aatcgaattc atcgaattag actcatttgt tatcttattt  13440
ttacaaatgc cattttgaca atcccagcag aagtcacaat tctttacata cgtacaccaa  13500
tatggaagct cctccttagg aggatgctgg gttcttggta attctggtaa ttcatgtgca  13560
agaatgagga ctgagtagcc caacaaaagt cctagaacct tcatgttgtg tccaaatggc  13620
acctgtcatt ttaaaaaaga tttaaatttt gctaccgcaa aaaaaatcca gtatgtattt  13680
ttttaataca tataattatt gaagtcttat aagataaagc cgagaacact atattttgta  13740
```

tagatgatgt atccggtatt caaactctct tataagtaca tgtaggaaat ggtcaattat 13800
tcaagattgg ctgagataac aacaaaacca aaatactcaa aagcataagt aatttcatgg 13860
ttgtactcag tcgtagattt ttgcagatcg caaatgcaac gcaaccagca aatacaaagc 13920
taaatacaag gtaaaaacaa taataccta taatgattgg ccaattctta tccctccatt 13980
tttccatgaa catttcatgt tcataaagtc taggatacga acaacatttc atgctatgat 14040
gattaggtat tttaagtgat atttcataaa aacaccacgg ggttgttggt gattgatagg 14100
taagaataag gatggttgaa taacctagta aaagtcctag aaaaaccttc atattgcgtt 14160
cataccacag atgttattta aaaaaaatat aaattttaca gtatgtgata tacacatacc 14220
acaaaaatgt tcttatatta actaaaatat gtgggcagag agcaattcat ataatgaata 14280
tatggtattt taggctcaat aaagtacata caacgatcaa taaaacgggt aatactacat 14340
ttactgatgt aatcattttg aacaataaga ggcatatcat ccaaaacctt atttttacaa 14400
ataccattct tacaatccca gcagaaatca cagtgttttc catacgtaca ccaatattca 14460
agttctctca taggaggcgt ataggtcctt ggtaaaattt gtttcgtata aaagatggaa 14520
aggggtcgat ttaaaactgg ctgtgctaac caaaccaaaa tactcaaaag aacgaaaagt 14580
ttcatggttg tactcagacg cagattctta caaagcgcac atacaaagca gcctgtatat 14640
gcaataccaa tgatgaaata gagacagtat tgctttatag ataattgttg atggtcaccc 14700
cccccccccc cccatgtttg catgaatatt tcatttcctg tatagggtct aggatgtaaa 14760
cattccatgc taaagtgatt aggcatttta gatgaaattt catataaaca ggattgagtc 14820
ttggaatcac ggaaaactct acagtttaca atagaatgat tggagtcaat gaaacgagat 14880
tccgttatct tatttttgca aatgccatct tgacagtccc aacagaaatc gcattgtggt 14940
acatacgtac accaatatga aagctcactc ttgggaggat gctgggttct tggtaagtct 15000
ggtaattcat gtgcgagaat gaggactgag tagcccaaca aaagtcccag aagaaccttc 15060
atgttgcgtc taaatgacac ctgcacttac aaaaaaaaat ttaaattttg aatataacac 15120
aaaaaaacca ccttaaaatt tcttatatta tttcttggat ctgccccgac gtcatacaat 15180
gtattaaaat tatagaccaa tcatcttttt gtatataggc taatcatctt tatatataga 15240
ttttagatgt ttgcttgttg tatcaactta actgctagcg aagaaaatgg ataaaaactt 15300
tctgtatttt tataggttga aatcatttta tgcacatcgc taggatctaa tattttattt 15360
tgaagaaccg aatgtgggct taaaattttt ttcttagaaa aaagtagaat cataatattg 15420
ctatgttttt gtttaatgat ttcttgtatc ttttttgtat acgggttggc acccaaacct 15480
atacaaaaat atacattact caaataacta ccttctatac ataatctttt ttccccacgt 15540
atttcctat ttatttccct atttatggaa ttaaaggata tcaatctctc taaggcacgg 15600
tcaaggtctg cgcctaaggc aaaacaataa tatataccta atttattccc agggcgtgca 15660
caggcaagaa acatcatgac gtttagccct aaacgtatat tttcctgaaa atacgcatga 15720
tgaacttcat caatattacc taagtatatg gccgtttgta aacgccaaag atctaaatga 15780
ggaaattttt tactaagata atgaataggt tttgtgagat taaaatctat ggcgaactta 15840
taccaaaatt ttaatacaag tgtatttctc gtcatttctt cttctttttc atctaaatat 15900
aagataaaac gattgtaaac aaagtctatc aataggtgaa aatcattgct attaaagctg 15960
tcgagaatca aaatattgtc ataataaatt tcgatcgcca gtaaaacctt ttttcgtttg 16020
acgagataaa caaacatatt atacaaccct acatctaaaa attctggatt ggctcctagt 16080
tggatacaca ggtctttagt ctgcttcgtt ttggcacaca tgatgccaaa attaatatca 16140
gcaccccata aaacaaataa cttgattaga tcagtctggt tttccttcac agcttttact 16200
aaggctctgt caagctcata gctgtcgaca tcagagcatg acatagagcc accggttacc 16260
attttacatt gcttacaaaa acctatgggt ccgttttccc accatagtcc aagctgttgt 16320
agaataaaaa tatcatcctc atgataattt gaaaaagcct tggtttctat caagactttt 16380
tttgtaagaa cctgtaaaga gttcatcgta ttattatgaa taacaggagt aaacgtaatc 16440
aattataaaa gtgatttttt cgaaaaaaac tttagatggt tgaaaatgat aatgtacatg 16500
ttcatacaaa aaatagatgc agtgatgtct aaaatcaaaa tttaattttc tatgtaaaaa 16560
gtacagactt acttatttgg gttaaattgt ttattttaaa ctttaattaa ccgtttgagt 16620
tagcgatgtt tgatttatct tccatactca tccggggggg gggggtcctt atagctctga 16680
cattattgtg gattattgaa tataatgaat acttcataga tgctaaacat tttaatagta 16740
gttctgaggc ttaattgtac tctataaatt tataaaaact ttttgatcaa aatttaattt 16800
cttataaaaa gagtacagac gtcgcttgtt taagcttcat catgtttcat tcattacttt 16860
ctacaattac gggggggggg agtcccctca tagctttagt attgctatgg tttactaatt 16920
attatgtaga atttatagaa gcatatgtac ctgaaagtat acctactcta taaaattaaa 16980
taatttcagt atattttttt tatgaataga acggaaatga tataaaaata atttaatatt 17040
gcaaaaaaaa ttcataatgt tggtatgtat tataaacata atagcatgtg taatttataa 17100
actgactcct ctatataatt attagatgag gtaccaacct acttatgata tgccgatgat 17160
agatattgta tactataaaa caaaattatt ttaaatgtat tcatggatac attataacat 17220
ttttaccgca aattgtctct cagcgaagaa aatgaatgaa acgtttctgt atattcatag 17280
gttgaaatta ttttacgcac ttcactaggt tctaatattt tcttatgaag tattgaatgg 17340
gggcttaaaa gtcctttctt aaaaagaagt ttcatcataa cattcttttc ttgtctaaga 17400
agagtttctt gtattttttt tgtataagga ttggcaccca aacttataca aaaatgtaca 17460
ttactccaaa taccataatt tgaaaagaaa gttatttccc tatttacttc atgattaatg 17520
aaacctatca acgtctctaa ggccgtattg atatttgcgc ctaaggcaaa acaatagtat 17580
atacccaatt tattttgagg gtacatacaa gcaagcgaca tcatgtcatt tggatctaaa 17640
cgtatatttt cctgaaaata tgcatgatgg atttcatcaa cattacctaa gtatacagcc 17700
gtttttaaac gccaataatc taggtgagga aatttcttac taagaaaacg aataggtttt 17760
ataagattaa actctatggc gatcttaaac caaaatttta atacatatgt atttttttatc 17820 atttttttctt tttcatctaa atttaagata aaacgattgt aaataaagtc tatcaacacg 17880
taaaaatcat ggctatcaaa actgtcgaga atcgaaatat tgtcataata aatatctata 17940
gctaataaga ccttttgttg tttaattaga tcaacaaaca tattatacaa ccctacatct 18000 aaaaatttttg gatcagctcc tagttgaata cacagaactt tcgtcctttc cgtcttggca 18060
catatgatgc cataattaat gttggcaccc cataaaacaa ataacttgat tagatcagtc 18120
tggtttttct tcacagccct caccaaggct ctgtcaagct catagctgtc aacatcagaa 18180
catgacatag agccactggt taccatttta cattgtttac aaaaacctat gggtccgttt 18240
tcccaccata atccaagctg ctgtaaaata aaaatatcat cctcatgata atttgaaaaa 18300
gccttgtttt ctatcaagac ttttttgta agaacctgta aagaattcat cgtattatca 18360
tgaatgaaag cagtaaatgt aatcaattat aaaattgact tattgaagag aaatgttaaa 18420
tgagtgaaat cggtgtttat gatgatgtac atgatcatac gaagaaacac gttcactggt 18480

```
gtccatgatc aaaatttaat gttttacgta aaaagtacag atgttaactg tttagtttaa  18540
acataaattt aacctttagt ttaaacccta gttaatgatg tttaatattt cttctatact  18600
cattcaggga agtgtaatga ttctaatact gttgttatgg attattaatg aaaactttac  18660
agatgctgga gggaataatt ttaatcatac tgttttaatg tagctatata agctttcatc  18720
aaaatttaat ttttttttata aaaatacacg aattaaacta aagtctaaac tttagtttga  18780
ctatttgagt taatgatgct taacttatct tccatgctta tcaagggggg gtcctaatag  18840
ttttgatact attgttgtgg attgttgaat ataataaata ctttatagat gctgaaatgt  18900
ttgaaaataa tagtacatca atgttgtaag tttgatcaaa atttaatttc tcataaaaaa  18960
ggtacacatc aacattgctc atttaagttt catgatgttt gattcattac ttcctacaat  19020
tactgggggg gggggggggt ctttaatagc tttagcattg ttatggtttg ctgactatta  19080
tgtagaattc atagaagcac gtttagatag taatatcact gcagtgtaga ttatgaaata  19140
catactaaac taatttcagt atattttttt tgttcatata agttaaggta caaaaatgat  19200
taaacattgc aaaaaaagaa aatcacaatg ctattataca tagtgatcat agtggcttgt  19260
atcatttcta aactagttcc aaatgaatat tgggcaatac atctattttt tatcattatg  19320
atttttatgg tatatatgta tgaaaagtta gatatacatc aaaaatctca gttctggaat  19380
tataccatgt caggcttatc tggacataac gtacaggtaa catgtaagtg ttactaaata  19440
ctatgaagta tctatttttt ttgttgtaaa aaaaagaact tgatagtatt ttttaaaaaa  19500
taaaataatt aattgtacgt caacttcctt attttattct ttaaaaataa ctcgtaagta  19560
ttatttatct attttttgaa aaaatagatg taatcggttt catcatttag gtgtgtattt  19620
ctttttagca tctatcaaga attcattgtt tagtgatatg aaaacaatga atgatcatta  19680
tcttctattt aacaaccacc taaataaatg aacgtctttt tcatcttaac tgattaccaa  19740
aagttatttt gcgaaaaggc atacatatga tcaatatcag acctacaatg aatatttcca  19800
taatatccct ttattgtaat aattctattt ttgcattccg atatctcatc atctgtgcta  19860
ttatatgttt ccataactgt ttcatcatca aacataaatc ctgttaaata ggcaaaagac  19920
tttaatcccg gatagatttt taccattttc ctgagagccg tgtatagctt gtaataaatg  19980
gccaaaaata tgcaataaag cgtagaaaga gagtaatttt tggcataaaa gattttgaag  20040
gtttgatgaa tggctaaatc gcatataata taagatacga ttttaaagcg cacctgttca  20100
cgcagatttg ttgaaaaatt cgtggaaaga tttaacaaat aaaaggttat taatagttgc  20160
tcatcattcc ccttatacga catcgtcaga cgctctaata ttttactact aggcacatct  20220
gccacatgtt gaacatttaa agcctgttct tcttctgtgt tacggcaaaa gagccgtgcg  20280
tattcaggtg aagctcccca ggataacaac gtccttgcta cggctaaatt tttttgacg  20340
atgactttta tcagaaataa gtctttattt ttgcattgat cactatgcga atttgtatag  20400
ttgacgccgt tgcattgagt acattgatat aatgttttac aattccagcg tagccctaaa  20460
tggtataaaa gaactgtatt ttcgacataa gcatgctgat taacgatgtt tttgagacaa  20520
cacgtcgtta aggacaccat attgtctcca atttgttaga taaaagtctt tactaaaaaa  20580
atagattttt agttttaaca atcgagattt tattatttgg atgcatcatc aaaaagattt  20640
ataagtataa gaggttgtat aagaaaaaaa tgatgttata ctatttatgt taaaatttaa  20700
tttatcatat aaaaagtaca gatttaatca gttggttaaa ctatttagtt aattaaacta  20760
aatagtttaa ccatttagtc agactacttg gttagcaatg tttgagcttt cttccattct  20820
```

tatccggggg ggggggtcct aatcgttcta atactattgt ggatagttga atataatgaa 20880
gactttatag atgctataat gatgaattct agtatgcctg tataaaataa ttaacctttt 20940
tgatcaaaat ttaatttttt tataaaaagc tacagagtag tgttttatta aacgtggctt 21000
atttaaaagt tacacaatgt taaaatctct acttacttta attctttgtg gggttttatt 21060
aactttatcc atattatggc ttactactta ccatgtagaa cttatagagg caatagatga 21120
tttctacgac tgaaatatag aatagtccat tttctatttg taaaataatg atttatattc 21180
tttcctaaaa atgatacttt atatggtttg aaaacaaata ttaacaactt gatttttttt 21240
tctataaata aactataaat gaaaatagta aaactcatag agtcttataa gtgaacatct 21300
tcataatgtt actcaaacgt tggactatta aaaaatattc cgtgtgcatt attgctttta 21360
atcagtatga ttactttata cgaagccgct attaaaacgc ttatcacaca ccgaaaacaa 21420
attttaaaac accccgatag ccgtgaaatt ttactagctt tggggttgta ctgggataaa 21480
actcatattc ttgttaaatg tcgtgaatgt gggaatatga gtcttaccgg aaaacacagt 21540
acaaaatgta ttaacattaa ttgtctactt attcttgcca taaaaaaaag aataagcgta 21600
ttgttgatac cttgatagga atgggcgcgg atgtaacata tatacatctt ttaaagaata 21660
agataaaact gtcatacaac cagctgtcta tgcttaaaag caactcgcag atttcattga 21720
aggagcttca tgctatatgc tatcttttat atggtcggct tcccaaaaaa attaaacaag 21780
ggatgcgact gtgtaaaaca atggcgggac tatgtggtga acttttatgt gcatttttag 21840
ctccgtaaat gataatatgt atttaaaaca aacagatatt accaaaatat attctatgta 21900
cataatatct gggaaattat tttttttct catacccta aatataaaaa tattgggttt 21960
cttcactaaa ctttagaggt aaaaattttt ctttgttttg caccatcatg tatgggttta 22020
ggctgtccca gggattgttt atttgaatat ttcctaaata ggaacacaac gccatgatca 22080
tatatctttc attctggtaa gctttttgat acatcttcaa agatgccgta cctccgagtg 22140
tgtaacagca aacaaacgtc cgtacttttc catgggtcgc agcccattcc attccgtagc 22200
tcagcatctt ttgctgtatt tttttattcg ctttataaaa aaagttttc atccattcca 22260 cgttctcata aaaacaggca cttaaaaaga gcactagggg tagtgtagtc ttattataga 22320
atgtaggaat gtatgtttta gttatttttt tcaacgcgtg ttccatacta tgttttaccg 22380
ccataaaaat acaaaaccaa taccaacttt ttctataaaa ggttttgctg tacacatata 22440
aacgagcaaa atatatttca aactctatat tctttttata aaaaaactcg agacagtcgt 22500
ttatgttacg actttttcta aatacctcaa aaacagtaat taattcactg tcgctgtgga 22560
aatgttcgta agctaactgt ttaatgtctt taggggtcaa ttcttttttt gggagcagtg 22620
gtttgagatt cggcaaaggt cgtctaaagt agtgagcgaa cttttcattc gctccccaac 22680
acaaaagccg ataagccagc atgtagttat cacgttttac cgcgtaaata agcaaatagt 22740
ttatattgat acatgtacca tgttgctgcc cgtttggaca tatgttgccg cattctgaac 22800
acttatgaat gagatcatag ttcttacaac ataaccccaa acgggttagt acttctttgt 22860
cacgttttaa aaactcgaca tgattcttta atgttaatgc tttgagcgca atgttaaata 22920
aactctgcat tttattaaaa tgaggttagt atcatgtttt agtataaaat ttagcggctg 22980
tttacataat gctaaataaa cttaacgttc ctactaaacc aaaaaaaatc aaattgacta 23040
agtcatagag aatttgacga tgttggtagg taattttta acatggtata tattttttta 23100
gggtcggtta tattaggtaa taaaagagga cgtgccgtta aagtattttg cttaagatcc 23160
tttagatcct tacaaaaata tagattgttc gtctgatgat gccactgtgt tgcagtgatg 23220
gcttgatcaa tatcacctcc caagacaaaa cagtagtata tcgttaaaaa gttgtaatct 23280
ttcatacaag ccaactgcat cattttatcg atgtccatat gaacgatctt ttgctcgtat 23340
atttcatgaa ggtcaaatac attgttgaag taaatggcgc acatgagtcg ccacatacta 23400
aggtgcccat atgtttgata gaaaaaggag atagctcttt taagcttata ttttactgct 23460
atggcatagc agtatttaac gaatacgttc atgggtacat tatctaagat ataaaatatg 23520
aaaaacttta actctcgatg aatctcttcc cccatttcct gtacatttag agcttccaac 23580
ataggatttt tatcaaatat ttcatgacat aaaataatgt tattgctcgt tttatgacgc 23640
attaaaccgg tgaaaatttc cttattattt aaactatctt tagctcctaa ctttcgacac 23700
agctcctgag tttgttccgt cctagcacag gtcagcccat aataaatgtt tgctccccac 23760
tcggtgaaca gccttattac gtcatagtta ttttctttta tggccatgat taatgccaca 23820
tcaagatgaa gaagttcccc cttaaagggg gttgagctta aaataacgta attacagtag 23880
tgacataagc taatgggctt gttttgccac cataagccac aatattttaa aatataatga 23940
tactcctcag gcacgctctg tttggccaca gcctttttgg ccagggtttg caaggagagc 24000
atgataactt cttgaaaaaa aaactcaaat taagttccta cttttttaaa atattagtat 24060
ggacagatct accatcatat gaaggaattc tttcatcgtt aaacactgaa gagataatac 24120
tttcatcgta tagagaatat catgtcaatc catatattga atgttatata tcattaaacc 24180
catcattaat atagtgttta tgtgctatgg acaggttttt tgaatgataa tcttttaaca 24240
tacgttttat aacttcggga tcagtttctt ttaaagataa agaatcattc atgttataac 24300
aatttaatga taacatgctg gcaatgaacg agttgtcttt ttgatgcgct agagtctttc 24360
cctcctcaaa ggcattggcg cctaagtcta tacaaaagaa tatgtttccg atattataga 24420
actgaataga atgaaacatg gcctgattga tatcagcccc taagacgacg caacagtaat 24480
aaatcgttaa atagttatag ttcttgcgac aggcccactt tagcatttca ttcatgtcta 24540
tgcgaatcct ctccttttcg tacacttcgt gaagttcaaa cacattattg taaaaaaggg 24600
cgcacataag ccgccaccga tgtagatgag catatctctg ataaaaatag caaatcgcct 24660
ccttaaggtt acattctatt gccatcgcgt accaatattt agtaaacatc tcgcttaata 24720
tatcggtttc taccattaat ccctccagtt gttcataaat cattcccttt acttcaaaac 24780
gatttatggt atctaaaatg ggattattag aaaataccte atggcagaaa atgatgttac 24840
tgctagttag atcacgtttc aatgtgtaaa aaaatcgtaa aatttcctgg tcatttaact 24900
gttctttggc acctagctgc ctgcacaggt ctcgggtgtg ctccgtgttg acagaaagca 24960
aaccgtagtt gatgtttgca ccccactcgg tgaacaattc tattagatcg tgattgtttt 25020
cctccacagc tttcaccaag gccgcgttaa gatttgtgcc gttcttaaaa tacggcgtcc 25080
atattttctt ttgatgatac atgatagggc cattatgcca ccatagaccg cagcacttca 25140
aaaaatgagg atggcatttg gccggatact ggctggccag cacctttttg gtgagagtct 25200
gcagagagag gaccatattt cttttttttg aaaaaatcaa attaaaaaaa tcatgcttgt 25260
ttagcataca tgtaatattg ttataattac gttataatta cgttataatt acgttataac 25320
tatattataa caatggtata acaatggtat aacaatgtta taacaatgtt ataacgatgt 25380
atcattgatg tcatcattca actaggccaa catacttttt aatttatagt tttttaatag 25440
atgatatatt ttgttaggat ctgcttcttt taacgttaat agcgaggagt ctgcactata 25500
aatgtctaat gataaatgat gagatatcaa atagtaattc cgttgctctg ctagggcctt 25560
tgcctcttca aaggcgtcgg ctcccagatc tatacaaaag aacaagttat ccatattata 25620
aaatcgtacg caggcaagca tagctgaatt aatattagct cctaagagaa aacaataata 25680
tatggttaaa aaattgttat cttttgtgca ggccatccgc atcatttcat ccacgtccat 25740
gcggatcttt tccttttcat acaaattatg taggtcaaac agcttattaa aacaaagagc 25800
acagattaac caccacgtat ttagatactt aaaatgttgg taaacataag aaatggcctc 25860
cctaagatta tcctgcaatg ccactataaa acagtatatc gttaacatat caccatccga 25920
catattactt aatatgtcgg tgtcttctac taacctttc aacttccaat atatggatga 25980
ccttatttcc cttataatga cataggctgg aaagggatta tcattaaaaa gtttaagaca 26040
taagataata ttactgctag tagtgccagg gtgtattaat ttaaagaaca tgtgcataat 26100
cttcttttta tccacgcggt acttggctcc taattcccag caaaattctc gaacaggcgg 26160
cgtattggcg caaattaacc catagttgat gtctgcgccc cattctgtaa acagttttat 26220
taactgatag ttgttttcct ttgtagccaa cattagtgcc gtattaaggt ccaagccgtc 26280
tgcaaagctt ggcagcttta tcagcatatg tttgcaatca agggaaattg gggccttata 26340
ccaccatagt ccgcagcgtt ctaagataac atggtactca atagatactt gctgtctggc 26400
tagtaccttt ttggcgaagg attgtaagga aggaaacatc ctgtttcttt tttttaaaa 26460
atcaattatc tttgttcata atcaagaaaa atccccatat ttattgagtg ataatttttt 26520
aacatgcaat ttatttttc agggtccgta acgatcgaca acagagaaat aaccggattg 26580
taatgcttta atgataaggc atgggctatc agataatttt ccttttgttc tgccaaagct 26640
ttgccctcct caaaggcatc ggcacccagg tctatacaaa agaacaggtt tccaagatta 26700
tagttttgta tggaaacaag catggcttga ttgatgttgg ctcccatgat aaaacagtag 26760
taaatggccg aatagctata atcttggatg caggctatgt gcatcatttc atcaatatcc 26820
atgcggaccc tttctatttc gtacagctcg tgaaggtcga acacgttgtt gtaaaaaagg 26880
gcgcacatga gccgccacct atgtagacgc gggtatttct ggtaaaagta gcggatagca 26940
tctttgaggt catagtccac cgctatcgcg taccagtatt tggttaaaac agtgctaaag 27000
ctatcatcat ggtccagcat gaaggttatc tccatgagcc ctcttaactc ccacatgatt 27060
tccccctca gatccagatt atctataatc cttaaattgg ggttattgga aaacacctcg 27120
tggcaaaaga taatattgct actggtttta tcgcgcgttg tatcaaagaa aatttttaaa 27180
atatactctc tttctaaata ttctttggct cccagctctt tgcacagatc acgggtattt 27240
tccgtgagag cacaaatcat tccatagtta atatctgcac cccattcagt aaacagcttt 27300
atcaagtcat gattattctc cttcacggct ttcatcagtc ctatgtttaa ctcgatacct 27360
tgactaaaac aggttgacct tataaataat ttattgcgtc gaatatgaag cataatgggg 27420
ccattatgcc accacaggcc acaacacttc aggacatgat attgatctac cggtatacac 27480
tgcccggcca gtactttctt cgtgagggat tgcagggaag gcaacatgcc tttccatcct 27540
ttgacggaaa tcaaattatc tactaataac tatcagtgtt tatattaagt atttagatat 27600
tatcccgggc tggatacgta gtatcgctat tcacatgtac ttccaactct agccggagcc 27660
tgcagggtca tttattttta atattgattc ttttttgtat ttaatcattt agagaaggtc 27720
atcataggag ccagatgttc tctctccaga acttatgtcg aaaaacatta cctaaccgta 27780
aacttcctga attttttgac gaatatatat tacaactgct gggattatac tgggaaaacc 27840
atggaactat tcaacgagca ggaaacaact gtgtgcttat acagcaacat accctcattc 27900
ccgtaaatga agccctgaga acagcagcat ctgaagaaaa ttatgagatc gtgagccttt 27960

```
tattagcgtg ggaggggaac ctttactatg ctattatagg ggctctagag ggcaaccgcc  28020
acgacttaat tcgtaaatat gatgaccaaa tcaaggacca tcatgaaatt ctgccattca  28080
ttgacgatcc agtcatattt cacaaatgcc atatcatgcg gcaatgcttt tttgattgta  28140
ttttatatca agctgtaaaa tatagtaagt ttcgcgttct tctttacttt aaacatagat  28200
tagaggatga tttgcccttc actcatttac ttattgaaaa ggcatgtaaa gatcataatt  28260
atgaagttat taaatggata tatgaaaacc tacatatcta caatatgata gatacctttg  28320
aatgtgctat tgcccataag gatctacatc tatattgttt ggggtataga tttatatata  28380
acagaatcgt acccgataag tatcatcatt tagatattcg catgctttca agcctacaac  28440
tcctacataa ggtggcagcc aaaggatact tagattttat cctagaaacc ttaaagtatg  28500
atcataataa agataatata aatattattc taacacaagc tgcaacctat aaccatagaa  28560
aaattttaat ctatttcatt cctcaatcaa cccacgcaca gatagaacaa tgtttactag  28620
tggcgataaa agcaaaatct tccaggaaaa ccttgaactt actactgtct cacctaaacc  28680
tttccatcaa cctcatcaaa aaaataagcc attatgttgc cacttacaat tcaacaaata  28740
taataggcat tctgagtatg cggcggaaaa agaagatata tttagatatc atattgacaa  28800
aatttgtaaa aaaagctatt tttaataagt ttgtcgttcg atgtatggat acattttcta  28860
taaacccgga aagaatcctt aaaatagccg cgcgaataaa taggatgatg ttagtgaaaa  28920
aaatatctga acatgtttgg aaaaatcatg cggttagact taaatacctt aaacatgcgg  28980
tacacacgat gaagcataaa gatgggaaaa atagactcat gaactttatc tatgatcgct  29040
gttattacca tatgcaaggg gaagaaatct ttagcctcgc aagattttat gcaatccatc  29100
atgcaccaaa gttgtttgac gttttttatg attgttgtat cctagatacg atacgattca  29160
aaagccttct tttagattgt tcacatatca taggtaaaaa cgctcatgat gctaccaata  29220
tcaacatcgt gaacaagtat atcggcaacc tgtttgttat gggagttctt agcaaaaaag  29280
aaatcttaca ggactatcca tccatttatt ctaaacaata catgccttag tttatttttt  29340
ttgcggccga aacattattc ttaccctaga aaacgcttat agtcatctta aatcataggt  29400
aaggaagatc atcatatttt ttgaaacgta attttttaac gcatgatcta tgatttcagg  29460
gtccgtgctt ttaggcaacg gggtggtggc cggactataa atctttaggg ataaaatgtt  29520
ctttataagc tcataccctt cccctaaagc tgtagtaccc tcttcgaaaa catcagcccc  29580
cagatctata caaaagaaca tgttttctat attatagtac tgtattgagc taagcatggc  29640
ttgattgatg ttggcgccca ggacatagca gtagtacatg gttgaaaggt tgtggtcttt  29700
gatgcaggcg atccgcatca tctcttctat gtccatatgg atcttgtcct tttcatacgc  29760
ctcatgaagg tcaaacacat tattaaaaca aagagcacat gttaaccgcc acgtattcag  29820
gtgtgtatat ttttggtaaa aatactgtat ggcctctttc aggttatagc gtatggctat  29880
agcgtaccag tatttgagta gtaatgtact gagcgaaaac tcattattta gcagatcggt  29940
ttttactatt aactccctta actcccagaa aatttctatc ctcattttta tattatttac  30000
tttttgtaat atcggattgt tggaaaacac ctcatggcat aaaataatgt tactactagt  30060
tttatgaaac tttagatcta taaaaatttg taaaatttct tcttcattca aggtttcctt  30120
ggcacctagc tctcgacaga ggtcccaggt gtgctccgtg ttgacagata ccagcccgta  30180
gttgatgtcc gccccccact ctgcaaacag ttttataagg ttgtagttgt tttcccttac  30240
agccttcact aacgccgtat ttaggtttaa gccctcttta atacctgctg attttatgag  30300
```

-continued

```
ccttaggtta tgatcaaacg tgatcggagc atcatgccac cataggtcat aacactttaa  30360
aagataatgt tggttcgtgg gcacgcattg tccagccaac accttttgg tcagagattg  30420
cagggaaggc aacatgtctc ttcatctttt aaaaaaaaat caaattaatt agccgaataa  30480
atttttcttt cgagggcttt ttaaaagagc tctttaagag ctctttaaga gctttttaag  30540
agattaaaaa attattcttg ctggcattct gccaagtatg cggcattcct atcatctata  30600
gtatattatg agaatattcc caaatgatgg ataagttttt tgatttataa tcttttaata  30660
aactgcttat ttcttcgggg tcctttaagt ttagtggcaa ggaagcatct gagctgtaaa  30720
tatccaaagc caaactatgg ctcagaaaat tataaccttt ttgttccgct atggcacgac  30780
cctcttcaaa ggcattacca cccaaatcta tacagaaaaa tatattaccg atgttataat  30840
attgtactga agtaagcata gcttggttga tgttgccccc cagcgcgtaa cagtaatata  30900
ttgttaatgg attgttatcc ttggtagaag ccagacatat catgtcatgg acgtctattt  30960
ggatgttttc cttgtggtac atctcatgaa gctcatatat tttgttataa tacaggagac  31020
atttaatcg ccattcatta agatccgtat atttctcatc tagaaaacaa atggcgtcct  31080
tacaatcgta ttgtactgct ttggcgtacc aatacttcac tagtaaacca tttaactcgt  31140
ccgtttcttt tatttctatg agcccccata gtcttttata aattaagccc cttaattgta  31200
taacaaattt gttttctaaa ataggattat tcataaaaat ttcatggcac aaaataatac  31260
tgccgctggt tttattgtgc attatcctgg taaaaatacg gaaaatatcg ttgtcctcta  31320
gagtttcttt ggcgcctagc tgtctacaca actctcggat gtgcttcgta ttgatagaaa  31380
gcaaaccata gttgatattt gcgccccact ctgtaaagag ctttatcaga ctatagttgt  31440
tttccttaac agctattatt aatgccacac gaaggtctat atcttctcct aaaaatcctg  31500
attttatttg tattcggcca cgatccatac aaagcttgag aggagcatca tgccaccata  31560
ggccacaata tttcaaaatg cagtgttcat ctattgacaa acactggctg gctatcgtct  31620
ttttgacgag ggtctgcaga gagagcggca acgacatgtt tctttttcac caaaaaaaat  31680
caaatgttct cgtctttaaa ggttaattca tgttcttaaa atgttcattt catgatagtg  31740
attaataata tggtttaata acgctagaag gcttgtttat aagacagtca taagcagtct  31800
ataagacagt ctataagcag tctataagac agtctatgac ttagtctata actataattt  31860
ctggatgggc tgtaagatac tcttcggctc gtttcagatt ttttgaagta tatgtcttta  31920
gcatatcata tatttcctgg ggttcggtta catctaatac caaggtcaca tcacggctga  31980
aaagctgctt tactaagaaa atgttgctca agttatacat ataagctttg tgcgcaatga  32040
gttgtgccct atcaaaatcg gcagccccca aatcaataca gaaaaacatg tttaaagtat  32100
tattgttata gatagaaaga ttcatgccat aatcgagact agcccccaac ctatgacagt  32160
aataaatggc cgcgtaattt ttttcccgca agcaagcaaa tttcatcatc agattagggc  32220
tgatgcaaat ctctttttca cgacacaact cgtgtatgtc aaaaatgtta ttaaaataaa  32280
ggctacaagc tacccgccaa tagaggtgat ttttatgcct tttatagaaa tagtgaatag  32340
cctttgtaaa attatgtcgt aatgccaggg caaaccaaaa ctttgttaat aggtggtgcg  32400
ccgtatcccc cgtcaacgga atgtttgaac aggtgtacgt aactgtgtct aaagtggttc  32460
tagttacggt ttccaagagt ggattatgac aaaacatgtc ataacccagc agaactcctg  32520
cacaggattt tagcctggcc acttctttta aaatttccag aagacggggt tcggatacag  32580
gcgttaagcc tcccagttcc gcacacagcc gctttagata cacggcagga acacgtataa  32640
gcccatattc aggatttgcg ccccaatcca caaataaacg tataagttca agattatcgc  32700
```

```
tcttcacggc ctttactagc gccgcttcga gacaaagatc atcctcagaa aaacactgta  32760
aatgtttata cgaaaaaact tgcttacaat tgttacatag gtgaatagga cctaaatccc  32820
accacaaacc aaaacgctgc aacgtataat catagtcact tgaaagataa ttgcatgcca  32880
caactttttt ggccaacgtt tgtaaagaca acatactaag tttaaaacat cttaaatcta  32940
agctagctaa ctttcaagaa aaccctctat ccctaagaat atatcttata actagactta  33000
tagcagtaaa aatcaacttt ggttattctt tttaatataa aacgtctaat tacttgcaaa  33060
ggactataaa gcccattttc ctcagctaga atttttattt tttaatgaag tagggggata  33120
tgttttccct tcaagacctt tgccgaaagc atctttttat tcttcccgat gtttttggcg  33180
agcatgtact acaacgatta ggactgtatt ggagatgtca cggctccctt caacgcatag  33240
gagacgacca catactcata cgacgggatc tcatcctttc caccaacgag gccttaagaa  33300
tggcgggaga ggaaggaaac aatgaagtag taaagctctt gttactgtgg aagggaaatc  33360
ttcattacgc cgtcatagga gccttgcagg gtgatcaata tgacctgatc cataagtatg  33420
aaaaccaaat cggcgacttt cattttatct taccattgat tcaagacgcg aatacgtttg  33480
aaaaatgcca cgctttagaa cgtttttgtg gtgtttcatg tctgctaaaa catgctacaa  33540
aatacaacat gctccctatt ctccaaaaat accaagaaga gctgtctatg agagcgtatc  33600
ttcacgaaac cctatttgaa ctagcatgcc tatggcagag gtatgatgtc cttaaatgga  33660
tagagcaaac catacatgtt tacgacctaa agattatgtt taatattgcc atctccaaga  33720
gggatctgac tatgtactcc ttaggatata ttttcctttt tgatagaggg aacaccgaag  33780
ctacgttgct aacgcaacat ctcaagaaga cagcggccaa agggctcctc cactttgtgc  33840
tagaaacgtt aaaatacggc ggcaacatag ataccgtcct gacccaagcc gtaaagtaca  33900
atcatagaaa acttttagat tattttctgc gtcaactacc tcgtaaacat attgaaaaac  33960
ttttgttgct ggccgtgcag gaaaaggctt ctaaaaaaac attgaactta ctgttgtcac  34020
atttaaacta ctccgtgaaa cgcatcaaaa aactaccgcg ctatgtgata gagtacgagt  34080
ccaccttggt gataaagatt ttattaaaaa aaagagtgaa cctgatagat gccatgttgg  34140
aaaagatggt aagatatttt tctgcgacga aagtgaggac gatcatggat gagctttcga  34200
ttagtccgga aagagtcatt aagatggcta tacagaaaat gagaacggat atcgtaatcc  34260
atacttctta tgtttgggag gatgatctag aacgtcttac tcgtcttaaa aatatggtat  34320
acaccataaa gtacgaacat gggaaaaaaa tgttaattaa agtcatgcac ggcatataca  34380
aaaacttatt atacggcgaa agggaaaaag tcatgtttta tttagccaag ctctatgttg  34440
ctcaaaacgc ggccacccaa ttcagagaca tttgtaagga ctgttacaaa ctggatgtgg  34500
cacggtttaa accgcggttt aagcaactaa tattagactg tttagaaatt attactaaaa  34560
aatcttgcta tagtatcctg gaaatcttag aaaaacatat tatttccctg tttactatga  34620
aagttatgac tgaagaagaa aaaaacctat gtttagaaat attatataaa gtaattcatt  34680
ataaaacaat acaatgttaa aattcaatag atatccatca ttaatattga ttatattttc  34740
gaatattatc ttctatggtg caagataatc atctagcgcg tgaaacatgt cctcttctct  34800
tcaggaactt tgtcgaaaaa agctgcctga ctgcatactt ccagagtttt ttgacgacta  34860
tgtattgcaa ctgttaggac tgcactggca agatcatggt tcccttcagc gtatcgagaa  34920
gaaccagata cttgttcaac aggaacccat ccatatcaat gaagcactca aagtagcagc  34980
atcggaaggg aactatgaaa tcgtagagct gttgttgtca tgggaggcag atccccgcta  35040
```

-continued

```
cgccgtcgta ggagccctag aaagcaaata ctatgacctg gtttacaaat actatgacca  35100
agttaaagac tgccatgata tcttgccgct gattcaaaat ccggaaacat tcgaaagatg  35160
tcatgagtta aacagcacct gttcactgaa atgcttattc aagcatgctg tgataaatga  35220
catgctgccg attcttcaaa aatatacaga ctatctggat aggtgggagt attgcagcca  35280
gatgctgttc gaactggcat gtagtaaaaa aaaatatgag atggttgtgt ggatagaggg  35340
agttctaggc gtcggcaaag ttacatctct tttcaccatt gcgattagca acagagacct  35400
acagctgtat tctctgggct actcaattat ccttgagaat ttgtactcct gtggacagga  35460
ccccaagttt ttactaaatc atttcctgcg agacgtttca ataaaagggc ttctaccctt  35520
tgtaatcaaa accatagaat atggtggaag caaggagata gccataactc tggctaaaaa  35580
atatcagcat aaacatattt tgaaatactt cgaaacctgg gaaagctagg ttcagtatgg  35640
tgtactcact attgtagtga atcgtatcct gtaaattttg taaaaaagct taaacttttg  35700
accacatcat attgttttag aaatctcaaa ccagtgaaca acagtcttat catacattaa  35760
aattccagta aaatttatat tttttttggt aaacaaatgt tttctcttca agacatctgt  35820
cggaaacatc tttttcaact tcctgacgct tttgatgaat atatattaca agcgctagga  35880
ctatactggg aaaaacacgg atctcttcaa cgaataagaa aggacgctgt gtttgtacag  35940
cgaaacatcg tcctttctac caatgaggcc ctgagaatcg cagcctcaga gggaaacgaa  36000
agggtaataa aacttctgtt atcatgggag ggaaattttc attatgtgat cataggagct  36060
ctagagggtg accaatatga cctaattcat aagtatgata gtcaaattaa agactaccac  36120
atgattttat cattgatcca aaatgcaaat acctttgaaa agtgtcatca gttatccaat  36180
agtaatatgt ggtgtcttat acagaatgct ataaaatata atatgctccc tattctccaa  36240
aaacacagaa atattctgac acatgaggga gagaatcagg aattgtttga gatggcatgt  36300
gaggaacaga aatatgacat agttttatgg ataggacaaa ccctaatgtt aaatgagccg  36360
gagtttattt ttgatatcgc cttcgaacgg atagattttt ctttattaac aatgggttat  36420
agccttcttt ttgataacaa gatgagtagt atagacattc atgatgaaga agatcttact  36480
tcattaccaa cagaacacct cgaaaaagca gccactaagg gatgtttctt ctttatgcta  36540
gaaactttaa aacatggtgg aaatgtaaat atggcagtct tatctaaagc tgttgagtat  36600
aatcatagaa aaattttaga ccattttatt cggcggcaaa aatgtttatc acgtgaagag  36660
attgaaaacc tattattaac cgccataacc aattgtgcat ccataaaaac gttaaactta  36720
ctcttgtctt acctaaacta ttccgtaaaa aatatcattg gaaaaatagt acaacatgtc  36780
ataaaagatg gtgattatac catcatatta cttttaaaaa aaaagaaaat aaacctagtg  36840
gaacctgttt taacaggttt tatagattat tactatagct attgttttat aaaacatttt  36900
atccaagagt ttgctattcg tccggaaaaa ctgattaaaa tggccgcgcg aaaaggtaaa  36960
ctaaatatga ttatcgaatt ccttaacgaa aaatatgttc ataaagatga tcttggaact  37020
atatttaaat atctcaaaac cctagtatgt accatgaaac ataaaaaagg aaaagagaca  37080
ttaattgttc ttattcataa aatatatcaa gatattcatc tggagactaa agaaaaattt  37140
aaattattaa gattttatgt catgcatgat gcaactatcc aatttctatc tatgtgcaaa  37200
gactgtttta atttagccgg ttttaaacca tttgttttag aatgtttgga tattgctatt  37260
aaaaaaaatt accctgatat gatacaatat atagaaattc tatcgaaatc tgagtaaaat  37320
ttattttttt gatcagagta agaaaatgtt ctccctccag gagatctgtc gaaagaacat  37380
ctactttcta cctgactggc tcggtgagca tgtgattcag cgactaggtc tgtactggga  37440
```

aaaacatggt tctcttcagc gaatcggaga caactatgta cttatacaac aggacctcat 37500
catccccatc aatgaagccc taagaatggc aggggaggag gggaatgatg aggtggtaca 37560
actcctatta ctatgggagg gaaacattca ttatgccatc ataggagctt tggagagtga 37620
ccattatagc ctaatacgta agctctatga ccaaatcgaa gactgtcacg acatccttcc 37680
cttgattcaa gacccaaaac tctttgaaaa atgccatgaa ttagataaat cttgtaacat 37740
tttatgtctc gtattacacg ccgtaaaaaa cgatatgctt tgcattcttc aagagtataa 37800
aatgcatcta agtggagagg atattcaagt ggtgtttgaa acagcatgcc gttcacaaaa 37860
aaacgatatt gtgtcatgga tgggacaaaa tattgcaata tacaaccccg aagttatttt 37920
tgatattgcc tttgataaga tgaatgtgtc cttattatct atagggtata cgcttctttt 37980
caatcatcat ataaataata cgaacgaaaa tattaattct ttattgacac aacatcttga 38040
atgggctgcc ggcatgggcc ttcttcattt tatgctggaa actttaaagt atggcgggga 38100
tgtaacgata atagtcttgt ctgaggccgt aaaatatgac cacagaaaga ttttagatta 38160
ttttctccgt cgaaaaaact tgtaccaaga agatcttgaa gaactattat tgttggcgat 38220
acgtgcagat tgttctaaaa agaccttaaa cttgttatta tcttacttaa actattccat 38280
aaacaatatc cgtaaaaaaa tattacaatg tgtaaaagaa tatgaaacga ccgttattat 38340
aaaaatttta cggaaaagaa agataaatct gatagagccc attttggcag actttatagg 38400
atatcatagc tatacctata tggtagattt tatgcgtgag ttttccatcc atccggaaaa 38460
aatgatcaaa atggctgcac gagaatcgag ggaggacttg atcataaaat tttccaaaaa 38520
agtttgcaaa gagcctaaag atagacttca ctatctcaaa agcttagtgt atactatgcg 38580
acataaagaa ggcaaacaac tgttaattta tacaatccat aacttataca aagcttgtca 38640
tctagagagt aaagaaatgt ttaatttggc acgattttat gcacggcata atgcagtgat 38700
ccagttcaaa tcgatttgcc acgatctctc caagctcaat attaatatca aaaacttgtt 38760
gttagaatgt ttaggtattg ctattaaaaa aaattacttt caacttatca aaacaataga 38820
aacggatatg cgttatgagt aacattttta gatgagggaa gattctacca aactaactaa 38880
gacctttcgc tagaatgtat cttattgtta atatagatga gatatgtcat tgtgaaaaaa 38940
tagattaggt aggttgtgaa aaacagatta aacttaaaat tatgtgtatt atgtaaaatt 39000
ttagaaataa aaatttattt tttttattga gggtacggaa aatgttctcc ctacaggacc 39060
tctgtcggaa gaacattttc ttccttccaa atgattttag caagcatacc ctacaatggc 39120
tgggattata ttggaaagag catggatccg tccatcgagc agaaaaagac agcataatga 39180
tacagaatga attggttctt tctatcaatg atgctttaca gcttgcagga gaggaggggg 39240
acacagatgt agtacagctc ttgttattat gggagggaaa tctgcattat gccatcatag 39300
gagccttgaa gactgaaaaa tataacctaa tatgtgagta tcatagccaa attcaggact 39360
ggcatattct cctacccatg attcaagatc cagaaacatt cgaaaaatgt catgatttaa 39420
gccttggatg tgactttatt tgccttctcc aacatgctgt aaaatacaac atgctttcta 39480
ttcttgtcaa atataaggag gatctactaa atgcaaggat taggcatcgt atccaatccc 39540
tgtttgtttt ggcatgcgaa aatcggagaa ttgaaattat tgattggata ggccaaaatc 39600
tgccaattcc tgaacctgat gccattttta gcattgctgt tgctacaaga gatttagaac 39660
tgttttcctt agggtacaag attatttttg attacatgca aagacaggga atcattcaat 39720
taaccaatgg agttcgcatg gttgtgctaa atcgtcacat tagcatggca atagataatg 39780

-continued gtcttttacc ttttgttctg gaaactttaa aacatggtgg gaatatacat agagccttat 39840
cttatgcagt aacacacaat agaagaaaaa ttctggatta tcttattcgc cagaaaaata 39900
tagcccctaa tacaattgaa agacttttat atctggccgt gaaaaatcaa tcttccagga 39960
aaactttgaa cttgttgcta tcttacataa attacaaggt gaaaaatgtt aaaaagctgg 40020
tagagcatgt agtaaatgag aaatccactc ttgtgttaaa aattttatta gaaaaaaagg 40080
aaaatctagt ggatgctgtt ttaacaagac ttgtaaaaca ttctacatat ttccaggtga 40140
gagaatttat ccaggagttt tccatcagcc cagaaaaatt cattaaaata gctgtgcggg 40200
aaaagaaaaa tgtgttaatc gaggctattt ctgaagatat ttgggaaaat cccacagaaa 40260
gaattactta tctcaaacag atagtgcaca ccataaaata tgaaagtgga aggcgatttt 40320
tggtagacat cattcacagc atttaccaaa gttactcact aaaacacgaa gatattctta 40380
aactggcaac attttatgtc aaacacaatg caatcaccca ttttaaagac ctctgcaaat 40440
atctttggct gaacagagga acagaaagta agaaactgtt tttagagtgt ttagaaattg 40500
ctgatgagaa ggagtttcct gatattaaaa gtattgtgag tgaatatatt aactacttgt 40560
ttactgcagg agctattacc aaggaagaaa tcatgcaagc ctatgatgct ttagagtagc 40620
catgtattaa cattctgaaa gtagaataaa atatactata tactaaaaac caaattagcc 40680
atttttaact atcttcttct taaaaactct ggataaaaat ttattttttt taatttgggt 40740
agggaaaatg ttctcccttc aggacctctg tcggaagaac accttcttcc ttccaagtga 40800
ttttagcaag cataccctgc atttgctggg gttatactgg aaggggcatg gatctatcca 40860
aaggataaag aatgatggtg tgcttataga gcatgatctt actctttcca tcaatgaagc 40920
cttaattctt gcaggagaag agggaaacaa tgaagtagta aagctcttgt tactatggga 40980
aggaaatctt cattatgcca tcataggagc tttgaggact gagaactata acctagtatg 41040
tgagtaccat agtcaaattc aggactggca tgttctcctc cctttgattc aagatccaga 41100
aacattcgaa aaatgtcatg atttaagcct tgaatgtgat ctttcatgcc ttctccaaca 41160
tgctgtaaaa tataacatgc tttcgattct tgttaaatat aaagaggatc tactaaatgt 41220
actatttagg caacaaattc aaggactatt tattttagca tgtgaaaatc ggaagcttga 41280
gattcttacg tggatgggtc aaaatctgcc aattcctgat cctgagccta tttttagcat 41340
tgctgttgtc acaaaagatt tagaaatgtt ttccttaggg tacaagattg tttttgaata 41400
catggaaaac caaggacttc atttaaccca ggtagttcgt atggttatgc taaatcatca 41460
ctttggcatg gtaataaata aaggactttt accctttgtg ctggaaattt taaattatgg 41520
tgggaatgta aatagagcct tatcttatgc tgtcacacaa aataaaagaa agattttaga 41580
ccatgttgtt cgccaaaaga atataccca taaaaccatt gaaagaatgt tgcatctggc 41640
tgtaaaaaag catgctccca ggaaaactct gaacttgtta ctatcttaca taaattacaa 41700
ggtgaaaaat gttaaaaagt tgttagaaca tgtagtgaaa tacaactcta ctcttgtgat 41760
aagactcttg ttagaaaaaa agaaaaacct gctggatgct actttgacaa gatatgtcaa 41820
agattctaca tactttcagg tgaaagaatt tatgcaagac ttctccatca gcccagaaaa 41880
attcattaaa atagctgtgc gggaaaagag aaatgtgttg atcaagggta tttctgaaga 41940
tatttgggaa aatcccgcgg aaagaatcag gaatcttaag cagatagtgt gtaccataaa 42000
atatgaaagt ggaagacaat tcctgataaa tatcattcac accatttacc agagttattc 42060
tttgaaacct gaagaaattc ttaaattggc aacattttat gtcaaacaca atgcaaccac 42120
ccattttaaa gatctctgca aatatctttg gctgaacaga agaacagaaa gtaagaaact 42180

```
gtttttagag tgcttggaaa ttgctgataa gaaggagttt cctgatatta aaagtattgt  42240
gagtgaatac attaactatt tgtttactgc aggagctatt accaaggaag aaatcatgca  42300
agcctatgct ttggagtatg ccatgtatta aatttctgaa tcagtaagca atagatagat  42360
tttagaatat gctgtattaa gttagtttct gaataagtaa ttaatagata gattttagtt  42420
tatgtaaaaa tgttaacatt tgttcataag ttttagatac cattttagag ttactttttt  42480
agatattact attttagcca ttattatctt aaataatcac tattttagat aggtccccgt  42540
attaaaaacc aaattaacca ttatctatgt ttttaataat actttttaaa aaccctccat  42600
aaaaatttat ttttttcat aaaagtagag aaaatgttct ccctacagga tctctgtcgg  42660
aagaaccttt ttcttccact tgagccctta ggcaagcatg tggttcaacg gctgggatta  42720
tactgggaag gccatggttc agttaaacga gtgggtgatt gctttatatg tgtagaccag  42780
atttggatgc tatcaatcca taaggctata caaattgcag cctcggaagg aaatgagaac  42840
attgtcaagc ttttcttact atggaagggg agtctacaat atgccatcat aggagcctta  42900
gagggcaggc aatatgatct gattcaaaaa tattacaacc aaattgggga ctgccatcag  42960
attctaccac tgattcaaga tccagaaatt tacgaaagat gtcatgaatt aaatgttaca  43020
tgtacctttc aatgcttatt tcaacatgct ataagagata acatgctgcc cattttccaa  43080
aaatatggag aagatctgaa tggaaacagg agaatggttc aacttctgta tgagatggca  43140
tgccgattac aaaattatga tatcatcaaa tggataggat ctaacctgca tgtttataac  43200
ttggaagcca tttttagcat tgcttttgtt agaaaggatt taactttgta ttctttaggc  43260
tacatgcttc ttctgggtag aatgagtact gaagatagaa actttatctc aatcataaca  43320
cgccatcttg aatacgcatc aaaaaaggga ctttttgact ttgtactaga atctttgaaa  43380
tatggaggtc aagtggatac agtgttgttt caggctgtaa aatacaacca taggaaaatt  43440
ttggcccatt ttattcatga aattccccgt gaaacggttg aaaagctgat actccatgct  43500
gtggagtcac gggcctccag aaaaacattc aacctgcttt tatcttccat aaactactgt  43560
gtgaaccctt ttgtcaaaaa actactgcac gctgtggtga aacacaagta catgcttatc  43620
ataaagcttt tgctcgagcg gcccaaaaag aagataaacc tggtagatgc tgctctattc  43680
aaacttgtaa aatactctac ttatacagaa atagtaaaat acatgggtga gttttctgtg  43740
gacccaaaaa gggtggtcaa aatggcagca cgactcatga gagtggacct gattaaaaag  43800
atttctaatg atgcatggga agataaacta gagagaatca agcaccttaa acagatggta  43860
aataccatga accacagaaa tggaaaaaat ctattgatgt acaatattca caatattact  43920
ggatatacct atctgaacac caaagaagca tttaacttaa caagatttta tgctgtccac  43980
aatgcaacat gtttgtttaa agaaatgtgt aaaagctgtt ttgtacatga taaaatacag  44040
ctcagagaat tgcttgaaga ttgtttacat attgctaata ggcatgatta tatccagatt  44100
gcagaaaccg cagatgaatg tatcaaatat atagatctta ttacatttaa gtaaaccatg  44160
tatatatcaa gtaaatccag attaaatcag gctaattgta aatagttgta gataccatat  44220
aatgaatgtt ttattaggat agtagttcag ttaagatagt agtttagtta agatagtagt  44280
ttagttaaga tagtagttat gttaagatag tagttctgtt aagataatag tttagttaaa  44340
actagttcat gttaagttaa tagttttgtt aagacaatag ttcatttaag tcaatagttc  44400
agttaagtca atagttttgt taagtcaata gtttagttaa gtcaatagtt tagttaagtc  44460
aatagtttag ttaagtcaat agttatatta agacattagt tctgctaata cattagtttt  44520
```

-continued

```
gttaagataa taaaaattta ttttttttca tcagggtaga gaaaatgttc tccctacagg  44580
agctctgccg gaagaacatt tacattcttc cttacccctt ggctaagcat gtacttcaac  44640
aactagggct gtactggaag ggacatggat ctcttcaacg aatcggagat gaccatgtac  44700
tcttacagca ggacctgatc ttttccatca acgaggcctt aagaatggca ggagaggaag  44760
gaaacaatga agtagtaaag ctcttgttac tatgggaggg aaaccttcat tatgccatca  44820
taggagcttt agagggcgac cgatatgacc ttatccataa atattatgat caaattgggg  44880
actgccacaa gattcttcct ttaatccaag acccgcaaat ctttgaaaaa tgccatgaat  44940
tgagtaactc ctgtaatatt cgatgccttt tagaacatgc agtaaaacac gacatgcttt  45000
ctattcttca aaaacacaag gagcaaataa gattacacat ggcattaacc caaatactat  45060
ttgaattggc gtgtcatgaa cgtaaaaatg acatcattag atggatcggt tattccctgc  45120
acatacacca tctagagact atttttgatg ttgcattcgc ccataaaaat ttatccttat  45180
acgttttagg gtatgaactt ctcatgcaca aagtaaatac agaggctgca tatatagaat  45240
tacccaattt gctatcatat caccttcgaa ctgcggcggc aggaggtctt cttaacttta  45300
tgttagaaac aataaagcat ggtggatatc tggataaaac ggttttatcc gcggctatca  45360
ggtacaagca taggaaaatt gtggctcatt ttattcatca ggttccccgt aaaaccgtta  45420
aaaaactgtt actctatgct gtgcaggctc gggcccccaa aaaaacactg aacctacttt  45480
tatcttcctt aaactactcc gtgcacacca tcaccaaaca actcgtacac aatgtcgtca  45540
tctacagttc cacgcttatc gtaaagcttt tactcatgcg gcgaaaaaac aagttaaacc  45600
tagtagatgc cgttttagcc agacttgtaa aatattccac ctatacagac attgtacaat  45660
tcatgggtga gttttctgtg agcccagaaa gggtgatcaa aatggctgca cgggaatcca  45720
ggacctttct gattgaaatg atctccaaag ctgcttgggg aaatcaccca cagacgttga  45780
ttcatcatct caaacaacta accaatacca tgaagcctca atctggaaaa gaccacatca  45840
tatataccat ccactatatt tatctaaact ctaatatgct ggtagcggag gaggaaaaaa  45900
atatttttaa attagcaaaa ttttatgcga atcataatgc ggtaaacagg tttaaacaaa  45960
tttgtgaaga ctattatata ttagatgcac gatttaaaac acttatttta gaatgttttg  46020
aaattgccgt ccagaaaaac tatcctagaa ttgcaaatat tgtggatgac tatattcgat  46080
tcctttttta caggggaaat ataaccgagg aagaaattcg tgaagcctat tctttaaaag  46140
atgctgaggt ttatgtagat ttaaaatggt tacaacaagg agaaatggtt taaaccaaat  46200
ccggtttaaa ctaaatccaa tttaaactac atttggttta tcattagtca ttgaaaccat  46260
cgaaaaaaaa gctatttgtt tatccccata aactcatctt ttttttgtct caaagtttga  46320
cactaaaatt cagtgtttta tagtgtttat aattaagtgt tttgcatgca ttgcagaaat  46380
tttcatcttt tttaattggt tcaataccac atgtcataca atatgttgtt tgattatcaa  46440
gattaacttt atgaaaggaa agtaagtgag ccgcaaattt aaaagtaaaa tatctttcat  46500
ttaaaatgat cttatgaatg tattttcgat aaggaggaat gaaagcattt gccaaaataa  46560
atcgcataaa aggcttggaa aaacccatat cttctaatct tttgtgggta taaaccctat  46620
tttggtgttt tacaaaaact tcattgttat aatagtcgtt atagctatca atcatttttt  46680
taagtcctat aatgcccaag gttgcacgca taaagccaca gtttctgctc caaaaagcat  46740
gcacctgtaa agggtgcttt tcatataacc aattacaaaa tttcattccg caacagtagc  46800
atgttatttc agtgggggat gtatagaata atccggcatt cgaaaatttt tcataatttt  46860
ttatgtcatg gattgcgaag ctttgatttc gtgcatctat ggagctatag cctacatatt  46920
```

taggttttac ttcaaataat cgcaaagaga tgtatggatc tatcgtattt attttaggaa 46980
acatttcata attttaaatt cttatatata atataaaaaa aattacaaac atttgtaatg 47040
atcatcctca attgaaggct gagttgtagg ctttattttt ctaattatac gaagaaggta 47100
ggttctcata aagccttcaa gatgactatt gatgtttcca atacattttc tcaatgagtt 47160
cataaaccca gacattttgc taatggcttg gcaaagtgcc aacaagttgt ccacaaagta 47220
ctggtagatt gccactagct atagctagct atagtgagcc aacctctctg tatgtatttt 47280
atatatttca ttttttaata gatttaatat ttttataaaa aatatttagt tttttataca 47340
agaatgtcga caaaaaaaaa gcccacaatt accaagcaag agctttactc cttagtagcg 47400
gcagataccc agttaaataa agcattgatt gaaagaatct ttacaagtca gcaaaaaata 47460
atacaaaatg ctttaaagca caatcaagaa gttattatac cacccggaat caagttcacc 47520
gtcgttacgg tgaaagctaa acctgctcgc cagggccata atcccgccac aggagagcct 47580
attcaaatta aagctaaacc tgaacataaa gccgtaaaga tacgagcatt gaaacctgtc 47640
catgatatgt taaactaaac tataaagtca tattcttctt tatcgttatt atcttcaata 47700
tatttttgcc aatcgaaatc gaataaattc agatcctgga catttaaata cttatcatcg 47760
tacattttaa tataatttaa acatgagttg ttgtcaaaaa cttttagcgt ttttgttaaa 47820
attatcatat gaataatttc cttattaaga gttgccggaa taatacaaaa cctattttta 47880
ggtacatcat ccatgataat agtaaaatta gtaaaaattg tttcttgttt ttcttttgtt 47940
tcaaataaac gttgtaaggt taaaggtttc tcgttcaatg gtttctttga agataaaaag 48000
aatgtataat ctggtttaaa ggtatttttg gtttcaatcg tgattccatc tgcttgagca 48060
tatactaaac cagaccaaat ataacggtcc actattacaa tataatttag cttaagtagc 48120
actgcaattt ctgcgataaa ttcactacga tgttttgtaa ataatttatg taattgttcc 48180
gatgacattt ctatggtttt atttaacacc tgcaatataa gatcaccggt ggtcgtgtct 48240
ggattaggaa aatgtataca tatagcatta taatccatgc attccaatgt ttcttttaat 48300
ttcattgcct gtgtgctttt tcccacacca ttgattccct cgatggcaat gagtattcca 48360
cgcatgatta ataaaaggaa aaaaagaatt cagtttttaa catttcttac aaatcttttt 48420
ttatacaaca ttgtacaaca ctgcattagc ggtatatgat gttatagctt cattaaatat 48480
ttgcttttat ataatcttta ccaacctata tttggtagat cactgcagat ggtcataaat 48540
aggccataac taagataaaa attatttcag acgctactac ggtagtatta ttaaaatcat 48600
gtgtggcaat gtatgacgtc ttaatagata aaacatttaa ggaaaacaaa tttgaataaa 48660
aaaataattg ttatgatggc gttgttacac aaagaaaagc ttatagagtg catctatcat 48720
gagctagaaa atggcgggac aatattgctt ctaacaaaaa atattgttgt gtcagaaatt 48780
tcatacattg gcaatactta taaatatttt acctttaatg acaatcatga tctgataagc 48840
aaagaagatc ttaaaggagc aacatccaaa aacattgcta aaatgattta taattggatt 48900
ataaaaaatc ctcaaaataa taagatttgg agtggtgagc cgcgtactca aatttatttt 48960
gaaaatgatt tatatcatac aaattacaat cataaatgta taaaagattt ttggaatgtt 49020
tcaacttcag tcggtcctca tatctttaat gatcgtagca tttggtgtac taaatgcaca 49080
tccttttacc catttaccaa cattatgtcg cccaatatat tccaataaat tagatatctt 49140
tgctattaaa atagttaaaa accttatagg ataattaggt actttattac gataaattat 49200
gatattttat aattagttac tttattataa ttaatctctt tattaatgaa ttatcataag 49260

-continued

```
ataactaatt atttttttcc atatatcaga taataaatct gatatgggct aaaagtatgt  49320
ttcaaactat ttacaataga atttctgtta agaaaacata cataatttga ataaaatttt  49380
tttaaatatc accgaaacaa tcaacatggt gttaatagag tttttaacag gtttcttcta  49440
tttatatgga aagagactgt tttccattag taaagtcatg gacatgatat gtctagacta  49500
ttataccatt attcctgctc ctctggcgat gatgttagcg gcaagactaa aaaactatga  49560
cctcatgaaa cgactgcacg aatgggaaat ctctattgac tacgctctac ttgtagtaga  49620
tgatgtgccg tctattgact attgcttaag tcttggcgct agatccccga ctagagcaca  49680
aaaaagagaa ctgctgaggg acaacacgtt taatcccgtg tataagtatc ttatgaactg  49740
ttccggcttc ccaacaaaga gagaaaaaaa cattccttgt gatgttcaat gcgaaagact  49800
gcaaaaaaac attataaaag aactggtatt taactgctct gtactgcttg aaatggtact  49860
gcacacagaa agagaatatg catacgccct acactgtgct gcaaaacata accaattgcc  49920
catcctcatg tattgttggc aacaatccac agacgcggaa tctattttgt tgaaaacctg  49980
ctgttctgat aagaacatca attgttttaa ctattgtatt ctatatggcg gcgcccaaaa  50040
tttggatgct gcaatggtgg aagcggcaaa gcacgatgcc cggatgctga taaactactg  50100
tgtcatgctt ggtggaagat ccttaaacga agcaaaagaa acggctgcca tgtttggaca  50160
cattgaatgc gcacaacact gttttaaact gcagtcttac gtcgtggaca catcgaatac  50220
agacgacact gattaaagcg acaatcttac gtcatgaacg actgtctttt gagtatctat  50280
acttacatta tattttttta tgaaaaaaat ataaaggttg tatacaaacc tttgtataca  50340
agaaatttgg atcattaaac aataattaat ttggacacag gaaacgatct agatcgatca  50400
aaaagctatt ttttttgcac acagaacatt tagataattg agagattact ttccatactt  50460
gttaagcttt tttacacaca ggaactttgg attctgttca ggaagttttt catagacatt  50520
atgtttacag ccagtaataa taattttggg ctttttctta aaccaccggt ggaaaacatc  50580
cagcttgtaa agagggaaat gcatgtagag aggttttggt agtcatggtt aagagatttg  50640
actaactcca tgtttcctgt aaagactgcc cagtcccaag cagtaaaacc tctatgatag  50700
tctttttgag tcggatctgc tccaaatttt atgagagaaa gcatatttaa agaacggccc  50760
cgtattgcgg ccttcatcac aggagtcatc ccattaaaat tcggtaaaca aattctggtc  50820
ccatttttc cgaaatagcc caacacccct tccaggatta aatgattttt tttctcagct  50880
aaataatgta aagcagagtt tccatcttta tccctcctat gagggttaat tatttctcca  50940
ggataagatt cttgttcaaa aagaaatttt aaaaagtcta tacgtccgta gatgcatatc  51000
cacatgaata ccgaggatcc atttttatcg catctattga caatccacgg atctgtttta  51060
aaaaattcct caaatagtgt aagattccca tttctaatat gtttttttaat ccatttaaca  51120
aacaagtttt ctatctccct ttctggaaac atgtgttcca ttttgaatgt cgcccctact  51180
ccactatatg attttactcc tttaattttt aatgtccttt tttttcggac ttctttggat  51240
aagctgttta ttaccatctt taaatgcctt atagcgggga ggagccaggc ccttttccca  51300
tatgtgcggt aattcttggt gtttatgctt gcctttggca taaccaggcc agtatttttc  51360
gatatattca gggtttgttt ttacgtattc tttaaaggtc cgataggctt cttgaataca  51420
ggtaggctca ccggtataat ttccatgttc atcttccttt aaaaagccat taaccctgtc  51480
ctttctccac ttaagattgt gctttccaaa aatgcgatca agatcttgcg cctgctgggg  51540
tggaatcata aatccctttt taggtcgaag ctttttattt tttccatagc ttcggccatc  51600
gcgttgcgaa acagtggtta ggacgcctga tagtctttcc atgggcgtcg catctaatcc  51660
```

```
tatccatcca ccctgatgaa tatcaatggc aacaagctct cctttatttt gggcaagcca  51720
agtttccaag aatgccatgc tttcttccca gggataaggc ccgccaacac cacgggttgt  51780
ccaatcttgc aaggactcca ggtccgacac ctggtaaggc tctaaagaag acggttcctt  51840
gtttttgtac tgcaaataag atttaatgac ccatttatac catgtgtcga accgcagcgt  51900
ggcgcctcca aagtgaaagc cgtcgttgat tttaggatat ctgcaacata tttcaaccgt  51960
acgtttgagt tctgcaaaag cggccttcca aggaagtctt tcgctgcggg taagacggtc  52020
tattttgccc tgcgtgccat agcgtatggc atgtcgtgcc aattgcaaca attctgacac  52080
cgatccgtgg gccccgatcc agtttatcgg ataggcaacc tccgaagggt ttaaaagatg  52140
ctcgtaaaag cgtggatctt cagatgccaa ggcgtctgca aaggggataa tgctagaaaa  52200
cctgtctaga catacgtttt ctgtgtttac ttctaaaggt agaaaaatgg ttgcgtgagg  52260
cttttgaacc tgcttgttca gcggtctgca tatgctttga ataatgtctc taggactatg  52320
tcgcggcgct gcaaaaaata ccgcgtttag ttctggaacc tctacgccct cttgaaagag  52380
tcgacagttt aataaaataa cgggttcctt tgaggaacaa aattctgtaa atgttttgag  52440
gataacctgt cgcggcaggg ttgagtgagc tatcagggca tagacccctt ggtctaccaa  52500
cgccgcgtat agctccttgg cctgtttaat atcacgggta aataccagca ttttaggagc  52560
cggtatattg gtttttaaat aggctaaggc cattataatt tgctttacta tgatctgttt  52620
cgtggtctcc tctttggtac tcggttggtg ggccaattta ggcgcggcta ccatctgcaa  52680
ttcaaaatca tttacatagc cggcctctat gccttctcgc agatagtagc gaaaggcaac  52740
gccgccaaaa agttcacgat ttttcatgga aagcggggtg tcgtacctgg gcgttgccgt  52800
taaaaaaagt cggtgccctt ttttaaagtt gagcaacacg tgggtaaagg gccgtgtctc  52860
ccattcgccg caaatccggt gacattcatc gctaataata agatcgaaat catccaccag  52920
tagcgtggag gattggtagg tggcaatcac aagaagagaa ggggcctccc gtatccgttt  52980
tgcaataaag acaggattgg tggtcatttc tatattgtcg tgatttagca caatgcgggt  53040
ctggtcagac cccacaagca aaacgttctt caaagaaatt ccatactgat agagtttttc  53100
cagagtctgc cgtagtaggg acaggcccgg caccaggtac aaaacttttc cttgaagata  53160
attggagagg ataagatagg cgacgcgagt tttgccgcat cggcaggcca tctgcagaat  53220
ggccctccca cttcgccgca gctcctgata gcccatattg gccgcctcct tctgataaag  53280
tcgatcctcg attgcagtcc gtgtctcatc tgtagaaaaa aataatacgt catctgcgaa  53340
atgttcatct tccacaggag ttatcaccag gtgtctcagt ttctccttgc ttatcagcgg  53400
atcagagggc aaagatggct caaccactat cgtggaatca ttcatctcat aggcgggaga  53460
atcacacaaa gtatagctta tgtccagaca gtttgcaaca tcctcagcca attgttttat  53520
tttttcgggt aaaagacata cgagttcttt gtttttgacg cgaaaaaaact gtgcacaata  53580
taacacccct gcttcaattt tttgcgcatc cttctttgta gatgtttcca atgtgaaaca  53640
atacttccat tcatccgtaa aacaggttgt ataagatcca tcatgaagcc tagcggccaa  53700
gtttcctgtg tgcccaactt tatgtaagga ttgggcctcc agccagggat gaaccgccac  53760
gtaaaatcct gcgcacatgc tatatcaaat tgcagtttct taataactgt acacaggatc  53820
tgaaaaacat gtgattacaa aatttagata agaaatattt aatattaaaa atcacagaat  53880
acatgtcact gtgtagagag aaagccaaaa actcctcttg accgccgtgg gaaatcatcc  53940
agggtagtag gttgtgtttc ataaagttgt atgccgtagt gatcaccgtg gactccagat  54000
```

```
ggttattggc atctttgcaa tactttgcca tcttggcaga aaagacgata aatccacaaa  54060
ttctacccca gttgataaga tccttaaaca gctcagtcac aaccccagta aactgggttt  54120
taatttcttg aacactcgta agagaaaagg taattgtaac ctgtttgttc aaacactcat  54180
cataataggt taaaattttt tttatttgtt gttgatatgg gctaagctca tgctctgaaa  54240
tatcattaat gtaatattta atatatccca ctagtatttc attaatgata ttatgatata  54300
ttaactcttc tccctccata gcggcaccct atattttttt atttaggttt caatgttatc  54360
acaattgcga tacaattgtg atacaattgt gacacaactg tgttgtatac aacaaatgtt  54420
aggccacgta tagcaaccta tatgttaaga aatattttta tcccaacatt agttggaaac  54480
gagcagccgc aaagaagtca tttaaaataa gccatttaaa gatttagaat ttatatgtat  54540
acaactgtac aatggaagca gttcttacca aactcgacca ggaggaaaaa aaggctctcc  54600
aaaatttca tcgttgtgct tgggaagaaa ctaaaaatat tataaacgat tttcttgaaa  54660
tccctgagga acgatgcacc tataaattca actcatacac aaaaaaaatg gagcttttat  54720
ttacccctga attccacacc gcctggcatg aagttcctga gtgcagagag ttcatattaa  54780
actttttgag actcatttcg ggacatcgag tggtattaaa aggccctaca tttgttttta  54840
caaaagagat caagaatctg ggcattccta gtaccatcaa tgttgacttt caggccaaca  54900
ttgaaaatat ggatgatcta cagaagggaa atctcatcgg caagatgaat atcaaagaag  54960
gctaaataaa acaactaaca tcaaaaaaca ttaaaggcta tgttgtggac gatgcctttg  55020
tctcaatagt ttcgaggtca tccaataact catgtaacgt aaaaaagttg gtccattttt  55080
ttgaaaacat taaaagacgt tcgtcttcat aaataaaaaa gtcattcgaa ggaaaaatga  55140
tatactcaat accatagtct tgtaatattt tttttaggtc tctcagggtc cagggattta  55200
ccaggcttct acgcgaagtg agcatcataa aaatatctaa tattttttgc gccataagcc  55260
agcgcggatt ctcattggcc cacaaatcaa caataattct cttatcaacc gtgagcattc  55320
ctacttgatt cgaagaaatg attagatgcc cagcagtcca ccccatgagt agataacgca  55380
gcgttgtaga aatgtcacat atggaaggca ttcctccaca acatgaaccc aaattaggat  55440
gcgtgtgaaa cacaaacata gcaggcttgt tggccaccct gctataaata tcagcaggca  55500
tcatagcctc gctgccaaaa taaatgttct ctcctgccct ataggggctt ggaatgattt  55560
ccactatctc gggtacaccg tttatcatat taatgcggcc gcaccattca cggtcatcgt  55620
ccaaaaattt tttgatggca ccccgaacat tgtcccagtt aagcaacaga gtattcacaa  55680
tctcattacg ctccgcccag tattccttaa aacttctttt agacttgctg agctgttccc  55740
aggattcgaa ctcagtccaa tgtttttttt cttttgggga agacttccct tttgaaacat  55800
tttttgcggc tccaccatct acactatgat tttccaaaat aatctccttc atcgtttgag  55860
ttatatgggc attgctaagc accttagtgg taacctgttt acctatgtga tttagcagaa  55920
aaccaagttt gtccatttgt gtctcaacca tttattctta acaaaacaaa aaaaattaaa  55980
aatcatcgtc gtttaaaaag agtttgaagg caaacgcatc atccttaaca cagttctgat  56040
actgcgtagg tcttaactcg aaaaagttgg ttttttctac ttcattaaga aagaatttag  56100
tcatctgagg aaaagggttt cccaccttat aaatgctttt gcactgcatc atgaagcaca  56160
aattatctgt aaagtagcgt atatattgaa atagcatttc ttttgaaaaa ccgggaactc  56220
ttcctcttgc cttgtcaaag gcatagttaa taaactcatc caccaactcc acagcctcct  56280
tcaaaatttt gtgaatgatc ttttcctcgg gaatgttata cacgtaattt gagataagaa  56340
aacacgcaaa actacagtgc atcccttcat cacgtgagat aaactcatta tagcttacaa  56400
```

-continued

```
gccccggcat aatattctgt tccttaagaa actggatcgc cacaaagtgg ttttgaaata  56460
aaatgccttc tacggcggcg aagcccacca gccgctcacc tagagtgttc ctgtcggggt  56520
ccatccactg ccgcacccac tgcgccattt tttttatgat agggtgtttt tcaatgccgc  56580
taaagatgcg ctgttgttcc ttctcatccg ggatcagcgt ttttacctgt attgagtagg  56640
cttcgctatg aacgcactct tgggcagcct gcattgtata aaagtataac acttccttta  56700
ctttaatttc gcgcataaaa ttggttaaaa ggttttcgat aacaatttcg tcggcaacaa  56760
caaagaaggc taaaatttgt ttataaaatt cgcgctgtgg ctttggcatg gcttcccaat  56820
catcaatgtc cttacacatg tccacctcct gcgccgtcca cgtcaaactt tctaattttt  56880
tataccagtt ccaacattcg gggtgctgaa taggaaaaat agtgaaacgt tgggaatttt  56940
caattagtaa ttcctccata tttgaaataa atattaacat cttcaaattt attggctgcc  57000
atggagacgt tttttattga gacgttggca tctgatgtgt atggaaaggc gttaaatgtt  57060
gatttagata gactatcgca ggcgcaggtt aaatataccc ttcaagagct tatttcctac  57120
tgcagcgctc taaccatttt acattatgac tattcaaccc ttgcggcgcg tctttcggtg  57180
taccagctgc accagtcaac ggcctcctcc ttctcaaagg cggtgaggct gcaggccgca  57240
caatcctgct cacgcctgtc cccccagttt gtggacgtcg tttacaagta caaagccatt  57300
tttgacagct acattgacta tagcagagat tacaagctgt ccctcctggg gatagaaacc  57360
atgaaaaatt cttatttgtt aaaaaataaa gatggggtca tcatggaacg cccgcaggat  57420
gcttatatgc gggttgccat catgatctat gggatgggaa gagtggtcaa tatgaaaatg  57480
attctgctaa cctatgacct gctttcccag cacgtcatca cacacgcgtc gcccaccatg  57540
ttcaatgcag gcaccaaaaa gccacaactc tccagctgtt tcctgctaaa tgtaaatgat  57600
aatttagaaa atttatatga tatggtcaaa acggccggca tcatttcagg cggcggcggt  57660
ggaatagggc tgtgcttgtc aggaatacgg gcaaagaata gttttatttc tggtagtggt  57720
cttaaaagta acggcataca gaattatatt gtgctgcaaa atgcttcaca atgctacgcg  57780
aaccagggag gcctacgtcc cggagcctac gccgtctact tagagctgtg gcaccaagac  57840
atctttacat ttttacaaat gcctcgccta aaaggacaaa tggctgaaca acggcttaat  57900
gcccctaatc tcaagtacgg cctatgggtc cccgacctat tcatggaaat acttgaagac  57960
caaatacaca acagaggcga cggcaaatgg tacctctttt cgccggatca ggcccccaat  58020
ctacataagg tctttgattt ggaacggtcg cagcacgaaa acgcacaccg cgaatttaaa  58080
aagctttact atcagtatgt tgctgaaaaa aggtacaccg gcgtcacaac ggccaaagag  58140
attatcaaag agtggttcaa aacagttgtt caagtaggga atccctatat cgggtttaaa  58200
gatgccataa atcgtaaaag taatctttca catgtaggca ctatcacgaa ctccaatctt  58260
tgtattgaag tcacaatccc ctgctgggag ggtgataagg ctgaacaagg tgtttgtaat  58320
ctggccgcag taaatctagc cgcctttata cgtgaaaatg gctacgacta ccgtgggctc  58380
atagaagcat caggcaatgt cacagaaaat ttagataata ttatagataa tggctactac  58440
cccacagaag ccacgcggag aagcaatatg cgtcaccgac ctattggcat cggggtcttt  58500
ggcctagccg acgtgtttgc gtctttaaaa atgaaatttg gttcacccga ggccattgcc  58560
atggatgagg ccatccatgc ggccctatac tacggggcca tgcgacgatc catagaactt  58620
gcaaaagaaa aaggaagtca tcccagcttt ccggggtctg cggcctcaaa gggtctactg  58680
cagcccgacc tatgggttcg ctgtggtgat ttagtttcct cctgggaaga acgcgtggca  58740
```

-continued

```
cagacgacgc agggtgtgtt gacgccgaaa aggtggtcgc agctacgcct ggcggctatg  58800
cagggacttc gaaatggata tgtcacagct cttatgccca ccgcaacctc ctcaaattct  58860
acaggaaaaa acgaatgttt tgagcccttt acatccaatc tatatacacg tagaacgtta  58920
agcggggagt ttattgtttt aaataagtat ttaatagacg atttaaaaga aattaatctt  58980
tggacagaag ccattcaaca gcagctacta aatgcgggag gtagcattca gcacattttg  59040
gatataccgg ccgagatccg cgatcggtat aaaacctcca gggaaatgaa tcaaaaaatt  59100
ttaacaaaac acgcggccgc acgaaacccc tttgtatccc aaagtatgtc cttgaactat  59160
tacttttatg aacctgaact aagccaggta cttacagtgc tcgtcctagg ctggaaaaaa  59220
ggtttaacta ccggttccta ttactgtcat tttagccctg gagcgggtac ccaaaaaaag  59280
attataagaa actctgagaa agcgtgtaat gcggactgcg aggcgtgtct tctgtaggtg  59340
tctcgcggta aaagagcagc ggggaccata tggtaaaccc caacaagagg ataatgaata  59400
aaaaaagtaa acaggcatcc attagttcca tattaaattt ttttttcttc tatataatgg  59460
aatattttgt tgcggtagac aatgaaacct ccttgggggt ttttacttct atagagcaat  59520
gtgaagaaac gatgaaacaa taccccggcc tccattatgt cgtttttaag tatatgtgtc  59580
cggcggatgc agaaaataca gatgttgtat atttaatacc ctcgttaacc ttgcataccc  59640
ccatgtttgt agaccactgt ccaaatcgta ccaaacaagc acgacacgta ttgaaaaaaa  59700
taaacttagt gttcgaggaa gagtctattg aaaattggaa ggtttcagta aatactgtgt  59760
tcccccatgt tcacaacaga ttatctgcgc cgaaactttc catcgacgag gctaatgaag  59820
ccgtagaaaa gtttttgata caagcaggac gactcatgtc tctgtaaatg tctcttcctt  59880
tatgggtgac gtctcttcct ttgccgagga agtctctgtt atgggcaaga ggtttgaaac  59940
aacgcaagga ctctgcttaa tctgctgtct cacaaaggga atcaaactac ctgctttcgt  60000
atttttaatg tagtaattac ccttgttgtg atgaatttta agaccatagc gtagtcccag  60060
tactttatta atgaatttta aaattgtttg agggtccgtt ttattgggct ttttaagctt  60120
aaactcaaag ctgatcgcgc ttaaatcata ctgaacaaat tcatcaacga gtttcgtcat  60180
taattgttca ttggtcaata tattagggtc ctgaacgcat ttaaagccgc acttagttaa  60240
tagcataata gcgtacatat gagattgaaa actataatta aattgtagat catgatgctc  60300
tgcgtgttgc atggcccatt gatgaaagtt taattcctga gtttgtaaca tagtgagcga  60360
ctcgtatact gtctttccgc ggcttatttg gacacggcca gtatagttct gttttgtcat  60420
aaaactattg tattgttcaa caaatttggg agtaatttta tgaccgtgcc atgcataaaa  60480
ttcgagtagt ttatactttt catacgcaaa taggtcttgc tggtctactg tgatgccttc  60540
ctttaagttt tgtttaattt gtaaagcttt attggcatca atggtttcag ccgaggcaat  60600
gtttacatag tcctggtgtt taatttccat tttaatgctt gtatattgtt tgactgtctc  60660
cagcttttca cccgtcagta taaacacctt agcgccggtg tcggcgatct ggttaataaa  60720
tcgggttata aagtgatttt ttgatagatg ttgtatccgc attgtttcga gccatagatg  60780
gtagtatgga gttttataat atatcggcct acctgtttcc ttactatacg tgaaggaaag  60840
ctggtgattg cttatggtct gaaaaagggt gtcacgtttt tgtaacgtaa acatttcaat  60900
gtcttcgatg gtttctggat agtaattttg tttcccctgt aagcagattt tataacactt  60960
actttttaat tcacgcacgc ggcccaacat ttggcaacat gtttctacgt cacacgacat  61020
attgttaaaa aagccgtata aaacatcaaa tctcttatct tcgtatgaaa cacccgctga  61080
aatcgtgggc gtatagataa ggatatcaac gagcccccaa taatacgata cattattaaa  61140
```

atgggattcc cgttcatgag cagtgctttt agaactataa aacccaattt ttttttccgg 61200
aaactttttt tggataaatg attgcaacag ccgggcctcc attaatgaat ttgtagggat 61260
aacaattttt ttgtcttcta gcaaatcctt taaaaggtta tttaaccaag tttctcgtga 61320
agaggtaaaa taatacgtgt catgctgggc ccttttatat tgattccagt gaaagaagat 61380
agggacatcc ccgcgaaaac gctgtagaat attatacgtt cgatttccta ggtttgcgtc 61440
caagcatata acataatttg ccgtttcgag catccacatg aaaatggcaa aagagggagc 61500
aaagtatttg tgcaggccgc tattgaattg attaaaaatc gattctacct catccaaaat 61560
aagtaggtct acaggctcgg ctgtggaggt tagccggaaa agtgattcta cctgaatgat 61620
gactctttcg tagctgtcca aatctccagt tacttcgctg tacaatgtga aattcggtag 61680
ccgggattgt atatttttg agaagatctg tcgaaacgtc acaaaccgta tggtttgttg 61740
ttttgaaata gaattattgc cgtagtattt ttgcaaatag ttgcgcagtt ggacggtttt 61800
acctattttc atttgagcct ttacaacaag cgtagggact cgttcatatt ctcgcatact 61860
actttcatca tagatgtgtt tttgagtatc aggcagttct tcaaagagaa tggactcatg 61920
aacctctatg ctctttgtca tcacttggtc cacatatgtt tccacaaaat tatttgtgcc 61980
ggaaaggctg cccatgagaa ggctatgttt attgtcatgg cgacagtgtt gatacacttt 62040
gtttcccgtg actcttaaaa ttagggtatt gtccttatca tgcatacgct tacatatttc 62100
gcagtaactt ggacttgtac gtttaaacaa tactaaattt ttatgaacac ggaggaagca 62160
atgattttta catagtgttc ctgcaaattt taatacctct tcaagttcac tttgttggat 62220
agtatcgcag gaactcggtg ttgtttcttt tacatttgtg aagatacaag gtaaacacgt 62280
cgtttcaaag gggttgcta taagggtatc actctttttc gtggttgtac tggtctcaaa 62340
cacctctgca agctcctcat taaacatttt aacacgcatg ctaccttttt tatgagaccc 62400
tatgatgcga aaattttgaa tacttttgtt gacctggggg tcaacaaaag gataaacgtg 62460
tttgggaaga ttttctaaca ctttggatgt aaagactttg gcctcattat tgtttaatac 62520
tgagtatgta taaagtatga tatgaaagga gtatttaagt tctcgctttt tatttaatcc 62580
gatagaatct gttagcaaaa tttgttcacg cgttagattg atgttataag gtaaagaata 62640
tgtctcgtaa aatacatcca tgatgacgtt aattatcatg tcaaggatgt catagacatt 62700
gtcttcgaca ttatcattgt catcaacatt gtcatcagag tatgacttat ttaccggaaa 62760
gtcgatgtca aattttaagc gctgaggcaa aaacccaaat accacttcgt ggaaacactt 62820
ctgctcaaag ggctgagccg cctcccactc ccaaaagtca tcacgacttg aaaaaactct 62880
aaaaagatta ttatattcat ctcgcaccac gaagtgattc tttaaggttt cgagagaata 62940
tttatcctct acggcttctc cttgggagtt acagcgaaga aacttgaatg tttcttgcat 63000
tttgatattt aaaattaaat caattatgat gcggccgcta atgcggcggt tgacgcggcc 63060
gcgccgctga cgcagccatc atacataaag cggcatggcc gttttataac gactagtcgg 63120
ccgttatatg acgaactata taaaaatgaa ttcttttaat tagagttaag tattgttgat 63180
tgtataatcc atcatggttg agccacgcga acagtttttt caagatctgc tttcagcagt 63240
ggatcaacaa atggacactg taaaaaatga cataaaagac attatgaaag aaaaaacgtc 63300
ttttatggta tcattcgaaa actttataga acgttacgat accatggaaa aaaatattca 63360
agaccttcag aataagtacg aagaaatggc ggccaacctt atgaccgtca tgacggatac 63420
aaaaattcag cttggagcca ttatcgccca acttgagatt ctaatgataa atggcactcc 63480

```
acttccggca aaaaagacaa caattaagga ggctatgccc ttaccttcat caaacacgaa  63540
taatgaacaa acgagtcctc ccgcctcagg caaaacaagt gaaacaccta aaaaaaatcc  63600
cacgaatgcg atgttcttca cgcgtagcga atgggcatcc tcgaatactt ttcgagaaaa  63660
gtttttaaca ccagaaattc aagccatatt ggatgagcag tttgcaaaca agaccgggat  63720
cgaaagattg catgccgagg gtctttacat gtggagaacc caattctctg acgaacagaa  63780
gaaaatggtc aaagagatga tgaagaagta atatttttgg taaaaatatt tttatcaaaa  63840
tttttacca aataataaaa atatttttac ttttttttctt cataatatac atagaatgcc  63900
tacaaaagct ggcacaaaaa gtaccgcaaa taaaaaaaca acgaagggct cctccaaatc  63960
tggttcttcc agaggccaca ccggcaaaac ccatgcttct tcgtccatgc attccgggat  64020
gctctataaa gatatggtaa atattgctag atctagaggc attccgattt accagaatgg  64080
atcgcgtctt actaaaagtg aattggagaa aaaaattaaa cggtcaaaat gaatataatc  64140
aggaaactta agcctggaac aattagcctt gtgctgggac ccatgtttgc cggcaaaact  64200
acgtttctta ttcattgcat ttacatgctc gaacgtttgg aaaaaaaagt agtcttcata  64260
aaatctacca aaaacacccg agacaaaact attaaaacac actccggtat acagctacga  64320
cccaaacaat gtaaaatcat agaaagcaca cagttatctg acgtgggttc tctcaccgat  64380
atccatgcag ttgtcgtaga tgaagcgcat ttttttgacg atttaatcac atgccgcact  64440
tgggcagagg aagaaaaaat tattattctt gcgggactca atgcttcctt cgagcagaaa  64500
atgtttccgc ccatcgttcg tatttttcct tactgcagct gggttaagta tattggccgc  64560
acctgtatga aatgtaacca acataatgca tgctttaatg tgcgtaagaa cgcagacaag  64620
acgcttatcc ttgcgggagg aagtgaactg tacgtaacat gttgtaacaa ctgtctaaaa  64680
aatacattta ttaagcagtt gcaacctatt aaatattaaa aatcttatac aataatggat  64740
cattatctta aaaaattaca agatatttat acgaagctcg agggtcatcc ctttcttttt  64800
agcccgtcga aaaccaatga aaaagagttt attactctgc taaaccaggc cttggcctca  64860
acgcagcttt accgcagcat acaacagctg tttttaacga tgtataagct agatcccatt  64920
gggtttatta actatattaa aacgagtaaa caagagtatt tatgcctgtt aattaatcct  64980
aaactcgtta ctaagttttt aaaaataacg agctttaaaa tttacattaa tttcaggctg  65040
aaaacttttt atataagtcc taataagtat aataattttt acaccgctcc ctctgaagaa  65100
aagactaacc atcttctaaa agaagaaaaa acttgggcaa agattgttga agaaggagga  65160
gaagaatcct aagtcgctta catttttttt tgctattttt atagaatgta cacgcatgtt  65220
gatgttgtcg gaatagctga agcctcagcg gccctctacg tgcaaaaaga tagggatcgc  65280
tacttagacg tgctaacaac cattgaaaac tttatttacc aacacaaatg catcataaca  65340
ggggaaagcg cccacctact ctttttaaaa aaaaatattt atctttacga attttactcc  65400
aacaatgtgg cggagcacag caaggctttg gcgaccctgc tttataaact tgatccggaa  65460
tacctcactc gttacacagt actcattacc aaaattccca accattggta tgtgattaac  65520
gtagatcagc gagaatttgt gcgcctatat gccatcccgg cagttaaaca acacttaccg  65580
attcccattt taccccttcta ttgcaccagc gcactcaccc agcaagaatt gttttgttta  65640
ggacctgaac tgcagttaat acaaatatat tccaagctct gtaaccccaa ctttgtcgag  65700
gaatggccta cgttgctcga ctacgaaaaa agcatgcgga tgttattttt agaacagttt  65760
ccgcaaagat tggaaatgac gggcgggaag aaggaggaga aggaaaagca tgaaagtatc  65820
attaaaaaaa taatactaga aatggtctct acccgtcagc gaatcgttgt tgggggttac  65880
```

atacaaaaaa acctgtacaa ccatgtactc aagaatagaa atcgtttaca gcttattacg 65940
agcttaaata tttatgaaga aaaagatatc atccagcaat tttgtgattc aaatggactg 66000
aagatcaaaa tacgtatcaa caatccgctc ttgcctacaa atccggaatt acggcgtttg 66060
actatttatt ttaatcataa taatgatgat gatcagtcat atctaatagt agatatgtac 66120
aacacgggaa gctatgagct agtgcctaca aatcagataa acacgcttga tggcagcttt 66180
ttaataggaa cacccttcgt gcaagcgcga tttttgttgg tagagatctg ggtgcttatg 66240
cttattgcgc agcaaactaa aaaggacacc aaaaaaataa tacaattttt tataaatcaa 66300
tatgaaatgc ttatgaatag tccttggccc agtatggagg ccctttttcc ctcaagcagt 66360
aaaagatatt taggcaacta tgtagaccct aacgcgctca taaagtgggc acaactcaaa 66420
ttaaaaagaa taccgccttt ttatcctgga aagccggatg aagaatcatg ttaagccgat 66480
taaaaaatca tgttaagctg gttgaaaaat catgttaagc tggttgaaaa actcttggtg 66540
aaagcacgga tgtaatatta acattggccg ctcgcatttc gtgttgaaat acgatggaag 66600
agcgacggct atctaccatg ccgatatcgg cctggacatc acagttcatg cacttgtaga 66660
tgggatgact cgcgttatag atggcaggct cgccacagtt tctacagatg taggagatgc 66720
agccatccga gtcgtcgtgc gatttttcta tgatggtttg catggcgccc tgcgccgtaa 66780
gcacccaatg ctccatttct cccagacgaa gacctccgtg cgatcgtttg ccgtccaacg 66840
gctggcctgt gagggcatcc gtgggcccat agcttgcaac ggcgtatcgg tcatccagca 66900
caaatttttg caggcgctgg tgataggtcg gtcctatgaa gatggccgca tcaaagtact 66960
cgccggtctg gccgttgaac attttttggc atccattgaa gcgtagacct tcttgcgcca 67020
gtctttctga aagaagctgc acattaatag gcaggaatgc ggtgccgtct gttaccaccc 67080
cctgtagggc atttgctaga ccaaccgtgg tttctatcat ttgaccgttg gtcattcggg 67140
agggatgtga gtgggggttt acaatgaggt cgggctgcaa tccgtcctct gtgaagggca 67200
tgtctgaagt gggcagggcc agcgccgcaa tgcccttgtt cccgctgcga gaactcattt 67260
tgtcgcctat attgagattt ctttcatagc gcaggcgcat gaggccaaag atctcgtcat 67320
taggcccatg ggacgcatcc acagcatcca cgacggccgg ctcatcgaag ccgtacatga 67380
cagaccggtc gatgtatttg ttgagttcgt ctttttcgcc ccgtattttg gccacttttc 67440
ctataatgat gtcgcccttt ttgaccaccg ttcctacggg cacgaatcca tctacaagct 67500
tttcgtaatt agcaccaggc ttaagatttt tggtgattaa agggtcgggc ttcccaaacg 67560
actctatatc gctttctaat tctacttttt cttctcggta gaaggtgccg gcaaagccgc 67620
ccctgtcaat aaaggactgc gacacgatca cagagtcctc ctgattgtag ccgccgtaga 67680
tcatataagc cacaatggta ttaagcccgt tgggtatgac atagttatgt gctatggtct 67740
ttacaagcgg catttcattg taaaactgga agaagcggtt catgtcgaca cgatatggcc 67800
agctaaagca ataccagccc cccgtttgcc ggccttggtt tgtttcatag gtaacacgcg 67860
caggttgggt acagtttgcg tagggggaca ctagggcggc aaggcccaaa atagcttggg 67920
gcacgtccac gtgtgtgaaa cgacgcgtta catcatgttt atgtttgcgt agctcgatga 67980
tggagaaggc aacaagacag ttttccgcct cctcgggggt aatgaactca cagatgccct 68040
gtgctacgag atcttcaagt gtaagcgttc cggctaaaat gtcttttgcc atttgaggcg 68100
taaatcgcgt attttgaatg aaagggattt tatgtttttc ccagtcttta tcgccttttt 68160
ttctggcctc tgcggccttg tagcaggctt gattgtattt ttcaatatta ttatctacaa 68220

-continued tgagtagggg gcgggtcagc ctaccgacgt ccaaccaaaa ttctacttcg tctaccatgc 68280
tatcccagta gatggtggta tggggatgca caaccttgcc ctcacggcga agcattctat 68340
accgctgagc aagctcaaag gcattggtgc agcagccgat ccattctccg ttgataaata 68400
cgcgcgctag gccctttcgt acaatgtcct tgttggaaac atcggctaac tgttgaatgg 68460
ccggatctga tagaaggcgt tgttttaacg aaagtacttc tccggcggtg cagacattgg 68520
cagtgatggc taactgttta gacatgccta ctttttcacc agtatcggct gactgggcta 68580
cgcagatgta tccaggatag gatgcgtgca cgcgacgcat catgtcagcc ctttctgttt 68640
gtttggatgc gttggtggtg ttatgagtat ttaccgtacg caatgctgaa atggtattta 68700
ataaattttt tctttccaaa ctttgagtag atactctgtt tacaatgggg cgctgtcgca 68760
ccatgatggt tttatttcct gaaatgatag actgttccat actgcgatta agatcggagg 68820
cggtattttt tgataaagcg gcagaaaatg cctcgataat gtttcgctga gtaagctcct 68880
caaaggctgt ttgtttaaga agttctttga acccattgat gatgggtgct atcacggaag 68940
tattaaaaat agccttaaag gccttggcga gtgagacccc tgagccgtgc acccgcttgg 69000
tgcggtagct atcacggtcc gtgggtggaa acacattcat aatgacaaga agtattttat 69060
gaataagcag gcctaaaaag cgcagctttc gtacacgtgt atctgcggtt tggcccatgt 69120
gtggcagcaa tattttgtct aaaatagtaa gttgtctttc atttaagtat tgtaccgcat 69180
tttcatcgct tttgtaagca gatgggtttg agacaaattt ggaaaccttc tcggataaaa 69240
actggataat tttttctcgg ttcagctcgt gttggaccgg ttgaaatatg gggtctaaaa 69300
catgaatgga tttttccaga atttctatca tgaaggtatt cacaagggag ttggattcta 69360
gatcaaatac cacttgctca atgatgctgt catcgcctgt cattccaaac atgcgaaaga 69420
tgagatacca aggtatgcga agttttgaga acttggtgct attgatttca atggtaatgg 69480
cgccggtggt catgtagcgt ataataattt gagagctatt ttcgaaggca cctcccggtt 69540
gggagataaa ctcgccgcga atgatttcat tattcccttg ttgcatggta tggtaatgga 69600
tgtgaagcgt gttaaagcgg atgttttcta agaggtctac gacccattcc ccgcctcggg 69660
ctataaagta gccgccgggt tcattagggt cttctcctat ttcttttttt gcggtttttg 69720
ataggtgatg agtgtggcag cggttgctgc cccgcatgat gggaaatgta gatacctgaa 69780
aaggaggaat acttgctcgt tttacctcct gccgaccatt gctgtagtgc gccgttaaaa 69840
taacctcggc ggctagatta accgggcccg aataggaaag gccacacagg cgtgccttat 69900
tgggtagtaa atttatcttg tttccctgtg aatagtttcg atgttgcggg cgttcaatgt 69960
tcacatctgt aaagttaaat tggatctgaa ctgattcccg aagcttatct atttcagtat 70020
ggtcgcgttg gtctttataa gtaatatcca cgttaaacat ttgttttaca atttgcggaa 70080
ttccattgtc cataagatcg tcgaagcttt tgatgttata ccctatcaat cctgtagagt 70140
ttactgcagc ggagataaag ctcagcatat cagcctctgt aagctcctca ttatccacgg 70200
tttcaatggg gccgtaggtt atttgcggcc gcaagggttc catgattatg aagtactaca 70260
ttaatattca gttattcttt aaaataaatc tttatttata aatcttattt ataatataag 70320
aatgccttat gcaagagaca tcacaaagtt tattacggca acggaaccag aggtgggtct 70380
tcccctgttg gcgctgcagc gctccaaatc catcataggg gttattcttc ttgtaataag 70440
tttgttattt attttcattg gcattattat attatcagtg agtagtggtc ataccacagc 70500
agcctctata tttatcgtat tgagtcttat cctaggtggc ggtggttttt ttcttattta 70560
taaagataat tcttaaccca cataaaattt gaaaaaatat agagtaagaa aatgtccaat 70620
tactattatt actatggcgg ggggagatat gattggttaa aaacagtaga acccactaat 70680
tttttaaaaa tcgggttgcc ttaccaggca cacccattac atcttcaaca tcaggcaact 70740
actcccccat ctatcttaga aaaatttaaa cgagcagaca ttcttcttaa tgaggtgaag 70800
gccgaaatgg acccactcat gttacaacca gaaaccgaaa aaaaactatt ccagatattg 70860
agtagtattg atatgttcaa aggtctgcga aaaaaagtag aattcacgta caatgctcaa 70920
attgttacga atgcttggct taaaatgtat gagctgctaa ataccatgaa ttttaataat 70980
acatctcagg cattttgcaa ttgtgagctt ccaggagggt ttataagtgc aattaaccat 71040
tttaattata caatgatgca ttaccctact tttaactggg tagcttcctc cctttacccc 71100
agttcggaaa cagatgccct ggaagatcac tatggtcttt atcagtgcaa tccggataac 71160
tggttgatgc aatctccttt actgaaaaaa aatatagatt ataataacgg ggacgtaacc 71220
atcgctagca atgtaaaaaa cctagcgctt agagccacac aaaggctgac gcccatccat 71280
ctatatacgg ctgatggggg tattaatgta ggacatgact acaataaaca ggaagaatta 71340
aatcttaagc ttcactttgg tcaagccctt acgggtttgt tgagtcttag caaaggcgga 71400
aacatgatac tcaaacacta taccttaaat catgcattta ctctttcttt aatatgtgta 71460
ttttctcact tttttgagga actatacatt accaaaccta cctcctctcg gcccacaaac 71520
tctgaaacct atattgtggg taaaaacaga ttacgcttat ttacccccaa ggaagaacaa 71580
gtccttctaa aacggctaga attttttaat gatacgcccc tcgtagacct aagtctttac 71640
caaaatttac ttgaaagcgt ttactttgcc gtagaaacaa tacatctaaa acaacaaata 71700
gaatttctaa acttcggaat gaaatgttat cgacattttt ataacaagat taaactactt 71760
aacgattatt tagctccgaa aaaaaagatt tttcaggata ggtggcgtgt gcttaataag 71820
ctttatgttc ttgaaaaaaa gcataaactt aagctttgtg cctcctaggg atctgttgct 71880
taatttaaca gatgcaatct taacagatgt aaactaaaaa gtgtgttcat acaaggattg 71940
tatttatgaa tatttattaa catataaggt tgtgatgtaa cactgtataa cctatataac 72000
tacactatga agcacggcgt ataataattt atattgaaca cgatgttgac tcatttattt 72060
gcaaacaaat atttgtttgc aagacgtttg catgcattta ctaatatgtt gttgactagt 72120
ttatttgcaa actagatgtt tgattgcaaa ctagatgttt gcacgtattt atttgaacta 72180
atatacactc cttgttttat ttgttatata cacagcatac ataagtgtat attgtttaca 72240
cttatgttta taactcgacg taataacatt ttacacgctt ttttttgca aatcttaata 72300 atattgtatg ataaatcaaa caatgtctta tatatgtggt ttattatttt aggcgccgca 72360
agatgtactc cattctcatt gcatgcttgg tgttattact ctgtctagtt atatatgtcg 72420
gtcatcgtgc cgatcatgca cgaaaatatt tagaaggaat gtggcatgga gatccggttt 72480
ttctaaaaca gtcggggcta caatcctttt atctctacat acaacctgac catacatgtt 72540
tttttagcat tgtgaataaa aatggtgaaa agctgatgga aaccaaaata ccttgtacga 72600
taacaaataa aatatatatg ttttttaaac ctatttttga atttcatgtt gtgatggaag 72660
acatacatag ctacttccct aagcagttta actttctgtt agatagtaca gaaggtaaac 72720
ttattttaga aaacaatcac gttatttatg ctgtattgta taaggataat ttcgccaccg 72780
cactaggaaa aacggttgaa aaatatataa cacaaaatta atcatgtttt ctaacaaaaa 72840
gtacatcggt cttatcaata agaaggaggg tttgaaaaaa aaaatagatg attatagtat 72900
attaataatt ggaatattaa ttggaactaa catcttaagc cttattataa atataatagg 72960
agagattaat aaaccaatat gttaccaaaa tgatgataag atattttatt gccctaaaga 73020
ttgggttgga tataataatg tttgttatta ttttggcaat gaagaaaaaa attataataa 73080
tgcaagtaat tattgtaagc aattaaatag tacgcttact aataataata ctattttagt 73140
aaatcttact aaaacattaa atcttactaa aacatataat cacgaatcta attattgggt 73200
taattattct ttaattaaaa atgagtcagt actattacgt gatagtggat attacaaaaa 73260
acaaaaacat gtaagtttat tatatatttg tagtaaataa tatttttaat tacttaaaat 73320
ttttatatat aagtttttga tactatatta taaaacatat gttcataaaa tgataatact 73380
tatttttta atattttcta acatagtttt aagtattgat tattgggtta gttttaataa 73440
aacaataatt ttagatagta atattactaa tgataataat gatataaatg gagtatcatg 73500
gaattttttt aataattctt ttaatacact agctacatgt ggaaaagcag gtaacttttg 73560
tgaatgttct aattatagta catcaatata taatataaca aataattgta gcttaactat 73620
ttttcctcat aatgatgtat ttgatacaac atatcaagta gtatggaatc aaataattaa 73680
ttatacaata aaattattaa cacctgctac tcccccaaat atcacatata attgtactaa 73740
tttttaata acatgtaaaa aaaataatgg aacaaacact aatatatatt taaatataaa 73800
tgatactttt gttaaatata ctaatgaaag tatacttgaa tataactgga ataatagtaa 73860
cattaacaat tttacagcta catgtataat taataataca attagtacat ctaatgaaac 73920
aacacttata aattgtactt atttaacatt gtcatctaac tatttttata cttttttaa 73980
attatattat attccattaa gcatcataat tgggataaca ataagtattc ttcttatatc 74040
catcataact tttttatctt tacgaaaaag aaaaaaacat gttgaagaaa tagaaagtcc 74100
accacctgaa tctaatgaag aagaacaatg tcagcatgat gacaccactt ccatacatga 74160
accatctccc agagaaccat tacttcctaa gccttacagt cgttatcagt ataatacacc 74220
tatttactac atgcgtccct caacacaacc actcaaccca tttcccttac ctaaaccgtg 74280
tcctccaccc aaaccatgtc cgccacccaa accatgtcct ccacctaaac catgtccttc 74340
agctgaatcc tattctccac ccaaaccact acctagtatc ccgctactac ccaatatccc 74400
gccattatct acccaaaata tttcgcttat tcacgtagat agaattattt aatatgtact 74460
atatattaat tatttaacct ttcaagctgg tcttcattta aatttaaaat ccactaataa 74520
aatgtatttt ctagtagcag atcatcgaga acatcatgtg attccttttc ttaaaaccga 74580
tttccatcac atgcatcaaa atcctataca aaaaaatcaa gctctcctag aaatcaaaca 74640
gctttttact ggagattatc tcatctgcaa aagcccttct accattctgg cctgtattga 74700
acgaaaaacc tacaaagact ttgcggcttc tttgaaagat ggacgttata aaaatcgcca 74760
aaaaatgctg tcgctgcgag aacaaaccaa ctgtcaactt tatttttttg tagaaggccc 74820
ggcatttcct aaccctcaaa aaaaaattaa tcacgttgcc tatgcaagca ttattactgc 74880
tatgacgcat cttatggtta gagatcatat ttttgtcatt caaacgaaaa atgaggccca 74940
cagttcccaa aagcttgtgc agcttttta tgccttttct aaggaaatgg tgtgcgtcgt 75000
tcccacctcc ctcaccccca cggatgaaga gctatgcatc aagctatggt cttctctttc 75060
tggtatttca ggcgtgatag gtaaaatctt ggcaaacact tgttccgtag ctcatttggt 75120
tcatggaaag ctttcatcgc agaatattga tcagttaaaa actccctcca accgaccatt 75180
ccccaaaaaa gtaaaacgta tgcttataag cattagcaaa ggaaataagg agttagaaat 75240
aaaattgctc tcgggggttc ccaatatcgg gaaaaaatta gctgccgaaa ttttaaaaga 75300
tcatgcgctt cttttttttc taaatcagcc cgtagaatgc ttggcaaata tacaaatcgt 75360

-continued

```
tcaaaaaacc cgtacgatta agttgggaat gaagcgagcc gaagcgattc attatttttt  75420
aaactggtgt ggctctgccc atgtaaccga tgatagccaa aatatcacag aggcgtcgcg  75480
gtccacaatg caggtcgcga cgcagtccgc cgcaatacag cccgctgcaa cgcagccatt  75540
gcacgaagta tcagatgatg catcatcaga tgcttcatca cccgtagggt atcaaacatt  75600
atctaaagaa atgttattga acacagcctg atgttaataa ttcactacat ctaaagaaat  75660
gttaacctcg atactaaaaa gtcattgaac acaactactg gggcgctaag ttgtccaaca  75720
catctaaaga aatgtcaaca tcctcgatgc taaaagggtc atcgagccgg tcaataatgt  75780
cttccccaaa aagtccggga gaactgtagg ccgagatgtc gtccatggag ctatcttccc  75840
cagagcacac aaagtcctct ccaaaaatca taaagttaaa tgcaccgggc ttacttaaca  75900
gcttttcgct ttgaataata gtgttgagtt ctgtcagcgc aaactctctc acaatattca  75960
caacccagga gggctcttta atttcataca gcgttaagaa acttatacat aaaaattcta  76020
tagagtaaag caaggcgctg gcaggatctg ttacccgtag gtgtttaaat gtagtgtgat  76080
attcattcac aacgttaggc agcacctttt ccaaatcctc cttttcctcg tacgacaggt  76140
gctttacaag cctttcaaca tgtataggag gcttgttaaa tgtactaacg tgccgcaaac  76200
agttataatt atataagaaa atacgtacgg cagagtcgac cgccatgagc cttggatcat  76260
ccattgaggt aggtggtggc ggggcaccct ggccttccct gatgtctgcg taggagcgcc  76320
cctccatggc ccctatggcc tctatcacag caggactgat atccaaaatc ttggccgtct  76380
tgattatttt tccgtaatcg aaagtccatg gctcctgtgg aggcttgggt tgtgtttcgg  76440
tggagggcgt ggtcatatct ttctttattt gaatagaacg gatcgacatc ttttccttat  76500
cgtactggtc tttataatta ttataatagt catgaactaa ttcgggttga gaaagatgat  76560
cgtatataat ataggtaaaa agtccgcact tgacacattt tttatcctgg aagtcgtgta  76620
atcctccctt ggggcagcgt gactcgtaga aggcataaaa ggtgttaaat tctaagctcg  76680
cctttagggc tgtttggacc ttttttatgt ttaattgccc cacctcatgt tgtagcacgt  76740
ggcatacaga acagcgtaga tcggcaagtg cataatggtt gtcaattttt tttatgacgt  76800
ctttgcgtgt tacttcaatc tcggcgggtt tctgcgaact gtctacggcc ttgtaaacgt  76860
aaatggtcca cttatgagga agcccccttt catcgtatag ggttgaaatg ggaagccttt  76920
tatactcaaa cagccgagtc cgttggtcgg ctcttcctgt gttaggatca aatatgttat  76980
aaaatccttg ctgagcaagc agggcctttt gctcgccata agcattttcg tacgttttga  77040
attctgcaag ttcggagtta aaattaggtg cattttgtaa atacttaaga aataattcat  77100
aggctctaag gtaaatgaga gttgaggttt tttcctcatc ccgtcctccc caccacaccc  77160
gcaggctttc ttcttgaaaa tagatgtcat tcagacgcgt caactgcgta aaatcaggcc  77220
gatatttaga ggtataaatt ttatcataaa attctttttg cgataatagc tcggccgggg  77280
tacgtcctat cacggtttta aactcatatt cagcctcctt gggagtccgt ggtttgtgca  77340
tagggatgct gccgtcaata cgggccactg tggcagcata atcatacatg gggtccagca  77400
gaatctctgt caaaagtacc ttggtgtcgt cctgcacgct aagcccttgt agcccatttt  77460
ggtggataat ttttttgaaa gcctcccgaa aattattagc aatccactga tccgtaatct  77520
cagatagctg atttattata ccgctatatt gctgcatcat tttctccaaa agaaaggtca  77580
cgtatgcatt caaagagcta tccgccttca ttccatgaat ggtaatcgta agaaattctt  77640
tatttttttg cgagctataa atgagattca aaatataggc atagatgtag atcacagcat  77700
```

acagctgcgt taaaggatcg taatcctctt cctttttaat attttcgatg ctatacacga 77760
gcggcaggca gacatttacg gctatattgg caaactgttt cacgtctaca agctttccaa 77820
agtggataaa cgtgcaggcc ttcatggttt cctgccaaat aaaaacacgg agcttactat 77880
taagatcgcc gatgatgccc acatctgccg tacgatcctc ttgaataaaa tgggccagct 77940
cttcgccaca aattttgcaa aagtaggagt aaataagccc ctggttgttt tctttctcct 78000
tgtttattcc tgaaaatttc attagcttgg ttcgcatggt gtcgtaggac gcttctgccg 78060
cttgaagctg tataagcatg tccacatggg gacaaagcag cttaaacccg caggctttgc 78120
atagattcca attggtggta ttgttttttt ccttgtagag tacacgaata ctttctaata 78180
cttttaataa ctccgcgtat tgaagacccg aacgcaactg ttttaccagc ttgagatgag 78240
cacatgcatt tttttcttgg agttcccact gtttttaat gtttaggtat tctgttgtaa 78300
taagttctgc ctcctgtttc ccacaggctt taatgacttc ttgaaggatg ctgttagggt 78360
catccacttt accctccatt gtaagaattt cacgtatagc atccgactgc accctaccta 78420
ttttttcttc cataatttta aaatactgtc tcgcctgggt aatgacctct gtgagcttca 78480
tgtccacctg ctgcagaatc atttgctcct tttcacgctg ttcagcatgt tgtaaaaact 78540
tttgttctac agggttccaa agcacctcca aatagcctgc tctatatagg tcataaagca 78600
agggcatgta tcccgatgta aaaaccgggg acaccgagta catcgtagac aactctttta 78660
aaaaaaatat cacgcgctta atgttctcct ccggttcaat ctcctcggtt tcaacgatat 78720
tagatatatg actgccctga tcctcacggt ctagctttcg gtgtaccatc tcctctgcta 78780
gccgattaat gagccagcta tgcccgccgc tccgcaaaaa cttataaagt tcgatatact 78840
ggtgcgtaaa ctggatgatg ttttccttgg tggttacgac aaccccttct ccgttttttt 78900
tccaggtttc ttgatccacg catttcataa atactcgaat aaaattggtc aaattggctc 78960
ctgaggcgac gtagcccaag gtttcaggcg agaaggagcc tatctcagcc atacgcataa 79020
aacactgcgg ggaaaaagtt tttagccgca acttaagtcc atagatttca atgggggctt 79080
ctgcgggaac ggccaggtgc gtcccattaa ttaaaaaaat ttctttgcgt gtgctagggc 79140
gaacacgtaa ttcctttttt ttttcactca cgatggggac cacatcgggg tctaccagca 79200
gttgacgtat gtaggcctct atgggcatgg atagatcggg cagctttgac tgctcggcgc 79260
gaacatggtt cacaaaatct tttagagtga aaagaaagtc tattaaacgt atgtttttta 79320
tatcattaga ccctttaagg gtagagtaga tttcatccac tagtgcctcg atttcctcat 79380
tattgagcga taagatatct gtgccacggt ggactatttg cgcgatcgta attacttcct 79440
ccattagata gaaactgaat attatattta aaataaatac aaaatgtcaa atgaaagttt 79500
tcccgaaacg ttggaaaact tactttcaat gttacagacc aaacagcaaa acgcaattca 79560
gtcagaggtg attgaatggc tgcacagctt ttgtgaaacc tttcacttaa aaatacactg 79620
ccataaacag tttattccta gcggggaaaa aaaacgagct aaaatacccg ctcaagaaac 79680
acagggaaac acgcagccct cccaccatgt gtaccgggtt gttctctcca gagcacagcc 79740
agtcaaagca caggaatctc tgctaacaac catgtgcaac ggactggtgc tagatgcaaa 79800
cacatggaca tgcctagcca ttcctccgcc tgcgcccttt caacaggcga cccgccaggt 79860
ccaacacttt taccgtaaca atttctacga agtggttccc atccaggatg gcacccttct 79920
cacaatctac cactgggatg accctgaata tggcccctcc tggtgcctag caagtaccca 79980
cggatatgat gtgagtaact actgttggat aggcgacaaa accttcgccg agcttgtata 80040
cgaattgctg cagcagcact ctacctgcga cgtcaccctg gaaaaaaata aaacgcgggg 80100
aacgcgtctt ttctttgata acttaaatcc cgattactgc tatacgattg gaatccggca 80160
ccataattta cagccgctca tctatgaccc tcaaaatatt tgggcgattc aatctacaaa 80220
cctaaaaacg cttaaaacgg tatatccaga atactacggc tatataggca ttccaggaat 80280
tcagagtcaa gttcctgagc ttccccagta tgatttacct tatctaatac gatcttataa 80340
aactgctatg aatcaagcca aaaatgctat aaaaaatggc aaaaaagaca agggatactt 80400
taattatggc tatttactca tttcgcgagc gcctgccatt actaaaagta cttctaatgt 80460
tttgttaaaa tcgcctctgc tggtattttt acaaaaaagt gtgtaccaga aaaaacacaa 80520
tatctctaac agccagcgac tagaatttat tatactgcaa aactacttga tgcagcattt 80580
tcgagatcat ttcattgctc tatttccgca gtacatatcc tattatacga aataccaaaa 80640
catgttgaat atgattatcc atagtattgc aactaaagat aaagatcatc cctttgcagg 80700
agccgtggta aaaaaagtgt tggaagatat tgaaaacgcc gaaaacatta ttgatcatac 80760
aaccattcaa aactatgccc atcaaagcaa gtacgccatg ctttacttgt caattatttc 80820
ccatttttaa tctaatacgg ccaaagccgc gggtttttta ataaactaac atttaaaaaa 80880
actgttttat taaaaattat aatactttta ttatatatgg aacatccatc tacaaactat 80940
actcccgaac agcaacacga aaaattaaaa cattatgttt taatccctaa acacctttgg 81000
tcttatatta aatacggaac gcatgtccgg tactacacca cacaaaatgt tttccgagtc 81060
ggtggctttg tgcttcaaaa tccctacgaa gccgttataa aaaatgaggt aaaaacagca 81120
ataagactgc aaaatagttt taacacaaaa gcgaaagggc atgtaacgtg ggccgtccca 81180
tatgataata ttagcaagct atatgccaaa ccagatgcaa ttatgcttac catacaagaa 81240
aatgttgaaa aagctcttca tgctttaaac caaaacgtac tgacgctcgc atcaaaaata 81300
cgttaaatat aatttttgta gaggataaaa agctatttta gctaaaaaat aattcatata 81360
cgtttatgca gaggaagaac ggtggctttc aaattcagat tgcatccacg tagaccgtag 81420
cgtttttttt gcttctggtt tatatcgtaa accgtaataa acatcatcat ttgtatccgt 81480
tggatctttt tcccactccg gataaaaaat cggttttctt ttttttggtc gtttttttgca 81540
gtaagctgta aattaaggga atatagctta tcgaaaagtt gttcctgatc catataaata 81600
gcagcatata ttaaaaaaaa taaaaaaaga cgcttcaacg agtcagtacc actgcttgcc 81660
aacgatttac gttggttggt gcattatggt gatatagtaa tgagtgcctg cacaagtgct 81720
tgcacaagtg cctgcacaag tgcttgcaca agtgcttgca caagtgctta cacaagtgct 81780
tgcacaagtg cctgtacaca ttactgcatc gccaaagcac ctgcaatgcc tacttcctca 81840
acagagtacg ataactaaat gcttttaagc accgcttgcg tcgatgtgtc cttcggggca 81900
atcgggttca attggatcca atattattag tcataattac ctaatactta ttcaatttta 81960
tcttttttac cttgtaagat ttaaacagcg ttttagcttg tttaaagcaa cgtttaaaac 82020
aagctaaaat gctgtttaaa acaacgtttt aaacaagtta aaacaaataa gcttataaat 82080
ataccatgac aaaattagcc caatggatgt ttgagcagta tgtcaaagat ttaaacctaa 82140
aaaatcgagg gtccccctcg ttccgcaaat ggctcacatt gcaaccctca ctgctgcgct 82200
attcgggtgt gatgcgtgct aacgcctttg acatcctaaa atatggctat cctatgcagc 82260
agtcaggtta tacggttgct acgcttgaaa tccactttaa aaatattagg tcttcctttg 82320
ccaacattta ctggaaccgt gatagcgagg agcctgagta cgtctgctgt tgtgccacct 82380
atcaatcgca cgatggcgaa taccggtatc gatttgtttg gtaccaaccc ttcatagagg 82440

-continued

```
cttataatgc catagaggcg gccctggatc ccctggaaac cattatcctg aacctcattg  82500
cggcacgaga tctagacttc gttgttcaca tatttcctta taataagggc catgaagact  82560
atttggcctc cacgcaactt attctcaaaa tctttattgc gacgctttta atggacattt  82620
taagaattaa agacaacacg ttggacgttc acttaaattc cgactatatt attgtgatgg  82680
agcggctttg gcctcacata aaggatgcca tagaacactt ttttgaagcc cataaggact  82740
tactagggta cttaattgcc tttcgcaatg gggggaactt tgcaggaagt cttagaccct  82800
cctgtgggca aaagattgtt cccctaacga ttcgagaggt cctacaaatg aatgatatta  82860
atttagccgt atggcgggag gtgtttatta tgcaggaatg ttccgactta gtcatcaatg  82920
ggatagcgcc ctgtttcccc atttttaaca cgtggacgta tttgcaaggt attaaccaga  82980
tttttttga aaacacgtct ttgcaggaga aatttaaaaa agattttatt gcccgagagc  83040
tttccaaaga aattatcaag ggccaaaaaa cgttgaatga caaggagttt aaaaagttaa  83100
gcctacatca aatccagtac atggaatcct ttctacttat gtcggatgtt gccattatga  83160
ttaccacaga gtatgttggc tatacccttc aatccctgcc gggtattatt tcgcgatcca  83220
gctatttatc cccatcgtg aaaaacattt tgatggacga agactctttt atgtccctac  83280
tatttgacct atgctatggc gcctacgtgt tgcataaaaa agaaaatgtg attcacgcgg  83340
atttgcacct gaataacatg acctactacc atttcaaccc aaccagtttt acagatcgca  83400
acaaaccagg aaaatacacc ttaaaggtca agaatcctgt gattgccttt ataaccgggc  83460
ccaaagtcga aaccgaaacg tacgtgttca agcacataga tgggttcggc tgcatcattg  83520
actttagcag agccattatg ggccaaaacc atgcaatcaa gcttgagcgg cagtacggcc  83580
tcgcttttgt aaacaccttt taccgcaatc aaagtgagca tattttaaag gtattacggt  83640
actattttcc tgaaatgcta accaatcgcg aaaacgaaat acagggggtg attttatcaa  83700
actttaattt ctttttcaat agcattactg ccattgattt ttacgccatt gctagaaacc  83760
tacgtagtat gctttctttg gactatttac acacctctga ggtgaaacga aacgtagaaa  83820
tttcgcaaac atttttggat acatgtcaat ttttggagga aaaggccgtg gaatttttgt  83880
ttaaaaatct tcatactgtc ttatctggca agccggtcga aaaaacggcc ggggatgtgc  83940
ttttacccat cgtatttaaa aaatttttat acccaaatat tcctaaaaat atattacggt  84000
cttttaccgt aatagatgta tacaattata ataatataaa gcgttattct gggaaagcta  84060
tacaaacgtt tccaccctgg gctcaaacca aagaaatctt gacgcacgcc gagggtcgta  84120
catttgaaga tatttttcct agaggagaat tagtttttaa aaaggcttac gcagaaaaca  84180
accatttgga caaaatttta cagcgtattc gtgagcagct tgctaatgaa aatttgtaag  84240
gcttgcagtt cttgtatggt cagaacctat gtcgatggaa acattatttt tcgctgcagc  84300
tgcggcgaaa gcgttcaagg ggatagtcag aacttgctcg tctctagcaa ggtgtaccac  84360
accggggaaa tggaagataa gtacaagatt tttattaaaa atgcaccctt tgaccccacg  84420
aattgccaaa taaaaaagga ttgcccaaat tgtcatttag actatttgac acaaatctgt  84480
attggaagcc aaaaaatcat tatattggtg tgccgctgtg gctatatgag caacagagga  84540
taaaccatat catcccaccg aattatgaca ttcctttaaa accgtccgcc taaatagttt  84600
tcacaccttt ggtggcagac tattttataa aaagtaatgt tggttcatga agataaagtg  84660
tgccaaagaa acttttataa acaaatgatt aatgtaggtg ctagtcgtgt gtacttaaac  84720
agggtattct atagccaagt attttctata gccaagtatt ttctatagcc agtattagtc  84780
aagtatttag atgtcagggt atttttatag ccagtatttt tctatatgta caaactattc  84840
```

cagtaaacat atgtgtgttc tttattgagc agcatcatgg cattaacaag tttattaaac 84900
tgctctaatg ggcattaaat gacaactcgg tgcttagcaa aagtgcctat accttttaac 84960
aattagggcc gggaggcatt cccagctttt ttctataatc agccatacag taccccctgag 85020 cctcatacac gggaataagg tccttccatt ccttgttggg atcggcgggc cagctctcaa 85080
atgaggtgtg aatgtaaggg tcctgttctt tttccttaat gaagcgttta atctccattt 85140
gatgttgttt actttttgt ttgcggcgga gcgtgttccg caccaatacg taaaaaatac 85200
caagaatcac acataaaaga attattaaaa aaaatatcat catcgcgggg tttaaaaaac 85260
gatcccatgc aacaggaatc gttcttaaaa ccttgtctgg cagggctgta aacatgaagt 85320
ctcctcctat aatcggggtg ggactgtagc ctaacagttc aaggtcctgt cgttctagat 85380
acttattggc gaactgccca ccctttgccc ccgttttttt attaatcaag cagcgctgca 85440
ttttccacca ttctaaatct tcaggagaaa gctcaatgcc atatatcaac tttaacgtta 85500
ttgcatcttt ttcaatatcc ttatcaattt ggctgagctt ttgagcttta agcgggtcta 85560
gtgtgtactt ccatttaaac ttagtgtcct gtagtttggc tacatgaaat acggaacatt 85620
tcggcggggc ctttgtgacg cccttacact gcggaagttt atcattagga caggcgcata 85680
gatgagactg cgccacagca tcgcgaacta catcgcagac ggagtacatt ttcctcctat 85740
gttaaacaat aaattttttt catagctgaa atttgtgggc ctatcttttc ccttgcccgg 85800
ataataatta taagggagtg ttgaaacatc tgggagagaa ttgcttaaaa aatgggtttt 85860
tgggaggggt aactgcgact gttgtacgtc gttggccagg gagattctat atgccgggct 85920
aaaggtgcaa cgttcctgtg aacaacttag tacgcgcgtt gttaatacaa atggactggt 85980
attagcaaac ctcgtaaact cttccggact tgtttgtttt tgtatgatgt ttagcaggga 86040
gtctgccttt tcgagaatcc aaagcgtcgc attgtagtaa aataaaaata gcgacttatc 86100
ggcaggcgtt gcaaaagcgc cgtatagaaa ataaagcagt aagtactggg gagacaccac 86160
aataaggtta tcttgaatga tagatatcgc tagctcttta aacatagtgc taaaaaaatg 86220
tatgtcgttc gtcttgaata tagggggact atagtccatg tagggctcac atatctcagt 86280
caggtgaagg cccatttctt ttatgacttc ttccgggttg tacgtcgcta acaccagcgc 86340
gggataggct ttgggcatat ccacggtaag tgttatgttt ttatcattct tatggtagga 86400
gtaagatggt tgtggaaatt ctgttttcca ctccgggact ttgcaggtaa ttctcagctc 86460
atttagagtc tggtacagga gggcgtatgc cgcaaagccg tgtatggcca cttgtttaaa 86520
gggaattgaa aacgttttac tttcgtatgt cgacttcaca ggaacaacgg gaatggggta 86580
atatttttct atgaggttat accgctgcaa atccttttta aacctgctaa aaacatcttc 86640
ccttggtggg ttatcaaaag gaaagcaaaa tgctaggtgt agcccggccc gctggtaatc 86700
ggggtgaatg attttaaggt ttttatacgt taatgtgggt atggtgttaa agatattggg 86760
gggcatatat gaaagatcag caacccacac aaagtccgtg cgcacccgca tggtctgcac 86820
atggatggcg cgcaccgtgc ccacctgctt gaagcccttt tcatacaaaa tgtcagcaag 86880
ttcgtaggcg tcctcaacgt ggttggggga aaacatatca aagtcgggtc tttctccctc 86940
gggataaatt gagctgcctt taagatgcag ggcataatca atggcaatcc ccccgtacaa 87000
aataagcttt ttctttatga taaattcgcg gaccacctcc aaagccgcct caatctccac 87060
ggcatttgcc tcacgttttt gagcaatgag ccggtactta gaaacattaa aatcagtctt 87120
tagtaaagac gtcataaata gtgtttaata tatattaaag gtttgaataa aatactaaat 87180
agtaaaaatg gatgccctat taaaggaaat agaaaagtta tcgcagccat ccttgcagaa 87240
agaaaacaat gatgtatgcg atctctgttt tatgcaaatg aaaaaaattt ctaactatca 87300
gcttttatgc gaagagtgcg gtcagctgaa ggactggttt gaacctgaat ataatgaaaa 87360
attcacggta tattctcgtc taaagatcgt gggtgccaat agttcctatc accagcgcga 87420
tttggacaag gccaactcaa gtgactatag ctccttgcaa tttcatcaca ttttagagga 87480
gctcaaatcc ctaaatgtta agtatatgga tgcggggcaa aagccctttc ctattcaggt 87540
gttaaaagaa actgctcaca gttataacca agtacaacaa catcgggtca tacgcagcat 87600
tacaaagctt cagatcttag ccagtattct acgtagcatt tgtttaaaat taaacattgc 87660
ttgtacggtg gcagacgccg cgaggtttac tcaacttaat accaaaggga tctcaagggg 87720
catggatctt ctgcgctccc tatttgtaga caataaaatt actttaaacg ttgatttaaa 87780
ccctatagac agctttatta atagtaccta cagtgcctta caaattaaac aaatccacca 87840
agaactgcag gaggaaaatg tttataattt aaaagaaatt gttaagagct ttatattata 87900
cgcggatgag aagaacatcg gcgtcgatct taacaggaga accgttgtga ttgctacgat 87960
gtataatgtt ttacgccgtg cctactaccc catagaaatt gatacggtgg tgtatcaatg 88020
taaaatacga aaaaatacaa ttacacgtgc tcttaaaatg tatgaggatt actactccca 88080
ctttaagtct ctttatgagc agtatcattt aaacgcggca aaaaaattaa tttaaactaa 88140
acgtttaaac taaatgttta aactaaacgt taaaactaaa catttcgact aaagtttaaa 88200
acctagtcta acagcgggat gcccatttcc ctggggttcc atatttcaac aattttttga 88260
ccttcgggtg ttaccttgat gcagcgcatg acgagcagtg gaattttcct attaaagagt 88320
tcttgcttag ctatatcaat aggactgcta tatttttttt taagcattgt agatccatta 88380
attgccaatt gttgcgctct aacggcgacc aaccttgtgg cctcaaaggt ggttaaaacg 88440
ttggaggtaa tgcgctcgtt atcgggtata atgaccaatg tttgcgacga ggcctgcaca 88500
aagccctcgc agatggacgg agactccacg atctcgtcct tgtcctcgga ctcctcctca 88560
ctgtcgacga ggttctcctc ttccgtttcc acatattcct ccacgaggtc atccatgata 88620
agatcctcgt tgtcattatc agccatatta cactgttatc aaatgtactg tttaatacgc 88680
aaatggattt actacgtttt aattgtatgt cttcatgtgc aggctctagt ggaaagtaat 88740
tttctcacaa tttttggcac cgttacactt gtgcccacaa aaacccgcga ttttttttatt 88800
ttatattact tttggaagta cgagtttaac cagtcgcttt caaaccttat gcgtctatct 88860
cgccaaaaaa cgctcacagc ggtgttggat attaccttta aaaaaataac attaattttt 88920
accacagagg gcgtattgcg tatggattct acgaataagc caggcgtgcc actcgatata 88980
gacccccagt tcattgacct tgatagtatt ttaatggaac tggatcatta ggacctctcc 89040
cgcccattta aatttttagt ttctacaata ataaaatgcg cgaggaatca tgggaagacc 89100
acgataccat tcagctcacc gctcagcgca aatacctcgc cgaggtgcaa gctctagaga 89160
ccctttttgac tcgagagctt tcagtctttc tcacagagcc aggcagcaaa aaaacaaata 89220
ttattaatag aatcacagga aaaacctacg cacttcccag cacagagcta ctaagactct 89280
acgagcatct cgagcaatgt cgcaagcaag gcgccctcat gtattttttg gaaagacagg 89340
ggacctactc gggtctcatg ttggactatg accttaaact caatacaaat gctgttcccc 89400
cgctggaacc ccccgcgcta tcacggcttt gccatcgaat atttgtgcat ataaaaaaca 89460
gcagtgtgct gcctgagggc agccataaaa tccacttctt ttttacatta aaacctgaag 89520
tggttcaggg caaatatggg ttccatgtgc tcattcctgg tctcaagctg gcggcttcta 89580

-continued

```
ccaaaaaaag cattatagga tccctacagc acgatgccac cgtacaaaaa attctacacg  89640
agcagggcgt tacaaatcct gagtcctgtc tggaccccca ctccgcctcc gttccctcgc  89700
tcctctacgg ctcctccaaa ctaaaccaca agccctacca actgaaaacc ggctttgagt  89760
tagtctttga tagctctgat cccgactaca ttcccattca tcaaataaaa aatttagaat  89820
cttataattt agtttctgag ttgagcctta cgaatgaaca gggaagcctt gtaagacctg  89880
tctattgcgc ggcagacatt gccgctgaga aggaggaaga gatcccgacc gaggatcact  89940
cgctctccat attaatgcta catgatcccg aagcccggta tttacataaa attttaaatc  90000
tgcttcctcc ggagtattat gtagagtacc ccctatggag caacgtcgta ttcgctttgg  90060
ccaatacatc cgctaactat cggcccctcg ccgaatggtt ttcgcaaaaa tgccctgaaa  90120
aatggaatac gggaggaaaa gagaaactag aaaaactttg gaatgatgcc tcgcaccaca  90180
ctgaaaagaa aatcaccaag cggtccatta tgtactgggc ccacaaacat gccccccagc  90240
aatacaaaga aattgtagaa caaggctact tttccattct cgctgaatat gtgtatagct  90300
ataacggcat gcttgagcac tacatgatcg ccaaagtcat ctatgctatg atgggcaaca  90360
agtttgtagt ggacgtggat tcaaacggga agtacgtttg gttcgaattt gtgctaccgg  90420
gccagccaat gaatcaggga gaaatatgga agtggcgcaa ggaggtaaac ccggatgagc  90480
tgcacatcta tatttccgaa aacttttcaa gggtgatgga ccgaatcacg gagcacatca  90540
aataccacct cagtcaaccc catgaaagca atattttaaa ttattataaa aaactattaa  90600
aagcctttga acgctctaaa agtaaaatct ttaatgacag ctttaaaaag ggagttatca  90660
ggcaagctga gtttttattt cgccaaagaa gctttattca aactctggat accaatcccc  90720
acctactggg ggttggcaac ggggttctct ccattgagac catcccggct aagctcatta  90780
atcattttca cgagcatccc attcatcagt acacacacat atgttatgtg ccctttaatc  90840
ccgaaaaccc ctggacaaaa ctattattga atgcactcca agacatcatc ccagaacttg  90900
atgctaggct gtggatcatg ttctacctaa gcacggccat atttcgcggc ctgaaggagg  90960
ctctgatgct tttgtggctt ggaggcggct gcaatggaaa aacttttcta atgcgacttg  91020
tggccatggt attgggcgat cactatgcct ccaagctcaa catcagcctt cttacaagct  91080
gcagagaaac cgcggaaaaa cccaacagtg cctttatgcg gcttaagggg cggggatatg  91140
ggtactttga ggaaaccaac aaaagcgagg ttctaaatac gtcgcggctg aaggaaatgg  91200
taaatccggg cgatgtcacc gctcgagagc ttaatcaaaa acaggaaagc tttcagatga  91260
cggccaccat ggtcgccgcg tccaactata acttcatcat tgacacgacg gaccacggca  91320
catggagaag actgcggcat tatcggtcaa aggtgaaatt ctgccataac cccgaccccca  91380
gtaaccccta cgagaaaaag gaagatcctc gctttattca cgagtacatc atggatccag  91440
actgccaaaa cgcattcttc agcatactcg tctatttttg ggagaagcta cagaaggaat  91500
acaacgggca gattaaaaaa gtgttttgtc ccaccattga gagcgaaacg gaggcgtaca  91560
gaaagtcaca agatacgcta cataggttta tcacagaaag agtcgtggag tcgccctccg  91620
cagaaactgt gtacaaccta tccgaggtcg tgacggccta cgcggaatgg tacaacacca  91680
acattaacgt aaagcgccat attgccctcg agctatccca ggagttagaa aactctgtgc  91740
tagaaaaata ccttcagtgg tctcccaaca aaacgcgaat tctaaagggt tgccgtattt  91800
tgcataaatt tgaaacgctg cagcccggcg aatcctacat tggggtgtcc acggccggca  91860
cactcctaaa cacacccata tgcgagccaa aaaataaatg gtgggaatgg tcccctaatc  91920
```

cctctgcccc tcctgagaaa gaagcgtctg caccaactcc ttagggaata tccttagaag 91980
catgtctttc ggcagagcca ttaccggtag caaaaaagca acattgagta tattatatgc 92040
cttagcctgc tcataagcgt cctttttttt catggtattt tatgttttta aatattttta 92100
attatttttt aaatacgatg aacagttcgt gctccgaagg ctgtttacta aaaatcggtg 92160
tgaatccgca ttctttaaat atggtttccc attcggggat ggtatggaaa tccatgtctc 92220
tacgaatagt atggtgccca agtgcgtcct gcaggctgtg aagccagaag gcctcctgac 92280
cttgatgaag gtcgtacatg ataagaaaac catcaggttt caacagatgg taaagcttgt 92340
taaaatcgtt tatcgtaaga tgatgcgccg ccataggtaa ccctatgagc tccacagagt 92400
tttcatgctg gacatcgtcc atatcggtat aaaacgtttc acagtaaatg agacgcttaa 92460
acgagtatcg atgacaaaca tttatttcca agtaggtttg cactacgttt ttaggtatat 92520
cgggaatcat gttgattaag gttgtttcgg gaaacttaat catctgacta ggcttcattt 92580
tcaactcttt aaaggatttc ccggagaagt gaaaatgggt ctttacgtat ttatgtaaaa 92640
atacctgaat gggcagaggg ggctcctcct cttcgttctc gacgcctccc aaaatatttg 92700
gaatttcctg acgtggcaaa agaaagttta tgtccacgtt tacgaatcca tcgaggacgg 92760
acacaaagct tggctctaat ctccattcca tatactgttt agaaacggga gatagcataa 92820
tcctaggcgt cacaatgcac gaagggtttt taatcaccgc atcgtggtaa gaaaagtgta 92880
ttccatttct tccagtataa agaagcctat gttcgtcgta gcagaaacaa ttaaggcggt 92940
atgcctcata catacactgt ttcaaagtac aaacacgttt taaaaaggtt tctgcattgg 93000
cggaggccaa gcggttttgc cattggtgga aggggttcaa tcctacaatg gccagctcgt 93060
ttaaaatatc ttcgcggcgc gctaaaatct gcaccataga agaatacttt agcatttttt 93120
tttcgcacca ttcgcgaaga tgtttagcta cattattaac cttattattg ataaagtata 93180
cgatggcatg ttggaagcct tcaaaaataa agagcccctc caaaagatca tctgccaata 93240
gaagatggat gttggtgtaa gcattgtcaa tattttgtag aaacggcgga atgcctgcca 93300
aaaccgcttc agcaagcata gctccgttcc gttgtttact gtccaataga ttcgtaagtt 93360
ttttgtccgc aacagacacg acggctagga tggttgcaat gtcagaaatg gcggcttgcc 93420
agaaataacc cgaaaagcac atgcgcgctt cttctataga taaaaacgaa aagcgagagg 93480
caatgtctcc gagctgcgtg agttgaagac ctttttctcc tctggttaaa aggcctgcca 93540
caatggcccg ctcaatggct gatgccagcg catccgtggg gggaggatcc agcatatcaa 93600
tctcctctgc cttaaacacg ccttccttat ttttttaat cgtttctacg acaatgctaa 93660
gaaaaatggc cccagggcct tccgtaatga tttcaggata ctgctgcact ggtatttgct 93720
caaagacgtg ttttgtgtaa agcgggtaaa agtgcccagg aaatactctc cctacacgcc 93780
cctttctttg ctcgatacgg ctttgagccg cggggcgcgt aataagccct cccgcccatt 93840
cgggatagta ggtttcaatg cttctgttcc acccgggatc tatgacgtac ttcagcgttt 93900
caatggtaag gcccgtttcc gcaacaaccg tggaaacaat gacccttctt aaaggttttt 93960
ccactttagc ggttaaggga tttttcaccc acagattctt aatttccgct ttcaggccaa 94020
ggtaggcctc attttcctgc gcaatcgcct cactatcgat cggcaaaatc aacattaacg 94080
gcagcttttc tttggcaagg tccatatttg cattattcag caacatcgaa aggaagcgta 94140
tttcagccat accgggcatg aaaattaaaa tatctgcttc cgtgggacga tcatgaatgt 94200
tttctttatg aatagtgaga gccgtttcgc aggcggtctt aatgtagttg ttggtgttat 94260
acagcggcca gtgggtttcc acaccgtact gtcgtccttc caccaaaata atgttttctt 94320
ttccgatacc aaaataggtt gagtatttat gggtatcaat ggtggcggag gttaaaatta 94380
caaagggaat acgcagcgcc cctatgcttc ctctttgcaa catgcgctga agcatacttt 94440
taatatacat gagcataagg tcgatgccta gggctcgctc atgggcctca tctataatca 94500
taaaggcata gcgggaagct atctcatcat ccgtcattgt atgtagctgc gccaacagaa 94560
cccccgcggt tgcataaata aggccccgat tgggtttttc cgtcagaggc ttcgtttggt 94620
agcccactgt ttggcctaat atcatgtcgg ggtagtgggt tgaggcgccg atgtctttgg 94680
cgagggtcac cgcggttagg actcttggct gggtacaaat aaccgagcgt cccaagtatt 94740
tttggaaaga atgcgtgttt tcatttctca gaattctgaa cacgtgtacg ggtaaggccg 94800
tggattttcc ggaaccagtg cgtgacttta taatgagcac ccggtctgcg agggaggttg 94860
gaatggcccc tccaaactcc gggagacgtt gttttatcca agtgatgatg taatgaatag 94920
gaacatcatt cttgtgctca gcgggcacgt tatagagatg accaggctcc aataaagtcg 94980
gttttcccat attctattgt tttaaggatt gattgttcat aaatattttt atactctgac 95040
caagaaatta tttttttatt aagccggtta tttacgttgt tatggaacgc gaaggtccag 95100
tactgaaagt cctccgagtt gtttaatgtc aagggatttt ttgtaagata cgaaaaggcg 95160
tggtgctggc acctggtgca tggcagagac tcgataaagt tcagtatcca ttggatggct 95220
tcatattttt ctttccagct aggagcgtct gaaaaaaaga tagcatatag atgcaaggat 95280
cgccagtatt taggtcccca atgcaacatt tataaccttt tgaaaaatct cattccatat 95340
agaggtaaat attttttttc catggagaat ttttttgcac tcttgaaggg attgcgccac 95400
atcgtcaaat gtttttttgtt ttccatgtat tttggcgtaa ttccagccag tatctgtgtc 95460
atggtcctta atgtcatccg ctaactgaaa ggcatgtcca aaacaatggg cagccctttc 95520
aatcatccca atgtcttcaa cggatccagt tcctaaaacc cagcccataa taaacgcgat 95580
cttaaaaaag ggaatggttt tttctggagt gtctactaac tgaccggaac ccgcgctgtt 95640
tagagagtgg cttacaaagg tacacagcag cgctcccagt tggttgggat ccggaaacct 95700
tggacagtgt tccttaatcc agtcgatttg ccggcaaata ttttgaaatc cttgcatggt 95760
tagcgccaga gcgctcatct gcgccttggc tacgccaaag cgggcccaca ctgtatcttt 95820
atttcgccgc ttcacatcgt tgtcaaagga gggcatatca tcgataatca aagaagctac 95880
gtgaaagtac tccgctgcta gggcggcctc tgccggataa ataggcgccc caaaggaatg 95940
ttgcaactga caggcccgaa caatttccat caggataatg ggacggatat acttcccacc 96000
tcttagagcg taagagcaag gctctgttag ttgtccctta aagtccccat cttcaatagc 96060
attatttaag atggtctcaa actcttcact aaaggtttta taatttttag gattcagtgg 96120
atgtattcca tgaaaaagcg cgacactacg cggtgctgtg attctaaaat acttaggttt 96180
gcgcgtatag gatattaaaa taataataag aactacaatg atggagatat agatgagatg 96240
caacatgctg agttgtctcc ccgcagggaa tggtcctttt ccgcgcttgt taacggtacc 96300
gaggaggcgt tgaaatcttt aggaaaggtg ctgtctagtt tggaatctcc aattcctccc 96360
gtatatttag gtatataatt attgtgtcta gaaattgttt gctttgaggt atcaaaatat 96420
tcagcctgac cgctatttct tttagaataa ttcggtatag ggcttgagta gttggcaata 96480
ctcttaaacc ggggcaccaa ggtaacaata ttttccatat aatgggtttg atacgctttg 96540
tttaaaaatg ggcttaccgg ctttatgctt gttagttgtg cattgagtac cggtatgtct 96600
tctaggattt gtggctttat agaatgatta gcaaacacag aatgtagtat attagatact 96660
tgtagcatat gtctatttgc ggaaaattcc tggtattctc tgccgtgttg cgaatctttg 96720
ggcggaaggg gaccaagcat cggcacgtcc gtgtaggtac tggtggattt tatgagttcc 96780
tgctctatgt tcggtttgac atgtggattt cctaaaggaa tacctctacc tgcaatccct 96840
ttttctaccg acgcaggtag attgtgcgct aaacacaaaa tattgtacac gtctttgtgc 96900
ggaatatatc cgttatagtg ctggcccggc atctgatcgc caaggtgctg ctcatgctta 96960
atggtaccct ttgttctgag tttaggaaga tcctcgtacg aaaaaaattt tgtgtgctcg 97020
ctgaacctcg tagaaggaac cgaactattt tttgggtttt ttaaggaagg caatgaggaa 97080
ggctgggtca gacaattttt ctgtgtgccc tttaagctag ccacctgcgg aaatgttttt 97140
ttttccgtac gaacaacatt gcgcctaatt aggttttccg tatgggttga aaaagcagga 97200
cgatgatttt taaaatgatt aaaaagttta ttttttggaa tggagctgta cggctccaga 97260
tcttgcgcat cgccgtaacc aatgtttttg tgctgagggt tcagcataaa agaaaagtta 97320
cgtagatcac tgagttgcaa tccctttca gccttttcag gactattagt gtattcattg 97380
tatacaggcg cggctccatt tttgttgccg cagtaccggg aatttagtat attatcagaa 97440
taccggttat gacgcggcaa atcgctttcc caaagaggtg gatctgacct ataatcggct 97500
aacagctttg aagcataatc atgatacatt gtatataaaa gttaattatt atattgagaa 97560
ggcataatta cttcttgtag gggtacaaga ggctttgaat caggcaaact gacgggtttt 97620
gaatcggccg gctttggacc ggcaggtatc tttttaggtt gatcttcttc tagctcatta 97680
gacacggatg ggggagaaat aggaggaata atttcatctc cgcccttata tttgtcatgg 97740
atagaagaaa caattacatc catgtttgat ttattataaa tgtcgtttaa ctggtgattt 97800
aaaacataat aatgcaaaaa taatagggct acaatgcata tatatacgta aatagccgtc 97860
ttcgttttc gtttttatc caccggcgga ttacaaattg caaaaaatac aactaatacc 97920
accgctgtaa tgattaaggc cacaatgaaa ggattttgaa aggatgtttt gaacggttcg 97980
cacgtataaa ttttttctcc taaattattg atacccgcaa taaaatctac attcatttta 98040
tatatttata aattatgaaa aatttagagt tacatctccg ccggaccaat cattgctaaa 98100
atttgaagat tcttcaaaaa ggcccgactg gttgaatgtc ttctgctcag gtttccaaaa 98160
attttccaag aatggatttt gaacaatagg ctcatcttga ttttcttctt caaggatatt 98220
ttctttgata tcaagaacag cttctttaaa ctcaggtgta tcttgattaa actcaggttt 98280
atcctgatca atcgcaaaaa tattatcttc ttcagatata tcctgtttaa tcgcaagaat 98340
agtttcttcc tcaggtttat cctgatcaat cgcaagaata ttttcttctt caggtttatc 98400
ctgaccaaac tcaacaatat ctttctcgct aaatccgttt ttagtgtgaa gctcttggtt 98460
ttgaagagaa ttatcaaaat ctattttagt tgttgtccta gaccgtggca cgggatagtt 98520
atctaatggt ttacttacta tagtcctcga atgtggcacg ggataattgt ttggtgactt 98580
gctggttagc tcttggcttg ttaatagttc ttgttttctc aataattcca tctctactac 98640
ttctttttga tccgctggtg tctctttttg gtattcttca ttagaaaaat gttcagaggg 98700
taatgtttca ataaactttg tgagtggata gctgctcttt gatgtagaag agcgttgaat 98760
ttgctgataa aggagttgaa caagtcgccg gtattcactc tgtctttttt catatttttt 98820
acgtagcgtg gagagatctg ctaagagcga cttgttttca gatgttaatt cttcaatttg 98880
atgaagaagg ctgcgattgt atgaactaag tcttgcatac gtttcttcta attctgtctc 98940
cggctccaca taggcctgtt ttcgcagaaa tttattgtat agttccattc ttttttgag 99000
cagaaaggta agactataat cttgcatttc tttcgtaact ttatggtagt tttctttccg 99060
gtttttgata ataaagggca gcatttttttc tgttgtgata aaggtgccca gattgctaat 99120
gtagtcgcac agtagcaatt ccaagataga ttctttcttt tcaaggctta tagattggct 99180
gtattcttta ggtatgaaag aatcaacaat cgttgttacg aagtttgaaa agtttaatgt 99240
tttgctgtta atttgggtaa tgttacaaaa atatttgtaa aaactatcta gcattttttc 99300
ataaagtttt ttattttgtt taacccctaa aatatagccc tttacttgat actgatattc 99360
cgtaacaatg gaatgttttt tgtatagtgc atttttgtat aaaaagttat aaaaaatgtt 99420
gataaaatac gcaccaaggg tttcaaaaat acttataacg tgggattctt cctgatccat 99480
tatatcatat gtaatattat tttaataaaa aattactgac gaataacatg caaaaaaaat 99540
atgtttaaac ttattttaag ctagcactta tttaaaagtg ttttaaacac gttttaaatt 99600
gtatgttaat acacttaaaa attaagccga aatttgctcc aataaggatt acttttatca 99660
atgaccacct ctttactata aacggcttta cataatttta ataatgcttt agagccaaag 99720
ctgaaggcag tgggaagcgg cactgtacta tggtaaaaat gttgccgatg ttcatcctcg 99780
cggatgtaca caagtttcct atatccttta aacacaatat ggctaatttc ttccacatac 99840
tccttatcct gtttggaata gcggttgctt tgacgggaaa aattcgacat acaaatagag 99900
gcatttgtaa aaatggaaac aaatgcgttt ttacgaagat tggcgggtaa atcggtatca 99960
tcttggcagc aaataatcat cgaaataaaa cagtgacgat tttggtaaaa aaacttttta 100020
aaaatttctt ttgtaaataa tgggtgcagt tcggccgcgc agtcgtctaa tattaaaagt 100080
aaacgaggat taagattgat atagtttaac gtaaactttt catcctctgt aaggcataag 100140
tttttataca tatgaatgtt ctgtataata atttttttta aaagttgctg ataaagcgat 100200
gtaatctttt cttctttttt ttggtccgtt tgttcagcct ttaagcactc cacttttgca 100260
atatttttgt tttcctttg ctgtatatcg atcggaagtt tatgatacaa tgtttttagc 100320
atatcgatgt tgtttactcg actgtagatg gaggacatca tagtttgccg ctgccagatg 100380
gcctccaaaa agcgttcagc gcccttgttg tcattttttt tttgcttatc ggcgagccac 100440
aagcggtagt gtattagagt tggatgtaca aaaccctcat atgaacgatt tgagggttcc 100500
gagggggcaa ccactaaaat ttgttcaata tggggttgca ggattttcat aatatgttta 100560
acgtacacgg ttttgcctgt ttttgagggg ccatatagca cagttgtttt atctataaaa 100620
tgatgtgctt tgaactgtag ttcaggaatt agcttccctg aatgggtcgt tagggccatc 100680
tctatattat tacaattctg cttttgtata taaaatttct ttttcgagtt tattattatt 100740
gttgacccac atatctaccc gtatcgtatc atcaggcaca ttgagcattt caagcgcatt 100800
atctaactgt ttttttgttt ttatcagctc gctttcttca tcgggggtta aattttcttt 100860
actaagcagt tgcttaattt tttcttcgca gtcgtctata aaatcatact ctcgagcttt 100920
tttgatattt ccagatgctt tttctaggtt ttttagctcc ttaaaggaaa gcagtccctt 100980
aatcccgcta tccgtgtgaa aggttgaatt atagatggag agccccggag catccgggcc 101040
agtttcttgt atattttttg ctttttgtg gtaaatagta tttcgtaaaa tctcttttcc 101100
tatctttagg tcttcctcat gacggtccaa aatccgtttt attatttcat tattttgatt 101160
aaaataattg tagcgctctc tgttggcctt aaagcttccc aggagtgtcc agttgcctaa 101220
ttgaatggat gaaacctctg agaaaatctg gtctttatat ttataataaa attcatcaac 101280
cttttgttgg ttgctgctat ccaccacatc ataaataatg aaggcaaact ctaggtcggg 101340
tttttctggg tagatgcttt ccgtagcggc ccgcaactct tcgtaattat cctcaatgta 101400

```
ataattccac ttataaaaag tatcctgagg tggaatatgc tgcgaaagat atctagtaat 101460
ttttgtgtta aagagaatgg gtttaaacgc cctcggattt tcaagcatat gtttaatgct 101520
ttggtgaagt tctatatttt gtaatatgtg ggctgctgcc ctatagccct gtggggtttg 101580
ggtgattgca tcaatatcgg cctgaagctc attaggcaca tttaatgttt tttgcatgat 101640
gtgtaaaggg atgcgctcag gatctgctaa atcggtgtat tctgtgcttg tacaagtgct 101700
tgcacaggta tctacattgg tatctgcaca catgcttgca caggtgtcta cattggtatc 101760
tgcacacatg cttgcacaag tgtctacatt ggtatctgca caagtatacg cactttgagc 101820
atgaagatta ggatcaaaca caaaatgttc tcgtaaaaag ctatcgatcg ttgttttagc 101880
ttccttgctt ttctgcgtct gggttttgca gctatctgct atagataaaa ttgtatttac 101940
taccgattca gagggaacat cattagtttc ctgtttcaaa gtatcaacta acgttattag 102000
ctcactgaga agagttttgg tcgtgtgggt aggttttgaa taggaaggca tccattcctg 102060
cagagctttg aagacatatc caataaagct agtcattata agacgtcgaa tatactgctc 102120
ccgcaaattt gtaaaagagc aaaaggccac cctgctatca tttttgaact gtttgtaagg 102180
gttcgtcctt tggtaaagct gtttaagcgt ttcttcggat atttcagtag agggatcctc 102240
caatacgttt ttgagaagct catcaatatt aaattctgcc atatcttaga gtttattata 102300
tacatattaa agctttaata taaggggggt ataacaatgg acgaaatcat caataaatac 102360
caagctgttg aaaaactttt taaggaaatt cagcaaggat tggccgcgta tgatcaatac 102420
aagaccttaa ttagtgaaat gatgcactat aataatcata tcaagcagga gtattttaac 102480
tttttaatga ttatttcacc ttatcttatt agggcgcata gcggagaaac gctgcgaaac 102540
aaagtaaata atgaaattaa acgtcttatt ttggttgaaa atatcaatac caaaatatct 102600
aaaacgctgg taagtgttaa ttttttacta cagaaaaaac tttcaacgga cggggtgaaa 102660
acgaaaaaca tgtggtgcac caataatccc atgctgcagg taaaaacagc ccacaacctt 102720
tttaagcaac tatgcgacac acagtccaaa actcaatggg tacaaacttt aaaatataag 102780
gaatgcaagt attgtcatac cgacatggtg tttaacacca cgcagtttgg gctgcaatgt 102840
cctaactgcg gttgtattca agaattgatg ggaaccattt ttgatgaaac acatttttac 102900
aaccatgatg ggcagaaagc aaagtcaggt atctttaacc ctaaccgtca ctatcggttt 102960
tggatagaac atattcttgg tagaaatcca gaacaagagt tggggaccaa acaagatccc 103020
tgcggaacca aggtgttgca acaactaaaa aaaattatta agcgcgataa taaatgcatc 103080
gcgcttttga cggtcgaaaa tattcgaaaa atgttaaaag agataaaccg cacagactta 103140
aataattgtg tttctcttat attgcgtaaa cttaccggag tagggccgcc tcaaatatca 103200
gagtcgattt tactacgagg cgaatacata tttacagagg caattaagat acgggaaaaa 103260
gtgtgtaaaa aagggcgtat taataggaat tattatccgt attatatata taaaattttt 103320
gacgccattt tgcctccaaa tgataccacg aatcgacgca ttttacaata tattcatttg 103380
caaggaaatg atacgctagc taataatgat agtgagtggg aatctatctg tatggagctc 103440
cctgaaataa aatggaagcc cacagatcga acccattgtg ttcatttttt ttaaagatga 103500
agatttttta gatgattttt tttagttttt taaaagacga aaaaattttt taaaagatga 103560
atattcttaa accccgcaaa ttactttttt ttaggtactg taacgcagca cagctgaacc 103620
gttctgaaga agaagaaagt taatagcaga tgccgatacc acaagatcag ccgtagtgat 103680
agaccccacg taatccgtgt cccaactaat ataaaattct cttgctctgg atacgttaat 103740
atgaccactg ggttggtatt cctcccgtgg cttcaaagca aaggtaatca tcatcgcacc 103800
```

cggatcatcg ggggttttaa tcgcattgcc tccgtagtgg aagggtatgt aagagctgca 103860
gaactttgat ggaaatttat cgataagatt gataccatga gcagttacgg aaatgttttt 103920
aataataggt aatgtgatcg gatacgtaac ggggctaata tcagatatag atgaacatgc 103980
gtctggaaga gctgtatctc tatcctgaaa gcttatctct gcgtggtgag tgggctgcat 104040
aatggcgtta acaacatgtc cgaacttgtg ccaatctcgg tgttgatgag gattttgatc 104100
ggagatgttc caggtaggtt ttaatcctat aaacatatat tcaatgggcc atttaagagc 104160
agacattagt ttttcatcgt ggtggttatt gttggtgtgg gtcacctgcg ttttatggac 104220
acgtatcagc gaaaagcgaa cgcgttttac aaaaaggttg tgtatttcag gggttacaaa 104280
caggttattg atgtaaagtt cattattcgt gagcgagatt tcattaatga ctcctgggat 104340
aaaccatggt ttaaagcgta tattgcgtct actggggcgt ccagctataa aacgtgactg 104400
gcgtacaaaa agtccaggaa attcattcac caaatccttt tgcgatgcaa gctttatggt 104460
gataaagcgc tcgccgaagg gaatggatac tgagggaata gcaaggttca cgttctcatt 104520
aaaccaaaag cgcaacttaa tccagagcgc aagaggggc tgatagtatt taggggtttg 104580
aggtccatta cagctgtaat gaacattacg tcttatgtcc agatacgttg cgtccgtgat 104640
aggagtaata tcttgtttac ctgctgtttg gatattgtga gagttctcgg gaaaatgctg 104700
tgaaagaaat ttcgggttgg tatggctaca cgttcgctgc gtatcatttt catcggtaag 104760
aataggtttg ctttggtgcg gcttgtgcaa atcatgaatg ttgcatagga gagggccact 104820
ggttccctcc accgatacct cctggccaac caagtgctta tatccagtca ttttatcccc 104880
tgggatgcaa aatttgcgca caagcgttgt gacatccgaa ctatattcgt ctagggaatt 104940
tccatttaca tcgaatctta cgttttcata aagtcgttct ccggggtatt cgcagtagta 105000
aaccaagttt cggtacgcat tctttgtgcc gggtacaatg ggtcttccaa aaggatctac 105060
aagcgtgtaa acggcgccct ctaagggtgt ttggttgtcc cagtcatatc cgttgcgagg 105120
aaacgtttga agctgcccat gggcccccat ctgggacgtg ccctgaatcg gagcatcctg 105180
ccaggatgaa tgacatgcac ccaatatatg atggcccacc atatcatgga aaaagtctcc 105240
gtactgggga ataccaaagg taagcttgtt tcccaaggtg ggggtacccg tatgcgggcg 105300
tactttattg tattcaaacc ctactggaac ataaggctta aaatgcgcat taaaatgcac 105360
caaatgtgtt tcttcgattt gactcaaagt gggttcggga tcgggtttcc cataactttt 105420
gttcacattt ttaatgttag agatcctgct attcagcaag tcttgggcca atataatctt 105480
gtcggccttc ccatcgttag caataagaca aaaagctcct cctgatgcca tatataatgt 105540
tataaaaata atttattgtt tttattaaat atggcggttt atgcgaagga tcttgataat 105600
aacaaagagt taaaccaaaa attaattaac gatcagctta aaattattga cacgctcttg 105660
ctggcagaaa aaaaaaactt tttggtgtat gaactacctg cccctttttga cttttcctcc 105720
ggcgaccctt tggccagtca gcgcgacata tactatgcca tcataaaaag cctcgaggag 105780
cgcgggttta ctgtcaaaat atgtatgaaa ggggatcgtg ccctcctttt catcacctgg 105840
aaaaaaatac aatccattga gataaacaaa aaagaagaat atctgcgcat gcacttcata 105900
caagacgaag agaaagcatt ttattgtaaa tttttagagt ctagatgagc ttttacgcaa 105960
tgttgtacag tgttgtatat atgtcttgta agcatttgtt gtagagtaat aagtaaaaga 106020
taaataaaaa tgactattaa aataaagccc aaaccattaa aaatattttt atctgttaga 106080
tttaatttaa taaatggctc atggaatgtg tggtgcgccg ctgcatgagg tgtggccgca 106140

-continued

```
tgggatgtgg tcgcataaga tgtagctaca tgggatgtgg catttgcttg catgtaagga 106200
tcatgatgtg ttgggtcttc atcccagcaa taatcgccat ctttatctag ctgaattgta 106260
taccccatta tatatcactt attatttttt tttaatgttt catgaatttc attataggcg 106320
gtgaaagggt cctcaggccc cttctgtaaa agattataga gatcttcgga cgctttatgt 106380
ttcgtgcgaa ttaaggcggg atataacaaa agagagggcc ccagttccaa acaaatttta 106440
cttagcgggc tcatattttg caccaagttt cccactactt gcgatgtttc ataacgcatt 106500
ttaaagagct ttatcataaa agtgttatgc aggccggtgt agtctggcct atagttaagg 106560
aaggggattt ctctggtacc gtcaaacacg atctcaagtc ctctagcaag cccgatcaaa 106620
atttcttcag caatggatga gtatctaatt cctacattac gaagcgtaag catttctata 106680
acatcatcta tttcctgcat agaggaatct attgtaggaa ttttaatatc atctgtgctg 106740
atttgttcat tcccaagata ggtaagcagc atattaattt tttctagctt tactagctta 106800
gtcttacgct cataatcatg atcttttta taaaaagagt tgggatcacc gttggaccgt 106860
agatgattaa taaggcggtc tacttgcttt gtactaggtt taatactttt ttcactatac 106920
tcgctttcag catagtggtt tttacgatct cttttagaaa tagctgtttt ttgagatgcc 106980
tcagactctg catatttttt tctatgcgta gaaagagaat aaccgcggtc attacgtgaa 107040
ctactgttgc atgcaaggcc tcggcgcgtc ttaccgctgc gcacactgcc attgcgtata 107100
ctgccatcgc gcacactgcc gctgcgtata ctgccattgc gtatactgcc gctgcgtatg 107160
ctgccgctgc gtatgctgcc gctacataca ctatcactac atatgctgtc agtacatacg 107220
ctatcgcggc gtatgccgcc gtgtacctta tcgccgcccc tacccgaggg tttttagat 107280
ataatactgt gtggggagtc aagcgaaaat tcagggtcat taaagttaat gcccaatgac 107340
tttgccaatc cattaagctc ttcatcaaaa tgatcggtag gaaaactttg ttgcttgccc 107400
atgacctgtt tttcaagttc ctccaaattg gcttgctcat ttatatggag attattcata 107460
agcgtcgtaa ttccagcaag atttgctcct tctaaaaatg tggtgtcctc catcggatat 107520
actatactat ttaaaagctt ttaaataaaa atgtgtttgg aagaaatgct ctcttcaagc 107580
gtgtgtagct cagatataaa tgcctcctca gaaagctttc caccatactc ctttctcatc 107640
gtataggagg gcgccggttt aatgtaggaa atccactggg aggtaaaaaa ccggtacaac 107700
atatttagca gctcgcgggc ctcccacctt ttgggctccg tatagtgcac atcaacataa 107760
gaggcggcgc atgaaaagct gcaaaagttg ccgagaacgc ccatctcaat ctctcctcgc 107820
tcattttcac gcatataggt gggcacgaat tttgggacag tcttgaaata gagatgacat 107880
gtccagcatt taaagctaga atgggtaacc catttggaaa cagtggtgaa tacggagggt 107940
agcttttttt cgacctcggc ttcatcgtca ttcgtattta acgtatcggt ggcagttttt 108000
ttggattgca agcattcttc aatggtaatc ccggataagt ataaaatatt aggacaatta 108060
gtttccataa ttttgatagt tatttttata caacatggat ttaattaaag ataaatggag 108120
gacgaaacgg aactgtgttt tcggtcaaac aaggtgacga ggcttgaaat gtttgtctgc 108180
acatacgggg gaaaaattac cagccttgca tgttcgcata tggagttaat taaaatgttg 108240
caaattgctg agccggtgaa ggcattgaac tgcaactttg gccaccagtg cctaccgggc 108300
tacgaatctt taataaagac tccgaaaaaa actaaaaaca tgttgcgccg tccgcgcaaa 108360
acagaaggcg atgggacttg cttcaatagt gccattgaag cctccatttt gtttaaggac 108420
aagatgtata aattaaaatg ttttcctagt accggggaaa ttcaggtccc gggcgtcatt 108480
tttccggatt ttgaagacgg aaaaaacatt atacagcagt gggtagactt cttgcaacat 108540
```

caacccattg aaaaaaaaat ccagattatt gaatttaaaa cgattatgat taattttaag 108600
tttcaaataa acccagtgtc tccccgcgtc atcattcatt taaaaaaatt tgcagctttg 108660
ttggaacaca tccctactcc atatcccata cgtgaaataa agcctccatt agaagactca 108720
aaagtatccg caaaatttat ggtcagtccg ggaaaaaaag tacgcattaa tgtttttctt 108780
aaaggtaaga taaatatttt aggctgcaac acaaaggaat ccgcggagac catttatacg 108840
tttttgaaag atcttatcag cgtacattgg caagaaattt tgtgcgtgtt accggtaccc 108900
gattaaagaa tgttttcatt aataaggtaa tcgactatgc taaaaagaat aacaagaaaa 108960
ataccttgaa gaactatacc aaagtaggta ggttttctgc atgtcacggc atggttaaaa 109020
ttgctaataa tgtagtccac aaaagcattg ctcaatacga ctaaaaatag taaaaaaagg 109080
ataagtgctc tttttatatc catatacttt aaaacttatt ttttacacta ataatttcct 109140
gcggccgcaa tataaactgt aggtcatcta taacgcccag acctgttaaa agtagagtac 109200
tatgttttaa gggatttaaa atatccgccg caagaatgtg aatataattt tcaaagtggt 109260
ttacaggaat gcgtaagcgt ttttttttgc actgcggttg gtttagggtc gaatactggc 109320
aggaggtata tatattaata agaccgcggt cgatggtttc aatatcttca tagaattcaa 109380
tgcgcggcgt caaaagtttt ttaagatgtt gacataactc atcatacgtg taggactgga 109440
ggggggaaag aagggtgtag tcaaagttaa aaatgttttt ttgaagaacc tttaaagcat 109500
gttccgcgtc cgtggtttcc aaaatatgtt ttatggtatg aatgtcattt aaatctacaa 109560
agtctgacag ctttgtgtag aactcggtga cggaggttat tttctggaaa tcggtttttt 109620
gaaaaagatt ttcaatgtgt ttgcgggttg agttgctttg cagtccatac aagacatcaa 109680
aaaattcaat cagcaaaaac ttatacaaat ggttaatata aaaagctttg ttggccttat 109740
tctgctgagg atatggttcc tctaggggat atagaatggc ttggtctata tccctaggat 109800
caatagtcaa tgttgcgatg ggaagctttt ccagcgtagc gggaagagtt tgggttggag 109860
cgtagtaaaa gtatagcccg gtttttccct ctgaaagaaa gcccacaaat tctttttta 109920
tattttgcag caccgctgag ggtacgattt cgtactgttt atactgtttg ttgaaaaggg 109980
taataaattt ccaggtttct tcaaagcttg caatctgggt gggccgcaga tcaaagtcga 110040
tgggaatgtc gtcatgaatg taggatgata gtcttatagg aaaataaata gggcgatcgg 110100
tgtctgaatc gataagtaaa gcataacaaa agttatgcct gttgataagt tttttaccaa 110160
ccgtgtagcc gggaatgttt ttcacgtcat ggatatccca ccagttatcc ttgcacataa 110220
actcgctcat agactggatg acctccatca cagggtcatc ttcggtaaaa atatactggg 110280
cctcactgtt tttcagaaat ctttttttgct gggtgatggc cattgggtag atcccttcgt 110340
ccgtgtcaaa gataatggct atcttcttcg atgggctaag aatttttttgt attgtgctgg 110400
gggacacctc aaacccgatg tcgccctgtt tatctttaaa aaagacacag tgaaggtcgt 110460
agcatatggc aacaaggtcc agaaagatgt cctgccatgt ggtgtcccat tgaagcagtt 110520
ggttttttttg ttcaacaaag gtttgtaaga taaggtttgc cagctccgcg ccgctggaaa 110580
acatgttgcc ggccccattc cccaaaatat agtactgcgg tgtgttggcc gcctttgcaa 110640
tttcaatggc aagggccttg ggggcaagat ccaaaattcg agcaagggaa taaaaaagcc 110700
cggcattgct aattccaagc atggtttgct ccaccccccac aatgcaaaaa atgtcgggct 110760
cttttatcgt atttaaaaac agttcatctg ctatctggtg gggtagaaag gcaatccggt 110820
tcaccggtat ttttttttcca taggacaagg tatgacgcga tgtttgtgta ttaagatcct 110880

-continued

```
ccaggtcttg ttctacaaac gtgtgcttgg tgaggcaggt attgttaata tagaaccgct 110940
ttgtgcccag cagggccttc gtcttttggc agcacggcag acagtaattt agggggtggc 111000
ggccttctag taggcttaga tgagggtagt caggatgcgg gcagctatag taggcaggta 111060
ccccctccgt gaaattccaa tactttacta gctccttgcg cttggctggc ggcatggact 111120
tcacctcggc ctctgagtaa atgacgggtg gccgtgggtg ctggcatagg acggagtaaa 111180
ccgttgcctg cgtgtcgtac ttgcgcaggt catacaggtc ggggtcctgt tcttgaagcg 111240
cacgtagctg agaggctccc tttccttgtt gtttatcgtg cagttgagag agtttattaa 111300
ccaaaatttt gtcaggcccg gtgatcaagt tatctaaaaa cacaaatagg taaacccaaa 111360
gatagttaaa ctcttcctgg gtaatgttaa acatttctat tttgatatct gtaaccctat 111420
ggtagatgcg aatgttgcgg ccgccgtaga ttgtttccca ccgggccgca acatttgtgt 111480
caaagaggta cgcatacgtg ttttggagca acgcaacatt gatgtccatt ttgcgccccg 111540
gaccggagga aataatgatc atccgttcga tttcgtgggg atcatacgaa taaatcccct 111600
ttttaaataa aaaattgtag accccggttt gctggaggcc ccgcacggaa ataatccctg 111660
cttgctcgta ttcccgccaa cgacttttga gctcggtaaa tcccttgcta gaaagcgtat 111720
agggccaaaa ggtggacacc gacatggagc tgatagaaat ttggatgtcc tcgttggagg 111780
gaaggggcag actccctcca cgaggaaacg cggcaggccc catatcatta attgtatgaa 111840
taataggatt tatgaaatta tttagggtgg acaccacgga gttaaagtcg tggcgctcgt 111900
tttctgacca attgctttcg ataaagtagt gcccattatt ttgtatggta agaataaagg 111960
ccttttttatt gataaagcgt attaaaataa tagtgggtac acggaatgtt ttattgctga 112020
atttttcagg ctccgtggaa gttatgtggt gtttggaaac cacggtggga cctgttttac 112080
tataaaagaa caccaccagc tgaggaatat cgggagtagc tggaaatagg tcgaaaacat 112140
tgcgcacatt aatttgaata tttacgaggg gtgaaatttt aatcattgcc gaggtgacgg 112200
ccaacgtgcc gcgtgttagt ctattcccct cgtacttggc aatgacttgt tgtgctctgg 112260
catacgtaaa gtttattagt ttttgctcta ggagaagcct ctttttaaga ctggtcaagg 112320
atggagaaag agcaggatac tgtttttcca tttgtaaggg agattgtacc aatagtttaa 112380
aggcatcggg ggaaagaaga ggccaatact tcataataag gccgtaatag agtaagtcaa 112440
attggtaatt atcctctatg gcaatggaga tttggcgccg catgggggcc actagcgtgt 112500
tgaggtctgc tacaaagatg tgatgaatgt tttttatgag ctggaagctg tcgagcgctt 112560
ccacatagag ctcatctttt tgactttcca tagatgcgtc gatgttcacc ccacccacct 112620
gttgaaactc ctttttgtag tcgcgaatgt ctaacgccac cccgctaccg cttaacaata 112680
ggcgatacgt tacctgaagc gcattgtttt gaaaaaagaa aatgtgttgt ctataagggg 112740
ggatccctgt ggcaacgtaa attttttctc gaatgtcttt aaaagtgtct tcagggaaaa 112800
tactatactc gctatacatc gtctcaattt ctggcatcat cacgtttgtc tcctcgccac 112860
gatcctccac aaaaagtttt tcaaactcat ctaaatcatc gctatctcca cccaccacgt 112920
attgggaaag ctttttctcc caatcctcgc cgtaaaaatt ttgtaaaatt tctttgtcct 112980
taggggttcg ctgcaggtct ttgcggcagg cctgtaacac gtttgcagga acggatccca 113040
aaaaaataaa cgtcttcgtg tactcatttt ccacaggatt ataaagagta actcgtagag 113100
gatttgttaa aaagtcattt tggaaatcca ttatacccgg tatagaaaat aaaatttaaa 113160
ataaaaacgg atgatatcta tcatggaccg ttctgagatt gttgcacggg agaacccggt 113220
gattacccaa cgagttacaa atctcctaca aaccaatgct cctctactat tcatgcccat 113280
```

tgatatccat gaagtacgat atggagccta cacacttttc atgtatggtt ccctcgaaaa 113340
cggttacaaa gcagaagtaa ggattgaaaa catcccagtt ttctttgacg tacagattga 113400
gttcaatgat acaaaaccagc tttttttaaa gtcgctactg acggctgaaa atattgtgta 113460
tgaacggctg gagacgctca cccagcgtcc tgtaatgggg taccgcgaga aggaaaaaga 113520
gtttgcacca tacattcgaa tattttttaa aagcctgtat gagcgacgaa aagccattac 113580
ttacttaaat aatatgggct acaacacggc cgcggacgac acaacctgtt attaccgaat 113640
ggtttcccga gaattaaaac tacctcttac aagttggata cagcttcagc actattccta 113700
cgagcctcgc ggcttggtac acaggttttc cgtaaccccc gaggatcttg tttcctatca 113760
gaatgatggc cccacagacc acagcatcgt tatggcctac gatatagaga cctatagccc 113820
tgttaaggga accgttccgg acccaaatca ggcaaacgac gtggtgttca tgatatgcat 113880
gcgcattttt tggattcact ccacagagcc tctagcgagc acgtgcatca ccatggcacc 113940
ctgcaaaaag tcctcagagt ggaccaccat tctatgctcc tctgaaaaaa atttgttgtt 114000
aagctttgct gaacagttta gccgctgggc tcctgatata tgcacagggt tcaatgattc 114060
tcggtacgac tggcccttta tcgttgaaaa atctatgcag cacggtattc tagaagaaat 114120
ctttaacaaa atgagccttt tctggcacca aaagctggat accattctaa aatgctatta 114180
cgtaaaggaa aagagagtca aaatctcggc cgaaaaatcg atcatttcct ccttttttgca 114240 taccccctgga tgcctaccca ttgatgtccg caacatgtgt atgcagcttt accctaaagc 114300
cgaaaaaaca agcttgaaag cgtttttaga aaattgtggg ttagattcga aggtagacct 114360
gccgtaccat ctcatgtgga agtattatga aacacgagac agcgaaaaaa tagccgacgt 114420
ggcctattac tgcattatag atgcccagcg ctgtcaggac cttctggtgc gccacaatgt 114480
tatccccgat cgcagagagg taggaattct gtcatacacc tcgctgtatg actgtatcta 114540
ctacgcggga ggacacaagg tatgcaatat gctcattgcc tatgccatcc atgatgaata 114600
cggccgtatt gcttgcagta ccattgcccg aggtaagcgg gaacacggaa aatatcccgg 114660
cgcctttgtg atagaccccg ttaaagggct tgaacaggat aaacccacca caggtctcga 114720
ctttgcgtcg ctgtacccct cactcatcat ggcctacaac ttttcgccag aaaaatttgt 114780
agcctctcgg gatgaggcaa atagcctcat ggccaagggt gaatctcttc actacgtctc 114840
ctttcacttt aacaatcgtc tcgtggaagg atggtttgtg cggcataata acgttcctga 114900
taaaatggga ttgtacccaa aagtactcat cgatctactt aacaaacgga ccgcccttaa 114960
acaagagctt aaaaaactag gtgagaaaaa agaatgtatc catgaatccc atcctgggtt 115020
taaggaacta cagtttcgcc atgccatggt agacgcgaag caaaaggcgt tgaaaatttt 115080
catgaacacg ttttacggcg aggcaggtaa caatttgtcg cccttctttc tgcttcctct 115140
agccggagga gtcaccagtt cgggtcaata taatcttaaa cttgtctata actttgttat 115200
caataaaggt tacggcatca agtacggtga caccgactca ttatacatta catgcccaga 115260
tagtctttat acagaggtaa cagacgcata tttaaacagc caaaaaacga taaaacatta 115320
tgagcaactc tgccacgaaa aagtgcttct gtctatgaaa gccatgtcta cactatgcgc 115380
cgaggtgaat gaatacctgc gacaagataa tggcaccagt tacctacgta tggcctacga 115440
ggaagtactc tttcctgtgt gctttacagg caagaaaaag tattatggta ttgctcatgt 115500
aaacacaccc aattttaata caaaagaatt attcatccgc ggaatagata tcattaagca 115560
gggtcaaaca aaactcacca aaacgatagg aacgcgaatt atggaagaat ccatgaaact 115620
acgccgccct gaggaccatc gcccccctct tattgaaatc gttaaaacgg ttttgaagga 115680
tgctgtggtt aacatgaagc agtggaattt tgaagacttc atccaaacag atgcgtggag 115740
accggacaaa gacaacaaag cagtccaaat ctttatgtct cgcatgcacg ctcggcgtga 115800
gcaactaaaa aaacacggcg ctgcagcatc gcaatttgct gagcccgagc cgggagaacg 115860
cttctcctac gttatcgtgg aaaaacaggt acagtttgat atccagggcc accgcacaga 115920
ttcctccaga aagggggaca agatggaata cgtctctgaa gcaaaggcta aaaatcttcc 115980
tattgatata ttgttttata tcaacaacta tgttctaggc ttgtgcgcga gattcattaa 116040
tgaaaatgaa gaatttcaac cccctgacaa cgtcagcaat aaggatgaat acgctcagcg 116100
ccgagctaaa tcctacctac aaaaattcgt gcaatccatt caccctaaag acaagtctgt 116160
cattaagcaa ggcaatgttc atcgacagtg ctacaaatac attcaccaag aaattaaaaa 116220
aaaaataggc atctttgccg acctttataa ggaatttttt aacaacacca caaaccccat 116280
cgaaagcttt attcaaagca ctcagtttat gatacaatac tttgatggag aacaaaaagt 116340
aaaccattct atgaaaaaaa tggttgaaca gcatgctacg gctagtaatc gagctggtaa 116400
gcccgctggt aatccagccg gcaatgcgct gatgcgggct atatttacgc agctgattac 116460
ggaagaaaaa aaaattgtac aagccttata caataagggg gatgcaatac acgatcttct 116520
cacctatatc attaacaata taaattacaa aattgccacg tttcagacga aacagatgtt 116580
gacgttcgag ttttccagta ctcatgtaga actgctatta aagctgaata aaacgtggct 116640
tattttggct ggaattcatg tggcaaaaaa acatctgcaa gctttttttgg attcatataa 116700 caatgaatcg ccgtctagaa cattcattca gcaggctata gaggaagaat gtggcagtat 116760
taaaccatct tgctacgact ttatttccta atacttctta agaaactctt taaacaagga 116820
cttcgcatgg tcaaaggttc taaacccatg gcccttatga ttcgccaaaa aagcggtttc 116880
atcaagattt tctaaccctt tcacggatga agaaataagg tgttcggcct cgtttgccca 116940
ttttctatga tttttttca cctcgggttc tagatctgtt ttctccatat actcattgtg 117000
gtcatatttt tttttgggag gaggcgtggg tggaggaatg ggtggaggaa gtacacccga 117060
ctttcccgct tcaaccgttt tataaaaaaa tagaagcata atacaaagaa taaggactat 117120
cgcaaatatg ataaccagtg tcccagtcga gggcattttg ttatataagt aacgtttttt 117180
ttatttttta taattcgaat gaagaaccat gttgaatagt cttctactca aagacatttt 117240
gttatacggt aaatgagaat ttataaaatc cgaatatcac tatcatactg tttatctgag 117300
aaggtctcac tgggtcctgt gatggagaac ccatactctg taatgctggg gtttataatg 117360
tggtcaggac tgacaagcac atttctgaac tgcgagagtt ctaggtttag acgcagtcgt 117420
aatagtcgct gtatatttgt aataaaatatt agattgcgta tgaggcgagt gtcaaagcga 117480
tcctttccaa tttgtactaa ggtgggcttt tgtattccaa ctcccacttg tttaacgatg 117540
gaccagggtc cttcttcccg attttgttcc gtgatatagg tcagcacact attttctgta 117600
tatgaggtat gatgtcgcat attaatacct ggtgccattc caactggcgg ttgtgcaatt 117660
cgggctgtac cgggacccaa ccatcgtgga gttttataaa catatcgttc tagcgtattt 117720
aaaaattcct taaggttatt tacgagtagc atgaagggtg ctattaaaac aggtggatgg 117780
tttataacca ttgtcataaa ccattgcatt gcttcaatat cattttgtaa tgcttgacgg 117840
ggaggcgggg caggtaatcc acgtatgttg aataaagcgg ttaattgtgc accggctgtt 117900
tggggcgtaa tattttgtat taaatttatc atcgaattgg cttgcccggc atttcctata 117960
agatcgatta aattggttat ttgacctcga tattgttgta cccagttttg aatggcagcg 118020
atgatctcag gggttggatt gttttgaatt tcaggtgttt gtattagatt attcacttct 118080
cttcgtgtat cttcaagctg agtcctaaat gcatttaact cgcctataat ttggtttcta 118140
tcaataacat ttcttaaacc tcgaactgtt tcagccaatc gtatagtacg cacaatttca 118200
tgtaaggcct ggtttatgta tattgacatg ggatggcccc accgctcacg tccacgttga 118260
atacctgcgg ccaaactagg acctgcctcg tcataatcaa attgtgtagg ataaaggctt 118320
ccaaatagca ctttattgaa aatttggtca gaaagaaatt tagggcggcc catatttagc 118380
gcgttgtccc ctctaaagat gcgtgacatg tatccggcgt tgcctttgga tagtaactca 118440
ttcccatatt gagtaataga gaccgagaca taggggttta taagaagttt tagcataaat 118500
tctcgagtat ttatgggggg acgattcgga atgtttaata cctctgcaac atctggttga 118560
ggagccgtgg tgtccagaga tcgtactttt tcagccgaaa tgccgtacat aagacaagca 118620
atttcttcaa aactatagtc atagttgtaa atattggcaa gtggtataga tcgcatcagc 118680
gcatttacat tgataggtat aatattcata tcaaacaagt taaatatgcg ctcgcgctct 118740
ctattagagc caagagtgcg tgtttgacct ttcggcgaca ctattttgtg aatatgattg 118800
atttgctcct cttggtaaga gctttccacg aaggaaatta cgtcttgcaa tgttttacga 118860
agcgaataca ctgcattcat ccctattccc gctgttataa tgggtttatc gtctctgttc 118920
tcgctaataa gattaactcc accaaaagta ttttcattgt acatcatcac tgttttaaaa 118980
ctacggatat ttatgataaa tcggagagcc tgaatggcgt gggtataaaa gtgttcaaat 119040
cgcgtgggag taatttgttc gcgagcaact accgtttcat tatagttttt catgataagc 119100
tgtactccgg gcatatctga gagctgtacc ggatcatttc ccagtaattt tcttgtgccg 119160
tatagtagtt taaactcggg ggagccgctt tcaaggttcg ggtaaagaag aggatcatat 119220
acctcattat tttctattct taggtcatgt aaataataga gcgaaagtga aaatggcata 119280
agaggctcct tattgtaccg ggacatatag ttttgaatga agtgttcttc tgtttcaaga 119340
tagatgggat gatcggtaag ctcgtgcagg acctccatgg cagaatctgc cagagtgtga 119400
gagcctctaa tgatcccgtc gatcactgcg accagtcgct ttcgcacaac atcgctcgta 119460
ttattttgtg cgtctcctag gggcataagc gtaacattgg gacgaaatac gccgccaatt 119520
ccccgcaggg ccgcctgacc gacggatagt cctgtcgcag gaacattgtt attattataa 119580
taaataacgg aatcattatt ggctcccaag agtgccgtca gattagggcg agctagttgg 119640
acatttgtgt attgtataaa ttgttttaga agctctccct ggctaataag aatattaaac 119700
attttgttaa atagtggaag attggctcta taattttctt taaggtaaat gggaatttct 119760
gttaaagtag aaataagatg ctgactcagg ccctggcgat tggtatcctt aataagccgc 119820
tgaagtataa gtcccaaaga cagaagaagc accgactgct ctgtggggtc gcctctatga 119880
ccaaagacgt tgttattgcg tgctaagtca gggtgagcat atcccatctc catcactgct 119940
tggctaaagt tcccattagc gaatgcatta ataagattta gatatatttt tccgctggga 120000
gcatcataaa atcgggtaat atatgaagct atgagctggt taaacaccat catcatacta 120060
cgattatttt gaataccata gtctgatccg tataggcgat aacgtcgaag gttgtttgcg 120120
gcatcattga cattggcata ggttctgagc gctatgttgt cccagtagct aagagtattt 120180
tcctcctggg cgttgttggt acgaataaga ttggagagtc taaagtctcc tagtgccacc 120240
tgctctacac gaagtccaga gttattctcc aaagcatcgt aaaatacgag tctactgaat 120300
actcttccgt attgttcaaa gcgttcagag gattggggat tgttatttat ttgaatatta 120360
gccgcgtccc ttctttgcgc cccacctcga agttgcagta cattataagg ctttgtaagc 120420
aaggtgtagg ttttattaat gatttggtta accccctcca ggcccaattc accgccagga 120480
agcggccttc ctccggcatc ggtaggtggt ttaataagtt tgtcaattaa atgttcttcc 120540
aaccagtaaa atgagccagg attagatcta ttttcatagt attgaataat gtttttatca 120600
atatgcgggc gtagaagatc aagaaaatac ttcgtgtcgg ccatcaaaga atcaattaag 120660
gaaataagac ctgtaaaatc taaatgcact tgagcggtgc tggtttcagg gaagcgaact 120720
tgaaccattt tgttaaaact ggaggtcatt tcgaagatat tggtcaacag gagctgcatg 120780
attcgctgat tatctactaa ataccttgcg gccaactctt gctccggacg aactcctcca 120840
ccagcaggaa tacccacata tggtacaatc caagcaaaaa gagtttctgt ggttaaattt 120900
cggtcttggg ctgctgcagc cgcttcggta gtgggatcag ggtacaccat agaaagccgc 120960
atattgattt ctttaatgac taatcctgga tttctaatct cagagatggc cccgtgtttt 121020
cttccgagcc agtcaataag attggcgcgg ttcacgttgg cagcttgtgt ctctcgtaac 121080
cattcgataa tgctttttg aatcgtatct aggtctaaac ctttaatgtt attacgaaag 121140
ttattaagaa gtacgtaaat agcactcaat aagttaagac ctgtaataac ggtttcatga 121200
aacagaaata ttttgttaac atctgtatct gccagtgact cagagccttg aataagtttt 121260
gaaacgattt gaattttatc ggtatgctcc tttttgagtt cattgatagc ctggcgaatg 121320
agttcttggt aggaaatttt gcccaattct tgttgcagac tgggatcttc aaacatctca 121380
ctaagctgtt tcctaaattt ttgtaccaaa tcccactggg agttgggctg cagcattcct 121440
gtttggacat ccacagagtc tatattgtat agtgccgggc gccacttggg ggtaggctgg 121500
gttgaaggac taataaacct atcggaggga agtaattgtg aggattgtgt atagccatcc 121560
tcatcaggaa gaatggagta gttggtttga ttcatcattc caaaatcatt catagttcgc 121620
gcttcctgaa caatgcgttg aaatttttcc cattcggtgc gtgtaatgac accgaatctg 121680
cggtttattt catttacaaa atggataagc gctttttgg ttgcttcttg ttcaccatac 121740
tctaagttaa agtgttggta aatgacgttt atttctttga taagctgacg aatttcggtt 121800
tctgagtagt caccaatgtt aataagctca ataggacgca taaagataat gcgaataagt 121860
cctgagaaga ttccttccag ctcaggaagc atcgagatct gtacattttc atctctaaag 121920
gaaaacaact tttgataaaa ttcggcgagg cggggaaggc ggaagtaaag ctctgctgcc 121980
tcgggaatta cctcgggctc tagctcatcg gcaccccca atatcatacg cgtgggtata 122040
agtttgtaca cgggctcagg ccgttcaaac atgtcgtaaa tccctaatac aataaaaatc 122100
ttggcggcca tacttttcag catgaaggtg aagaagacgt cctcggtttc ccagcgggtt 122160
gatagggcgt cgttaactct cacagtagag aggtagaccc gctgagccgc ttcctcggca 122220
gtctgtgcaa gcgccatcct ttgtcctcca atttctgatt gatttagatt tttaagtccc 122280
acggaaagcg cagaatgttg aagatattca agcaaggttt tatagatttg caggggcgac 122340
atgggcacca tttgccgcag ctcctctccc ccaagcatgt ccccaatccg ggcaaaggca 122400
ttgatgatat ttttaagcgc ctgaaagtta gaaagagagc gcccgataag gtcgcgaatg 122460
tttttagcct ggcttgctct gacgggacgg agggtaccaa cgcttcggcc ttgttggatt 122520
tcagccgcaa ctttttcgta gtagtggccc gcaggagcat tatccgtaaa gacgttggag 122580
tcgttgcctg tggaggtggg aaaactttca aagacttgtg caagcgtgtc ccctgttgtc 122640
tcggtgaacc atcgtcctat aatgcgcacg ccatccagca tctgttggac tgtttgaata 122700
gaatctatgt tgtttacaaa cgttttggta atgtttttaa gataaagatc tagcccttcc 122760
agagctcgat agaatcggcg ttttacatca tactccagct cgatggcgct tacggttgcc 122820
ttccagtcta cttcctgggc acctccagga tttgggccca cgtgtcctct ggcaagatct 122880
acagccggag aattaatgcg cgcatttttt tccgtatcca actgcatgag gcgtcccgca 122940
atagcatctc cgagaatagt ggcatagttt tcctcgtagg attgaaactc ctgtttgtta 123000
tgcgttaaat tggagtaaat ctgggccaca taatagtaat acataaaggt gttaattgcc 123060
tggttgaggt caacctgcga tcgcgcggcc ttgctgagcc caagctcttc aactgttagg 123120
gcagcaccgc ctacccttgt acactcgcag tcctcctcgc ctccatactt tttttgcaca 123180
atatcggtat aaaaatcaat aatctgtagc aagcgagagc aggagtcata aagattttta 123240
aaattagggt cggttttaga tatctcctcc aaaacatttt taacaagcgt aagctgtgtt 123300
aagaaggttt cgcgttcttc tcgtgcggcc gcattggtgt aaaagccgat aagacttaga 123360
tcaagtgcga tggtgcccat atcattaatg cgcgaaagag catctcgaag cctcgttatg 123420
ttcggcgtca aggcaatttc tttaacaagt ttgatgccta ttttttttcac attttccaaa 123480
aagtcgttat aggcttgtgt gcttttattc aaaaattcca tgaggatgtg ctttctatcc 123540
agtctttgcg cttcaatcct cctatctagt ggcgttttct cctcatcgcc cccctttttg 123600
gcacaactgt tctcaaggat tttgtggcgt tcattaaagg tctgtcgcaa caggttcacg 123660
gctttttcaa actcagcaat gttttctgcg gagacaagac cactaaacct tttgaggtca 123720
agctccttgt caaactccgc ccagtttttg ctttgaaggt actgttcaac cttgagtcct 123780
actttctgga gagccttatt aattttattc gcaacagacg cagcaatacc tagattacaa 123840
agtgtgtacg aaagtacttt tccaaaattt ttggttccca agacactatt tgtatcattt 123900
aaaagtttaa taatatccac ctcatccgtc tgcagtttat caagttcctt ttgggtggga 123960
gttaaaatat tgtcaataaa attcgttaaa atgttgattt gcaggttttg ttcatttaaa 124020
agtcgacgat atactgcttc aatcatggtg actgcattaa tgacttcctc attgggggct 124080
gctttggtta cctccgtcac catgcgctcg tgaagttgct taatggcgtc gtttaacagc 124140
ttgatatttt caagtgtatt ttctatactg ccgtgtacat caagatactc tgcgcgcagt 124200
ccatgagtta gggagttaat gtacagaact atttgtcgac atatactggc ggccccttcg 124260
gtggtatcta taagcttatc ctgacctaaa tcaataaatt cctggttaat ggcgtctgca 124320
atcattttac agacggtctc ctgtttttcc gcattttttta caaaggtgga accggctcga 124380
ggatcgggca gttgtttttt gatatcttta agaatatctt cgatgggctg ctttgtgtct 124440
actttgaacc ctattttggc aatcgccctg ataattcctt ctataatccg cagctttgct 124500
ttactcgata cggagtctat gtgataatct ttaatgtgtt gtacaggatt tttgtccccc 124560
ccgccattaa aatatcctcc ccctgaaaaa ggacgagttt gtctttgtat atgatcctgt 124620
aacttcgcat atatatttgc ttctgatgaa ggcagtggtc tactagaggt tgaagatcca 124680
cggttaccca ttataataaa aaaaataaag atttaaaact acaaatattt tgctgtttat 124740
aaacccaatc atataagact aactaaaaca ttaaatgtag gtgagataaa agcttatttt 124800
ttttaaaagt ttaataacca tgagtcttac cacctctttt tcttcttcct ttagaggggt 124860
tccataaatg gtttgaataa aattatgtgc tctaataacc ttgttaaaat caggtgcctt 124920
tccatattgt tcaatatgtt gcacagtctt ttgtgcaagc atatacagct tggagtcttt 124980
aggtacctcc gatgagggct cttgctcaaa caacgtttca aaggaggatg tgcattcatt 125040
ggtttcatta tcattttttt catgaatgtt ctccgaagat gctgaggatt ccgtctcctc 125100

-continued ttcaaacagc acatgcagaa tcatattcca ttcttcttga gcctgatgtt cagtataccc 125160
ttgccctgca tatatacgag cagatttcac aatatcatac ttaacagtac taagcaatgt 125220
ttttatagcg gtcgtaacaa ttctaccgct attgataatc tcaacagaaa accaattata 125280
caggctaccc gcatgaaaca caacttgtga agatgatctt aaatccgttt tgaagatgac 125340
ctccattttc atggatatat ttaaaataaa atccattcaa ttttaaaatt ataaaataat 125400
aagaagatgc cctctaatat gaaacagttt tgcaagattt ctgtatggct acagcagcac 125460
gatccagatt tattagaaat tatcaacaac ttatgtatgc ttggcaattt atccgcggca 125520
aagtacaaac acggagttac cttcatttac cccaaacagg caaagatccg cgatgaaata 125580
aaaaaacatg cctactccaa tgacccttca caagccataa agaccttaga atcactcatc 125640
cttccatttt acattcccac tccagcggag ttcaccgggg aaatcggctc ctacaccgga 125700
gtgaaattag aggttgaaaa aacggaggcg aataaagtta ttttaaaaaa tggagaagcg 125760
gtcctagtac cggcggccga ttttaagccc tttcctgatc gccgactagc ggtctggatc 125820
atggagtcag gctctatgcc cctggagggt ccccctata agcggaaaaa ggagggtggg 125880
gggaatgacc cgccggttcc taagcatatc tcgccgtata ctccgcgcac gcgtattgcc 125940
attgaggtgg aaaaggcctt tgatgactgt atgcgtcaaa actggtgtag tgtcaataat 126000
ccctatcttg ccaagtcggt ctccttgctg tctttcttgt cgctcaacca tcccaccgag 126060
tttattaagg tactgccgct tatagacttt gaccccttgg tgacctttta tctacttctt 126120
gagccctata aaacgcatgg ggatgacttt ttaattccgg aaaccatttt attcggccct 126180
accggatgga atggtacaga tctgtatcaa agtgccatgc tggagtttaa aaagtttttt 126240
acccagatta ctcgccaaac ctttatggac atagccgatt cggctactaa ggaggtagat 126300
gttcccatat gttactcgga tcccgaaacc gtacattcct atgccaatca cgtgcgtact 126360
gaaattttgc atcacaatgc cgtcaataag gttacaacac ctaacctcgt cgtgcaggcc 126420
tataatgagc tcgagcaaac caataccata cgacattacg gccctatttt cccggaaagt 126480
accatcaacg cactgcgttt ttggaaaaag ctgtggcagg atgaacagcg atttgttatc 126540
cacggcctgc accgcacgtt gatggatcaa cccacctatg aaacctctga gtttgcagag 126600
atcgttagaa atttacggtt ttcgcgtccc ggcaataact atataaacga gcttaatatt 126660
acaagtcccg ctatgtacgg cgacaagcat accaccggag atattgcgcc caatgataga 126720
tttgccatgt tggtggcctt tatcaacagt actgactttt tatacaccgc gattcccgag 126780
gaaaaggtag gggggaatga aacccaaacc agtagcctta cagacctagt tccaacacgg 126840
ctacactctt ttttaaatca taatctaagc aaacttaaaa tcttaaaccg cgcgcagcaa 126900
acggttagaa atattctttc aaatgattgt cttaatcaac tgaaacatta tgttaaacac 126960
acgggaaaaa atgaaatact aaagttactt caagaataag tatgttgata cctgtggtgt 127020
gttttacctg tgggtttcct attggaacct acgcggcaat tttgacaagg gctcgtaccg 127080
agtatattaa aaccaaaatg ggcggaacat tgccgcaaaa tatcccatta gatgcttctc 127140
tccagattga gttaaaagac ctcattacag ctctgggaat cccaatgcgg gtgtgttgtc 127200
gcactcattt aattactacg ttggattatc gtaaatatta ttaatatcta aaattgaaaa 127260
aatattttta atgttactag taaaaatgac tacacacatc tttcacgcag atgatctcct 127320
acaagcattg caacaagcaa aagcagaaaa aaatttttca tctgtatttt ctttagattg 127380
ggataaatta cgcacagcga agcgtaatac aacggttaaa tatgttacgg tcaatgtcat 127440
agtaaaaggc aaaaaagctc cgctaatgtt taactttcaa aatgaaaaac atgtaggaac 127500
cattcctccc agtaccgatg aagaggttat acggatgaat gctgaaaatc caaagttttt 127560
ggtgaaaaaa cgtgacaggg atccctgttt gcagttcaac aaatacaaaa tctcgccgcc 127620
attggaagat gatggtctca ctgttaaaaa gaatgagcag ggtgaagaaa tataccccgg 127680
cgacgaagaa aaatctaagt tgtttcaaat tattgaactg ttagaagaag cctttgaaga 127740
cgctgtgcaa aaaggtcctg aagccatgaa aacgaaacat gttataaaat taattcaaag 127800
aaaaatttct aatagcgcgg ttaaaaacgc agacaaacct ttgccgaatc ctatcgcacg 127860
cattcgtatt aaaatcaatc ccgctacaag tatactaaca ccaatattgc ttgataaaaa 127920
taagcccatt actttacaga atggtaaaac aagctttgaa gagttaaaag atgaagacgg 127980
cgttaaggcc aatccggata atattcataa gcttatagaa tcgcattcta tacatgatgg 128040
catcattaat gctagatcta tttgcatcag caatatgggc atttcatttc cgctttgctt 128100
ggaaatggga gttgtaaaag tttttgaaaa aaataatggg attgatgtga actccattta 128160
tggctcagac gatatttcaa ctcttgttaa tcagattgct attgcttaaa caatttgctc 128220
aaaacaagct tataaacgtt tcttaggtat gcgatacgta aatcctaatt ctttaataag 128280
ttctttttca gtagtgattt ttagaggtac taaagtttga tttttaaata atccatactg 128340
atttagctta taattctttt tttttaacgc agctcgaatt cttattaaat aagaaacggg 128400
acccgtaaaa tgaagtactg cgtatggctt ttcctcggct aaggccgtaa aaagatcaag 128460
ttgatatgtg ttttttttcc attcaataaa aagtacacac tttcgttctc cgcagacttt 128520
tacagaaaaa gaaagatcct ttatgcgaat gttgggcagg acgtgtttta aaagtttttt 128580
ttctggaaca ataataagaa gatccacgtc attaagcatt ttctcttcgc gtcttaagct 128640
accaacagca acgatgtttt ttgataaaat ttttataagt tgtccattat attcaaacgc 128700
aagtcgggag cgtaagtcat ttacaatttt ttttccttga ataagcgtta acattttata 128760
tttaatatta aaatcttttc attttatata ttatatacgc aaaatggcac ttgatggttc 128820
aagtggtgga ggctctaatg tagaaacatt acttatagta gcaatcattg tggttattat 128880
ggcaatcatg ctttactatt tttggtggat gccccgccag caaaaaaaat gtagcaaggc 128940
tgaagaatgc acatgtaata acggaagctg ttccctaaaa acaagttaaa acatgcaatt 129000
atatgcatgc atataaacgc atgcatataa acgcatacat ataaaatgcg taaatactat 129060
ataaaaaact ataacatatc aatcaaggaa tcaacacttt tataattttc cgtaatatat 129120
ttttcatcca taatgatgtc agagtacatg gtccctatgc gaggaacaga gcccataagg 129180
gtaggcgcgg caataccgta aatgggattc acggcggagt caaccgcagc atctgtcaag 129240
acctggactg gagacgacaa ggccattcgc aacaacacgt tggaaggctc tcttgcatta 129300
agccctgcct tttctagaga ggtaacctgt cccgttcttg tcatgagatc tgcgtacatg 129360
agtaaatgac gatggttggg acccttgtcc cccataaccg ttctaatttc actaataatt 129420
ttttgccgtg ccgcttctat gccgtaaagc tccatggtgt ctcctataga ggacgatacg 129480
atggtgtatg ggtcgatgtt atcatcaagc attgcgccaa aaatattagt cccgtttgtt 129540
ttgatggcgt agatattgtc tagtcttacc agtttcccct gggcatccac acggtggcgc 129600
ataagcttaa caacattcgc atttttgatg cctggtattc ctctaatcgt gctatttaat 129660
agtttatcca ccacatttac ggcaattttt tcatccgtag ccattcgggt attggtactg 129720
cgtctaaagg cgctttcccg taggtatatg cgaataatga tgggaatccc tgaggccgtg 129780
ttttccacag aatgcatgat gtaggtgttg gggtgtttag ctcttagact attaataata 129840
ctttctagac taatgctttt taatatcatg gttgttttgt ttaattccaa gcggatacac 129900
cagtttgcaa tatcctctgg gggctgtagt agaggatggt tttccagaaa atccgtcatc 129960
cattccacat cacttgcaaa atcggggtac atcacatttt tttttgtgct tgaatacgtt 130020
tcgtacaata ggtgccactg caatatcaac cgttcgaacg ttataagctc tatgctgtta 130080
gcaatttctt gcgcatatgt tttatttgtt tccacttccg ggttctttag acgtaaaagc 130140
atttcagagg attgttcagc ctctacgggc ttcgcgctaa agatctcctg gggccgcaca 130200
attcccgact tgttggttcc cccggccacg gaccggtggt gggagtccag catatattgt 130260
gtcaagggct ctgatacgga ctgcgccgcc aggattccca ctgcctcacc gtagttaata 130320
agactttgag tatattgtag ccttatgagg tccaggatgg cactcatctg ctcgcaggta 130380
atgtttaatg ttttaacggt tgccagttcg atgcgaataa gcatgcgcat cagagaggca 130440
gcccgtttaa gataaacggg tatgggcgtt tgtagtcgtt cctgaatgtt gttaataaac 130500
acgtatggaa gatttttgca aaacgttttg accatcgcgt atttttgtag aatacttttt 130560
tcgtcgaagg gaagcacgcc actggtggag ctcagtagaa tgttttttac gatgctggcc 130620
acgtttaccg gcacctgtct aacatctgta agcagctgac tgaaattaaa attttcgacg 130680
tttaggaaga tctgtcgata tttatctcta tcctttttaa ggcgtgaaaa ttcttcttca 130740
aacaagggcg attgtatccc ggtgtacttg aatttgtctt caagttcctg gtccgacagc 130800
atgatggttt caaaccgtac ggtttcaagc tggcgcgcat caaggccgtc ctctccgtac 130860
aactgctgca caagacgcgt atcgatggaa acccgtcggt aataatccac aatacaggat 130920
tgaaggccaa agatggcttt acggttggca tagcctgtgg atgatgtcga taatgctttg 130980
ttgatcaagt cgaatcttcc attcatttcc ccaaagataa attcagggga ggtaaggccc 131040
gcaatatagc tgttgcagat gaacccgtag gcctgcgcct ccagggcaaa cctggggtag 131100
tacaccaggg tcctaccgaa ggaaaactgg ggttgaatgc gttgtgtatt aatttcaatt 131160
tggccgatgc ccgccatgat gtgaatcata ttggggtttg agcccttggc gccagtggcc 131220
accatctgaa aaagcccatt ggtttccgga ttaatggaat tcataatcgg ctttaaaatt 131280
ctatcgggaa atttaagcgc attcagctgc aatttttcgt agaagtcatg cgttgtcagg 131340
cctataggcg gcatgatgtc tccatgaagc agccggttgt ttatttcctc cgactcaagc 131400
agcagttcat tgataatttc ttggacctcc tgatgtgcct ccggggttag gagcatgtcg 131460
gccgtggaca ctgtgaatcc ggcgttgcgc acgtagttta gggcgagctg ctgggtcgca 131520
aatatcattt tcaaggcctg ctgcggccca tacctacgcg aaataaggtg atagattcca 131580
ccggaggaac ccgctccgac ggcctttttg tcaaggacgc cttcaatgag ttcgccgttg 131640
cgtatttgtg tagagatgtc ctgcttgtta taatgcatgt agggtgcata cacttctgag 131700
taccatgtgg gggctcgttg ataattgatg gggtctgcc tcagtagcat agatacaacc 131760
gatttgccat ccagcaggtc agttggggag tagttggcaa aacaaggtgg gtcggtttgg 131820
gttgtttgaa acaaccccat ggcgtgcagc ttgttcatca cattttttccc catgggggtg 131880 ttcgtgcgtg taagcaaaaa gcttcccacc gtggagtcct gcacctgccc attaacggga 131940
cccgagctct ttgtggaaat gaaccagttt cgcacagaac aaagtagttc ggcctcaacg 132000
cggctcatga cgctccaggg aacccagaga ttcatctgat ccccgtcaaa gtccgcatta 132060
taccaggcac atgcgctgac attcatttga aacgtagaaa tttttgggtt ttcaagaacg 132120
acaatccggt gaacccctat gctgcttcgt tcgagagaag gctggcgatt aaaaaacgcg 132180
acgtcgccag tgacgacgtc acggtaaagg atgtctccta cctccagcct aaagtcttgt 132240

-continued ttgagaccct caatgtcgtg aacggattgt gttatttgct tatacactct tgaacaacca 132300
gggtactggc gctttccatt taaaaaatag ggcattaatc tattaatatt ataatgttgc 132360
actgtttccg caacttgcag cgttcgtgca aaggaaatgg gatagccaac ctcgtccagg 132420
tgaaggtctg agttcccgca gatggtggac cggctgatcg accatacctg gctgcccagt 132480
agggatttac gaattcttcc ctccttgcga ggaagtcttc gcatgatgga gggagcaggg 132540
cgtgcccccca tgacgatccc acgctttccc gtgcctccct gggttgcggt ggtggaaacg 132600
gaatccaaca aaaagttata gtaaagttgc tgtatggttt gcaaattgcg gtcaatattt 132660
aaaggtattt tttggccgcg cacgatttgt aggtccttcg ggatcagcag attctttcga 132720
accagatact gaatcacgtt gttaatgtcg tgaaagcttt gggggcctga cccgattccc 132780
aatctgatgc caggtcgtat gctgatgggg gggatctgaa tggccttaag cacaagtttt 132840
tcgggatggg agtttttact tcgccccagt tttacaacgg tgtcgtaggt tacgcgcgaa 132900
aaaatctctc tgatgatctg cgggtacagt ttgtcaatct tgccctgctg atccgcccaa 132960
aaggtaaaat aatcttccga gtccttaaca attttggggt gtactgcctt acagacgtag 133020
cactgctttc cttcggtttg gcttgaagcc gcttcaataa gacgcttagg cctaataagg 133080
tgctcgtacc tctttaggtc aacgatggga gccccgcagt tgagacatat aacccttaac 133140
catcgtcgta tttcggcgat gaagagcggc tgaagcaccg gagcatgcat ctgcagtatc 133200
ccagggtgtc ccatacattg cttgcgctgg tgtgagcaag tgatgcattt ataatggtga 133260
tcggtggttc ccattcgcgc atcatagata ccccccttcgg cgggaagggt gccctcaaat 133320
aaattagaaa tggtaacctc cataacgcct tgcctcttat gatcattgtc accggcaata 133380
ttgaactgaa cggcggctat ttcggcatat ccagcctcca tatttttgct aaatacataa 133440
taaaacttca aatgttaaaa aaaataacat cggttggcat atttttttgt taaaaccaag 133500
tgttaaatga tttctaaaac atttatcggt tcacgaaaac ctaccgcacg ggcctgaaga 133560
ggaatgccag ttttggggga aagctcggca tattccacgg taagctcttt tccataaaga 133620
tgttttttaa ataaggcggg cgtgagtttt tgaaaaagag cataacgatc cgcgtacgtc 133680
aaatgcttag gagtgactac aaaccgcttt ttgtttggca attcgcaaac ccataaaatg 133740
gcgcctaagt cctttccctt ttttccctga gtatagtcca ctaaaataaa ttcagcgtct 133800
agcagcggtt tcagcttggc aagatgcgct gagtggtagt tgttgtatcc cggctcatag 133860
ggcccattgg cattgcgtac gatggctccc tcgtagccct ccttaataaa ctgcgcctta 133920
agcctaaggg cctcatccac attcttcacg ctaaaatttt caacttggtg gataaaggta 133980
agatcttcct tctgtttaaa aatatttgtt aatagctgtt gtctcttgtt ggaaggcatt 134040
tgaagctgat cactccaaaa acagtcaaac acgtaaaagt gcagctcgga ggaatctgtc 134100
ttcgcattcg cctgccccgc gatccattgc agaggtttgc ggtgtaaata aagctcacca 134160
tccaaatata ctctcacgtc tataaataaa taaagctgtt tgagctcttt tttaatattg 134220
tcaagaccta aaaattcctt tttcgtgcgc gaatacaaga gaatgctacc atcgccctgc 134280
tggcaggcca cagctcgaac gccattacgc ttgcgctgca cgatgggatc tgtttcttct 134340
tcaaaaaatg tcttaggaat tatattaaaa tattttacca gcataggggg gataattcct 134400
ctatttgtgt gggctccccg cttttgtctg gcatggcgat tatatttact aagggcgtcc 134460
ttgaatgcct gatggactac cgttgtggca ttttttttac ccaagttttt tccctcggta 134520
acacgtgtca tttttgatat ccgcaccgcc ccttcttcca caaaaaattt tgtgaaaatt 134580
tcagcaacgg cgtcttttac atctgtggaa aacatctcat ctgtgatggg aatgatcgtg 134640
ttgtgctgca ccacttgcac acaaataatc catgaggcct tttttccgct tttcgtttca 134700
gactcaatcg gaggaaaaca aaaaatgttg tttgaatatt gcccaggaaa ttgatttagc 134760
atggttttaa caataaaata agcctatcaa ttttttttata atttgaatag ttattccaaa 134820
ttcaatatgg cttctttaga taatttagtg gcacgatatc agaggtgctt taatgaccag 134880
tctcttaaaa atagtactat tgaacttgaa atacgttttc aacagataaa tttttttatta 134940 ttcaaaaccg tatatgaggc acttgtggca caagagatcc ctagcaccat ctcccacagc 135000
atccgctgca tcaaaaaagt tcaccatgaa aaccactgcc gggaaaaaat tttgccgtcg 135060
gaaaatcttt acttcaaaaa acagcctctc atgtttttta agttttcaga gcctgcatct 135120
ctgggctgta aggtctcgct ggccatcgag cagcccattc gtaaatttat cttggactcc 135180
tccattctcg ttcggctcaa aaatcgtacg acctttcggg tatctgaact ttggaaaata 135240
gagcttacca ttgtaaagca gctgatggga agcgaggtct ctgcaaaact tgccgctttc 135300
aaaacgcttc tgtttgacac cccagagcaa caaacgacaa aaaatatgat gacgttaata 135360
aacccagatg acgaatatct ttacgaaata gaaatagagt atacaggaaa gcccgaatcc 135420
ctaacggcgg cagatgttat aaaaattaaa aacacggtgt tgacacttat ttctccaaac 135480
catttaatgc taacagccta ccaccaggcc attgaattca ttgcctccca tatactgtcc 135540
tcagaaatcc ttcttgctcg tattaagagc gggaagtggg ggcttaaacg cctcctcccc 135600
caggtgaaat ccatgaccaa agcggattac atgaaatttt atccgcccgt tggctactat 135660
gtaacggaca aagcagatgg aattagaggc atcgccgtca ttcaggacac gcaaatttat 135720
gtggttgcag accagttata cagcctaggt accaccggca ttgaacccct taaaccaacc 135780
attttggacg gtgaatttat gcctgaaaaa aaagaatttt atgggtttga cgtcatcatg 135840
tatgagggca atctattgac gcaacagggg tttgaaacaa gaattgagtc tttaagcaag 135900
ggcattaaag tcttacaagc gtttaacata aaagcagaaa tgaagccctt tatttcgcta 135960
acaagtgcag atcccaacgt gctcctcaaa aactttgaaa gcatttttaa gaaaaaaact 136020
cgcccatatt ctattgatgg catcatttta gtagaacctg gcaattctta tctaaataca 136080 aacacccttta agtggaagcc cacctgggat aacacattag actttttggt gcgaaaatgt 136140
ccggagagtt taaacgtacc agagtacgcg cccaaaaaag ggttttccct gcatctacta 136200
tttgtaggca tctccggaga gctttttaaa aaattagcgc taaattggtg tccaggatat 136260
acgaaactat tccccgttac acagcgcaac caaaactact ttccagtaca gttccagcca 136320
tcggattttc cattggcatt tctttattac cacccagata cctcgtcatt ttctaatata 136380
gatggaaagg tccttgaaat gcgttgtctt aagagagaaa tcaatcacgt cagctgggaa 136440
attgtaaaaa tccgggagga taggcagcag gatcttaaaa ccggcgggta ttttggcaat 136500
gatttcaaaa cagccgaact cacatggctt aactatatgg atcccttttc ctttgaggag 136560
ctggcaaagg gcccttctgg aatgtacttc gccggtgcca aaaccggcat ataccgcgct 136620
caaacagcac ttatttcctt tattaaacaa gaaatcatcc aaaaaataag tcaccaatcc 136680
tgggttatcg atcttggaat aggaaaaggg caggacctag gacgttacct ggacgcaggg 136740
ataaggcatc ttgttgggat cgataaggat caaaccgcgc ttgcggagct tgtttatcga 136800
aaattttcgc atgctacgac ccgacagcac aagcacgcta ccaacattta cgtgttgcat 136860
caagacctcg cagagcctgc gaaagaaatc agcgaaaagg tacaccaaat ttacgggttt 136920
cccaaggagg gagcttcttc cattgttagc aacctgttta ttcactatct tatgaaaaac 136980

-continued acgcagcagg tggaaaacct ggccgttctg tgccataagc ttcttcagcc ggggggaatg 137040
gtgtggttta ccaccatgtt gggagaacag gtcttagaat tacttcatga aaatagaata 137100
gagctcaatg aagtatggga ggctcgtgaa aacgaagtgg tcaaatttgc tattaaacgt 137160
ctctttaaag aggatatatt acaggaaact gggcaagaaa ttggagtcct gttacccttc 137220
agcaatggcg acttctacaa tgaatatctt gtgaacacag cgtttttaat taaaatattt 137280
aaacatcacg gcttttccct agttcaaaag cagtccttta aggactggat tccagaattt 137340
caaaacttta gtaaaagttt gtataaaatt cttacagaag ccgataaaac ttggacaagc 137400
ctttttgggt ttatttgtct gcgcaaaaat taaatatttt ttcataagaa gtactaccca 137460
ggttttaaag aaatagctaa aaatatcata tggatactgc catgcagctt aaaacgtcta 137520
ttggtttaat tacatgtcgt atgaacaccc aaaataacca aatagaaact attctggttc 137580
aaaaacgtta cagccttgct ttttcagaat ttattcattg tcattactct ataaatgcta 137640
atcaaggtca tctgattaaa atgtttaata acatgacaat taatgaacga ctgcttgtca 137700
aaacactgga ttttgaccgc atgtggtatc atatttggat tgaaactcca gtctacgaac 137760
tataccacaa aaaataccaa aaatttagga aaaattggct tctcccggat aatgggaaaa 137820
agcttatttc attaatcaac caagcaaagg gctcaggaac acttctatgg gaaatcccta 137880
agggtaagcc gaaggaagac gagtcggacc ttacctgtgc catacgggag tttgaagaag 137940
aaaccgggat tacccgcgaa tattaccaga ttctcccaga gtttaaaaaa tctatgtcat 138000
actttgacgg taaaacagaa tataagcata tctacttcct tgcaatgtta tgtaagtcgt 138060
tggaggaacc caatatgaat ctttctttac aatacgaaaa ccgaattgcc gaaatttcta 138120
aaatttcttg gcaaaatatg gaggctgtac gttttattag caaacgccag tcattaaacc 138180
tggagcctat catcgggcct gcatttaatt ttattaaaaa ctatttacga tacaagcact 138240
aggatgccgc attaaaatgc cacataaggt aatacactag gaatgtcgca cacgcacaag 138300
aatacaacgt cgccggagat ttattatcta gtacacgttt tatgtatgta caatccgcct 138360
tcatttaata tattgagcgg atgtactatg tatttatttt aacaaaaaac attatttttt 138420
ttaatcttca tcatctgttt ttataaactc agtaatatca aaagtagctt gtggggtttc 138480
agagggttca ccttggttat cctccgtgag gataacatgt tcttcaggtt cgtcgtcact 138540
ggagaaccca tcatttaatt cctcttcact caacatctgt aaaaaatctt ccaagctttc 138600
gctatcgtta aaatcctcat catccataag aataatggta ccttcctcat cgtttcctcc 138660
ttgtttcgtg tctaaatagg cctgcatggc atttgcaaaa gtatcaaaat aggctgagtc 138720
agattgctgt tccaaaatat ggccttgcgt attaaatgtg gttgcatcgt tgttaaatgc 138780
ttgcaaatac agtaagggat ttatatccat tattattaag caaaaaaaat ttaaattatt 138840
tttcgaccga tgttaggtaa aattaaacaa ttgctatagg tgttaagcaa tgtttattga 138900
ttttaagtac tcaacaacca tgatgtaaat actatacagc acttttggat ttttaatcaa 138960
atccagatta atactaactt cttttgtgat acagttcgta ataatagtat cctgctcatc 139020
gttttgtaag atttctttta atatattttt ttttaccggg atactaagca attgattatt 139080
ttcttttaaa aactcctttt gatattcaat cgtcttattc attgaatatt tgtatataac 139140
tataattaca aatgttcaat gaattgttat tcatgtcggg agatggctat ttaaaaatca 139200
tgtcctattt ttctttgctc aataagcatc caaatatttt catggcgttt tattaattgt 139260
tcattattga acgtatcaca aagatcattt ataaattgca gatagtttat tatttctttc 139320
aagagagtaa caaacattac ttcagcagaa catataatag gtaattcagt ggcgttaaaa 139380
gaattttgat cttgttgata cgccaatggc gaggacttaa ggagatttgg gggtcttgcc 139440
caaaacccta ggctgctgtt cttgtttttt agggcgtcat aaagaaatga aagcacattg 139500
caaggcttaa gccgcgacat ctccttcccc ttgggccctt tccatatttt tagatctaag 139560
atctcatccg agcttataga gtaggtatag taaagttttt caaaaaagca tatctgcttg 139620
aagtcttttt tagaacgact ttcaagaagc atttctataa tgttaacaag ttttgttagg 139680
tttaaggcct gttcctgtgt aagctcctct tgcacgtgat agactgaaaa agtgtgctta 139740
ggaatgaaaa tactccccgt ggcactggcc tgttgtctgc caggtatata gtacacgctg 139800
ctgttagcaa gctgtaccgg cacaatttgc cccacttctg caacattatt ttgcgattcg 139860
gacgagggta tgacaatagt tacgggttca gtcaataggc tttcgccgag aataatatta 139920
ctgtcatttt taataatttt aacggccgct attaaatcaa aggcatttaa gtaagaaaca 139980
acagcagaaa atcttacatg catatatcct cttccgctat tattcgtacg cataataaaa 140040
caaggggagc gttgtataac gccagtaata ttaagaataa aactgttttt gaaacactta 140100
cccacataaa tgttttcaag ctccttcaaa agatgagcct ccacatttgt acaaaaattg 140160
gtaggatcat caatattcaa cgttgtctca aaaatttttt ggtcgatcat atctataata 140220
tattctgtct atttcaattt aaataatata cgaataaata acgagattat tttattaaat 140280
aagcaatggt gtatacactt tgtatttact ttgagatata ctttgtgtat cacaacgtgc 140340
cctaagatgt gtgcacaagt gacggcattt tgtcgttaaa aaggtaaaac cagcggattc 140400
catcctgcat tccatttggt tgattacgag cctccatttc tttttgcaaa aggttattgc 140460
gaatgagtaa gcagagcttg atggcactaa tctttgtaag gtttaaactt atgcccaatt 140520
ggtcagcaat tttttgttgc tcctcccgtc cgcgtgtttc gcatacggct ccccggttta 140580
gcatgcgaat atcagtaatc tcattctttt ttaaaacctg gataggtggg cggattttaa 140640
atttaagggc ctttcccttg ctttccatat agcctatgac gatgtcgttt tcttttcgtt 140700
taacattaat attaagcata taaagcggaa tttcatgcca ggttttatct tctcgcgagg 140760
taataagtcg cacggagtcc tccgtggcat agcccactag agtgttgtca tccccaggca 140820
cgtggcttat aattttaaaa atgtccggaa atggctgaat atcttttttt gaaaaagcga 140880
tgaaaaactt tttataaacc tcgacaaggg cccccatacc tgcaagatta tctataataa 140940
gtgcttctag catcgtatag tgaaatgaag cggggtagtg gatgagtacc tgctccattg 141000
gctcatcctg aaaatccttc tgaaactttt catacaatac ttgaaagggt tctttggtct 141060
gcgagtgttc gaggtatttg gtaatacgga tgctgtgcat cgcgggaggc tgaaaatccc 141120
gaatatatgt ttcaatatct aataccggtt cctttttatg gttaagcacc gcagcgacgt 141180
acaaatgctc aggctttgcc ggcacatgca taatggtgca aagacgattc tgtatccata 141240
attccttgca ctggtttttt gagtagcata gagaaatgag cgccagcgcg aagttgtcct 141300
ctgagaagag tttattatcg atggtaattc cctgtatgag cttgggagtg gaaacagcct 141360
tccatagctc ggagtacgtc cacacggggc gtgccataaa caaagatata ataatattag 141420
aaattgtttt tacctcttgc tccccgtatc cataggcctc aaaggtattg aggacggtgg 141480
ctccgacgtt tgccggcgtg atggatggac taaggggcag actttccaac ataggcttat 141540
caatcttaat ctggttggtg aacccatcaa tggcgtgctt tcgcagcgcc ttatccccct 141600
cctgtattaa aatgtattct tttaattttt gtgcgtactt agcgagctct ggccctccat 141660
cgggtgttgt cgatacgtac aaataaattg tcacgttgcg ctcactgggg gggagctcca 141720
tgtgtgaatt ttttcgcacc accctcccaa atacctgaat aagccgggga atatcaaggg 141780
gcaatgacat aatcatctcg taccgcacgg cctgaaagtt caaaccctcc acaatcacct 141840
tggacccgat gagaatacgc agctggtggc cttccaggtt ggacgaggcg ttaaaaagag 141900
ccaggcttcg ttcgcgtaca gcgggctcta tttcgctgtg cagaatggtg aaccgtactg 141960
gaataaactg atggtcgcta tgtgtgtgct catcgcgaat cgcggcgcag atggagcagc 142020
gggtcgttcc cacaggggac gaaacttcat ttaaaatgcc attactttgt aaaatttctt 142080
gcaagataag aacccccgac atgcggaccc gattgtggta aattaaaatt ttcccccggc 142140
cttgccgaat aatggaaaga atgtctttca tcatttgagt gtattttccg ctataaaagg 142200
ccaatcccga gatgtgcgtt ggtggctgca gcgacaaaaa gctgccactc acattaaagg 142260
gggctctacg cgaaggctca ataatctgta ccccgttttc cagaagccag tctgtgcttg 142320
ccatagaaag ggcggtgggg gtttccgtcg agttaaacag gccgtaagcc ttgggttccg 142380
tttgttttga aaattttggg ttgggaaaca ccatgtcata aatgctgtac gcattactcg 142440
agattttagg gtcagggccc agctgtttaa gcgtttcaag ctgatactca gacatggggc 142500
attcgatgaa atgtaagtac ggcaatgttt cgtctttata ggacaacatc tttccggcaa 142560
atattctttc ggggtaaaaa ttggtgttgg tatccaacaa aaaagatacc cttccggtgc 142620
tcagtctttc cacaagagct agggcgtcct ttttccattt aacggaatgc ccactgctgt 142680
caaacagttg ctggcgctgg aggggctggc cgttgggcag ctcatgccgc ggaaccaaaa 142740
ggtttaacag gtcgacgtat tccatgacac tcccggttac gggcgttgcc gacatgaaga 142800
cggccctggg ggcctggtga ggtggaaagg catccaggac atactgtaaa gcgatgccat 142860
aattatttcg ttcctggata ttgtacacgt tgtgtatttc atccgcaatg agcagtcctc 142920
ccctaagttg ctccatgatt ttttgattca cccggatgag gccgtttgtc tcggcctcgc 142980
taattttttg cacgaactga gatatatcgt tctcattcaa tgtatcttct gcttcgtcag 143040
aacgatgaaa cagagaaagc acatcaaagt ttttctcttc acccttactc gtaatattga 143100
aaagcttgga tgcaaattcc ttatagccgt aaaactgaaa aaagcctccg cggtttctat 143160
cggttaaacg gcgctttaac gtactaacga acccatttag atgccgtgat tcgaccgacg 143220
tggtgctgcc agactgcttt gcaatgtgaa gaagccggtg tagctcagcg acctccttgt 143280
aagaaacaaa tcccagctca ggacgtctta gcatttctgt ttgaatgatg gcgcgtgtaa 143340
agcctaccac aaaaatccag ggcgcatttt caataaaatt catgtagtgg ttcataaatt 143400
gacgcgcgat ggcaatcgcg gcaatgcttt ttcccgtccc ggtctgccag tttaataaaa 143460
gacgcgagta gggcgtgttg ggattttgaa agttttggac gaaaagctgg gcattatgca 143520
attggagacc cttgatggaa ggaaagggcg acgcgtaggg gtcacacgga aaaaacgctc 143580
gcccccccct ctcgcagcca ggcccaccga tctggacaaa atgagcccgc agatcacgaa 143640
tgagctcttt ttggtcgaca ggaggggaaa tcaacgattt aaactccttt cttcgcgcca 143700
actgctgcaa aaagtctgcg gcatccaatt cgggatacgc catattatca taaaaaaata 143760 aacctttta tgaaaacttt tatgtgattc tgtattgcaa ttgtttttta tgaatactgt 143820
aaataagcgt atcaacttgt ttttctaacg aagaggcgtt attctttttt tctggatata 143880
aaataataat aagtataata attaagacta aacagcaggc aatcactatc aaactcatat 143940
tatacttact tttttataaa aagtattata tcttatgaat gcgcaagttc agctaattgt 144000
tcgtcgcttg gaatgtggga ctgcagggag gtggagtttt tcctttttct aaagaatacc 144060

-continued gggaaatggt ggtgaggctc aggttgttgt acatagtagc taggaggagg tttaggtatg 144120
ctcgacttgc agtcaatagt ccggttatag taaacgatgg caacgatgat aagaataata 144180
atgagcaaaa tcaaaatgcc caggagaatc gcagttgttc cgggatattt ggcgattgta 144240
tgggctaaaa ggccttgggt gctttgttta attccctcgc gggttgacag gttatgagaa 144300
agcagtggag acgtttcagt gtccatttat tacaattgaa cagttatatt aatctcaaat 144360
aaaatataac acaaaattaa ttatggccat gcaaaagtta tttacgtata tttacgagtt 144420
tattgaatat cgtaagatgg tgctgttgga agaaaaggta ccatatgata agtttgttca 144480
aatggtactt aatacaggat tttttcgtat taacgcggag acgctgaatc acggaatcgt 144540
atccgtgttt atctttggag caaatggcaa gtacgttcac cacggaggcg acatgagaac 144600
gcttttaacg aatacgctta atgaaaaaaa acattatgaa gaattaattt taatcgttga 144660
taagcccgtt ttaagcaaaa aaaatatttt agatataatc gtcgagcagc gcgctgcaaa 144720
tcccacgatt gtaataaaca tatatcccta ccacctgttc tgcattaaca ttcccaaggt 144780
gagtgccatt cctaaacata aactaattac tcaggaggag gcgcaggagt ttttaggtcg 144840
cgaatatctg caaccgcagg acctcatgca aattagcgcg tcagaccccc cggtggtctg 144900
gctgggagga agaccgggag actttgtgca aattgagcgg ccctcagaga cagctatgca 144960
cgctgttgtt atccgcttta tcaccaagtc caaaatttga gtcccgtgtt taaagatgac 145020
agacagctaa gtaagcatat ctgtaaaatt gtcgatgtcc tctgtggata gagcgctttc 145080
ctctgagcag caaatttttt catacatctc catgggggat ggcgaggctt taatagtatg 145140
taggtcacgt aagaactgtt gtatgatggg atatttgtct tttaaaaact ggggatgttt 145200
cataactgga attatttgaa agataaagac cttccatcca aagtagccaa ccacatttgg 145260
catttcggga cacgcggttt cataaggcat agaatagtga atagtgtact gatctttttg 145320
atacagcgtt tcaagtagtt ggcgaaatgt ttccgcgtcg agcgtgccaa aatcttgagg 145380
agcctcggtg tgctcctgtg tagagcagat cgtgatgatt ccccaggcaa gcgggagcat 145440
ggactctgga gggtggatat ccgtattggt ctcattattc gatcccagct gatgaatgcc 145500
gcacacgcga aacatggcct cgacgtagat gcccatagag ataggcggcg aaagggcaag 145560
accggattgt atttgcggca tatagtagga gggcaccgag ttttttattt ttcggttgaa 145620
tggggacttt atttctacca gcacggggat gcgtttcgtg gcctcatagc gtacgttgtt 145680
aaaaattgtt ttgatttccc aggactgttg agtgtatccc agcgttaggt gacaaaaccc 145740
atcggggcta ttactatgtc cggggtatcc caaataggtc ccatcaatat gaatattgtc 145800
acctatgacg gtggtttggc agaacaactc aagcagatct ttactaacac gctcaaaaag 145860
ggttccccag ctacaagcag cgcggttcaa attcttctta aaaagatttg ctttttccgc 145920
caaggttata taatagcttt tgtaagggtt taaacctaaa acgctggcaa ggtcagagcc 145980
acccacctga gtgcgacgaa tagcatgcca ggcatcggag cgctgctgag gagagtcttt 146040
aaacaggcgt acaaaggttt ccattatact tgttttaaca ggaattcaat ataaaaagtc 146100
aacacagttt gcaatttttc caatctcaag atatagccat acattttttt ttccaattgg 146160
cgaatatgtt taagctcatg tgtttcaata ttagcatccg gaaatttaaa tgcataaaga 146220
tgttcaaagg cctgatttat acacgtatca aaggatctgt ggtatgttat tagcttcagc 146280
atgtgtgcca gatcttcaag atggtctaaa tttatacggt tttccacgtg gtggatcatg 146340
tctgccacat cttgagcccc catccagggg atcacaaggt actcccccct aaagatgatt 146400
cgtcgttttt ttaaaaaatc atgaaaacgt tttaaagctt caagaaaggg gcagttgggc 146460
tttgacccca aaatgctgac gacgatatcc tcgggcatga tgtattcgca gtgaggatag 146520
tagtttacgg actctaattc agcggcccgc cgttttattt cgtatcttgc ccagttattc 146580
agagagtact ccacgcctcc gaccacaaca gacatcctat ctattaaaaa ataacaataa 146640
aaaccttatg aaatctatgt atagtggccg ctaaaatgtc tatattagaa aaaattacgt 146700
caagtccctc tgaatgcgca gagcatctta caaacaaaga tagctgttta agtaaaaaaa 146760
tacaaaaaga gctcacctct tttttggaaa aaaaagagac actcggttgc gattcggagt 146820
cctgcgtaat tacccacccc gccgtgaagg cctatgcgca acaaaaggga ctggacctct 146880
ccaaagaact ggagactcgg tttaaagcgc caggacccag aaacaacacg ggtcttctta 146940
caaacttcaa tattgatgaa acgctgcaga ggtgggccat aaaatacacc aagtttttca 147000
actgtccttt ttccatgatg gactttgaga gggtccatta taaatttaat caagtggata 147060
tggtaaaggt atataaggga gaagagctac aatatgtaga aggcaaagtg gtcaagcgtc 147120
cttgtaacac cttcggatgc gttttaaaca cggacttttc aacgggcact ggaaaacact 147180
gggtagccat ctttgtggat atgcggggcg actgctggag catcgaatat tttaattcga 147240
cgggaaattc tcctccaggt cccgttattc gttggatgga acgggtcaaa cagcagctat 147300
taaaaataca ccacaccgtg aaaacgcttg cagttaccaa cattcgtcac caacggtcgc 147360
agaccgagtg cggcccctac agcctgtttt acatcagggc acgcctcgac aacgtgtcat 147420
acgcccattt tatatccgct aggattaccg acgaagacat gtataagttt agaacccatc 147480
tgtttcgcat cgcataaact aataaagttt gaattcttta taggaataaa aatggaagcg 147540
tttgaaatca gcgatttcaa agagcatgcg aagaaaaaaa gcatgtgggc tggcgccctc 147600
aacaaagtca ctatttcggg tcttatgggg gtctttaccg aagatgagga ccttatggcg 147660
ttacccattc acagagacca ctgccccgct ttgttaaaaa tttttgacga gatcatcgta 147720
aatgccacgg atcatgaaag agcttgccat aacaaaaacaa aaaaggtaac ttacattaaa 147780
atttcgtttg ataaaggtgt gttttcttgc gaaaacgatg gcccgggaat ccccattgca 147840
aagcatgagc aagccagtct tatcgccaag cgcgatgtgt atgttcccga ggtggcttca 147900
tgtcactttt tagccggaac gaacatcaat aaggccaagg actgtatcaa ggggggaacc 147960
aacggcgtcg ggctgaagct cgccatggtg cattcgcagt gggccattct taccaccgcc 148020
gacggcgcgc aaaagtatgt tcaacatatc aaccaacgcc tagatatcat tgagcctcct 148080
accattacac cctccaggga aatgtttaca cgtatcgagc tcatgcccgt ataccaggaa 148140
ctagggtacg cggagcctct gtctgaaaca gagcaggcgg atctttccgc ctggatttac 148200
cttcgcgcct gccaatgcgc ggcctacgtg ggaaaaggca ccaccattta ttacaatgat 148260
aagccttgcc gcacgggctc tgtgatggcg ctagccaaaa tgtacaccct gttgagcgcg 148320
cctaatagca cgatacatac ggcgaccatt aaggccgacg caaagcccta tagcctgcac 148380
cccctgcagg ttgcggcggt cgtgtccccc aagtttaaaa aatttgaaca cgtgtccgtt 148440
atcaacgggg taaattgcgt aaaaggagaa catgtcacct ttttgaaaaa gactattaat 148500
gaaatggtcg ttaaaaaatt tcaacaaacg attaaagata aaaaccgcaa aacaacatta 148560
cgagacagct gttcaaacat ctttatcgtt atagtgggtt ccattccagg aatagaatgg 148620
accggccagc ggaaggatga acttagcatc gcggaaaatg tttttaaaac gcattactcc 148680
attccttcta gttttttaac aagtatgaca aagtctatcg tggatattct tctgcaatcc 148740
atttctaaaa aagataacca taaacaggtc gacgtagaca aatatacgcg tgcccgcaat 148800
gcgggaggaa aaagggcgca ggactgcatg ctactcgcgg cggaagggga tagcgcactt 148860
tccctgctgc gcacgggact aaccctggga aagtccaacc caagcgggcc ctcctttgac 148920
ttctgcggca tgatctccct gggaggagtc atcatgaatg cctgcaaaaa ggtgacaaac 148980
attacaacgg actctggaga aaccattatg gtgcgcaacg aacagcttac caataataaa 149040
gtgttgcagg gaatcgtgca ggtattgggt ctagacttca actgccatta caaaacacag 149100
gaagagcgag caaagctgag atacggctgc attgttgcgt gcgttgatca agatctggat 149160
gggtgtggaa aaatccttgg actgctgctg gcctactttc acctgttttg gcctcagctt 149220
attatccatg gtttcgtaaa acgactgctt accccgctga tacgtgtgta tgaaaagggt 149280
aagaccatgc ccgtggaatt ttactatgaa caagagtttg atgcctgggc aaaaaagcag 149340
accagcttag ccaaccatac cgtaaaatat tacaagggat tggcggcgca tgacacccat 149400
gaagtaaaaa gcatgttcaa acattttgac aacatggtgt acacgtttac cctggatgac 149460
tcagcaaagg agttgtttca tatttatttt ggcggggagt cggagttgcg aaaaagagag 149520
ctttgcaccg gcgtggtgcc gctcaccgaa acccagacgc agtccattca tagtgtccga 149580
cgaattcctt gcagcctgca tctgcaagta gataccaagg cttacaagct ggatgccatc 149640
gagcggcaga ttcccaactt cttagacggg atgacgcggg cgcggcgcaa aattttagcc 149700 ggggggggtga aatgcttcgc ctccaacaac cgtgaacgaa aggtttttca gttcgggggc 149760
tacgttgcag atcacatgtt ttatcaccat ggcgacatgt cgttaaacac aagtattata 149820
aaagccgccc agtattaccc aggctcctcc cacctctatc cggtattcat aggcatagga 149880
agttttggct ccaggcacct gggaggaaag gatgcaggat ccccaagata catcagtgtg 149940
cagcttgcgt ctgaatttat taaaacaatg ttccccgcgg aggactcatg gcttctcccc 150000
tacgtctttg aggacggcca gcgggcggaa ccagagtact acgtgcctgt gttgccgctt 150060
gctattatgg agtacggcgc caacccatcg gagggctgga agtacaccac ttgggcccgg 150120
caactggaag acattttggc cttggtgagg gcctacgtcg acaaagacaa cccaaaacac 150180
gagctactgc actatgcaat aaaacataag attactatac tcccgctgcg gccctccaat 150240
tacaatttca agggccattt gaagcggttt ggccaatact actacagcta cggcacgtac 150300
gtcatctcag agcagcgaaa tataattact attacggagc ttcctctgcg tgttcctacg 150360
gttgcataca tcgaaagtat aaaaaaatcg agtaaccgca tgacatttat tgaagaaatc 150420
atcgactaca gtagttcaga aactattgaa attctggtga aattaaagcc aaatagtctt 150480
aaccgtatcg tggaagaatt taaggagact gaagagcaag attccataga aaattttctg 150540
cgcctgcgca attgtttaca ttcacatcta aactttgtaa aacctaaagg tggcattatc 150600
gagtttaaca cgtattatga aattttgtat gcgtggctac cttacaggcg tgagctttac 150660
caaaagcgtc ttatgcgtga gcacgcggtg cttaagctgc gcattatcat ggaaactgct 150720
attgtacgct acatcaatga gtctgcagag ctaaatcttt cccattatga ggatgaaaag 150780
gaggcaagcc gcattctaag cgagcatgga tttcccccgc tgaaccacac gctgatcatt 150840
tcccctgagt ttgcctctat agaggaactc aatcaaaaag cactgcaggg ctgttatacc 150900
tatatactat ctttgcaggc tcgagaattg cttatcgcag ccaaaactcg tcgggtggaa 150960
aaaataaaaa aaatgcaagc tcgtcttgat aaggttgagc agcttttgca agagtctccc 151020
tttcccggcg ccagcgtatg gctggaggaa attgatgcgg tggaaaaggc tattataaaa 151080
ggaagaaata ctcagtggaa atttcattaa acgctaccgg ttttatgatg tccaataggt 151140
gttaagcaat cagttcatca acattttttt caagaatttg aaaagtttgg ataatgttct 151200
gaatactttt ttctaaaaga gttatcaaat cttcttgtga ggccttatga ataattgtta 151260
ataccatttc ttgcttatgg ggaacacact gataccccac aaagctaata tcaggaatca 151320
tttcataaat atatgttttt agcagatttc cgatggtatg ggtttcatct tttatcgtga 151380
taatggcctt tgtttttttcc tcatccatgg aaaacagcac aagttccggc tgcggctctt 151440
caaagttttc ataaattttt tgaatgcttt ggattcggcc aataatgatc cggcaggcgt 151500
tttttaaata cgtgcgaacg gcctggttga tatgtggcag cggcaccgct ggaaagcaaa 151560
gccccaggcg gtggtgacgc gggtctgagg tcatagagct ttgcttgtaa ccgctaagcg 151620
ccatatattc ttttttatcc gttgggtact gttcaatgtc aaggtgggaa aaatgtgttt 151680
taacggcaag attaaaggcg gcatgctttc gtcctatgcc ctttttaata tagatatcct 151740
ctataatcaa cgattttccg ggttgtagga agccaatctc aaaggtagga ttaaaaatcg 151800
ggtatttaag cttagggcct gccacctgga tgagatcgcg gctatagatg gttttaacct 151860
cacagctatt gtttaaactc cgcagagcaa ataccagtgt ctcgtttttc gcataaatcg 151920
gaatgaaatt aatgcggttt ctaataaatt gttccgtcat aaacaggtcc gtggaatcct 151980
cgatcttata cccaccgggc ttaatatcta gcatataatt gggaatttca tcttgcaaga 152040
cccgcgacag gccgtggacc gcggctctgc taatgccctt aaagtccata acaacattga 152100
ccgggacgag gggcaactgc tcctcgagct gaaatagttt tttggccgca tttttaataa 152160
agaggttgga aaagtctatc aaaaaacggtt tgatttccac gttttggaaa attttttcca 152220
tttgtattat aaatatatct atatatattc aaattatggt agtttatgac ttgctcgttt 152280
ctttaagtaa ggaatccata gatgtgctac ggtttgtaga ggcaaacctt gcggcgttta 152340
accagcagta tatttttttc aatatccaaa gaaaaaactc gatcacgaca ccccttctca 152400
ttacgccgca gcaggaaaaa atttcgcaaa ttgttgagtt tttaatggat gaatataata 152460
agaacaatag aaggccctcc gggccgccgc gtgagcagcc catgcaccca ttattgccgt 152520
atcaacaatc ctcggacgaa cagcccatga tgccgtatca acagccccccg gggaatgatg 152580 atcagccata tgagcaaata taccataaaa aacacgcgtc gcagcaagta aatactgaac 152640
tgaacgatta ttatcaacat attcttgcat taggcgatga agacaaaggt atggacagca 152700
tgttaaaact tccagaaaag gcaaaaaggg atagcgatga tgaggacgac atgttttcta 152760
taaaaaacta acgacgtaac aattaaacaa aaataaaaat cattataaaa tgaatcttga 152820
atacgtccaa gttgttcaaa aatttaatca agtactccta gaacttacca aaaaagtatg 152880
taccgttgtg ggcgggagca aacccaccta ttggtatcac cacattagaa gggtttgctc 152940
agaatgtcca tccatgccga tgagtatgat aggtccgtat ctgaatgtct ataaagccca 153000
aattctaaca agggacaaga atttttttat gaatttcgat cccgcgcata atgagtacac 153060
ctttatcatt caaaaactaa aagaagcagc ccgaaatatg ccggaagacg aattagaaca 153120
gtactgggta aaactttttat ttttacttaa aagctacata aaatgtaagc cctttattaa 153180
ttaaagaatt gatgcataac taataaatgg ccggtcgtgt taaaataaaa cagaaagagc 153240
tcatagactc tactgtaaaa aacaaaaatg tgatgaatct gttccatgaa attataggct 153300
caaaaggcaa tattaatttt agcgttgtct ggcccaagtt taaaaaaatc aaacagagcg 153360
tttatgacta catttccact ctttctgtgc tggaaaaagc aaacgttatg caaaactttg 153420
aagctgataa gaaactgttg gaactttttg tacaaaagct gtgggctgcc tatgaaggct 153480
atttcaaata tcccgagatt gaaaaatatg aggtggaagg ccaggtaaat ttcaatctcg 153540
tacctcagtg cgtcctcgaa aagtttagcc agttgtatag gataagaatc aattcagagc 153600
ttgtcacact catcctaaac agctgtgcct ttatgagtaa atataacgat tatattctca 153660
aaaaagatcc ctacatacta accataaccc ccggcctatg cttttccccc attcccaact 153720
tcgaggacct aaattttaaa catctttaca acagtgataa aaattctcag catgacaaag 153780
agtttatcat gtttatatta tataagcttt atacggctgc cctaggagtg tacaatgcca 153840
tctcgattcc agacatcgac gtagaagacc ttgaaaatat catcctatcc tcggtgagcc 153900
agattaaaaa acaaattccg cgctgcaaag acgccttcaa caaaattgaa tcttcggtac 153960
acctgttgcg caaaaaattt aacacatatt acagtgacta tgtgggctca ggctacaacc 154020
caaccatcat tatggaacag tacattaaag acatatcaca ggattccaag aacatatcac 154080
cacgcatttc ctaccagttt agaaccatca tcaagtatta ccgcgacatg attgccacca 154140
ggcatcaaac gatggacccc caggtattaa acctcgtaaa gcacgtcgaa aagaaattag 154200
atatgcttga tagagaaaaa aattagtata tatagttatg gtgaatcttt ttcctgtttt 154260
taccttaatt gtgattatta caattttaat tacgactcga gaactatcca ccacgatgct 154320
tattgtttct cttgtaacag attatattat tattaataca cagtatacgg aacagcagca 154380
tgaaaacaat acatttttca tgccgcaaaa aaattctttt aacgaatctt ataataaaga 154440
caaaaaatct aatatacata ttccctacca gtggctggcg cctgaactga aggaagctga 154500
gagcaagtac tggtggggca attatgatcc tcatagcgag cccgttctcg ctggcgcatc 154560
ttgaatatct tcatacgtgg cacgtcacca tcaaaaacat tgcccaacag cacgggcttg 154620
atataaaggt ggccattgtg gtctcaacat cgcatttaaa taattttttg ccaatttccg 154680
gggcgcttaa catcgaatgt ataaccttcc ccagttgcgg catcaaggag atagacctcc 154740
tatgggcgcg cattaaacta tttcaacatt actgcgccat cggtgcccgt cttttatggc 154800
tggtaagtgc tgacatcagg ccccctgttt cagcgtggcc agccatcgcc gacagtctaa 154860
aaaagggagc agatgcggtc gttattccct acccctcccg atggaacaat cttataccta 154920
ccgtcatcaa agaaatagtt gtccaccaaa aaaaatgcct tgtggcggtg gatgcacgcc 154980
accttgatac agatacccag attgtagggg ccgggatggg ctgcatcgtc ctaaccctaa 155040
aggcccttat ggtgcgccta agtattggca aacagcccgt taagatactg tggcccgacc 155100
ttcacggcac tgccgagggc attcctctgg agggggtgga ggttggctgg tttttaaacg 155160
cttatgcgca taaattaaat atacgctgcc taggggctga tcatattgcg cagcacttaa 155220
cttaattctt tatttaaaaa gtccacgcat ccagtggcgg cctacattaa gggcctacgc 155280
acataaatat acactggcta gaagtacgcc ttcatttaaa ccattgaatt atttatataa 155340
tggctgcaaa cattattgca acaagagccg tgccaaagat ggccagcaaa aaagagcatc 155400
aatactgtct gctagactcc caggaaaagc gtcatgggca ttatcccttt tcatttgaat 155460
taaagcctta tgggcaaaca ggcgcaaata tcataggagt acagggctca cttacccatg 155520
ttatcaaaat gacagtattt ccatttatga ttccttttcc tttacaaaaa actcatatag 155580
atgattttat tggtggacgc atttatttat tttttaagga actggacatg caagcagttt 155640
ctgatgtaaa tggaatgcaa taccacttcg agttcaaggt tgttcctgta agccccaacc 155700
aagtagagct tcttcctgtg aataataaat ataaatttac atatgctata ccggtagtgc 155760
aataccttac cccaatcttt tatgatcttt cgggaccgct agatttccca ttagatactc 155820
tttcggtcca tgtggatatc ctctccaatc atatacagct tcctatccaa aaccataacc 155880
taacaacggg tgatcgtgtt tttatttctg gatataaaca cctgcaaacg attgaattat 155940
gtaaaaataa caagattttt atcaaaaata taccgccgct ttcatccgaa aaaataaaac 156000
tatatatact aaaaaatcga atcagaattc cgctatactt taaatcttta aaaacgtcta 156060
agtaataaca tttttatagt ctactcctag ttccgaaata ggctgaattt ctttttaag 156120 tcctttaaac caaggatgtg atacaagact cttaaaggaa agccgcttat tttcattaat 156180
tgttaaacat tccgtgataa actgttttcc cgtctctgaa atgttctcgg gaatataatt 156240
ttcccgtttc aggatatcat ttaaataaaa attttctgca cgaaatctaa aaagattaac 156300
cgcgaccata cctatcgtcc acacggttaa aggaagctgg tagtaataac cataataata 156360
aaattctgga cacacgtatt cccatgttcc aaacatatta tattggggac gggtttcgtc 156420
taatctaaca gcgcttccaa agtcaatgac cttaatgatc ttttgattta tgtctataat 156480
aaggttctca tccttaatat ccccatggat aaagcccttc tcataaatgt tttgtataat 156540
aagaataagc tggaatatta tttttttggc ttcggtttcc tcaagttttt taaagtaatg 156600
ataatgaagt agatcaacac tatttggaat atattctatg attagtatat gatacatagc 156660
attttcggta tattcgataa gcttaataac accgggagta tcttgcaggg ctttcaacac 156720
gatgacttca tttcctggaa tttctttttt agaaacgtac ttaaatataa tgggttgccc 156780
tacttgatga cccaaaaaga cgttatttct gccaccctca aacatgggtc tcgtcgcaat 156840
gaaatacatg tgctgcgttg tggagatcct ttccaccttt gctgtaggat aaaacgcata 156900
ttgtgcctgg ggattttta acattttttt aagctgttgt tccggcctgg acatgtttta 156960
ttagctttat atataaaggg ttagaaggtt taatttcaat atatgcctta atgatgggat 157020
tatattcgta aaaggtatag cctaatccta cgtctttgtt tttttggtaa aaaaactgtt 157080
tgccctcgta ggatatgcta taggctttta cttcggcttt tacaagcggt tggcagggat 157140
tgggcaaacg taaatcgcgt tcaaagtttt catgaaaaag caaagcattt gtgggctgac 157200
acatcagaca gccgctttcg ccattgaagg cacattcaat ggccgccctt tttagtaaat 157260
cgcggaaagc agaattaaga tggctctttt caagcccccct ttcgtgaaaa cgctcatcaa 157320
tcgttttttg ttcctgactg ccttcgggaa tactataaaa cattttttga ttagccaccg 157380
cgatgtacaa aaaaggctgt acggttttct cctcgggcgg tagcgcatcg tggctaccaa 157440
tgcgtataat gcgcgccttc acttgatcct ctcgggcctt atcccagtac ggctctagga 157500
tatgaacctg ccgcccgtat ttgagatcca atccctcagc tcctgtttta gagacgagta 157560
aaattttaat aacctctccg tgtatattca gcggcgaatt ccaaagctgc tggatcatgt 157620
cgcgctcttt agataaaatt ttccctgtaa taagcgtaaa tcgtgttatt ttggaggaca 157680
ggactaacgt atgggtcggc ccatcttccg caaagttttt caccataaga tctttcccat 157740
ccttatgaag gaggatggtg ttgtgccctt cttccaatac ttttaggggc tgaaggcact 157800
ggtagccctc tatttctaaa aagcgggcca cgacgtgaag gcccaattcc acaaactgtg 157860
agtaaatgag cacagggccc ggagacgttt taatattttt tagcatgcgt actattttgg 157920
gactagaatt ttctgtgaag gcctctttgg gcagctgctg aacagcctct gataattttt 157980
catcctcctt tactgttagc atttcggacg cgaagatgct gatcatacgg gaacgcacat 158040
agtaggagga gcctgactct tgctccgatc ctggcaggca gagggcggcg gcatttattt 158100
tttcatacat tcctgagctg gcgtgctttt ccgcgttttc aacgtctcgg gccagcagat 158160
attgcctata ctgctcgggt gacatttcaa ccttttctat aataagagga agctctgtgg 158220
ggaatagctt gttgagctca ttctggtttc cagcgtagct tatcataccc actaggcggt 158280
ttagtagttt gtccgcgttt aaagggctat tcgttgtttt attgacataa gcggtgtaga 158340
atctttcata gtgaagaggt aataagattc gcccgcttag catattaaaa cagggcacca 158400
tttcaaaggg gtccttcgaa cacggggtgc ctgttaaaaa cagaatacga atatttttag 158460
cttgcataat attattgtac agctggcggg catttgtttt atcattggcg ctattgataa 158520
ttcctctaaa gaggttgtgt gcctcgtcaa cgatgagcag gcatccattt agggaccctc 158580
ccgcctttat gatctgctgc cccatgttgt aagcgtctag ggacacaaac ctgaagcgcc 158640
gcgagatttt ttgtagctct ttggagtgat ccgtcgtttc cggatataaa agtttaataa 158700
gctttaacaa agactgttgg aagtttgagt gcaacgactt gggtgcgatc agaatcgggt 158760
tgtaaatatg tgaaagtgag atggcaagcg acaggctcaa aatggttttc cccatgccca 158820
tctggtgata gatgaggagg ccccgtgtgt tttccccctg gcctatccca aatttaggat 158880
ccgaaaaggc ggtgtaaatt aaaaactggt agtatttcag ggctcgtgca aagcgggcag 158940
tgagtgaggt gtctttgctt tcctgaagct ctttatattt ttcatatacc tcttttaggt 159000
atgcttctat ttggacgggg aaggaggtgt tgttgtgcac gcaagacatg actcgttata 159060
aggatcccat attaaaactt cattagaaga atagggctgc tgatagctag cgctgcactt 159120
aaaaatgggg tagccctttt tcttgtaaat ccggtgcctg tcgtagacct ggctagaaag 159180
cgggcttagt gtatctttaa tgtccacaac gatgcgtacc ttttttttcat ccgatccctg 159240 ccgggtaata cgtcccaaga tttgctccat gttgtttctg cggggcgttg ccatgatgat 159300
cgatgtcata tgcttgaagg aaatgcctct acgcccgtag ccataggtca gcaagataat 159360
ggaagcgctg tgtgcctgag aaagagcggt atttgaaacc ccgccgcata ggagcgccac 159420
ctccggaacg ataatttgaa catctttgaa ttctttggaa agcgcctgat aaaaaatttc 159480
taaaagtttg cgaaattcca cgaaaatgat gatgccatac ggctcatcgg tcccccattt 159540
gtgaggctca gcggtatgca gggagtaaag ccgctttgcc tcatttacga caagttgtat 159600
acgcgaagga tcttgaagta gtttatcaat ggtggcaatg gccgatacct tttcattaat 159660
atacacaggg ctaacgaagt caggatgtcc ctgatattcg atttccctca cgtacccgga 159720
aaaggttgtg gtgggactta cagtcctctg gggctgtcct agatggtgaa taataatctt 159780
gtccatacca tcgggccggt ccaggggtgt agcggacagt cctaatatcc gactaagttg 159840
tattttccaa aaaattttgt aattctccgg cgagtgtaat tcatgtgcct catctaacac 159900
gactagacca aagggctcaa agaactgctc aggcttcttg cgcagggtat taatgattcc 159960
cacgatgacg tcgtactctt tgctcgtcat gtccttttttc ttgcacgctg cattattgta 160020
agcagctaca cgtaggtggg gcaggagcaa tgttagctcg tcgatccact gtatttgaat 160080
cgccttggtg ggcacgatga ccagggtagg gtacaaaagt ttttgaataa tgctgatcgc 160140
aatacgcgtt ttccccaaac cggtatttag atgtaggtaa aagcgcccat agggggacag 160200
gagcttttta tgaatcttat cgaccatttc ttgctggtag ttaaatagtg gaaattctgt 160260
ttcaacgcat gggagggccc gcagcgacac ggggcgcgtc gtgtaaacca tgttaaacat 160320
ttcaaactgc ttttgcagca atatgggaaa ataaatgtat tccccctgca gcgtgaaggc 160380
agtttcctgt cttatggcta tgtgctttgg ctgcccgggt aatgcccgcg ccgtaacggt 160440
gagcgcctta agaacgcgcc cgaaatcatg ttgtaattta ctttgtagct tcttataatt 160500
tattcctatt ccagcaaagg atataatggc ctccattctc acgctggacg ggttatatgc 160560
agaggttcca aaattcttac cagaggcgtt acgagagggc tgtgctggca agaatcctct 160620
aagcttttat attcaacaaa ttttaaattt aatgggatgt gacggtaacg agtaccatgt 160680
tctttttacc agcagctccg aggaagcaaa tactcatatg atcatggccg ccgtgcgtcg 160740
ccatttgctg cggacgcagc aaaggcctca tgtcattatc ggagcagccg agccccctag 160800
cgtcaccgaa tgtgtgaagg cattggcgca ggaaaaacgc tgcgtataca ccatcatccc 160860
cctaaaaaat tttgaaatag atcctgttgc ggtatacgat gccatacaaa gcaatacctg 160920
cttagcgtgc atttcaggca ctaatgctgt tgtcaaaacg ttcaacaaac tccaggacat 160980
cagcaacgtg ttaaaaggta ttcccctgca ctcagaagtg agtgatcttg tttatcaagg 161040
atgtattcaa caaaatccgc ccgctgatag tttttcaata aatagtctct acggcttcct 161100
gggagtcggt gttttgggaa tgaagaaaaa ggtcatgcaa ggattggggc cgctcatttt 161160
tggaggaggg ctgagaggcg gaagccctaa tatacccgga attcatgcca tgtataaaac 161220
gctaacccag caaaggcctt ctatgaaaaa aaataaatac aatacatacg ctgttcatga 161280
aaactttaaa aaacatcagc atgtatatct acccataggg ggcgtgtctg cagaggacac 161340
gtctgcagaa aacatatcta caaaagacat gcctgttgaa ggcccgaagg gactcccggg 161400
ctatatttta tttagcgttg gccgtcgcgc cgaggagcta caaaaaaaaa ttttcactaa 161460
atttaatata aaggttggcc gtgttgttga cttacaagag atactgtttc gtatcaaaat 161520
accccaaaaa tactgggaga cattattgtt catccaatta agagataatt tgaccaaaga 161580
ggacataaaa agagttatgg ttgttttgat gcatttagat accatcactc ctcgtggctc 161640
tcttcctcct ccgagccact cttcttcttt ttcttaatcg tttttgtttg ttctataata 161700
agggaaaaga actccgtggg atcttgttcc ccgtacaggt tatctgcgac cataaggatg 161760
cttagaatgg taaacaggtg agaatacata agggtttgcg ttttaagaaa accctgacgt 161820
tgaatcataa ttgaaaacac cttgcaaagc cgactcatca gttgttctgt aatggcgtta 161880
agcattttct ggaatttttc ttggttttcg ggtgtgattt tatattcatg tagaaagtgt 161940
ttcacacctg aggagaagaa tctttcctcc ttcgagagcc catctttgat gatgggaagt 162000
tccttgatca gggcaaacca ttcctcctct tgggcttgcg gattctgaag atactgatgg 162060
cagatatggt ttagaatggt gcacacgtag ctaataagct ctgagctgat tctttggttg 162120
gttttcaaat gttggcgaaa gtagtttttc accgaagtgc atgtaataaa cgtcttcatt 162180
ttcttataat atacaacagt atgttgagtc tttaatttaa aattacaagg agttttctag 162240
gtctttatgc gtataggtgt ttctttgtcg taaattttca atagccgaca ttgtttgtga 162300
agcagtgttc tgagtagtga ctgtcgtgta aggctcagcc ggatgagcag gagcactcgc 162360
ggccgcaggt gcggccgccg gcccgccagt tgccatgact agtctgtccg taactgggtt 162420
gtccgtaact ggtttgtttg ttgctggtct gtttgttgcc ggtctgcccg tgactggctt 162480
gcctacactt gctgtagtcg ctccagctgg tttagaggta cctggttgtg gagtgacttc 162540
tacccactgc tgatcttgat aaggatttat aaactgtata tcttcctcct caatagcagc 162600
agctttttc tttcttgaag agaatagata gattagaacg atgataatga tgactaagac 162660
cacgatagca atgagaatag tatacatatg tgtggagaag aagcttggtg tagtgactgg 162720
tgacaaacac tcaccataat gccgcggata aaccggttga aaaaattcag aatccattta 162780
agatactatt ataaataata tataaaaatg ttgtggcgca atgaaattac agaatttatg 162840
gaccaacttt ccaagtattc tcaagaaatc ttaaaaacgt ttaagcaatt gcgtcctagt 162900
gaatataaac aatacaatga atttttaaca caagttacac cgttgctgca aaaaaacccct 162960
gaaaaaattc cagagttggt tgaccatata ttcaattacc tagacaacgt tgaaaaaatt 163020
tgtgagctcc tcgtgaatgc tagctcaatt attattagtt caaaaatacg agaacaagta 163080
aaacacggaa tgagcttcag ctataaagcc gacctcgact ccttggcgga cattctctct 163140
caaaaacagt acgtgcttat gcatctttca aaaaatattg cggccgagta ttttaatacg 163200
tgtttaaacc aagggaaatc caagttagat ctcaaagctg cctctgtatt tttatagtagt 163260
cgttcccgaa cggcaagctc agcagaactc tatagaaaaa tgctatacgc ctatggttca 163320
ccgcaggaaa ttaattatta tactgaaaaa gcccgaaata agacgttgga tgtggaggag 163380
agcgacagca tggccatcat cgaacgaacg gcccgacaca acctttccct tatgcacccg 163440
ctagaagcca tggggcttac ctttggggca accaacacgg acgccgaccc ggaggatctg 163500
aaggacaaaa cggtgataaa tttaacgctc ccgcaggcaa cagaaagcat cacctaccat 163560
cttaaatccc taatgcagct aaaaaaagta agtacggctt caggactaaa tacaaacatt 163620
ttgaaagcat ttgataatat tatttccacc cctgtgaaaa aaaataaaat ggcctccaag 163680
ttggcgcccg ggatggatgt cgtgttcact agcgataacg gaaaaacatt ttttactaaa 163740
aacattttaa gcaaaaacat gctagcgggg cccaaagagc gggtgtttgc atataataat 163800
ctcattagta atttaaataa ctcctgtttc atacaaaatc acaacgattt tttaagacag 163860
caggactctt ggcccttcta tgacgcgcac aattttacca acaagttttt aatgcagcct 163920
attttttcgg ggcagacccg tcctcggctt cagggagcca tggaggcggc gcatgtggaa 163980
acgcatctca cggcattttt acaaagtatt cagccctcta ggccacaaga tccctctgtt 164040
ttggcttccc ccaagttatc tgctctaatc ttgaactaaa aacagccttt cttggactta 164100
aatgatggtc taccagtttt tgaaataact tagagaacta tgaagatttt catgaaattt 164160
aaattagaga tttgcaaagg ttacttgcgg tcattttctg ttgaattaaa taattattcg 164220
aatagtataa tgtctgaaga tattcgtcgt ggtcctggca gaccgccaaa gaaaagggtt 164280
gttcccaact ttgagcgcaa gggcattctg gaaaaaccag ttcggccaca aagccgtctc 164340
gagttttcct atgataaccc gctgatattt aaaaatcttt ttatttactt taaaaacctt 164400
aaaagtaaaa atattttggt gcgatgtacc cccaccgaga ttaccttttt ttcacgtgac 164460
cagtcgcagg caagctttgt tattgccacc atcgacggaa aaaacgtgaa ccattattac 164520
gccagtgatg tcttttggct aggcatcaac agagagctcg ttgaaaaaat gtttaacagc 164580
attgatcgct cttttttaaa aattaccatc gttcaccgct atgacaagcc tgaaaccctg 164640
tttttatctt ttacggattt tgacattgac aaggagtgca cgtatcagat tacggtctcg 164700
gagcccgagc tcgatatgga ccttatcgaa atggaaaaaa gcatcagtga agaaagactc 164760
aagaactatc ctctgcgctg ggagtttacc tccaagcagc tcaagaaaac atttagcgac 164820
ttatcaaact acaccgagct cgtgaccatt gaaaaactcg gcggcgatac gccgctgcac 164880
ctgtatttcc aaaagtttaa ctccatctca taccacgaga tgtataaatc ttccaacaag 164940
atcaacctga cctcgaccat tcctaagtcg caggtgttcc agataaatgt taaaattgct 165000
cacatcaagt cgctggcctc ggctatggtc accgacaaga tccgcattct gtgcgaagaa 165060
aatgggaacc taatctttca atcggaaatg gatgccctta tgttaaatac gattaccttg 165120
aacaccacga tatagttcgg taacattaga tgttctaata tttagcatct aaataatacg 165180
ctgtagtccg gtcagggttg cgtcacagtt ttcccatttt tttgcctcgt cggcggtggc 165240
caccgttgcc ctatcattta cgcccggtaa gacaaagcta aaggcgttca gcggggcttg 165300
gcaatgcccg cccagcgtga aggagctcgg aggattttgc gcatcccgaa atcccttagc 165360
catgttgttt aacacttcgg ttacgtcaat cgagtgaagg gatcccttgg gatccgtgaa 165420
tgtaaagacg cagtttctaa agcgcatgta tgcgatggac gattcatcgg gggttttgaa 165480
ggtaacagtg ttccccttgc tgtacttaaa gggggaccat ccggtaaaat tataccaaat 165540
gaaagcaata ataattaaaa taaccaacac aatagttata gacaacacaa agtctgtagt 165600
gccgcccatt attaaataaa aatattttag accgccggct taaaatttac ttattgctca 165660
tagcttaagt ctattttatt catagcttaa gtttattgct catggcttaa gtctattgct 165720
tatagcttaa gtctatttta ttcatagctt aagtctattg ttcatggctt aagtttgttg 165780
ctcatagctt aactccatta ctgatagctt actgatcatg acttaaataa aaatattttg 165840
cccgcttaaa aattgtttag gtttgaaaaa ataagagatg gagggggcaa cttatcgtca 165900
ttgtgtttac ccccactgga agacatcaaa cggtaaataa ttataagaat caaaatgatt 165960
aatataaggg ttaaaaaagg atgattcatc acattaatta aaaacgtatt tataacgctg 166020
ttgcagttga aattttggta taggtcggaa atattgcccg agcctccgta ttctgcaatg 166080
ttctgacata tggtgagtcc ggaggggcac tgcttgttgg tcaaaatatt tctttgctcc 166140
gttgttttat aggcattttt atttccatta cacggagcaa acgcacattc aggccatagg 166200
gtgccggagt tcacacaggc acaatactgg ctatacgcat actcatcctt tgagcacaat 166260
ccctgtttat cgcatatgct cccaataata ttgtcatcct ccgccgtttg ttgatttgta 166320
tgcgagcgta aaatagcggc ccaggccttg ggctcctttt tttgcagctc ggaaatcgaa 166380
gggcctgtac agctaaagtc gacccaaata tcattgcatt tcgtggaaac tggcatgcaa 166440
gacataattg aaataattaa taagtatata tcatggcaac aaattttttt attcaaccta 166500
tcaccgaaga agctgaagca tactacccac cttccgtgat aacgaataaa cggaaggacc 166560
tgggggtaga cgtatactgt tgctccgacc tagtgcttca acctggacta aatattgttc 166620
gcctgcatat taaagtagca tgcgaacaca tgggcaaaaa atgcggtttt aaaatcatgg 166680
cgagaagcag tatgtgcacc catgaacggc tgctcatcct tgcaaacgga attggtttaa 166740
tagacccggg ttatgtgggc gagctcatgc tcaagatcat taatcttggc gacaccccgg 166800
tccaaatatg ggccaaagaa tgtttggtgc agttggtggc ccaaggtgac catgtgcctg 166860
accatatcaa catcctaaaa agaaaccaaa tatttccgct gtttgcgcct accccaagag 166920
gcgagggtag atttgggagc acgggcgagg ccgggattat gagaacttaa ttttattttt 166980
tttcttaaca taatgggagg ctctacaagc aaaaattcct ttaaaaatac gaccaacatt 167040
atcagcaatt ccattttcaa tcagatgcaa agttgtattt ccatgttgga tggcaaaaat 167100
tacataggcg tattcggtga tggaaatatt ttaaaccacg ttttccagga tttaaactta 167160
tcattaaaca caagttgcgt gcaaaagcac gtaaacgagg aaaatttcat tacaaatctt 167220
tcgaaccaaa ttactcaaaa tttaaaagac caagaagttg cgttaaccca atggatggac 167280
gcaggaactc acgatcagaa aacggatata gaagaaaata taaaggtaaa cttaacaacc 167340
acacttattc aaaactgcgt ttcatccctg tcgggtatga acgtgctggt ggtgaagggg 167400
aatggcaaca ttgttgaaaa cgcaactcag aagcagtcgc agcaaatcat ctctaactgc 167460
ttgcagggga gcaagcaggc catagacacc acaaccggca tcactaacac ggtaaatcag 167520
tactcacact acacctcaaa aaactttttt gacttcattg cagacgcaat ttcggctgtt 167580
tttaaaaaca tcatggtcgc ggctgtagtt atcgttctaa tcatcgtagg gtttatagcc 167640
gtcttttact ttttgcattc acggcaccgc catgaggagg aagaagaagc tgaaccactc 167700
ataagcaaca aggtattaaa aaatgctgcc gtttcgtaat aatttaatta aaagtaaaaa 167760

```
aaaaggtatt gttatagtga tggcagattt taattctcca atccagtatt tgaaagaaga 167820
ttcgagggac cggacctcta taggttctct agaatacgat gaaaatgccg acacgatgat 167880
accgagcttc gcagcaggct tggaagagtt tgaacccatt cccgactatg accctaccac 167940
atcaacttcc ctgtattcac aattgaccca caacatggaa aaaatcgcag aggaagagga 168000
tagtaatttt ctacacgata ctagggagtt tacttcactg gtccccgatg aggcagacaa 168060
taaaccggaa gatgacgaag aaagcggtgc aaaacctaaa aagaaaaaac atttgtttcc 168120
aaaattaagc tcgcataaat cgaagtaaaa attgaagcga aaaaaagtag aaaaaaaatg 168180
tttggagctt ttgtaagcca ccgtttgtgg tcagatagtg gttgtacgac cacctgcatc 168240
acaaacagca ttgctaatta tgtagccttc ggcgaacaaa ttggatttcc ctttaaatca 168300
gctcaggtat ttattgccgg ccctagaaag gctgtgataa atattcagga agatgataaa 168360
gttgagcttt taaagatgat tgttaagcac aatctttggg ttgttgctca tggaacctac 168420
ttagatgtgc cctggtcccg taagagtgcg tttgttacac attttataca acaagaacta 168480
cttatatgca aggaagtcgg tattaaaggg ttagttttac acctaggcgc tgtggagcct 168540
gaacttatta tggaaggact aaaaaaaatt aagccggttg agggggttgt catttacctg 168600
gaaaccccgc ataacaaaca tcatacatat aaatacagta caattgagca gatcaaagaa 168660
ttgtttttac ggatacgaaa taccaggttg aaacagattg gtttatgcat tgatacggct 168720
cacatctggt cttccggtgt caacatctcc agctataatg acgcggggca atggctgcgc 168780
tcgctggaaa acattcattc cgtgatccca ccaagccaca ttatgttcca cctaaatgat 168840
gccgccacag aatgcggaag cggtatagac cgacatgcaa gtctttttga aggaatgatt 168900
tggaaatcat atagccataa aataaagcaa agcggtttat attgttttgt tgaatacgtt 168960
acgcgacacc agtgtccggc tatattggag agaaacctcg ggtcttccat gcaattacaa 169020
accgctttaa ccgcagaatt tactacatta aaatcgttat taaaataagg atgagtttta 169080
gcgaatgtcc cttagttatt agtgcatgca aaaaatttct acaaaagcgt attacaatag 169140
agaatgaagc acttataaat gccttaataa ccgctttagc gcagaccagc acgttgaatg 169200
atctttgttt attacctatt caaacctatt tgcttagtta taaaaatgct tttgagtgga 169260
tacacttcgt atgtattgca atcaccacta ttttggataa taagtataac tggaaggact 169320
gtacggtaga tattaattat atttttctcc atgtaaccta tatttacaat attaaaacca 169380
aggaatacct agactactgt tcttaaactt tattttttct atatttacgc caaagagaat 169440
atttaaagtt tttttgaaaa aaataatata tgtagataaa attcagttac atgatatatg 169500
tgtaaacatg tgtggtaaac aacatatggt tatgctttat aagataaatg cgcataatat 169560
atgtaaacaa aatatggtta tgtgttaaat gcatataaat gtattttaac gtatatcttg 169620
tgataatgga tatatgcatt tattaaaaga ggctgtattt attataaatc ttgctaagga 169680
tgccattgtc aacatatatc ccatgttgga caaattgcgt tgcgatccag ttcttttttt 169740
ttgattttgt ttaatgctat cctttttgaa gggatggttg tccaccatat ttattcgatg 169800
ttcaatgaat aggtctgctt tttcgtaagg cagtgaaggt cgttccaaga ctccttgaac 169860
gatggacgtg ttttcttgga tccacttaaa aagcacgtgg cattcaaaaa caggacagtg 169920
attggatcct tggatatgct ttggacagcc aatgcttgaa gagatgtagt ccctttttctt 169980
taggacaagc ttctccacgc tggggcaaca gagatcgttc aagttctgga cggtcgcatt 170040
tggaatgttg aaacttcgta tccattcacc ctcgggtcct cccttatgaa gaaggagtat 170100
ttgctcatgg tccttagtaa tcttaaccaa atgttggaag atcatttttt tacctgcttt 170160
```

aaaggcctga agggtgtcag ttggcaaagc tattgaattc gggagtgggc tttcatcaag 170220
cgtgaaatgg tgaatgtgac gcgactggaa agaaaacgac cgttgattta ttttttcaaa 170280
gattgggtcg attccgccat gaaagaacag ctgcaagatt ttagaaggcg tatttttttc 170340
ccaataaaaa atgaccactt ctcgtgggat taaaatcgtc tgtgtcccat tttcattata 170400
taattggccc ataaagccat caacgtcaat caacaccaaa agcatggtat agagagcttt 170460
tagaaccgga gttcgttaaa aaaatacaaa gttcgtttaa aacgtgtaat gttactaaaa 170520
aaatgtaatg tttaaatgat aatgatacca catgcattaa tgaaaaaaac ttttaaattt 170580
ttgttttaat atttgcatga aaatggaaac atttttagtc tgtttatttc acaatgcaga 170640
tggtttacat caacagattc aggaaatttt gtatttattg cggatgcata tttacgaaac 170700
aaatctttac ttaaagcagg aactatcacg gcttatatat ccaaataggc aactttcttt 170760
tgtgttactt atgccccttt cccttctaag aaactgggat gacattgaat atttaacgga 170820
cgttgtagat gataagcaga ctctacatta cgcggcaaat ttgctgacaa actacgttct 170880
acatctatcc atgtttcaaa agctgacaaa accatacttc cttttagcgg tcaagcgggt 170940
cagcgaaaaa ctcaacaaaa agcagcgaca ttcattttac gaggtattgg taacctccga 171000
aaccttgaat aattatgaaa acctatctaa aaacatttta aatacgttga tgtttgccgt 171060
gcgctacgta tttaaaccta cgccgaacta ttcagaaatt ctcgcagagt tggaaaaaaa 171120
aaataaaatt caccatatta tttttaatat ggtaattacg gattttgcgc aaatccgtga 171180
acaacaaatg gataaacatc tgtgtgaaac aaataatgag cttcgtcagg aatgtaaaga 171240
aactattttt gatttaaagg tggtaggaaa tgtttagcca ataaactcat gcccgcattt 171300
tttacaggta caaaatatcg tggatggctc atcgagggcg cgtgtttgta cttctctgta 171360
ggtacacata cgctgcttgc agttgggaca cttataaagt tgtgacgtct tttcggcgac 171420
cttttgctgc gaacgtagag taatttctgt cttctccttt aaggcggcag aggggcaaag 171480
ctcggcgaac gtcatgctac caattgcctc cggttttagc tcgccagaaa ttagcttatt 171540
aagggcatcg ttatcctgtt gttggtgact tttttttcg cagttaataa tatgattgat 171600
cgtcccacaa cgggttgaat attcttctaa aaaggttttt tcttgttgct ggtacgtata 171660
atgataacac gaggcctcga ttttttgcgc gtattcggtg cataaatcag tatgttcctt 171720
aaaaaacata tgtttttgaa gcgttctaaa aaacatcatt tggatgatat cacgcatttc 171780
caaaataata tagggttcta gtcttttgga atctttcata actagatcgg tggtaatatt 171840
cttagtcata caatttatta aaaatggttt aatatattgt aaatattttt taggcgtgtc 171900
agcctgtaaa aaacattctt gttcaatctt atttgtaagg atagtatttt gcaaatactt 171960
atttagcaaa aatacgatag aatcgcgggc tatatgcatt ttcatataat ttttttttaa 172020
aatttaatac aaaaaaaaga agtatagact cttcttctag tccggttagt tcgttggttg 172080
cctcaacatg gagactcaga agttgatttc catggttaag gaagccttag aaaaatatca 172140
ataccctctt actgctaaaa atattaaagt agtgatacaa aaagagcaca atgtcgtctt 172200
acctacagga tctataaata gcatactgta cagtaactca gaactttttg agaagattga 172260
taagacaaat accatttatc ccccgctttg gatacggaaa aactaattgt aaccagtagt 172320
acatttaagg atagtttaag cagtaaatgt agaataacac agttaagcaa taaataacaa 172380
gtatatagga atatatagga atatatagaa atatatagaa atagctaagc ttaatactaa 172440
ttcagctttt tttttaacta aaacctgaat agatgcgaag tagcggacat atacatacta 172500
aaataagcca tacatttact ttcttcttga acatgaaacc ttttttttctt ctgttgttgg 172560 tatataaaca ataggactgt ttgctgaggt tgtatgatct tctacaactg ctgtctcagg 172620
atgacgatgt ttttttaaac taaaagtgta ggatggaatg agtggaatat agttatggct 172680
cgacttatcc tgtttcgtac aggaatattt tttacaaata gaacgcaaca agcatatgaa 172740
taaaaacaga aatgatatac aggagcataa aatagatatg aacactaagg ggtagcagct 172800
tttataacgt tccgtatttt tcttagctat caattgattt accgtaatat ttatctcggg 172860
aaactttgtt ctacaatatt ttgtttggta ttccagaaac tcatgtcctg gcttattccc 172920
gcagcttaaa aaatgataca aaaatgtgtt attgttacta aaattaattc ttcttaagaa 172980
aaactgcgga agacgcttta ggtacgtctg ttcctgtttt agtaggaagt agtataaggg 173040
acaatttctt tttccacaca ttagattatt gtaatatagg taggttgggg tgttggagcg 173100
aataagtttt ctgagtatgt tataatctat gacttgtaaa tcgttatacc ttaggtccaa 173160
aaacttgagt tctttaccaa agccacctgc aatttcagaa atatttttca tcccgcagcg 173220
gataatacgg atgtcctgaa acgtctttaa aatacttgta ttgtagtgaa tacttatgtt 173280 attttttgt aaataatcta tgtcatgaca agtgcatgaa atgccagcag cattgcttgg 173340
tatagtatta tatgcaggaa gaactatact actattgaga atagtcacat tgtacttata 173400
ccatgtatta ttttctgata taaagtattt gcaggtgacc tgtggtttaa tcctacctgt 173460
taagccactt cctaaaaaaa caaaaaaatat gaaaaccctt agcatcctgt atatactatt 173520
aaaaatttat aaaattttct gtttaaattt catttagaca aaaaaataat atatatacat 173580
cagcaagaaa ttatatacag attatataat tttctgattt ttttttgcca caataagcat 173640
cattatatgc attaaaatct caatactaaa cactaaaatc taaattctaa gcattaaatt 173700
ctaagcatta aattctatgc actaaactgt aagcactaaa atctaagtaa ctaaaatcaa 173760
cactaaatgt atgcaaccta aaatgtaaag cattactcat catcctcctc ttcttcatcc 173820
tcatcatcat aggttaagat atatgtgtca tcctccattt cttcacattc atcttcataa 173880
gcatcactgg gtattggtgg aacattggat gcagcatttt taaaatattc tatgtcttct 173940
ggtgaacact catctaatga ttttttgaca gtccttttaa cttccatggg atatgattcc 174000
aaatcctctt tatataagag tttacggtag cttttagctg catccacatt tgctggagaa 174060
tctggatttg gctcattgag cagtgaaatt acactaagaa gaatggtatc aatcttttga 174120
gccggagacc aagtcattcc ctgttcttca gcattgtctc cgtgtaagat agagatacat 174180
agttttccat cagagtaaat attaggatgc cacatttcag aggtgaatgt taatctgggt 174240
ggtgcatatg ggtattctgg aggaaaggcg atttttgcct tgaataagcc tccctcataa 174300
aaagtgtcag gtgggcccct taagatcaca tcccattcag tcatatcctt ctcattcacc 174360
gaaattttga aattctcaga gggattctct atcaggtgtc tgtactctgc tattaaaaac 174420
ctggaaacca tggttattta atattaatta aattccctgg tttattcctc cttaaaagta 174480
gatgaacctc ttttgttttt tattgggttc atttttacta aatttatgaa ctggaaaaaa 174540
ctttaacggc ataattatca aatgcgaagg gggatccgta taaaatccta gcttgccggt 174600
aatggctatt aagttaaatt tggtaccagt aacactaata tttaaaaagc cctgatcatt 174660
aactttccac attaaaagat tattatattc gaatgtttgt ccaatatgga caactttgtc 174720
accagatgtt acatttgatt tggttgttag tggctgaagc ttggcacaat caaaaataag 174780
cccattaaca ctaagatata gaggagtggg ttgatctatt ttctcatagt ttaatattcc 174840
atctttccac gtaatagctt gataattatc cgcagcaatg agttgaaatt ttataaatag 174900
tacaggggtt ttagttgtcg ttatacattt aaagggtgtt ttataaaaat aaaaataata 174960
attgttaaaa gtatgataat aatcgccaaa ataatttcat acattttttta taagaattat 175020
acatagtatg gtatttaaaa tattagctaa atttaaaaaa acttcatgat ttttaaaaca 175080
gggaaaaagg ggattaggtt gaataaaaaa ggtaagcact tgtctatata ttttttttac 175140
aatgttgcct tgagtcgcat ttttaactgg ctggggagta tcagagtgga atatcactgt 175200
agtaggtcta taaggtcttg ttaaaatatg atcggtcatt gttttcgtac tagtgtcatt 175260
tagggtcgac ctgatagctc gatataaagt tatagggggat aacctatcaa atacagtctt 175320
atctgtgctg aaatgtatat cgtcttcttt atcactaata atattaggaa tggctgtcat 175380
taaataatta ctacttgttg ttgtgggtga aatagttgta ctggtattat tggaaatggc 175440
tgtcattaaa taattactac ttgttgttgt gggtgaaata gttgtactag tattattaga 175500
aatggctgtc gttaaataat tactacctat tacaagtaaa ctaatgctaa ctacattttt 175560
aacctcaata aacctaaaaa gccatactaa atacctaaac aacatcctgt tataatatga 175620
gcagaaaaaa aaataagtat aattagggaa ttattcttat tcgcttacta ttaagaataa 175680
ttcagaatct tatttagtta gaaactatca taaagtgaat aggactcatc gtcggatgaa 175740
gattccgttt cagagatagt ttctttttct tcctcagaat aatctgttcc tacaatagaa 175800
tcggtgtcat cctcagaaag agaagtattt aaatatggac tatctatagc aatatcctct 175860
tctatctcgc aatcctcctc ctccatttcc atagtgtgta ggagaatatt tttatcatca 175920
tgctcacttc tttttttgtt gaaagatgaa ccgtcctcaa tacggttcat gttaagttcc 175980
ttcatcttat gtataatttc cgtaatccgt gatgtttttg acatgtaaga tggttttaag 176040
gttatatcca caataacagg agaatctcta tcattttcat ttgataaact ttgatctttg 176100
atttcttcgt ctaaaattct tgtctttttt tgggtactag atgaaataga ggaattcata 176160
ttctgaaacg atatatcaag gggagctgga cgcttttttc caattaaacc gtttttcgag 176220
atactatgat tagatgaatg atctttagcc aagctgtcct tggatatact atagttagat 176280
attttacctt taaataatat tcttctatac aagttattct taggtaaaga attagtatgg 176340
attcctatat ttttatctga aggagtgtcc atatcggaga acgtcctctt acgaatattt 176400
tgaccacgag ccatttcatc cactataggc agtattttgg ctggctatgg ttctttgttg 176460
tgacaattct atgagatttg attgcaaatc aatttttagt tttaaatata ttggtaccta 176520
ggacaaagaa agtatatata gccaataatt attccactaa attgatttcc agactgatgg 176580
gtatggagcc atgttgtctc tgcagacgat cgcaaaaatg gccgtagcaa caaacaccta 176640
ctccaagtat cactatccaa tactgaaggt ctttgggctg tggtggaaaa acaatacgct 176700
aaatggccct attaaaatat gtaaccattg caacaacata atggtaggag aatatcctat 176760
gtgttacaat catggaatga gtctggatat agctttgatt cgggcagtaa aggagcgtaa 176820
tatatcctta gtccagcttt tcaccgaatg ggggggaaat attgactatg ggcactttg 176880
tgctaacact ccatctatgc aaagattatg taaaagtttg ggagccaaac caccaaaggg 176940
ccgaatgtat atggatgctc ttatacatct ttcagatacc ttgaatgata atgatctgat 177000
tagggggtat gagatttttg atgataatag cgtgttggat tgtgtcaatc tcatacgact 177060
caaaataatg cttaccttga aggcccgtat acctctcatg gaacaactag accaaattgc 177120
cttaaaacaa cttctgcagc gatactggta tgccatggct gtacaacaca acttaacaat 177180
cgctatccac tattttgata atcatattcc taatataaag ccatttagtc tgcgctgtgc 177240

-continued

```
tttgtatttt aatgatccct ttaaaatcca tgatgcttgc agaactgtaa atatggatcc 177300
taatgagatg atgaacattg cttgtcaaca ggatttaaac tttcaaagca tttactattg 177360
ttatctttta ggggctgata ttaatcaggc tatgctaatg tctttaaagt atggtcatct 177420
ttctaatatg tggttttgca tagatttggg ggcggatgcc tttaaagagg caggggcgct 177480
tgctgagaaa aaaataaaag agtgttacaa cacatattag gtcttaatat ctttaagcga 177540
gagttgattc ccccctgtaa agatcctgat ccttatcaaa tccaaattct gttaaaaaac 177600
tacattctaa aaaatgtctc aactgttttt acatattatt gccagtagcc attgtttata 177660
tcagaaaata acccatttgt ttatcttttt ttgtggggca accattaaga cccgacgcaa 177720
aaaaagatta atcttttatc agatacctaa aacgttctat aagggagtct atgagatgga 177780
tcatattttg atggtcatag taagaagcaa gctttttggc gaaaacaacg gagttaaaga 177840
atttaacccg ctcatgtttg gataggactt ttaacagcga gccaaaacag tatttaaaaa 177900
tttggcaata gttttttgg gatgcaataa acaaacactt gatcagtgcc cgcttcactt 177960
tctgatcaga catgtttgcc gcataacagg cctttttaaa cttagtaata taattatgtt 178020
ccgcaagcac cattaacaag ggaacgatgg gaagctgctt ttcttggtga aatttacgta 178080
aatattcgat ggccaccgct tggacgactg tgtaatttac taagttagaa atgatagctt 178140
tcatggttgt aaaaatatac ataggatttt ctttttctgt atacagtttg aaaagcttat 178200
gattacgtga aatgatggcc atttttaata caagatggta tagtgtatct ttaggtaaaa 178260
atgccttgca agccgcgatg atgtcgatgt tgtctccatg aacagcgata gaaactaatg 178320
tttccaatct aaatgttttt atctgcatta atagaagaat gcagtcaatg ttattatact 178380
taataatact gtaatacacc gaatcaatga ccgtcatctg agaatcaagc tgacttatta 178440
gtaaatttaa cgttttttg gaggcatgac ctttgatcgc ggcactaagt gcacacagta 178500
tagcaaaatt gttaaataca ttttgattta ggagaaggag taatattttc cttcggttat 178560
agtacgcagc atctgtgatg attattggcc gataaatgtt aaaatgtgtt aacagctttt 178620
taaaaaaacg gaagtaattt ttttggatcg ctgtttgcat catcgaaata atgagataat 178680
cagggtatat aatgggtagg tcacatgcta cctctaacaa agaatagtcg cccaatctaa 178740
aggctgtgtt gaaaagcgta ctatcatcat acgtatcgag tacccctgct gttacaaacc 178800
aagcgataag atgaatgtgc cgttccttgc aagctatcgc aaatagggag tttcctatgg 178860
aatgtcgaat aatgtactcc ctattttttt ccaaaatgtt tggaaaattg tatagcgttg 178920
cggcatacag tagacactcc attctggcgt tataattttt acttttacat atgaataggt 178980
ggaagaactc gaataattct tgagaacttg ttaaatgcat aatatggtga tattttggtg 179040
tcgttaaatg gtatgagaaa atgcattcta atacatcttt tcggttatgc tttagcgcct 179100
gagctaaggc atattcaggc tcgacccata ggactagtgt ttctataatt gagatattcg 179160
cctgctttgc cagggcatac tttaagacgc tccggttaga aaaaatgttg ttatgaagat 179220
ggataaccgt atccattttt acgatgggac cattccagta tagtcctaaa tgctgtagca 179280
gatcttttgt tagttgtgaa gcgttctcgg gtgtcatata aatatgttgc agggcttttt 179340
tctgtaagga gaacatttcg tcgtaatcgt acaaaaaaaa ttaaaatttg ggcatggatg 179400
attcaaacat aacaaaatca agattttata acagtttgca ttaacctata catatatgca 179460
agtaaatgag atattatcta tcataacgaa tcaagggata tttgtatata tcaggagttt 179520
ctgaaataaa gatatgaaga ttatcatagt agtatccatc aatcacaatg caacttcctt 179580
taaggcataa tttagtaaac tcagcactcc catcttctgg atgctttaca actaacatta 179640
```

aaaactcctc agtcatatta tctgtaataa aataagatcc tcctggagcc atttgtagca 179700
tgtctcttat tcctacaaaa tcttttttgg gatggtaaaa actcagcagt ttcaaactct 179760
tttttagttt tttttcctgg tatttaagcc atttgttata aaacagtttt cttatgaaaa 179820
tgcatttgaa aatattggga atgtttaacc atgcttcttc cgagcacatc tccagatact 179880
tactttcttt gtttcccatg tctaatttat tgctcactaa gttagtaatg aatctatttt 179940
aataatctac tttactaatc tatcttaata acctatctta taatctatct taataaccta 180000
attataacct atttataatt ggctaatgct gccggcattt catgcctatc taaacaactc 180060
ctactaagca atctactatt acatatatag attcactttt tatatttgta aatcatgaga 180120
attataaaat cattactcat ttttattgta aattagtggg tatttgtaaa aatcttcaaa 180180
cgttttaaga tagttttcta gagagaagta atctttgcca tcaatatata atgcttttcc 180240
tttaaactcc agttttgcta tgtttagtga gccgtttcta gatctttttg ggcaataaat 180300
agattttcat tggttgcatc gtccgtaagc agaaaggtac cactaggcac gttaaaaaac 180360
atacgttcta tttcatggtc ggatttttga gaatagaaaa aatctaattt tttaatccgc 180420
gttaactctt ttttatcaat ctttccagac tgttttatat atactttatt gcaaatctta 180480
caatcctcta tggcttcatt atacttattt tgcttatcct ctattgacat gtccgtattt 180540
gataggtaac ttccgttaag gcggttcccc atggttttag atagattttt aattcagttg 180600
tatactttta ttatgaggct aaaatataga agtttgatcc taaaaaaata aaaagatttt 180660
gtacatttat ttatggttta tagcggtata gaggccgata aaaggtatcc gggtagtctc 180720
ctatgatatc gtcaattttg gtataataac agttgttatg gtagtattgt ccaaaccgag 180780
tatgtatgcg ccggtgaagc gtccgcccgc taatggtaca gttccaggtt aagacaatca 180840
tatcacaccc aaaaagagag gaaacagcat aggtgcccaa aggttcatta tataacatac 180900
gccgcatata ttttagtttt ttttctccat ggtaataatc acaggttttc atgtcctgct 180960
taataggatg attccccatg tatgataata tataataaat ttagttttta gctttttcaa 181020
aaaattgggc gctcgaaact aaattttcct tatcacagcg tttggagaaa gcgtatttaa 181080
agatatatct tcttctaaca agactgcaaa aaaaatctta ccccttattt ttataatgtt 181140
catcatagcg tttgaagata tcagaaggtg ccaggtttta taaaaatatc ctttaggatt 181200
tataacgata caagggtcta taaaatatat gcgggtataa tcttataaaa tcatcgattt 181260
tttcataata ttctccgttt atacaataaa gatcataaca gatattgatg cgtagatgca 181320
ttattcgcgt gttcgttggg cagctaaagg atatcacaac gtagtttttt ttaagaaaag 181380
acgaaactac ataagtccct aagggttcat tgaatagtaa acgccatatt tgttttaaat 181440
tttgttgttc accatagtag tattcgcact ttttcaagtc ttttttaata agcctattcc 181500
ccatgtatgc ttataaataa aaatttagaa atgtgctata ttatttgttg atgaatcatg 181560
aacacgtctt atatgttgat atgttacttt aaaaacattt gtattttcaa cagacgcgtt 181620
ctattcttat taagaatgat gccgtcttta ttttaaacct tggtttaaaa tttaaagaag 181680
tatttataaa ctataatcat gggaactttt tcagtaactg cctctgcaaa aagtgacgat 181740
gctgtttgta agtatttaga agaaccaata gatgaaaatt acagaaacat attaagaaat 181800
gagcatgtta aaaaaaattt aaatgaggct ctgaatcgac atattactac ctataatcca 181860
gtagttgatt ggtgtaataa ctattcaaca ttttcatctc aggatttcga tgaatataaa 181920
atttatatac atagcgatct tatggatgga cgacctcgtc caaaaaaaac atggtgtgtc 181980

-continued atcatgtaat gtttgttagt tttatataaa cgcaaaaata ttcttctagg agatgttgat 182040
atactaccta ttgaattcaa tatattaaag tacatttctg gctattccca ttacggtatt 182100
attattacta tttttaagag ctagatgtgg atttaagtaa taataacatt ctcccgttcc 182160
tcctagagac acctcatcaa attcccatcc tatgcaacct ttatgttgta aacataatga 182220
ttgacagcat tcatcttctt ttgaccaagt cgtccaaatc ctaccaagat ctatacgtgt 182280
ttttccaaat ggagattgaa gatcagcagt agtggcatta aacctataaa aaccaggtgc 182340
ataatcacat gaacggatcg taggatctaa tttaatatct tttatatctt gttttactgc 182400
ttctagacaa cttttatcag tacatgttcc acgtacacag tggtgtcctt tatccttaca 182460
atccgtatct gtcttacatt ttttttcgg cggtttatgt ttcagatggt aaaaacccag 182520
tattaaaata atcacaagaa taattcctat aagtacttga acaacaggat aaaacatttt 182580
aatattaaat atatttttta attaaatgaa tagatttaat ccaagtagta ttaaaatttt 182640
ttagaaatag tgttctacaa ataatgaaat gaatggtcca aaaaaaataa ggtgtacaat 182700
aatgtaatat attgttaggc taagtaaatt taatatttta aagtatttgg aaaaatattt 182760
tttaacatat gatgtctagg aatatttttt agacatttaa aaccatatag ttactttatt 182820
tattacactg aacttgaaaa gacttattac ctaaaatatt aatagatgaa gtaatattgt 182880
gtaattgagt ccataacatg ggtgggaaac aaaaatctcg taatatgaaa aataaacatc 182940
ctaaaaagag tgcaattgtt ataagtttat gtaactttat tttaaagtaa gaatataaaa 183000
atatgagtac aagaggaata ggggccatta ctaacattgg ctccaacatc ctgttgtcta 183060
caaaaaaaaa tatttttttt agcaaaaaaa aatccatgga aggatattaa tacacataat 183120
tatttgacat cacattagtg tacttaccaa atagtaatat acaaccatcc taatattcac 183180
ctttatgaaa tgatcccaac ctatacggta aaatagtata ggttttaata aagaaaaaag 183240
atattctgtg gtttttattt ttgtatagtg tgtgaataca aaataaaatc ccaaatttta 183300
accttttctt ttttttctat acaggatgtt agaaatagta ttggcaacgc tgctaggcga 183360
cctgcagcgg ctccgggttc ttacccctca gcagcgggca gttgccttct ttcgagccaa 183420
tactaaggag ctagaggact tcttatgctc agatgggcag tctgaggagg tactgtctgg 183480 ccccccttctt aaccgtctac tagaaccctc aggccctctt gatattttaa ccggatatca 183540
cctatttcgt cagaatccca aggcaggtca gttgcgcggc cttgaggtca agatgcttga 183600
acggttatac gatgctaata tttacaatat actgtctcgg ctgcggcctg aaaaagttcg 183660
caacaaggct attgagctat actgggtttt ccgagctatc catatttgtc atgctccttt 183720
agttttagat attgtacgat atgaggaacc ggactttgct gaactggcct ttatttgtgc 183780
tgcttacttt ggtgaacctc aggtaatgta tttgctctac aaatatatgc ctctgacccg 183840
cgcagttctt acggatgcca tccggataag tcttgagagc aacaaccagg tagggatttg 183900
ctatgcttac ttgatgggag gcagcctcaa gggactagtc tccgccccac tgcgtaaacg 183960
tctgcgcgcc aaactacgct cgcagcgcaa aaagaaggac gttctttcac ccccacgactt 184020 cttactgctg ctccagtagc tttttttgcc gcaggagcac cgcggatagg agctcctcca 184080
cgctcgcgat ccggcgctgg aagcggaacc gatcgaccgc cacctgctcc cagggaccct 184140
tgcgctcgat gtcgtcggct tcccacacct cgacggctgt ggcaaaatgg acatgcttcg 184200
cgtcgttcgt ccgtttttttg cgccgcctcc ccattattct tcctgtaaga ttagtgttta 184260
atacctataa taacataatt ttaagattta atataccaaa acttaaacta tttttgtata 184320
gtaactatta gcatgtctac acatgattgt tctctaaaag agaaaccggt tgatatgaac 184380
gatatatctg agaaatcagt tgtcgtggat aatgcacccg agaaaccagc tggagcgaat 184440
catatacctg agaagtcggc ccgcgaaatg acatcatcag aatggattgc tgaatattgg 184500
aaaggtataa aacgtggaaa tgacgtgcca tgttgttgtc caagaaaaat gaccagtgca 184560
gacaaaaagt tttcagtatt tggtaaggga tccctaatgc gctccatcca gaagaataat 184620
taaaaaaaat atttttttta gcaagttttt aaactattta aataaatgtg gtaaaaaaat 184680
tcacataata attaaagtga acgtgttaga attaatattt ttttataatc ggatataata 184740
tccattaaat caataaatga tagtgttgct accacactaa acaataacaa acagaaacgc 184800
acgatacctt tcctcatgat ttataatagc gtgttatcta aagatttttt tgaaaaaaat 184860
attaaatttt agttgattat ttttttcagt tacaacattg ctttagaaaa aatacctaat 184920
tactacatag caaataaagc gagcgcattg ttacaaacaa catttttttt gcgcctggat 184980
actcctatat atgagaacta taatacggta tattaatcct attaccaaca ttgtcaataa 185040
tagtatgtag gcaatgacat actttaaata ccaaatatcc atggttattt ctaaaaatct 185100
tgaaaaaacg ttaaatttta gatcggtcac ctacgacagt aatactaatt ttaataattg 185160
atgactgaaa tcataatata atgccgtgcg aaaaataatt atttttcggt taaagatacc 185220
attacataaa aaatatgcca tctactctac aagtgcttgc taaaaaggta ttggccttag 185280
gggagcataa agaaaatgaa catatatcta gagaatatta ttatcatata ttaaagtgtt 185340
gcggtttatg gtggcatgaa gctccgatta tactttgtta tgatgggagt gagcaaatga 185400
tgataaagac tccaatcttt gaagaaggca tattacttaa tactgcatta atgaaagctg 185460
tacaggagaa taattatgaa ttaataaagt tgtttactga atggggagca aacatcaatt 185520
atggattaat ttccattaat accgagcatg cccgggatct atgtcgaaaa ttaggagcta 185580
aagaaatgct tgaaggaaat gaatttatac aaattatatt caaaacatta gatgatacca 185640
ccagtagtaa tataatttta tgtcatgaat tattcaccaa caatcctctt ttagagaatg 185700
taaatatggg ggaaatgagg atgataattt attggaggat gaaaaattta acgaacctat 185760
tattaaataa tgactctatt agtgaaatat taactaaatt ctggtatggt atagcagtaa 185820
aatataatct taaggatgcg atccaatatt tttaccagag attcatggac ttcaacgagt 185880
ggcgagtaac atgtgctctt tcttttaata atgtgaatga tcttcataag atgtatataa 185940
cagagaaggt tcatatgaat aatgacgaaa tgatgaatct agcctgcagc attcaagaca 186000
gaaatttatc aaccatttac tattgttttc tattgggggg ctaacatcaa tcaagcaatg 186060
ttaacctcag tattaaatta taatattttt aacttattct tttgtataga cttaggggct 186120
gatgcctttg aagagggtaa gaccctggcg aaacaaaagg ggtataatga aatagtggaa 186180
atcttatcat tagatatcat ttatagtcca aatactgact tctcatcaaa aatagaacct 186240
gaacatatta gttctttgtt aaaaaacttt tatccaaaaa atctgttcgc ttttgatcgt 186300
tgcaaccccg gtttatatta ttcttagagg accgctacaa aaattatttt ttttcttgat 186360
caaagctcca aaataattat tagattaaag tcgcctatag cagcagccca ctccaaaaaa 186420
agtattttat agtacaaaaa acacgaaaaa tagtttgcgg ccggcggcaa actatttgtt 186480
gttgtctaaa acttaatgtt tttttaatat ttttaaatgc aaccatggat tgttggacta 186540
tcagggagaa gaactatagc tacatcatat tgtcaatact ggtaatacta ttaatatggt 186600
atcttatact taactattgt cgatcgaaaa aaaatgcagt tacaaacaac atgccgccac 186660
catacacggt gtcaagtagc tgttctcaat aatagggttg attgacgctc ttcgtaataa 186720
tatgttgatt gacgcatcat aaaatgctgt ggttgattaa tatgttgatt gtcgcctact 186780
ttattatata agtaatgatt tttgtataaa atacgggttt gtgagggctt tattttttct 186840
tattagaaca aagcatgcaa tttaaggcct acagcaagag taatttaaca cctacaacag 186900
taattttaag gtcagtaata atgtttaatt aaggcctgac cactaaaact taaacgattt 186960
tgtaaaaaaa aatgtctact ccactttctc tacagactct tgttaaaaaa gtgctggcca 187020
cacagcacat atctaaagaa cactacttta ttttgaaata ttgtggttta tggtggcatg 187080
aagcgccgat tacgatttgc attgatgagg atagccaaat attgataaaa tcggcaagct 187140
tcaaagaagg cttatcttta gatatcgcat taatgaaagt cgtgcaagaa aataaccatg 187200
atttaataga gttgtttacc aagtggggtg cagatatcaa ctctagctta gttactgtta 187260
atacggagta tacccggaac ctttgtcaga aattaggcgc aaaggaagct ttgaatgaaa 187320
gggatatttt acaaatattt tataaaacac gtcatcttaa aactagcagt aatattattt 187380
tatataatga attgttttct aataatctcc ttttccaaaa tatagagaga ttgagtttaa 187440
tagtttatag gggcttgaaa aacttatcaa tcaactttat attggatgat atttcattta 187500
gcgaaatgtt aactagatac tggtatagta tggcgatatt atataacctt actgaagcca 187560
tccaatattt ttatcaacga tataggcatt ttaaagattg gcggcttata tgtgggcttt 187620
cttttaacaa tttgtctgac cttcatgaag tatataactt agagaagacg gatatagaca 187680
ttgatgaaat gatgaagttg acctgtagta cgtatgatgg taattattcg actatttatt 187740
attgttttat gttgggggct gacatcaatc gggcaatgtt aacctcggta ataaactttc 187800
atattggtaa cttgttcctt tgtatagatt taggagctga tgctttcgaa gacagcatgg 187860
aactagcaaa acaaaagaat aataatatat tagtagaaat attatcattt aaaaattatt 187920
atagttcaaa tacctctctt ttatcaataa aaacgacaga tccggaaaaa attaatgcct 187980
tattagatga agaaaagtat gagtcaaaaa atatgttaat gtatgaagaa ttatctcatt 188040
gatacaaaat tattttttat aacagaactc tctgatggtg acaaatctcc gataggaata 188100
tatgacgtaa cataattatt tttttcgccc agaaaaaaat tataaatgtt attattgcca 188160
gcacttttat caactatacg tacaaaaagg tgttgaccaa aaaaataatt ttttttcttg 188220
atcaaagtat gtaaacgccc gcttacagca aggatcttaa gtgagagcca ttaaatttta 188280
ttgatagctg cttgccacca gtagaatacg gccaaaccac ctaacaggaa atacaaggcg 188340
gcccttcggc caataaggtg gataaaaatc acgcataaga cggttgtaac atagcacttt 188400
agtgcgaata tcaggaatgc caatagcatg tagataaggc accaaacatc gcagctatac 188460
atggctaaag atcaaccaga aaaggtttaa attttaacgc cggcccaaaa cttaaacttt 188520
ttttgatatt tttaagtgca gccatggatt ggtccggcca taggatgacc tatgcctacg 188580
tggcattctc attgatggca atagcaataa tatggtatat tctacttatc tattgccgat 188640
cgaaaaaaaa tgttgttaca agcggtaata cgctcgcttt agcgccaata tcgcatatgt 188700
gaaaaatgtt cgccgaaaaa aacattaaaa tttagaaccg ccgcggcatc tcaggggcgg 188760
caacattttt ttttatatgg atattgtcac acaccacctc atctatgacg caatatatta 188820
ctgctaatat caggttcccc aatagtatgt agagaaacca cacaagatag atattcatgg 188880
cgatttttga cgaaaaaaca ttaagtttta gcttctttga cgcctgtgta ctaataatgt 188940
ttaacgcctg tagtataata attgatacct acagcagtaa ttgataccta cggcgataat 189000
gtctctctgg ccgccccaaa aaaaagtatt tacggtaggg tttattaccg gcggcgtaac 189060
accagttatg gtcaattttg tctggcccgc cgcccagccg caaaaaaaaa tcaattacaa 189120

-continued

```
ccgcaaaaaa aaatatttcc ggccgcggcg tttcaaaaaa taatctttgc gaaataattc 189180

cgcatcttgt gaaatgaacg cctacagtaa taattttaat ctttgacacc tacagcagta 189240

gtaataattt taatctttaa cgcctgcagc agtactaata ttttaatctt taacgcctac 189300

agcagtagta ataattttaa tgtttaacgc ctacagcagt agtaat               189346
```